US007858784B2

(12) United States Patent
Buchwald et al.

(10) Patent No.: US 7,858,784 B2
(45) Date of Patent: Dec. 28, 2010

(54) LIGANDS FOR TRANSITION-METAL-CATALYZED CROSS-COUPLINGS, AND METHODS OF USE THEREOF

(75) Inventors: Stephen L. Buchwald, Newton, MA (US); Brett P. Fors, Cambridge, MA (US); David S. Surry, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/334,083

(22) Filed: Dec. 12, 2008

(65) Prior Publication Data

US 2009/0221820 A1    Sep. 3, 2009

Related U.S. Application Data

(60) Provisional application No. 61/013,174, filed on Dec. 12, 2007, provisional application No. 61/087,368, filed on Aug. 8, 2008.

(51) Int. Cl.
   *C07D 239/00* (2006.01)
(52) U.S. Cl. ............ 544/242; 548/414; 549/220; 564/184; 564/218; 568/13
(58) Field of Classification Search .......... None
   See application file for complete search history.

(56) References Cited

U.S. PATENT DOCUMENTS

| | | | |
|---|---|---|---|
| 4,885,376 A | 12/1989 | Verkade | |
| 5,231,202 A | 7/1993 | Hayashi et al. | |
| 5,508,458 A | 4/1996 | Zhao | |
| 5,510,554 A | 4/1996 | Regnat et al. | |
| 5,530,150 A | 6/1996 | Takaya et al. | |
| 5,663,426 A | 9/1997 | Albanese et al. | |
| 5,710,337 A | 1/1998 | Unruh et al. | |
| 5,710,338 A | 1/1998 | Unruh et al. | |
| 5,739,396 A | 4/1998 | Trost et al. | |
| 5,756,760 A | 5/1998 | Miyano et al. | |
| 5,767,276 A | 6/1998 | Zhang | |
| 5,789,624 A | 8/1998 | Unruh et al. | |
| 5,817,877 A | 10/1998 | Hartwig et al. | |
| 6,100,398 A | 8/2000 | Hartwig et al. | |
| 6,307,087 B1 | 10/2001 | Buchwald et al. | |
| 6,395,916 B1 * | 5/2002 | Buchwald et al. | 556/413 |
| 6,525,210 B1 * | 2/2003 | Zhang et al. | 556/21 |
| 6,946,560 B2 | 9/2005 | Buchwald et al. | |
| 7,026,498 B2 | 4/2006 | Buchwald et al. | |
| 7,223,879 B2 | 5/2007 | Buchwald et al. | |
| 7,247,731 B2 | 7/2007 | Buchwald et al. | |
| 2006/0173186 A1 | 8/2006 | Buchwald et al. | |
| 2008/0033171 A1 | 2/2008 | Buchwald et al. | |

FOREIGN PATENT DOCUMENTS

| | | |
|---|---|---|
| EP | 0503884 | 9/1992 |
| EP | 0731105 | 9/1996 |
| EP | 0802173 | 10/1997 |
| EP | 0849274 | 6/1998 |
| JP | 51132190 | 11/1976 |
| JP | 5097880 | 4/1993 |
| JP | 05097880 | * 4/1993 |
| JP | 07330786 | 12/1995 |
| JP | 09235289 | 9/1997 |
| WO | WO-98/15515 | 4/1998 |
| WO | WO-03/006420 | 1/2003 |
| WO | WO-2004052939 | 6/2004 |

OTHER PUBLICATIONS

Leroux et al., {A practical transition metal-free aryl-aryl coupling method: arynes as key intermediates, Advanced Synthesis & Catalysis (2007), 349(17+18), 2705-2713}.*
Ashburn et al., {Synthesis of Tetra-ortho-substituted, Phosphorus-Containing and Carbonyl-Containing Biaryls Utilizing a Diels-Alder Approach, Journal of the American Chemical Society (2007), 129(29), 9109-9116}.*
Demchuk et al., {A mixed naphthyl-phenyl phosphine ligand motif for Suzuki, Heck, and hydrodehalogenation reactions, Synlett (2006), (18), 2908-2913}.*
McEwen et al., {Role of through space 2p-3d overlap in the alkylation of phosphines, Journal of the American Chemical Society (1978), 100(23), 7304-7311}.*
Anderson, K. W. et al., "General Catalysts for the Suzuki-Miyaura and Songashira Coupling Reactions of Aryl Chlorides and for the Coupling of Challenging Substrate Combinations in Water", *Angew. Chem. Int. Ed.*, 44:6173-6177 (2005).
Anderson, K. W., et al.; "Monodentate Phosphines Provide Highly Active Catalysts for Pd-Catalyzed C-N Bond-Forming Reactions of Heteroaromatic Halides/Amines and (H)N-Heterocycles"; *Angew. Chem. Int. Ed.* 2006, 45, 6523-6527.
Aranyos, et al., "Novel Electron-Rich Bulky Phosphine Ligands Facilitate the Palladium-Catalyzed Preparation of Diaryl Ethers," *J. Am. Chem. Soc.* 1999, 121, 4369-4378.
Barder, T. E. et al., "Efficient Catalyst for the Suzuki-Miyaura Coupling of Potassium Aryl Trifluoroborates with Aryl Chlorides", *Organic Letters*, 6(16):2649-2652 (2004).
Bei, X., et al., "Phenyl Backbone-Derived P,O- and P,N-Ligands for Palladium/Ligand-Catalyzed Aminations of Aryl Bromides, Iodides, and Chlorides. Synthesis and Structures of (P,O)n -Palladium(II)Aryl(Br) Complexes," Organometallics 1999, 18, 1840-1853.
Bei, X., et al., "General and Efficient Palladium-Catalyzed Aminations of Aryl Chlorides," Tet. Lett. 1999, 40, 1237-1240.

(Continued)

*Primary Examiner*—Daniel M Sullivan
*Assistant Examiner*—Chukwuma O Nwaonicha
(74) *Attorney, Agent, or Firm*—Foley Hoag, LLP

(57) ABSTRACT

Ligands for transition metals are disclosed herein, which may be used in various transition-metal-catalyzed carbon-heteroatom and carbon-carbon bond-forming reactions. The disclosed methods provide improvements in many features of the transition-metal-catalyzed reactions, including the range of suitable substrates, number of catalyst turnovers, reaction conditions, and efficiency. For example, improvements have been realized in transition-metal-catalyzed cross-coupling reactions.

42 Claims, 26 Drawing Sheets

OTHER PUBLICATIONS

Bei, X., et al., "A Convenient Palladium/Ligand Catalyst for Suzuki Cross-Coupling Reactions of Arylbornonic Acids and Aryl Chlorides," *Tet. Lett.* 1999, 40, 3855-3858.

Beller, M., "Palladacycles as Efficient Catalysts for Aryl Coupling Reactions," *Agnew. Chem. Int. Ed. Engl.* 1995, 34, 1848-1849.

Beller, M., et al., "First-Palladium-Catalyzed Animations of Aryl Chlorides," *Tet. Lett.* 1997, 38, 2073-2074.

Biscoe, M. R., et al.; "Electronic Effects on the Selectivity of Pd-Catalyzed C-N Bond-Forming Reactions Using Biarylphosphine Ligands: The Competitive Roles of Amine Binding and Acidity"; *Angew. Chem. Int. Ed.* 2007, 46, 7232.

Brenner, E. et al., "New Efficient Nickel(0) Catalysed Amination of Aryl Chlorides," *Tet. Lett.* 1998, 39, 5359-5362.

Chemical Abstracts vol. 123; No. 15, Oct. 9, 1995, Abstract No. 197945; Columbus, Ohio, US.

Chemical Abstracts vol. 124 No. 25, Jun. 17, 1996; Abstract No. 343650, Columbus Ohio, US.

Chemical Abstracts vol. 127 No. 21; Nov. 24, 1997, Abstract No. 293410, Columbus Ohio.

Cornils, B., "Industrial Aqueous Biphasic Catalysis: Status and Directions," *Org. Proc. Res. Dev.* 1998, 2, 121-127.

Devasher, R. B. et al., "Aqueous-Phase, Palladium-Catalyzed Cross-Coupling of Aryl Bromides under Mild Conditions, Using Water-Soluble, Sterically Demanding Alkylphosphines", *J. Org. Chem.*, 69:7919-7927 (2004).

Ding, K., et al., "Highly Efficient and Pratical Optical Resolution of 2-Amino-2'-hydroxy-1,1'-binaphthyl by Molecular Complexation with N-Benzylcinchonidium Chloride: A Direct Transformation to Binaphthyl Amino Phosphine," *Chem. Eur. J.* 1999, 5(6), 1734-1737.

Fabbri, et al., "Binaphthyl-substituted chiral phosphines and oxides from binaphthophospholes and nucleophiles," *Syn. Comm.* 1994, 24(9), 1271-1278.

Fiaud, J., et al., "Preparation of Optically Pure 1,2,5-Triphenylphospholane. Use as Ligand for Enantioselective Transition-Metal Catalysis," *Tet. Letters* 1991, 32(38), 5089-5092.

Gelman, D. et al., "Efficient Palladium-Catalyzed Coupling of Aryl Chlorides and Tosylates with Terminal Alkynes: Use of a Copper Cocatalyst Inhibits the Reaction", *Angew. Chem. Int. Ed.*, 42:5993-5996 (2003).

Gill, F. D., et al., "Transition Metal-Carbon Bonds. Part XXXIII: Internal Metallations of Secondary and Tertiary Carbon Atoms by Platinum(II) and Palladium (II)," *J. Chem. Soc., Dalton Trans.* 1973, 3, 270-278.

Gladiali, S., et al., "Synthesis, Crystal Structure, Dynamic Behavior and Reactivity of Dinaphthol (2,1-b:1',2'-diphospholes and Related Atropisomeric Phosphacyclic Derivatives," *J. Org. Chem.* 1994, 59(21), 6363-6371.

Guram, S. A., et al., "A Simple Catalytic Method for the Conversion of Aryl Bromides to Arylamines," *Angew. Chem. Int. Ed. Engl.* 1995, 34, 1348-1350.

Grushin, V. V., et al., "Transformations of Chloroarenes, Catalyzed by Transition-Metal Complexes," *Chem. Rev.* 1994, 94(4), 1047-1062.

Hamann, B. et al., "Sterically Hindered Chelating Alkyl Phosphines Provide Large Rate Accelerations in Palladium-Catalyzed Amination of Aryl Iodides, Bromides, and Chlorides, and the First Amination of Aryl Tosylates," *J. Am. Chem. Soc.* 1998, 120, 7369-7370.

Hartwig, J. F.; Electronic Effects on Reductive Elimination to Form Carbon-Carbon and Carbon-Heteroatom Bonds from Palladium(II) Complexes; *Inorg. Chem.* 2007, 46, 1936.

Hattori, T., et al., "Nucleophilic Aromatic Substitution Reactions of 1-Methoxy-2-(diphenylphosphinyl)naphthalene with C-, N-, and O-Nucleophiles: Facile Synthesis of Diphenyl(1-substituted-2-naphthyl)Phosphines," *Synthesis* 1994, 2, 199-202.

Hayashi, et al.; "Catalytic asymmetric synthesis of axially chiral biaryls by palladium-catalyzed enantioposition-selective cross-coupling," *J. Am. Chem. Soc.* 1995, 117(35), 9101-9102.

Hiroi, K., et al., "Asymmetric Induction Reactions. VI. Asymmetric Synthesis of a Cyclopentene Derivative by Transition Metal-Catalyzed Asymmetric Vinylcyclopropane-Cyclopentene Rearrangements with Chiral Phosphine Ligands," *Chem. Pharm. Bull.* 1994., 42(3), 470-474.

Huang, et al. "Expanding Pd-Catalyzed C-N Bond-Forming Processes: The First Amidation of Aryl Sulfonates, Aqueous Amination and Complimentarity with Cu-Catalyzed Reactions," *J. Amer. Chem. Soc.* 2003, 125(22), 6653-6655.

Ikawa, T., et al.; "Pd-Catalyzed Amidations of Aryl Chlorides Using Monodentate Biaryl Phosphine Ligands: A Kinetic, Computational, and Synthetic Investigation:" *J. Am. Chem. Soc.* 2007, 129, 13001.

Lee, S. et al., "Palladium-Catalyzed Synthesis of Arylamines from Aryl Halides and Lithium Bis(trimethylsilyl)amide as an Ammonia Equivalent," *Org. Lett.*, 3(17):2729-2732 (2001).

Louie, J. and Hartwig, F. J., "Palladium-Catalyzed Synthesis of Arylamines from Aryl Halides. Mechanistic Studies Lead to Coupling in the Absence of Tin Reagents," *Tet. Lett.* 1995, 36(21), 3609-3611.

Mann, G. et al., "Palladium-Catalyzed C-N(sp2) Bond Formation: N-Arylation of Aromatic and Unsaturated Nitrogen and the Reductive Elimination Chemistry of Palladium Azolyl and Methyleneamido Complexes," *J. Am. Chem. Soc.* 1998, 120, 827-828.

Marcoux, J. F., et al., "Palladium-Catalyzed Amination of Aryl Bromides: Use of Phosphinoether Ligands for the Efficient Coupling of Acyclic Secondary Amines," *J. Org. Chem.* 1997, 62(6), 1568-1569.

Marion, N., et al.; "Modified (NHC) Pd(allyl)Cl(NHC = N-Heterocyclic Carbene) Complexes for Room-Temperatire Suzuki-Miyaura and Buchwald-Hartwig Reactions"; *J. Am. Chem. Soc.* 2006, 128, 4101-4111.

Old, W., et al., "A Highly Active Catalyst for Palladium-Catalyzed Cross-Coupling Reactions: Room-Temperature Suzuki Couplings and Amination of Unactivated Aryl Chlorides," *J. Am. Chem. Soc.* 1998, 120, 9722-9723.

Old, et al., "Efficient Palladium-Catalyzed N-Arylation of Indoles" *Org. Lett.* 2000, 2(10), 1403-1406.

Rataboul, F., et al.; "New Ligands for a General Palladium-Catalyzed Amination of Aryl and Heteroaryl Chlorides"; *Chem. Eur. J.* 2004, 10, 2983-2990.

Reddy, N. P., et al., "Palladium-Catalyzed Amination of Aryl Chlorides," *Tet. Lett.* 1997, 27, 4807-4810.

Reirmeier, T. et al., "Palladium-catalyzed C-C- and C-N-coupling reactions of Aryl Chlorides," *Topics in Catalysis* 1997, 4, 301-309.

Sodeoka, M., et al., "Stable Diaqua Palladium (II) Complexes of BINAP and Tol-BINAP as Highly Efficient Catalysts for Asymmetric Aldol Reactions," *SYNLETT* 1997, 463-466.

Sodeoka, M., et al., "Asymmetric Synthesis Using Palladium Catalysts," *Pure & Appl. Chem.* 1998, 70(2), 411-414.

Stambuli, J.P. et al., "Screening of Homogeneous Catalysts by Fluorescence Resonance Energy Transfer. Identification of Catalysts for Room-Temperature Heck Reactions," *J. Am. Chem. Soc.* 123:2677-2678 (2001).

Stauffer, S.R. et al., "Palladium-Catalyzed Arylation of Ethyl Cyanoacetate. Fluorescence Resonance Energy Transfer as a Tool for Reaction Discovery," *J. Am. Chem. Soc.* 123:2677-2678 (2001).

Strieter, E.R. et al., "Insights into the Origin of High Activity and Stability of Catalysts Derived from Bulky, Electron-Rich Monophosphinobiaryl Ligands in the Pd-Catalyzed C-N Bond Formation," *J. Am. Chem. Soc.* 125:13978-13980 (2003).

Tomori, et al., "An improved Synthesis of Functionalized Biphenyl-Based Phosphine Ligands," *J. Org. Chem.* 2000, 65(17), 5334-5341.

Trost, B., et al., "Asymmetric Ligands for Transition-Metal-Catalyzed Reactions: 2-Diphenylphosphinobenzoyl Derivatives of C2-Symmetric Diols and Diamines," *Angew. Chem. Int. Ed. Engl.* 1992, 31(2), 228-230.

Uozumi, et al., "Synthesis of Optically Active 2-(Diarylphosphino)-1,1'-bynaphthyls, Efficient Chiral Monodentate Phosphine Ligands," *J. Org. Chem.* 1993, 58, 1945-1948.

Vyskocil, S., et al., "Derivatives of 2-Amino-2'-diphenylphosphino-1,1'-binaphthyl (MAP) and their Application in Pd(0)-Catalyzed Allylic Substitution," *Am. Chem. Soc.*, Newsletter and Abstracts, 216th ACS National Meeting, Boston, MA, Aug. 23-27, 1998, #538.

Vyskocil, "Derivatives of 2-Amino-2'-diphenylphosphino-1,1-40-binaphthyl (MAP) and Their Application in Asymmetric Palladium(0)-Catalyzed Allylic Substitution," *J. Org. Chem.* 1998, 63, 7738-7748.

Vyskocil, "Synthesis of 2-Amino-2'-diphenylphosphino-1,1'-binaphthyl (MAP) and its Accelerating Effect on the Pd(O)-Catalyzed N-Arylation," *Tet. Lett.* 1998, 39, 9289-9292.

Walker, S. D. et al., "A Rationally Designed Universal Catalyst for Suzuki-Miyaura Coupling Processes", *Angew. Chem. Int. Ed.*, 43:1871-1876 (2004).

Wolfe, J. P., et al., "Palladium Catalyzed Amination of Aryl Iodides," *J. Org. Chem.* 1996, 61, 1133-1135.

Wolfe, J. P., et al., "Room Temperature Catalytic Amination of Aryl Iodides," *J. Org. Chem.* 1997, 62(17), 6066-6068.

Wolfe, J. P., et al., "Rational Development of Practical Catalysts for Aromatic Carbon-Nitrogen Bond Formation" *Acc. Chem. Res.* 1998, 31(12), 805-818.

Wolfe, J. P., et al., "A Highly Active Catalyst for the Room-Temperature Amination and Suzuki Coupling of Aryl Chlorides," *Ang. Chem., Int. Ed.* 1999, 38(16), 2413-2416.

Wolfe, J. P., et al. "Highly Active Palladium Catalysts for Suzuki Coupling Reactions," *J. Am. Chem. Soc.* 1999, 121(41), 9550-9561.

Yamamoto, T., et al., "Palladium-Catalyzed Synthesis of Triarylamines from Aryl Halides and Diarylamines," *Tet. Lett.* 1998, 39, 2367-2370.

Yang, B. H., Buchwald, S. L.; "The development of efficient protocols for the palladium-catalyzed cyclization reactions of secondary amides and carbamates," *Org. Lett.* 1999, 1, 35.

Zhao, et al., "Synthesis of Arylpiperazines via Palladium-Catalyzed Aromatic Amination Reaction with Unprotected Piperazines," *Tet. Lett.* 1996, 37(26), 4463-4466.

Anderson et al., "The Selective Reaction of Aryl Halides with KOH: Synthesis of Phenols, Aromatic Ethers, and Benzofurans," *J. Am. Chem. Soc.*, 128(33):10694-10695 (2006).

Vorogushin et al., "Use of Tunable Ligands Allows for Intermolecular Pd-Catalyzed C-O Bond Formation," *J. Am. Chem. Soc.*, 127(22):8146-8149 (2005).

International Search Report dated May 27, 2010 from PCT/US2008/086651.

\* cited by examiner

Figure 1
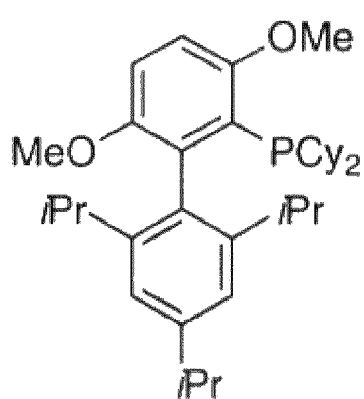
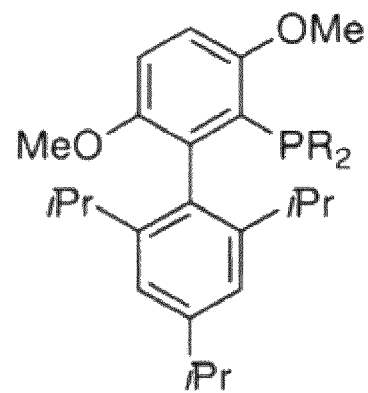
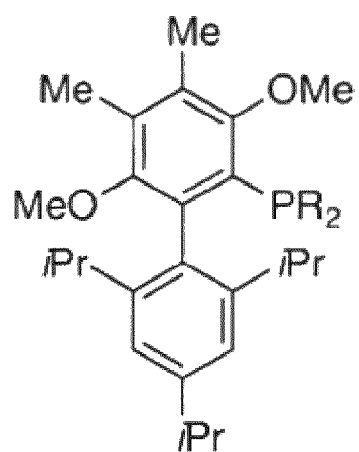
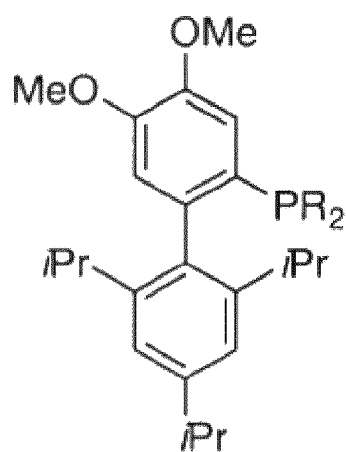
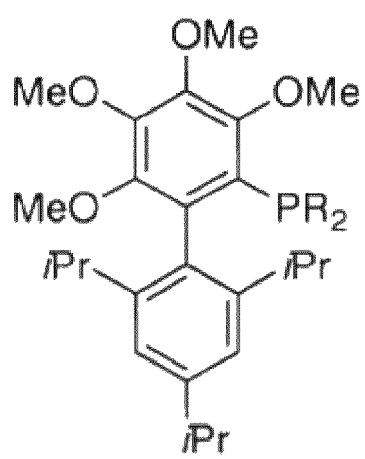
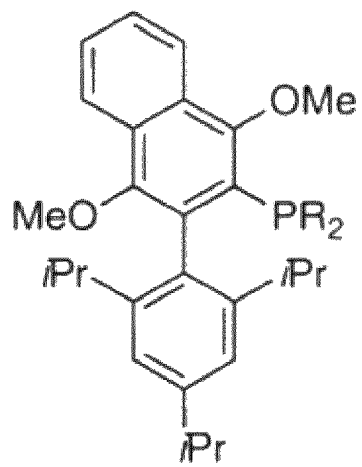

Figure 3
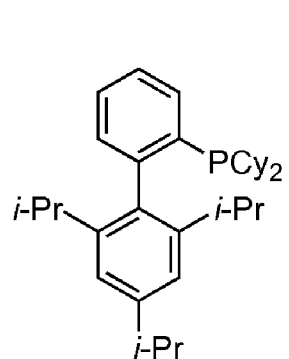
13, XPhos
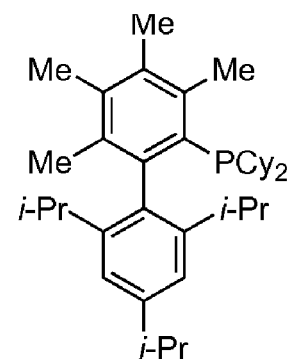
7

Figure 4

Table 1: Low Catalyst Loadings

R—Ar—NH₂ + Cl—Ar—R' →(0.01% Pre-Catalyst, 0.01% 1, NaOt-Bu, Bu₂O, 110 °C, 1h)→ R—Ar—NH—Ar—R'

Pre-Catalyst

| Entry | Aniline | Aryl Chloride | Product | Isolated Yield |
|---|---|---|---|---|
| 1 | 4-EtO-C₆H₄-NH₂ | 2,4-Me₂-C₆H₃-Cl | 4-EtO-C₆H₄-NH-2,4-Me₂-C₆H₃ | 93% (44%)* |
| 2 | 2,5-Me₂-C₆H₃-NH₂ | 4-MeO-C₆H₄-Cl | 2,5-Me₂-C₆H₃-NH-4-MeO-C₆H₄ | 97% |
| 3 | 4-Me-C₆H₄-NH₂ | C₆H₅-Cl | 4-Me-C₆H₄-NH-C₆H₅ | 99% |
| 4 | 4-EtO-C₆H₄-NH₂ | 4-MeO-C₆H₄-Cl | 4-EtO-C₆H₄-NH-4-MeO-C₆H₄ | 97% |
| 5 | 2,4-F₂-C₆H₃-NH₂ | C₆H₅-Cl | 2,4-F₂-C₆H₃-NH-C₆H₅ | 84% |
| 6 | 4-F-C₆H₄-NH₂ | 4-MeO-C₆H₄-Cl | 4-F-C₆H₄-NH-4-MeO-C₆H₄ | 99% |
| 7 | 3-F₃C-C₆H₄-NH₂ | 2,4-Me₂-C₆H₃-Cl | 3-F₃C-C₆H₄-NH-2,4-Me₂-C₆H₃ | 94% |

*Reaction was run with the XPhos pre-catalyst and XPhos.

Table 2: Difficult Heterocycles

| Entry | Aniline | Aryl Chloride | Product | Time | Isolated Yield |
|---|---|---|---|---|---|
| 1 | 2-aminopyrimidine | 6-chloroquinoline | N-(quinolin-6-yl)pyrimidin-2-amine | 1 h | 91% (37%)* |
| 2 | 2-aminopyrazine | 4-chloroanisole | N-(4-methoxyphenyl)pyrazin-2-amine | 4 h | 98% |
| 3 | 2-aminopyridine | 2-chloropyridine | N-(pyridin-2-yl)pyridin-2-amine | 2 h | 96% |

*Reaction was run with 3% XPhos instead of 1 for 1.5 h.

Figure 7
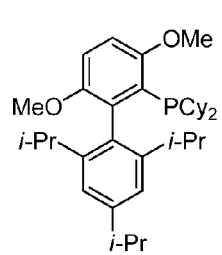
1, BrettPhos
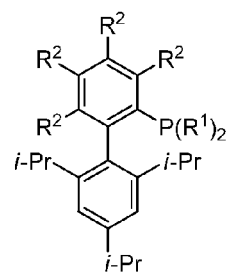
13, XPhos; R¹ = Cy, R² = H
8; R¹ = *t*-Bu, R² = H
7; R¹ = Cy, R² = Me
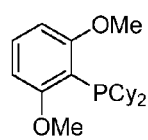
9
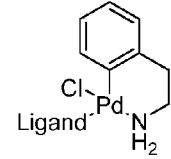
10; Ligand = 1
11; Ligand = 13
12; Ligand = 8

*Table 4.* Coupling of Aniline and 4-*t*-Butylphenyl Methanesulfonate[a]

| Entry | Ligand | Pd Source | Yield |
|---|---|---|---|
| 1 | 1 | Pd$_2$(dba)$_3$ | 0% |
| 2 | 1 | 10 | 98% |
| 3[b] | 1 | Pd(OAc)$_2$ | 99% |
| 4 | 13 | 11 | 4% |
| 5[b] | 13 | Pd(OAc)$_2$ | 2% |
| 6 | 8 | 12 | 0% |
| 7[b] | 7 | Pd(OAc)$_2$ | 0% |
| 8[b] | 9 | Pd(OAc)$_2$ | 0% |

[a]ArOMs (1 mmol), amine (1.2 mmol), Pd (1 mol%), ligand (2 mol%), K$_2$CO$_3$ (1.4 mmol), *t*-BuOH (12 mL/mmol), 110 °C, 3 h. [b]Using water activation protocol. Fors, B. P.; Krattiger, P.; Strieter, E.; Buchwald, S. L. *Org. Lett.* 2008. ASAP.

Figure 9

*Table 5.* Formation of Diarylamines Using Aryl Mesylates

ArOMs + H$_2$NAr' $\xrightarrow[\text{K}_2\text{CO}_3,\ t\text{-BuOH, 110 °C}]{\text{1 mol\% 10, 1 mol\% 1}}$ ArN(H)Ar'

| | | |
|---|---|---|
| pyrrole-N-C$_6$H$_4$-NH-(2,5-diMe-C$_6$H$_3$) 99% | (4-F-C$_6$H$_4$)-NH-(2-CO$_2$Et-C$_6$H$_4$) 82% | (3,4,5-triMeO-C$_6$H$_2$)-NH-(4-F-C$_6$H$_4$) 90% |
| (2-MeO-C$_6$H$_4$)-NH-(4-CO$_2$Et-C$_6$H$_4$) 82% | (4-Ph-C$_6$H$_4$)-NH-(4-Ac-C$_6$H$_4$) 97% | (3-CO$_2$Et-C$_6$H$_4$)-NH-(4-CF$_3$-C$_6$H$_4$) 84% |

[a] ArMs (1 mmol), amine (1.2 mmol), 1 (1 mol%), 10 (1 mol%), K$_2$CO$_3$, (1.4 mmol), t-BuOH (12 mL/mmol), 110 °C, 16 h.

*Table 6.* Screen of Ligands for the Arylation of Methylamine[a]

| Entry | Precat | Yield | Temp | MeN(H)Ar : MeNAr$_2$ |
|---|---|---|---|---|
| 1 | 10 | 92% | rt | >97:3 |
| 2 | 11 | 0% | rt | -- |
| 3 | 11 | 11% | 80 °C | 20:80 |
| 4 | 12 | 70% | rt | 82:18 |

[a]ArCl (1 mmol), 2M MeNH$_2$ in THF (2.0 mmol), Pd [10, 11, or 12] (0.01 mol%),[15] NaO$t$-Bu (1.2 mmol).

Figure 11

*Table 7.* Mono-arylation of Methylamine[a]

ArCl + H₂NMe (2M in THF) → (1% 10, NaO*t*-Bu, *t*-BuOH, rt, 2h) → ArN(H)Me

| 4-MeO-C₆H₄-N(H)Me | 3-pyridyl-N(H)Me | 3,5-(MeO)₂-C₆H₃-N(H)Me | 6-quinolinyl-N(H)Me |
|---|---|---|---|
| 92% | 90%[b] | 90% | 95%[c] |

[a]ArCl (1 mmol), 2 M MeNH₂ in THF (2.0 mmol), 10 (0.01 mol%), NaO*t*-Bu (1.2 mmol). [b]35:1 mixture of monoarylation to diarylation. [c]17 h reaction time.

Figure 12

*Table 8.* Coupling Reactions at Low Catalyst Loadings and Short Reaction Times $$\text{ArCl} + \text{H}_2\text{NR} \xrightarrow[\text{NaO}t\text{-Bu, Bu}_2\text{O, 80–110 °C, 1 h}]{0.01-0.05\ \text{mol\%}\ \mathbf{10},\ 0.01-0.05\ \text{mol\%}\ \mathbf{1}} \text{ArN(H)R}$$

| Ar–N(H)Hex, 4-OMe | Ar–N(H)Bn, 4-OMe | Ph–N(H)Hex | Ph–N(H)Bn | 2-Me-C6H4–N(H)Hex |
|---|---|---|---|---|
| 88%[a] | 97%[a] | 91%[a] | 90%[a] | 91%[a] |

| Ar = 2-Me-5-Me-C6H3; R = 3-CF3-C6H4 | Ar = 2-Me-5-Me-C6H3; R = 4-OEt-C6H4 | Ar = 4-OMe-C6H4; R = 4-F-C6H4 | Ar = 4-OMe-C6H4; R = 4-OEt-C6H4 | Ar = 4-OMe-C6H4; R = 2,5-Me2-C6H3 |
|---|---|---|---|---|
| 97%[b] | 93%[b] | 99%[b] | 97%[b] | 97%[b] |

[a] ArCl (1 mmol), amine (1.4 mmol), 1 (0.05 mol%), 10 (0.05 mol%), NaO*t*-Bu (1.2 mmol).
[b] ArCl (1 mmol), amine (1.2 mmol), 1 (0.01 mol%), 10 (0.01 mol%), NaO*t*-Bu (1.2 mmol).

Table 9. Selectivity of Primary Amines Over Secondary Amines[a]

[a]ArCl (1 mmol), amine (1.2 mmol), NaO$t$-Bu (2.0 mmol).

Figure 22
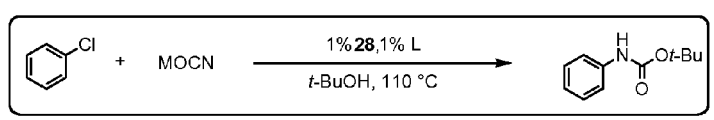
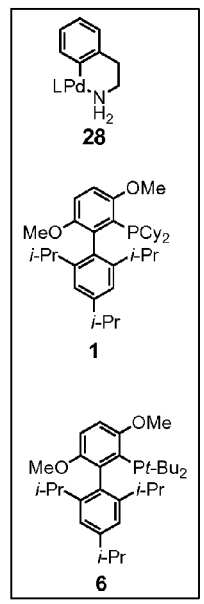
| MOCN | Pd Source | Ligand | Additive | Conversion | Yield |
|---|---|---|---|---|---|
| 2 equiv KOCN | 28 | 1 | - | 0 | -- |
| 1.2 equiv KOCN | 28 | 1 | K2CO3 | 0 | -- |
| 2 equiv KOCN | Pd2(dba)3 | 6 | - | 100* | -- |
| 1.2 equiv KOCN | Pd2(dba)3 | 6 | K2CO3 | 100** | -- |
| 2 equiv NaOCN | Pd2(dba)3 | 6 | - | 100 | 74% |
*A large amount of an unidentified biproduct was seen.
**Adding $K_2CO_3$ increased the yield of the biproduct.

100% Conversion after 24 h

LIGANDS FOR TRANSITION-METAL-CATALYZED CROSS-COUPLINGS, AND METHODS OF USE THEREOF

RELATED APPLICATIONS

This application claims the benefit of priority to U.S. Provisional Patent Application Ser. No. 61/013,174, filed Dec. 12, 2007; and U.S. Provisional Patent Application Ser. No. 61/087,368, filed Aug. 8, 2008.

GOVERNMENT SUPPORT

This invention was made with government support under Grant No. GM058160 awarded by the National Institutes of Health. The government has certain rights in the invention.

BACKGROUND

Transition metal catalyst complexes play important roles in many areas of chemistry, including the preparation of polymers and pharmaceuticals. The properties of the catalyst complexes are influenced by both the characteristics of the metal, and those of the ligands associated with the metal atom. For example, structural features of the ligands can influence reaction rate, regioselectivity, and stereoselectivity. Bulky ligands can be expected to slow reaction rate; electron-withdrawing ligands, in coupling reactions, can be expected to slow oxidative addition to, and speed reductive elimination from, the metal center; and electron-rich ligands, in coupling reactions, conversely, can be expected to speed oxidative addition to, and slow reductive elimination from, the metal center.

In many cases, the oxidative addition step in the accepted mechanism of a coupling reaction is deemed to be rate limiting. Therefore, adjustments to the catalytic system as a whole that increase the rate of the oxidative addition step should increase overall reaction rate. Additionally, all other factors being equal, the rate of oxidative addition of a transition metal catalyst to the carbon-halogen bond of an aryl halide is known to decrease as the halide is varied from iodide to bromide to chloride. Because of this fact, the more stable, lower molecular weight, and arguably more easy to obtain, members of the set of reactive organic halides—the chlorides—are typically the poorest substrates for traditional transition metal catalyzed coupling reactions and the like. Bromides have often been acceptable substrates, but have often required higher temperatures, longer reaction times, and have given lower yields of products.

Metal-catalyzed cross-coupling methodology to form carbon-carbon bonds has advanced organic synthesis. A., de Meijere, F. Diederich, Eds. *Metal-Catalyzed Cross-Coupling Reactions*, Vol. 2: Wiley-VCH, Weinheim, 2004. The Suzuki-Miyaura coupling is one of the preeminent methods for formation of carbon-carbon bonds and has been used in numerous synthetic ventures. N., Miyaura, *Topics in Current Chem.* 2002, 219, 11; and A. Suzuki, *Organomet. Chem.* 1999, 576, 147. A catalyst system that manifested high activity paired with extremely broad scope was recently reported. T. E. Barder, S. D. Walker, J. R. Martinelli, S. L. Buchwald, *J. Am. Chem. Soc.* 2005, 127, 4685; T. E. Barder, S. L. Buchwald *Org. Lett.* 2004, 6, 2649; S. D. Walker, T. E. Barder, J. R. Martinelli, S. L. Buchwald *Angew. Chem.* 2004, 116, 1907; and S. D. Walker, T. E. Barder, J. R. Martinelli, S. L. *Angew. Chem. Int. Ed.* 2004, 43, 1871. In addition, a catalyst system which provided excellent reactivity in the copper-free Sonogashira coupling of aryl chlorides/tosylates and terminal alkynes has been disclosed. D. Gelman, S. L. Buchwald *Angew. Chem.* 2003, 115, 6175; and D. Gelman, S. L. Buchwald *Angew. Chem. Int. Ed.* 2003, 42, 5993. However, this catalyst system was successful in coupling aryl alkynes only when the alkyne was added slowly over the course of the reaction. This fact is presumably due to competing non-productive oligomerization of the alkyne at higher concentrations in the presence of the catalyst. Further, a catalyst system and reaction conditions for the coupling of water-soluble aryl chlorides, and for the combination of difficult coupling partners in aqueous conditions, has been disclosed. Buchwald, S. et al., U.S. patent application Ser. No. 11/328,426, filed Jan. 9, 2006, hereby incorporated by reference in its entity.

Palladium-catalyzed C—N cross-coupling reactions are an important technology both in industry and academia. Schlummer, B.; Scholz, U. *Adv. Synth. Catal.* 2004, 346, 1599; Jiang, L.; Buchwald, S. L. In *Metal-Catalyzed Cross-Coupling Reactions* (Eds.: de Meijere, A.; Diederich, F.), 2$^{nd}$ ed., Wiley-VCH, Weinheim, 2004; Hartwig, J. F. *Synlett* 2006, 1283. In recent years, the palladium-catalyzed coupling of amines with aryl halides or sulfonates has been investigated. Muci, A. R.; Buchwald, S. L. *Top. Curr. Chem.* 2002, 219, 131; Yang, B. H.; Buchwald, S. L. *J. Organomet. Chem.* 1999, 576, 125; Hartwig, J. F. *Angew. Chem., Int. Ed.* 1998, 37, 2047. Unfortunately, these methods are still subject to undesirable limitations, notwithstanding the improvements in the substrate scope of palladium-catalyzed C—N bond-forming reactions realized by using weak bases, such as potassium phosphate or cesium carbonate. Old, D. W. et al. *J. Am. Chem. Soc.* 1998, 120, 9722; Wolfe, J. P.; Buchwald, S. L. *Tetrahedron Lett.* 1997, 38, 6359. Although the use of weak bases allows for the use of substrates containing ester, cyano, nitro and keto groups in the reaction, reactions of aryl substrates containing alcohol, phenol, or amide functional groups remain problematic. But see Harris, M. H. et al. *Org. Lett.* 2002, 4, 2885. Despite these considerable advances in the field, notable limitations remain for which improved methods will have an immediate impact on the chemistry community. Marion, N.; Navarro, O.; Mei, J.; Stevens, E. D.; Scott, N. M.; Nolan, S. P. *J. Am. Chem. Soc.* 2006, 128, 4101; Shen, Q.; Shekhar, S.; Stambuli, J. P.; Hartwig, J. F. *Angew. Chem. Int. Ed.* 2005, 44, 1371; Rataboul, F.; Zapf, A.; Jackstell, R.; Harkal, S.; Riermeier, T.; Monsees, A.; Dingerdissen, U.; Beller, M. *Chem. Eur. J.* 2004, 10, 2983.

Also of importance is the monoarylation of primary amines via a cross-coupling reaction. Although this transformation has long been proficient with aryl bromides, recent progress has extended the method to aryl chlorides. Wolfe, J. P.; Buchwald, S. L. *J. Org. Chem.* 2000, 65, 1144; Shen, Q.; Ogata, T.; Hartwig, J. F. *J. Am. Chem. Soc.* 2008, 130, 6586; Shen, Q.; Shekhar, S.; Stambuli, J. P.; Hartwig, J. F. *Angew. Chem. Int. Ed.* 2005, 44, 1371. However, despite this success, challenges still remain, including the monoarylation of methylamine, which has yet to be described. Because it is the smallest aliphatic primary amine and therefore most likely to undergo diarylation, methylamine is a particularly challenging coupling partner to monoarylate.

Due to their high stability, good atom economy, and low cost, aryl mesylates represent an important substrate class for C—N cross-coupling reactions. Until recently, no procedure has been published for the amination of these materials. Percec, V.; Golding, G. M.; Smidrkal, J.; Weichold, O. *J. Org. Chem.* 2004, 69, 3447; Munday, R. H.; Martinelli, J. R.; Buchwald, S. L. *J. Am. Chem. Soc.* 2008, 130, 2754; So, M. C.; Zhou, Z.; Lau, C.; Kwong, F. *Angew. Chem. Int. Ed.* 2008, 47, Early View. However, amination reactions of aryl tosylates, benzenesulfonates, and nonaflates are known. Anderson, K. W.; Mendez-Perez, M.; Priego, J.; Buchwald, S. L. *J. Org. Chem.* 2003, 68, 9563; Roy, A. H.; Hartwig, J. F. *J. Am. Chem. Soc.* 2003, 125, 8704; Huang, X.; Anderson, K. W.; Zim, D.; Jiang, L.; Klapars, A.; Buchwald, S. L. *J. Am. Chem. Soc.* 2003, 125, 6653. Recently, it was demonstrated that substitution of the phosphine-containing arene in biarylmonophosphine ligands can have profound effects of the observed reactivity in catalytic reactions. Ikawa, T.; Barder, T. E.; Biscoe, M. R.; Buchwald S. L. *J. Am. Chem. Soc.* 2007, 129, 13001.

However, there remains a need to develop improved ligands and reaction conditions (e.g., lower catalyst loadings) for a variety of cross-coupling reactions.

SUMMARY

One aspect of the present invention relates to ligands for transition metals. A second aspect of the present invention relates to the use of catalysts comprising such ligands in various transition-metal-catalyzed carbon-heteroatom and carbon-carbon bond-forming reactions. The disclosed methods provide improvements in many features of the transition-metal-catalyzed reactions, including the range of suitable substrates, number of catalyst turnovers, reaction conditions, and efficiency. For example, remarkable improvements have been realized in transition-metal-catalyzed cross-coupling reactions.

BRIEF DESCRIPTION OF THE FIGURES

FIG. 1 depicts selected ligands of the invention, wherein R is independently for each occurrence, for example, Cy (cyclohexyl), i-Pr, $C_5H_{11}$, Me, Et or t-Bu.

FIG. 3 depicts two "benchmark" ligands.

FIG. 4 depicts examples of cross-coupling reactions of anilines with aryl chlorides at low catalyst loadings using ligands of the invention.

FIG. 7 depicts representative ligands of the present invention, representative "benchmark" ligands, and representative precatalysts of the present invention.

FIG. 9 depicts examples of diarylamines that can be formed using aryl mesylates.

FIG. 11 depicts examples of mono-arylation reactions of methylamine utilizing a representative ligand of the invention.

FIG. 12 depicts examples of coupling reactions with low catalyst loadings and short reaction times utilizing a representative ligand of the present invention.

FIG. 14 depicts the synthesis and NOESY NMR crosspeaks of 17, 18, and 19, and the crystal structure of 17a.

FIG. 22 depicts a representative synthesis of an N-aryl carbamate from the coupling of an aryl chloride with sodium or potassium cyanate.

DETAILED DESCRIPTION

One aspect of the present invention relates to ligands for transition metals. A second aspect of the present invention relates to the use of catalysts comprising at least one of the ligands in various transition-metal-catalyzed carbon-heteroatom and carbon-carbon bond-forming reactions. The subject ligands and methods provide improvements in many features of the transition-metal-catalyzed reactions, including the range of suitable substrates, number of catalyst turnovers, reaction conditions, and efficiency. For example, remarkable improvements have been realized in transition metal-catalyzed aminations and amidations of aryl chlorides.

Ligands of the present invention show unprecedented reactivity in C—N cross-coupling reactions, for example. An exemplary ligand has allowed for the first Pd-catalyzed amination of aryl mesylates. Arylations of methylamine can also be performed for the first time with exceptional selectivities for monoarylation utilizing catalytic systems based on ligands of the present invention. Utilizing representative ligands of the invention, primary aliphatic amines and anilines can be coupled with aryl chlorides at low catalyst loadings and with fast reaction times, demonstrating the unparalleled reactivity and stability of these catalyst systems.

Figure 15:
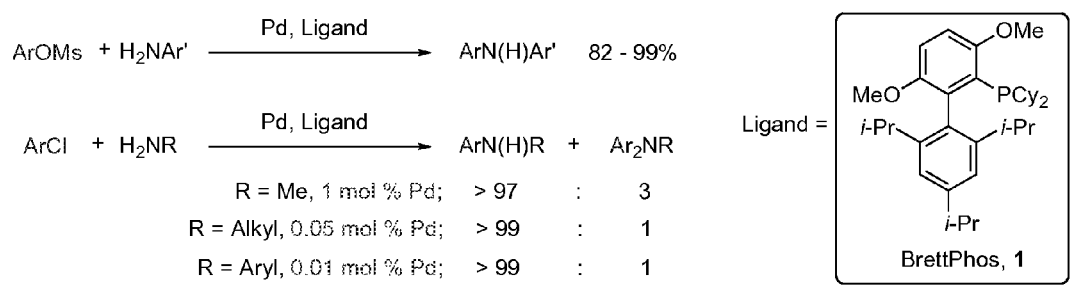
FIG. 15 depicts a summary of exemplary methods of the invention.

An aspect of the invention relates to a catalyst system based on new biarylmonophosphine ligands that shows excellent reactivity for C—N cross-coupling reactions. In one embodiment, a catalyst system of the invention enables the use of aryl mesylates as a coupling partner in C—N bond-forming reactions. FIG. 15. Additionally, the use of certain embodiments of ligands of the invention permits the highly selective monoarylation of an array of primary aliphatic amines and anilines at low catalyst loadings and with fast reaction times, including the first monoarylation of methylamine. FIG. 15.

Lastly, oxidative addition complexes of a ligand of the invention are included, which provide insight into the origin of reactivity for this system.

Figure 23:
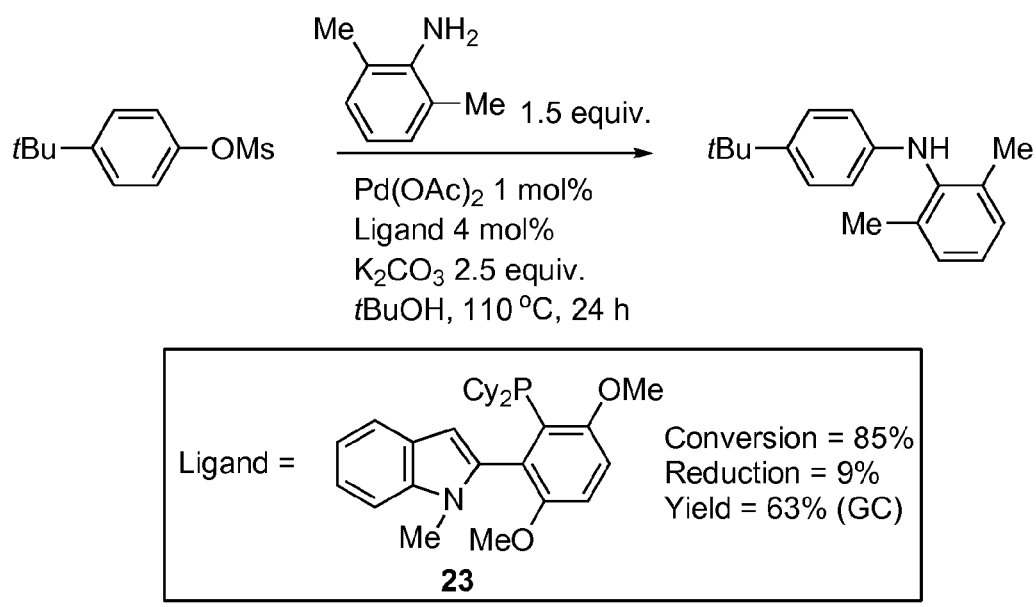
FIG. 23 depicts the cross-coupling reaction of an aniline and an aryl mesylate using heteroaryl-based ligand 23.

An aspect of the invention relates to a catalyst system based on new aryl-heteroaryl monophosphine ligands that shows excellent reactivity for C—N cross-coupling reactions. In one embodiment, a catalyst system of the invention enables the use of aryl mesylates as a coupling partner in C—N bond-forming reactions. FIG. 23.

DEFINITIONS

For convenience, before further description of the present invention, certain terms employed in the specification, examples, and appended claims are collected here.

The terms "biphenyl" and "binaphthylene" refer to the ring systems below. The numbers around the peripheries of the ring systems are the positional numbering systems used herein. Likewise, the capital letters contained within the individual rings of the ring systems are the ring descriptors used herein.

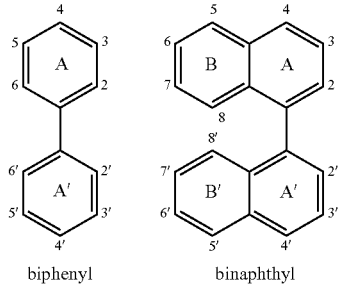

biphenyl                binaphthyl

The term "substrate aryl group" refers to an aryl group containing an electrophilic atom which is susceptible to the subject cross-coupling reaction, e.g., the electrophilic atom bears a leaving group. In reaction scheme 1, the substrate aryl is represented by ArX, and X is the leaving group. The aryl group, Ar, is said to be substituted if, in addition to X, it is substituted at yet other positions. The substrate aryl group can be a single ring molecule, or can be a component of a larger molecule.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined herein. Electrophilic moieties useful in the method of the present invention include halides and sulfonates.

The terms "electrophilic atom," "electrophilic center" and "reactive center" as used herein refer to the atom of the substrate aryl moiety which is attacked by, and forms a new bond to the nucleophilic heteroatom of the hydrazine and the like. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (s) constant. This well known constant is described in many references, for instance, J. March, *Advanced Organic Chemistry*, McGraw Hill Book Company, New York, (1977 edition) pp. 251-259. The Hammett constant values are generally negative for electron donating groups (s[P]=−0.66 for $NH_2$) and positive for electron withdrawing groups (s[P]=0.78 for a nitro group), s[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of the hydrazine or the like and the substrate aryl group. In general, the term "reaction product" will be used herein to refer to a stable, isolable aryl ether adduct, and not to unstable intermediates or transition states.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics" or "heteroaryls." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

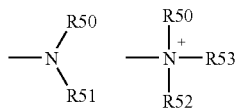

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

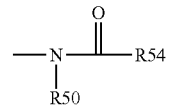

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

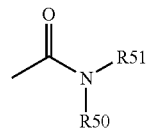

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

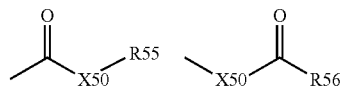

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C═O)NRR', where R and R' are independently H, aliphatic groups, aryl groups or heteroaryl groups.

The term "oxo" refers to a carbonyl oxygen (═O).

The terms "oxime" and "oxime ether" are art-recognized and refer to moieties that may be represented by the general formula:

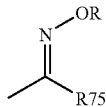

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

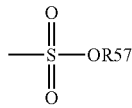

in which R57 is an electron pair, hydrogen, alkyl, cycloalkyl, or aryl.

The term "sulfate" is art recognized and includes a moiety that may be represented by the general formula:

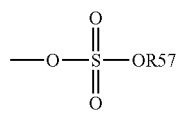

in which R57 is as defined above.

The term "sulfonamido" is art recognized and includes a moiety that may be represented by the general formula:

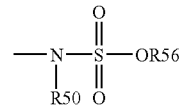

in which R50 and R56 are as defined above.

The term "sulfamoyl" is art-recognized and refers to a moiety that may be represented by the general formula:

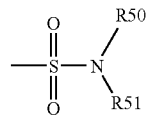

in which R50 and R51 are as defined above.

The term "sulfonyl" is art-recognized and refers to a moiety that may be represented by the general formula:

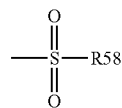

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

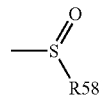

in which R58 is defined above.

The term "phosphoryl" is art-recognized and may in general be represented by the formula:

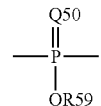

wherein Q50 represents S or O, and R59 represents hydrogen, a lower alkyl or an aryl. When used to substitute, e.g., an alkyl, the phosphoryl group of the phosphorylalkyl may be represented by the general formulas:

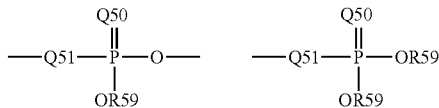

wherein Q50 and R59, each independently, are defined above, and Q51 represents O, S or N. When Q50 is S, the phosphoryl moiety is a "phosphorothioate".

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2 ed.; Wiley: New York, 1991). Protected forms of the inventive compounds are included within the scope of this invention.

A "polar solvent" means a solvent which has a dielectric constant ($\in$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred polar solvents are DMF, DME, NMP, and acetonitrile.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

A "polar, aprotic solvent" means a polar solvent as defined above which has no available hydrogens to exchange with the compounds of this invention during reaction, for example DMF, acetonitrile, diglyme, DMSO, or THF.

A "hydroxylic solvent" means a solvent that comprises a hydroxyl moiety; for example, water, methanol, ethanol, tert-butanol, and ethylene glycol are hydroxylic solvents.

For purposes of this invention, the chemical elements are identified in accordance with the Periodic Table of the Elements, CAS version, Handbook of Chemistry and Physics, 67th Ed., 1986-87, inside cover.

Various General Considerations

In certain embodiments of the reactions of the invention, there is no need to use large excesses of reactants, e.g., amine, amide, aryl halide, heteroaryl halide and the like. Remarkably, the reactions proceed quickly and in high yield to the desired products using substantially stoichiometric amounts of reagents. For example, in the amination or amidation reactions of the invention, the amine or amide may be present in as little as a two-fold excess, or in no greater than a 20% excess relative to the aromatic compound. Alternatively, the aromatic compound may be present in as little as a two-fold excess, or in no greater than a 20% excess relative to the amine or amide.

The reactions typically proceed at mild temperatures and pressures to give high yields of the product aryl amines, aryl amides, and the like. Thus, yields of desired products greater than 45%, greater than 75%, and greater than 80% may be obtained from reactions at mild temperatures according to the invention. The reaction may be carried out at temperature less than 150° C., or in the range of 20-100° C. In certain embodiments, the reactions are carried out at ambient temperature.

The reactions can be run in a wide range of solvent systems, including polar aprotic solvents. Alternatively, in certain embodiments, the subject reactions may be carried in the absence of added solvent. In certain embodiments, the subject reaction may be carried out in a polar solvent. In certain embodiments, the subject reaction may be carried out in an aprotic solvent. In certain embodiments, the subject reaction may be carried out in a polar, aprotic solvent. In certain embodiments, the subject reaction may be carried out in a hydroxylic solvent.

The ability to provide synthesis schemes for aryl amines, aryl amides, and the like, which can be carried out under mild conditions and/or with non-polar solvents has broad application, especially in the agricultural and pharmaceutical industries, as well as in the polymer industry. In this regard, the subject reactions are particularly well-suited to reactants or products which include sensitive functionalities, e.g., which would otherwise be labile under harsh reaction conditions.

The subject amine arylation, amide arylation, and the like can be used as part of combinatorial synthesis schemes to yield libraries of aryl amines, aryl amides, and the like. Accordingly, another aspect of the present invention relates to use of the subject method to generate variegated libraries of aryl amines, aryl amides, and the like, and to the libraries themselves. The libraries can be soluble or linked to insoluble supports, e.g., through a substituent of a reactant (prior to carrying out a reaction of the present invention), e.g., the aryl group, amine, amide, or the like, or through a substituent of a product (subsequent to carrying out a reaction of the present invention), e.g., the aryl amine, aryl amide, biaryl, or the like.

The ligands of the present invention and the methods based thereon enable the formation of carbon-heteroatom and carbon-carbon bonds—via transition metal catalyzed aminations, amidations, and the like—under conditions that would not yield appreciable amounts of the observed product(s) using ligands and methods known in the art. In certain embodiments, the ligands and methods of the present invention catalyze the aforementioned transformations at temperatures below 50° C., and in certain embodiments they occur at room temperature. When a reaction is said to occur under a given set of conditions it means that the rate of the reaction is such the bulk of the starting materials is consumed, or a significant amount of the desired product is produced, within 48 hours, within 24 hours, or within 12 hours. In certain embodiments, the ligands and methods of the present invention catalyze the aforementioned transformations utilizing less than 1 mol % of the catalyst complex relative to the limiting reagent, in certain embodiments less than 0.01 mol % of the catalyst complex relative to the limiting reagent, and in certain embodiments less than 0.0001 mol % of the catalyst complex relative to the limiting reagent.

The ligands of the present invention and the methods based thereon can be used to produce synthetic intermediates that, after being subjected to additional methods known in the art, are transformed to desired end products, e.g., lead compounds in medicinal chemistry programs, pharmaceuticals, insecticides, antivirals and antifungals. Furthermore, the ligands of the present invention and the methods based thereon may be used to increase the efficiency of and/or shorten established routes to desired end products, e.g., lead compounds in medicinal chemistry programs, pharmaceuticals, insecticides, antivirals and antifungals.

One aspect of the invention provides for a catalyst comprised of a new biaryldialkylphosphine ligand that shows excellent reactivity and stability in C—N cross-coupling reactions and overcomes many restrictions that previous catalyst systems have possessed.

Ligands of the Invention

Biphenyl-Based Ligands

In one embodiment, the present invention relates to a ligand represented by I:

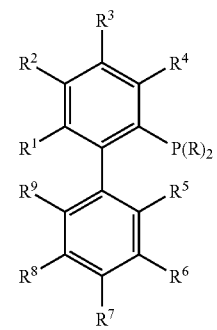

wherein

R is selected independently for each occurrence from the group consisting of alkyl, heteroalkyl, cycloalkyl, heterocycloalkyl, aryl, heteroaryl, aralkyl, heteroaralkyl, and —$(CH_2)_m$—$R^{10}$;

$R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$; or any two adjacent instances of $R^1$, $R^2$, $R^3$ and $R^4$, taken together with the carbons to which they are bound, form a five-membered substituted or unsubstituted aryl or heteroaryl ring; provided that at least one of $R^1$, $R^2$, $R^3$ and $R^4$ are —$OR^{11}$;

$R^5$, $R^7$ and $R^9$ are selected independently for each occurrence from the group consisting of hydrogen, alkyl, cycloalkyl, heterocycloalkyl, aryl, heteroaryl, aralkyl, heteroaralkyl, —$Si(R^{11})_3$, —$(CH_2)_m$—$R^{10}$, —OH, —$OR^{11}$, —$NH_2$, —$NHR^{11}$ and —$N(R^{11})_2$;

$R^6$ and $R^8$ are selected independently for each occurrence from the group consisting of hydrogen, lower alkyl and halogen; or any two adjacent instances of $R^5$, $R^6$, $R^7$, $R^8$, or $R^9$, taken together with the carbons to which they are bound, form a five- or six-membered substituted or unsubstituted aryl or heteroaryl ring;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

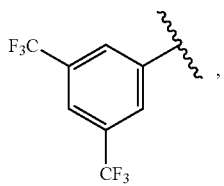

or

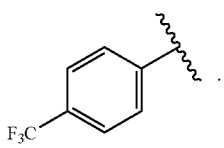

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

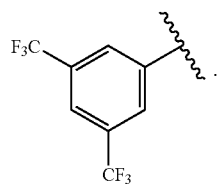

In certain embodiments, the present invention relates to any one of the above-mentioned ligands, wherein R is

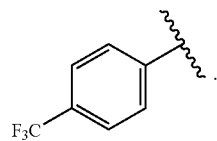

In certain embodiments, the present invention relates to any one of the above-mentioned ligands, wherein R is t-Bu.

In certain embodiments, the present invention relates to any one of the above-mentioned ligands, wherein R is i-Pr.

In certain embodiments, the present invention relates to any one of the above-mentioned ligands, wherein $R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$.

In certain embodiments, the present invention relates to any one of the above-mentioned ligands, wherein $R^4$ is —$OR^{11}$.

In certain embodiments, the present invention relates to any one of the above-mentioned ligands, wherein $R^4$ is —$OR^{11}$; and $R^{11}$ is alkyl.

In certain embodiments, the present invention relates to any one of the above-mentioned ligands, $R^4$ is —$OR^{11}$; and $R^{11}$ is Me, Et, n-Pr, i-Pr, n-Bu, i-Bu, or s-Bu.

In certain embodiments, the present invention relates to any one of the above-mentioned ligands, $R^4$ is —$OR^{11}$; and $R^{11}$ is Me.

In certain embodiments, the present invention relates to any one of the above-mentioned ligands, wherein $R^1$ and $R^4$ are —$OR^{11}$.

In certain embodiments, the present invention relates to any one of the above-mentioned ligands, wherein $R^1$ and $R^4$ are —$OR^{11}$; and $R^{11}$ is alkyl.

In certain embodiments, the present invention relates to any one of the above-mentioned ligands, wherein $R^1$ and $R^4$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^1$ and $R^4$ are —$OR^{11}$; and $R^{11}$ is Me.

In certain embodiments, the present invention relates to any one of the above-mentioned ligands, wherein $R^1$ and $R^4$ are —$OR^{11}$; $R^1$ is —OMe or —Oi-Pr; and $R^4$ is —Oi-Pr.

In certain embodiments, the present invention relates to any one of the above-mentioned ligands, wherein $R^2$ and $R^3$ are —$OR^{11}$.

In certain embodiments, the present invention relates to any one of the above-mentioned ligands, wherein $R^2$ and $R^3$ are —$OR^{11}$; and $R^{11}$ is alkyl.

In certain embodiments, the present invention relates to any one of the above-mentioned ligands, wherein $R^2$ and $R^3$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^2$ and $R^3$ are —$OR^{11}$; and $R^{11}$ is Me.

In certain embodiments, the present invention relates to any one of the above-mentioned ligands, wherein $R^2$ and $R^4$ are —$OR^{11}$.

In certain embodiments, the present invention relates to any one of the above-mentioned ligands, wherein $R^2$ and $R^4$ are —$OR^{11}$; and $R^{11}$ is alkyl.

In certain embodiments, the present invention relates to any one of the above-mentioned ligands, wherein $R^2$ and $R^4$ are —$OR^{11}$; and $R^{11}$ is Me, Et, n-Pr, i-Pr, n-Bu, i-Bu, or s-Bu.

In certain embodiments, the present invention relates to any one of the above-mentioned ligands 1, wherein $R^2$ and $R^4$ are —$OR^{11}$; and $R^{11}$ is Me.

In certain embodiments, the present invention relates to any one of the above-mentioned ligands, wherein $R^1$, $R^2$, $R^3$, and $R^4$ are alkyl.

In certain embodiments, the present invention relates to any one of the above-mentioned ligands, wherein $R^1$, $R^2$, $R^3$, and $R^4$ are Me, Et, n-Pr, i-Pr, n-Bu, i-Bu, or s-Bu.

In certain embodiments, the present invention relates to any one of the above-mentioned ligands, wherein $R^1$, $R^2$, $R^3$, and $R^4$ are Me.

In certain embodiments, the present invention relates to any one of the above-mentioned ligands, wherein $R^2$ and $R^3$ are hydrogen.

In certain embodiments, the present invention relates to any one of the above-mentioned ligands, wherein $R^1$, $R^2$, and $R^3$ are hydrogen.

In certain embodiments, the present invention relates to any one of the above-mentioned ligands, wherein $R^5$, $R^7$ and $R^9$ are alkyl.

In certain embodiments, the present invention relates to any one of the above-mentioned ligands, wherein $R^5$, $R^7$ and $R^9$ are Me, Et, n-Pr, i-Pr, n-Bu, i-Bu, or s-Bu.

In certain embodiments, the present invention relates to any one of the above-mentioned ligands, wherein $R^5$, $R^7$ and $R^9$ are i-Pr.

In certain embodiments, the present invention relates to any one of the above-mentioned ligands, wherein $R^5$ is —$OR^{11}$.

In certain embodiments, the present invention relates to any one of the above-mentioned ligands, wherein $R^5$ is —$OR^{11}$; and $R^{11}$ is alkyl.

In certain embodiments, the present invention relates to any one of the above-mentioned ligands, wherein $R^5$ is —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^5$ is —$OR^{11}$; and $R^{11}$ is Me.

In certain embodiments, the present invention relates to any one of the above-mentioned ligands, wherein $R^5$ is —$N(R^{11})_2$.

In certain embodiments, the present invention relates to any one of the above-mentioned ligands, wherein $R^5$ is —$N(R^{11})_2$; and $R^{11}$ is alkyl.

In certain embodiments, the present invention relates to any one of the above-mentioned ligands, wherein $R^5$ is —$N(R^{11})_2$; and $R^{11}$ is Me, Et, n-Pr, i-Pr, n-Bu, i-Bu, or s-Bu.

In certain embodiments, the present invention relates to any one of the above-mentioned ligands, wherein $R^5$ is —$N(R^{11})_2$; and $R^{11}$ is Me.

In certain embodiments, the present invention relates to any one of the above-mentioned ligands, wherein $R^5$ and $R^9$ are —$OR^{11}$.

In certain embodiments, the present invention relates to any one of the above-mentioned ligands, wherein $R^5$ and $R^9$ are —$OR^{11}$; and $R^{11}$ is alkyl.

In certain embodiments, the present invention relates to any one of the above-mentioned ligands, wherein $R^5$ and $R^9$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^5$ and $R^9$ are —$OR^{11}$; and $R^{11}$ is Me.

In certain embodiments, the present invention relates to any one of the above-mentioned ligands, wherein $R^8$ and $R^9$, taken together with the carbons to which they are attached, form an aryl ring.

In certain embodiments, the present invention relates to any one of the above-mentioned ligands, wherein $R^8$ and $R^9$, taken together with the carbons to which they are attached, form a six-membered ring.

In certain embodiments, the present invention relates to any one of the above-mentioned ligands, wherein $R^8$ and $R^9$, taken together with the carbons to which they are attached, form a six-membered aryl ring.

In certain embodiments, the present invention relates to any one of the above-mentioned ligands, wherein $R^6$ and $R^7$ are hydrogen.

In certain embodiments, the present invention relates to any one of the above-mentioned ligands, wherein $R^6$ and $R^8$ are hydrogen.

In certain embodiments, the present invention relates to any one of the above-mentioned ligands, wherein $R^6$, $R^7$, and $R^8$ are hydrogen.

In certain embodiments, the present invention relates to any one of the above-mentioned ligands, wherein $R^6$, $R^7$, $R^8$, and $R^9$ are hydrogen.

In certain embodiments, the present invention relates to any one of the above-mentioned ligands, wherein $R^5$, $R^6$, $R^7$, $R^8$, and $R^9$ are hydrogen.

In one embodiment, the present invention relates to a ligand represented by I:

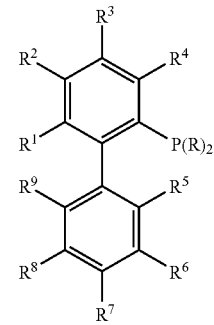

I wherein

R is selected independently for each occurrence from the group consisting of alkyl, cycloalkyl, aryl, heteroaryl, aralkyl, heteroaralkyl, and —$(CH_2)_m$—$R^{10}$;

$R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$; or any two adjacent instances of $R^1$, $R^2$, $R^3$ and $R^4$ taken together with the carbons to which they are bound, form a five-membered substituted or unsubstituted aryl or heteroaryl ring; provided that at least two of $R^1$, $R^2$, $R^3$ and $R^4$ are —$OR^{11}$;

$R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$;

$R^6$ and $R^8$ are selected independently for each occurrence from the group consisting of hydrogen, lower alkyl and halogen;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

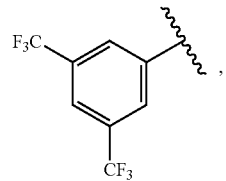

or

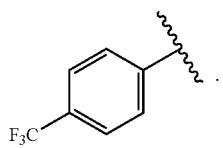

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

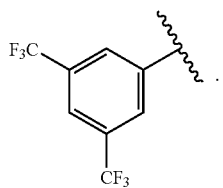

In certain embodiments, the present invention relates to any one of the above-mentioned ligands, wherein R is

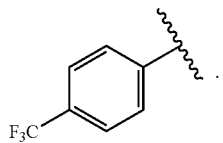

In certain embodiments, the present invention relates to any one of the above-mentioned ligands, wherein R is t-Bu.

In certain embodiments, the present invention relates to any one of the above-mentioned ligands, wherein $R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, $-OR^{11}$, $-N(R^{11})_2$, $-Si(R^{11})_3$, and $-(CH_2)_m-R^{10}$.

In certain embodiments, the present invention relates to any one of the above-mentioned ligands, wherein $R^1$ and $R^4$ are $-OR^{11}$.

In certain embodiments, the present invention relates to any one of the above-mentioned ligands, wherein $R^1$ and $R^4$ are $-OR^{11}$; and $R^{11}$ is alkyl.

In certain embodiments, the present invention relates to any one of the above-mentioned ligands, wherein $R^1$ and $R^4$ are $-OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^1$ and $R^4$ are $-OR^{11}$; and $R^{11}$ is Me.

In certain embodiments, the present invention relates to any one of the above-mentioned ligands, wherein $R^1$ and $R^4$ are $-OR^{11}$; $R^1$ is $-OMe$ or $-Oi\text{-}Pr$; and $R^4$ is $-Oi\text{-}Pr$.

In certain embodiments, the present invention relates to any one of the above-mentioned ligands, wherein $R^2$ and $R^3$ are $-OR^{11}$.

In certain embodiments, the present invention relates to any one of the above-mentioned ligands, wherein $R^2$ and $R^3$ are $-OR^{11}$; and $R^{11}$ is alkyl.

In certain embodiments, the present invention relates to any one of the above-mentioned ligands, wherein $R^2$ and $R^3$ are $-OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^2$ and $R^3$ are $-OR^{11}$; and $R^{11}$ is Me.

In certain embodiments, the present invention relates to any one of the above-mentioned ligands, wherein $R^2$ and $R^4$ are $-OR^{11}$.

In certain embodiments, the present invention relates to any one of the above-mentioned ligands, wherein $R^2$ and $R^4$ are $-OR^{11}$; and $R^{11}$ is alkyl.

In certain embodiments, the present invention relates to any one of the above-mentioned ligands, wherein $R^2$ and $R^4$ are $-OR^{11}$; and $R^{11}$ is Me, Et, n-Pr, i-Pr, n-Bu, i-Bu, or s-Bu.

In certain embodiments, the present invention relates to any one of the above-mentioned ligands 1, wherein $R^2$ and $R^4$ are $-OR^{11}$; and $R^{11}$ is Me.

In certain embodiments, the present invention relates to any one of the above-mentioned ligands, wherein $R^1$, $R^2$, $R^3$, and $R^4$ are alkyl.

In certain embodiments, the present invention relates to any one of the above-mentioned ligands, wherein $R^1$, $R^2$, $R^3$, and $R^4$ are Me, Et, n-Pr, i-Pr, n-Bu, i-Bu, or s-Bu.

In certain embodiments, the present invention relates to any one of the above-mentioned ligands, wherein $R^1$, $R^2$, $R^3$, and $R^4$ are Me.

In certain embodiments, the present invention relates to any one of the above-mentioned ligands, wherein $R^5$, $R^7$ and $R^9$ are alkyl.

In certain embodiments, the present invention relates to any one of the above-mentioned ligands, wherein $R^5$, $R^7$ and $R^9$ are Me, Et, n-Pr, i-Pr, n-Bu, i-Bu, or s-Bu.

In certain embodiments, the present invention relates to any one of the above-mentioned ligands, wherein $R^5$, $R^7$ and $R^9$ are i-Pr.

In certain embodiments, the present invention relates to any one of the above-mentioned ligands, wherein $R^6$ and $R^8$ are hydrogen.

In one embodiment, the present invention relates to a ligand represented by II:

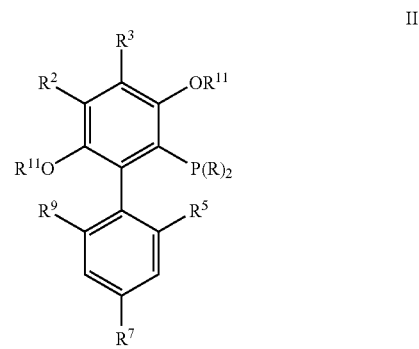

II wherein

R is selected independently for each occurrence from the group consisting of alkyl, cycloalkyl, aryl, heteroaryl, aralkyl, heteroaralkyl, and $-(CH_2)_m-R^{10}$;

$R^2$ and $R^3$ are selected independently for each occurrence from the group consisting of hydrogen, halogen, alkyl, cycloalkyl, heterocycloalkyl, aryl, heteroaryl, aralkyl, heteroaralkyl, $-OR^{11}$, $-N(R^{11})_2$, $-Si(R^{11})_3$, and $-(CH_2)_m-R^{10}$; or any two adjacent instances of $R^2$ and $R^3$ taken together with the carbons to which they are bound, form a five or six-membered, substituted or unsubstituted, aryl or heteroaryl ring;

$R^5$, $R^7$ and $R^9$ are selected independently for each occurrence from the group consisting of alkyl, cycloalkyl, heterocycloalkyl, aryl, heteroaryl, aralkyl, heteroaralkyl, —Si($R^{11}$)$_3$, and —(CH$_2$)$_m$—$R^{10}$;

$R^6$ and $R^8$ are selected independently for each occurrence from the group consisting of hydrogen, lower alkyl and halogen;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

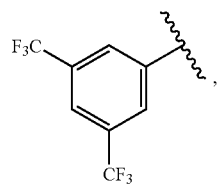

or

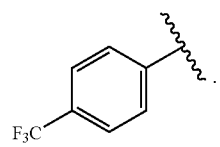

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

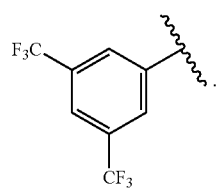

In certain embodiments, the present invention relates to any one of the above-mentioned ligands, wherein R is

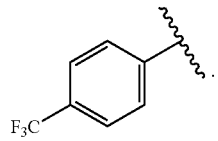

In certain embodiments, the present invention relates to any one of the above-mentioned ligands, wherein R is t-Bu.

In certain embodiments, the present invention relates to any one of the above-mentioned ligands, wherein $R^{11}$ is alkyl.

In certain embodiments, the present invention relates to any one of the above-mentioned ligands, wherein $R^{11}$ is Me, Et, n-Pr, i-Pr, n-Bu, i-Bu, or s-Bu.

In certain embodiments, the present invention relates to any one of the above-mentioned ligands, wherein one occurrence of $R^{11}$ is Me; and one occurrence of $R^{11}$ is i-Pr.

In certain embodiments, the present invention relates to any one of the above-mentioned ligands, wherein $R^{11}$ is Me.

In certain embodiments, the present invention relates to any one of the above-mentioned ligands, wherein $R^{11}$ is i-Pr.

In certain embodiments, the present invention relates to any one of the above-mentioned ligands, wherein $R^2$ and $R^3$ are selected independently for each occurrence from the group consisting of hydrogen, halogen, alkyl, cycloalkyl, heterocycloalkyl, aryl, heteroaryl, aralkyl, heteroaralkyl, —O$R^{11}$, —N($R^{11}$)$_2$, —Si($R^{11}$)$_3$, and —(CH$_2$)$_m$—$R^{10}$.

In certain embodiments, the present invention relates to any one of the above-mentioned ligands, wherein $R^2$ and $R^3$ are —O$R^{11}$.

In certain embodiments, the present invention relates to any one of the above-mentioned ligands, wherein $R^2$ and $R^3$ are —O$R^{11}$; and $R^{11}$ is alkyl.

In certain embodiments, the present invention relates to any one of the above-mentioned ligands, wherein $R^2$ and $R^3$ are —O$R^{11}$; and $R^{11}$ is Me, Et, n-Pr, i-Pr, n-Bu, i-Bu, or s-Bu.

In certain embodiments, the present invention relates to any one of the above-mentioned ligands, wherein $R^2$ and $R^3$ are —O$R^{11}$; and $R^{11}$ is Me.

In certain embodiments, the present invention relates to any one of the above-mentioned ligands, wherein $R^2$ and $R^3$ are alkyl.

In certain embodiments, the present invention relates to any one of the above-mentioned ligands, wherein $R^2$ and $R^3$ are Me.

In certain embodiments, the present invention relates to any one of the above-mentioned ligands, wherein $R^2$ and $R^3$, taken together with the carbons to which they are bound, form a five or six-membered, substituted or unsubstituted, aryl or heteroaryl ring.

In certain embodiments, the present invention relates to any one of the above-mentioned ligands, wherein $R^2$ and $R^3$, taken together with the carbons to which they are bound, form a six-membered, substituted or unsubstituted, aryl ring.

In certain embodiments, the present invention relates to any one of the above-mentioned ligands, wherein $R^2$ and $R^3$, taken together are —CH═CH—CH═CH—.

In certain embodiments, the present invention relates to any one of the above-mentioned ligands, wherein $R^5$, $R^7$ and $R^9$ are alkyl.

In certain embodiments, the present invention relates to any one of the above-mentioned ligands, wherein $R^5$, $R^7$ and $R^9$ are Me, Et, n-Pr, i-Pr, n-Bu, i-Bu, or s-Bu.

In certain embodiments, the present invention relates to any one of the above-mentioned ligands, wherein $R^5$, $R^7$ and $R^9$ are i-Pr.

In one embodiment, the present invention relates to a ligand represented by III:

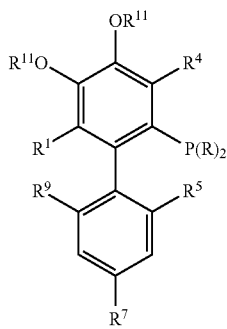

III wherein

R is selected independently for each occurrence from the group consisting of alkyl, cycloalkyl, aryl, heteroaryl, aralkyl, heteroaralkyl, and —$(CH_2)_m$—$R^{10}$;

$R^1$ and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$;

$R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$;

$R^6$ and $R^8$ are selected independently for each occurrence from the group consisting of hydrogen, lower alkyl and halogen;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand, when chiral, is a mixture of stereoisomers or a single enantiomer.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

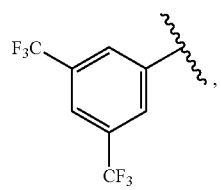

or

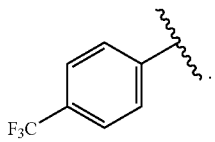

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

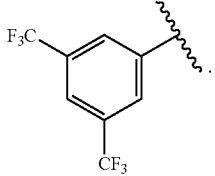

In certain embodiments, the present invention relates to any one of the above-mentioned ligands, wherein R is

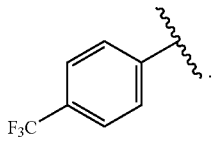

In certain embodiments, the present invention relates to any one of the above-mentioned ligands, wherein $R^{11}$ is alkyl.

In certain embodiments, the present invention relates to any one of the above-mentioned ligands, wherein $R^{11}$ is Me, Et, n-Pr, i-Pr, n-Bu, i-Bu, or s-Bu.

In certain embodiments, the present invention relates to any one of the above-mentioned ligands, wherein $R^{11}$ is Me.

In certain embodiments, the present invention relates to any one of the above-mentioned ligands, wherein $R^1$ and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$.

In certain embodiments, the present invention relates to any one of the above-mentioned ligands, wherein $R^1$ and $R^4$ are —$OR^{11}$.

In certain embodiments, the present invention relates to any one of the above-mentioned ligands, wherein $R^1$ and $R^4$ are —$OR^{11}$; and $R^{11}$ is alkyl.

In certain embodiments, the present invention relates to any one of the above-mentioned ligands, wherein $R^1$ and $R^4$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^1$ and $R^4$ are —$OR^{11}$; and $R^{11}$ is Me.

In certain embodiments, the present invention relates to any one of the above-mentioned ligands, wherein $R^1$ and $R^4$ are alkyl.

In certain embodiments, the present invention relates to any one of the above-mentioned ligands, wherein $R^1$ and $R^4$ are Me.

In certain embodiments, the present invention relates to any one of the above-mentioned ligands, wherein $R^5$, $R^7$ and $R^9$ are alkyl.

In certain embodiments, the present invention relates to any one of the above-mentioned ligands, wherein $R^5$, $R^7$ and $R^9$ are Me, Et, n-Pr, i-Pr, n-Bu, i-Bu, or s-Bu.

In certain embodiments, the present invention relates to any one of the above-mentioned ligands, wherein $R^5$, $R^7$ and $R^9$ are i-Pr.

In one embodiment, the present invention relates to a ligand represented by IV:

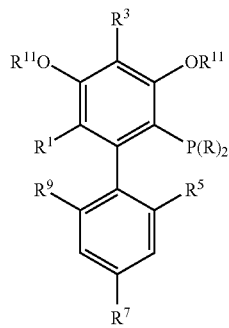

IV wherein

R is selected independently for each occurrence from the group consisting of alkyl, cycloalkyl, aryl, heteroaryl, aralkyl, heteroaralkyl, and $-(CH_2)_m-R^{10}$;

$R^1$ and $R^3$ are selected independently for each occurrence from the group consisting of hydrogen, halogen, alkyl, cycloalkyl, heterocycloalkyl, aryl, heteroaryl, aralkyl, heteroaralkyl, $-OR^{11}$, $-N(R^{11})_2$, $-Si(R^{11})_3$, and $-(CH_2)_m-R^{10}$;

$R^5$, $R^7$ and $R^9$ are selected independently for each occurrence from the group consisting of alkyl, cycloalkyl, heterocycloalkyl, aryl, heteroaryl, aralkyl, heteroaralkyl, $-Si(R^{11})_3$, and $-(CH_2)_m-R$;

$R^6$ and $R^8$ are selected independently for each occurrence from the group consisting of hydrogen, lower alkyl and halogen;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand, when chiral, is a mixture of stereoisomers or a single enantiomer.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

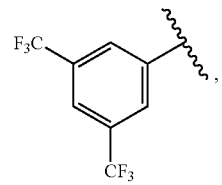

or

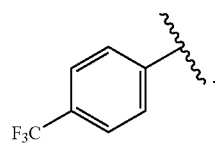

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

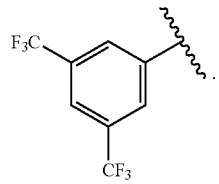

In certain embodiments, the present invention relates to any one of the above-mentioned ligands, wherein R is

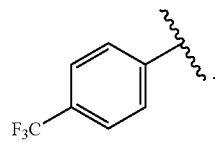

In certain embodiments, the present invention relates to any one of the above-mentioned ligands, wherein R is t-Bu.

In certain embodiments, the present invention relates to any one of the above-mentioned ligands, wherein $R^{11}$ is alkyl.

In certain embodiments, the present invention relates to any one of the above-mentioned ligands, wherein $R^{11}$ is Me, Et, n-Pr, i-Pr, n-Bu, i-Bu, or s-Bu.

In certain embodiments, the present invention relates to any one of the above-mentioned ligands, wherein $R^{11}$ is Me.

In certain embodiments, the present invention relates to any one of the above-mentioned ligands, wherein $R^1$ and $R^3$ are selected independently for each occurrence from the group consisting of hydrogen, halogen, alkyl, cycloalkyl, heterocycloalkyl, aryl, heteroaryl, aralkyl, $-OR^{11}$, $-N(R^{11})_2$, $-Si(R^{11})_3$, and $-(CH_2)_m-R^{10}$.

In certain embodiments, the present invention relates to any one of the above-mentioned ligands, wherein $R^1$ and $R^3$ are $-OR^{11}$.

In certain embodiments, the present invention relates to any one of the above-mentioned ligands, wherein $R^1$ and $R^3$ are —$OR^{11}$; and $R^{11}$ is alkyl.

In certain embodiments, the present invention relates to any one of the above-mentioned ligands, wherein $R^1$ and $R^3$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^1$ and $R^3$ are —$OR^{11}$; and $R^{11}$ is Me.

In certain embodiments, the present invention relates to any one of the above-mentioned ligands, wherein $R^1$ and $R^3$ are alkyl.

In certain embodiments, the present invention relates to any one of the above-mentioned ligands, wherein $R^1$ and $R^3$ are Me.

In certain embodiments, the present invention relates to any one of the above-mentioned ligands, wherein $R^5$, $R^7$ and $R^9$ are alkyl.

In certain embodiments, the present invention relates to any one of the above-mentioned ligands, wherein $R^5$, $R^7$ and $R^9$ are Me, Et, n-Pr, i-Pr, n-Bu, i-Bu, or s-Bu.

In certain embodiments, the present invention relates to any one of the above-mentioned ligands, wherein $R^5$, $R^7$ and $R^9$ are i-Pr.

In one embodiment, the present invention relates to a ligand selected from the group consisting of:

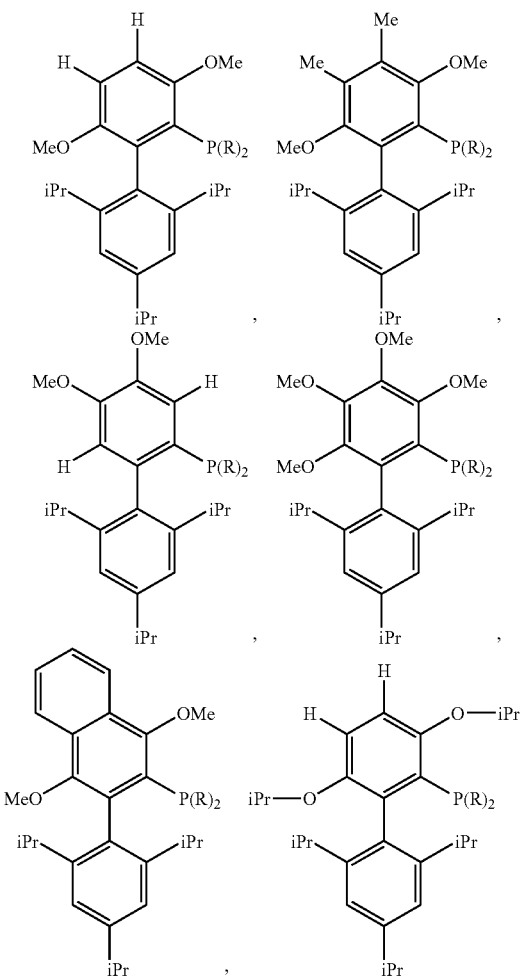

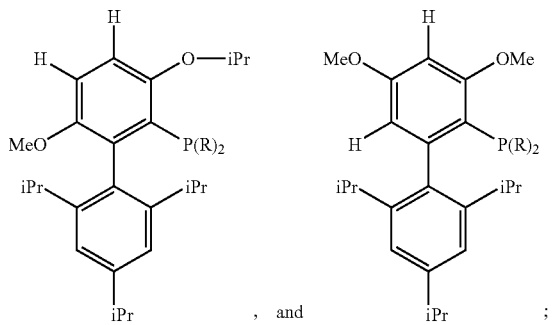

wherein R is selected independently for each occurrence from the group consisting of alkyl, aryl, and cycloalkyl.

In certain embodiments, the present invention relates to any one of the above-mentioned ligands, wherein R is Cy, i-Pr, $C_5H_{11}$, Me, Et, 1-adamantyl, t-Bu,

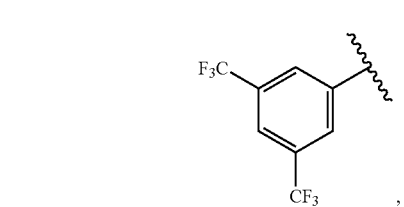

or

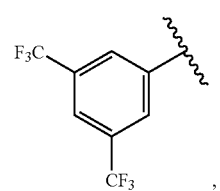

In certain embodiments, the present invention relates to any one of the above-mentioned ligands, wherein R is Cy.

In certain embodiments, the present invention relates to any one of the above-mentioned ligands, wherein R is 1-adamantyl.

In certain embodiments, the present invention relates to any one of the above-mentioned ligands, wherein R is

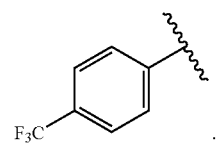

In certain embodiments, the present invention relates to any one of the above-mentioned ligands, wherein R is

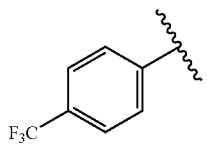

In certain embodiments, the present invention relates to any one of the above-mentioned ligands, wherein R is t-Bu.

In one embodiment, the present invention relates to a ligand represented by

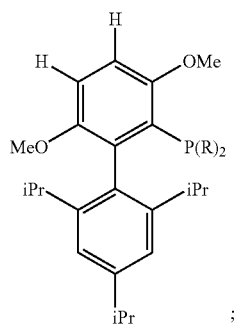

wherein R is Cy.

In one embodiment, the present invention relates to a ligand represented by

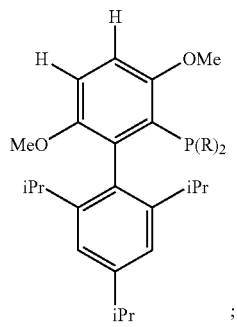

wherein R is t-Bu.

Heteroaryl-Based Ligands

In one embodiment, the present invention relates to a ligand represented by V:

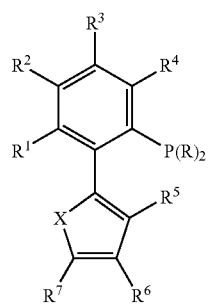

wherein

X is selected from the group consisting of O, $NR^8$, and S;

R is selected independently for each occurrence from the group consisting of alkyl, cycloalkyl, aryl, heteroaryl, aralkyl, heteroaralkyl, and $—(CH_2)_m—R^{10}$;

$R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, $—OR^{11}$, $—N(R^{11})_2$, $—Si(R^{11})_3$, and $—(CH_2)_m—R^{10}$; or any two adjacent instances of $R^1$, $R^2$, $R^3$ and $R^4$, taken together with the carbons to which they are bound, form a five-membered substituted or unsubstituted aryl or heteroaryl ring; provided that at least two of $R^1$, $R^2$, $R^3$ and $R^4$ are $—OR^{11}$;

$R^5$, $R^6$, and $R^7$ are selected independently for each occurrence from the group consisting of alkyl, cycloalkyl, heterocycloalkyl, aryl, heteroaryl, aralkyl, heteroaralkyl, $—Si(R^{11})_3$, and $—(CH_2)_m—R^{10}$; or any two adjacent instances of $R^5$, $R^6$, and $R^7$, taken together with the carbons to which they are bound, form a five- or six-membered substituted or unsubstituted aryl or heteroaryl ring;

$R^8$ represents hydrogen, halogen, alkyl, cycloalkyl, heterocycloalkyl, aryl, heteroaryl, aralkyl, heteroaralkyl, $—OR^{11}$, $—N(R^{11})_2$, $—Si(R^{11})_3$, and $—(CH_2)_m—R^{10}$;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

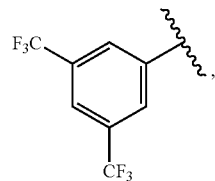

or

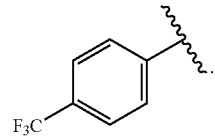

In certain embodiments, the present invention relates to any one of the above-mentioned ligands, wherein R is Cy.

In certain embodiments, the present invention relates to any one of the above-mentioned ligands, wherein $R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$.

In certain embodiments, the present invention relates to any one of the above-mentioned ligands, wherein $R^1$ and $R^4$ are —$OR^{11}$.

In certain embodiments, the present invention relates to any one of the above-mentioned ligands, wherein $R^1$ and $R^4$ are —$OR^{11}$; and $R^{11}$ is alkyl.

In certain embodiments, the present invention relates to any one of the above-mentioned ligands, wherein $R^1$ and $R^4$ are —$OR^{11}$; and $R^{11}$ is Me, Et, n-Pr, i-Pr, n-Bu, i-Bu, or s-Bu.

In certain embodiments, the present invention relates to any one of the above-mentioned ligands, wherein $R^1$ and $R^4$ are —$OR^{11}$; and $R^{11}$ is Me.

In certain embodiments, the present invention relates to any one of the above-mentioned ligands, wherein X is O or $NR^8$.

In certain embodiments, the present invention relates to any one of the above-mentioned ligands, wherein X is O.

In certain embodiments, the present invention relates to any one of the above-mentioned ligands, wherein X is $NR^8$.

In certain embodiments, the present invention relates to any one of the above-mentioned ligands, wherein $R^8$ is hydrogen or alkyl.

In certain embodiments, the present invention relates to any one of the above-mentioned ligands, wherein $R^8$ is alkyl.

In certain embodiments, the present invention relates to any one of the above-mentioned ligands, wherein $R^8$ is Me, Et, n-Pr, i-Pr, n-Bu, i-Bu, or s-Bu.

In certain embodiments, the present invention relates to any one of the above-mentioned ligands, wherein $R^8$ is Me.

In certain embodiments, the present invention relates to any one of the above-mentioned ligands, wherein $R^6$ and $R^7$, taken together with the carbons to which they are bound, form a ring.

In certain embodiments, the present invention relates to any one of the above-mentioned ligands, wherein $R^6$ and $R^7$, taken together with the carbons to which they are bound, form a six-membered ring.

In certain embodiments, the present invention relates to any one of the above-mentioned ligands, wherein $R^6$ and $R^7$, taken together with the carbons to which they are bound, form an aryl ring.

In certain embodiments, the present invention relates to any one of the above-mentioned ligands, wherein $R^6$ and $R^7$, taken together with the carbons to which they are bound, form a six-membered, aryl ring.

In certain embodiments, the present invention relates to any one of the above-mentioned ligands, wherein $R^5$ is hydrogen.

In certain embodiments, the present invention relates to any one of the above-mentioned ligands, wherein $R^2$ and $R^3$ are hydrogen.

In one embodiment, the present invention relates to a ligand represented by VI:

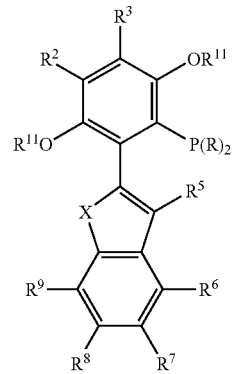

wherein

X is selected from the group consisting of O, $NR^{12}$, and S;

R is selected independently for each occurrence from the group consisting of alkyl, cycloalkyl, aryl, heteroaryl, aralkyl, heteroaralkyl, and —$(CH_2)_m$—$R^{10}$;

$R^2$ and $R^3$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$; or any two adjacent instances of $R^2$ and $R^3$, taken together with the carbons to which they are bound, form a five- or six-membered substituted or unsubstituted aryl or heteroaryl ring;

$R^5$, $R^6$, $R^7$, $R^8$, and $R^9$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$;

$R^{10}$ represents an unsubstituted or substituted aryl, cycloalkyl, cycloalkenyl, heterocycle, or polycycle;

$R^{11}$ is selected independently for each occurrence from the group consisting of alkyl, cycloalkyl, heterocycloalkyl, aryl, heteroaryl, aralkyl, and heteroaralkyl;

$R^{12}$ represents hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$;

m is independently for each occurrence an integer in the range 0 to 8 inclusive; and the ligand is achiral or, when chiral, is a single stereoisomer or a mixture of stereoisomers.

In certain embodiments, the present invention relates to any one of the above-mentioned ligands, wherein R is alkyl, aryl, or cycloalkyl.

In certain embodiments, the present invention relates to any one of the above-mentioned ligands, wherein R is Cy, i-Pr, $C_5H_{11}$, Me, Et, 1-adamantyl, t-Bu,

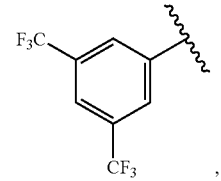

or

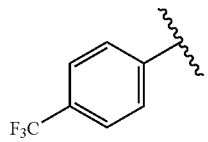

In certain embodiments, the present invention relates to any one of the above-mentioned ligands, wherein R is Cy.

In certain embodiments, the present invention relates to any one of the above-mentioned ligands, wherein $R^{11}$ is alkyl.

In certain embodiments, the present invention relates to any one of the above-mentioned ligands, wherein $R^{11}$ is Me, Et, n-Pr, i-Pr, n-Bu, i-Bu, or s-Bu.

In certain embodiments, the present invention relates to any one of the above-mentioned ligands, wherein $R^{11}$ is Me.

In certain embodiments, the present invention relates to any one of the above-mentioned ligands, wherein X is O or $NR^{12}$.

In certain embodiments, the present invention relates to any one of the above-mentioned ligands, wherein X is O.

In certain embodiments, the present invention relates to any one of the above-mentioned ligands, wherein X is $NR^{12}$.

In certain embodiments, the present invention relates to any one of the above-mentioned ligands, wherein $R^{12}$ is hydrogen or alkyl.

In certain embodiments, the present invention relates to any one of the above-mentioned ligands, wherein $R^{12}$ is alkyl.

In certain embodiments, the present invention relates to any one of the above-mentioned ligands, wherein $R^{12}$ is Me, Et, n-Pr, i-Pr, n-Bu, i-Bu, or s-Bu.

In certain embodiments, the present invention relates to any one of the above-mentioned ligands, wherein $R^{12}$ is Me.

In certain embodiments, the present invention relates to any one of the above-mentioned ligands, wherein $R^5$, $R^6$, $R^7$, $R^8$, and $R^9$ are hydrogen.

In certain embodiments, the present invention relates to any one of the above-mentioned ligands, wherein $R^2$ and $R^3$ are selected independently for each occurrence from the group consisting of hydrogen, halogen, alkyl, cycloalkyl, heterocycloalkyl, aryl, heteroaryl, aralkyl, heteroaralkyl, $-OR^{11}$, $-N(R^{11})_2$, $-Si(R^{11})_3$, and $-(CH_2)_m-R^{10}$.

In certain embodiments, the present invention relates to any one of the above-mentioned ligands, wherein $R^2$ and $R^3$ are hydrogen.

In one embodiment, the present invention relates to a ligand of formula VII:

VII

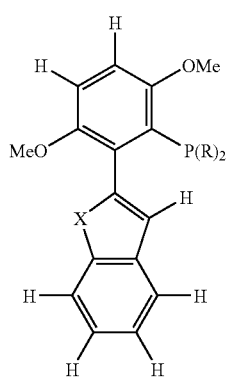

wherein, independently for each occurrence,

R is selected from the group consisting of alkyl, cycloalkyl, aryl; and

X is O or $NR^{12}$.

In certain embodiments, the present invention relates to any one of the above-mentioned ligands, wherein X is O.

In certain embodiments, the present invention relates to any one of the above-mentioned ligands, wherein X is $NR^{12}$.

In certain embodiments, the present invention relates to any one of the above-mentioned ligands, wherein R is Cy, i-Pr, $C_5H_{11}$, Me, Et, 1-adamantyl, t-Bu,

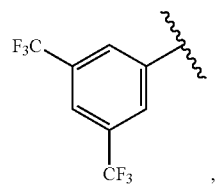

or

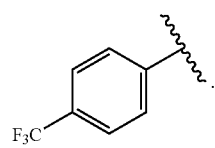

In certain embodiments, the present invention relates to any one of the above-mentioned ligands, wherein R is Cy.

In one embodiment, the present invention relates to a ligand represented by

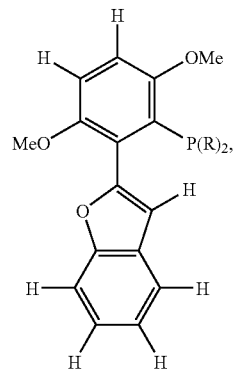

wherein R is Cy.

In one embodiment, the present invention relates to a ligand represented by

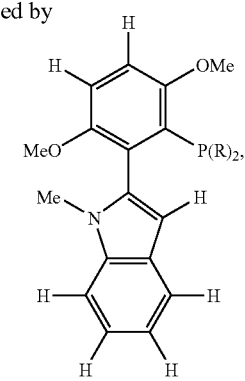

wherein R is Cy.

Exemplary Catalyzed Reactions

As described herein, one aspect of the present invention relates to novel ligands for transition metals. A second aspect of the present invention relates to the use of catalysts comprising these ligands in transition metal-catalyzed carbon-heteroatom and carbon-carbon bond-forming reactions (e.g., Suzuki couplings, Sonogashira couplings, and Stille cross-couplings). The subject methods provide improvements in many features of the transition metal-catalyzed reactions, including the range of suitable substrates, number of catalyst turnovers, reaction conditions, and efficiency.

One aspect of the present invention relates to a transition metal-catalyzed amination or amidation reaction which comprises combining an amine or amide with a substrate aryl group bearing an activated group X. The reaction includes at least a catalytic amount of a transition metal catalyst, comprising a novel ligand, and the combination is maintained under conditions appropriate for the metal catalyst to catalyze the arylation of the amine or amide.

Suitable substrate aryl compounds include compounds derived from simple aromatic rings (single or polycylic) such as benzene, naphthalene, anthracene and phenanthrene; or heteroaromatic rings (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like. In preferred embodiment, the reactive group, X, is substituted on a five, six or seven membered ring (though it can be part of a larger polycycle).

In certain embodiments, the aryl substrate may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidazole, quinoline, furan, pyrrole, thiophene, and the like. Suitable aromatic compounds derived from fused ring systems, include but are not limited to naphthalene, anthracene, tetralin, indole and the like.

Suitable aromatic compounds may have the formula $Z_p$ArX, where X is an activated substituent. An activated substituent, X, is characterized as being a good leaving group. In general, the leaving group is a group such as a halide or sulfonate. Suitable activated substituents include, by way of example only, halides such as chloride, bromide and iodide, and sulfonate esters such as triflate, mesylate, nonaflate and tosylate. In certain embodiments, the leaving group is a halide selected from iodine, bromine, and chlorine.

Z represents one or more optional substituents on the aromatic ring, though each occurrence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—$R_{80}$, —$(CH_2)_m$—OH, —$(CH_2)_m$—O-lower alkyl, —$(CH_2)_m$—O-lower alkenyl, —$(CH_2)_m$—O—$(CH_2)_n$—$R_{80}$, —$(CH_2)_m$—SH, —$(CH_2)_m$—S-lower alkyl, —$(CH_2)_m$—S-lower alkenyl, —$(CH_2)_m$—S—$(CH_2)_n$—$R_{80}$, or protecting groups of the above or a solid or polymeric support; $R_{80}$ represents a substituted or unsubstituted aryl, aralkyl, cycloalkyl, cycloalkenyl, or heterocycle; and n and m are independently for each occurrence zero or an integer in the range of 1 to 6. P is preferably in the range of 0 to 5. For fused rings, where the number of substitution sites on the aryl group increases, p may be adjusted appropriately.

In certain embodiments, suitable substituents Z include alkyl, aryl, acyl, heteroaryl, amino, carboxylic ester, carboxylic acid, hydrogen, ether, thioether, amide, carboxamide, nitro, phosphonic acid, hydroxyl, sulfonic acid, halide, pseudohalide groups, and substituted derivatives thereof, and p is in the range of 0 to 5. In particular, the reaction is anticipated to be compatible with acetals, amides and silyl ethers. For fused rings, where the number of substitution sites on the aromatic ring increases, p may be adjusted appropriately.

A wide variety of substrate aryl groups are useful in the methods of the present invention. The choice of substrate will depend on factors such as the amine, boronic acid, ketone, or the like to be employed and the desired product, and an appropriate aryl substrate will be made apparent to the skilled artisan by these teachings. It will be understood that the aryl substrate preferably will not contain any interfering functionalities. It will further be understood that not all activated aryl substrates will react with every amine, amide or the like.

The reactive amine, amide or the like can be a molecule separate from the substrate aryl group, or a substituent of the same molecule (e.g., for intramolecular variations). Nitrogen-containing molecules, such as nitrites or cyanates, may also be coupled by methods of the present invention and should be considered to be included in the term "amine, amide or the like."

The amine, amide, or the like is selected to provide the desired reaction product. The amine, amide or the like may be functionalized. The amine, amide or the like may be selected from a wide variety of structural types, including but not limited to, acyclic, cyclic or heterocyclic compounds, fused ring compounds, aryls, heteroaryls or their derivatives. The aromatic compound and the amine, amide, or the like may be included as moieties of a single molecule, whereby the arylation reaction proceeds as an intramolecular reaction.

In certain embodiments, the amine, amide, or the like is generated in situ by conversion of a precursor under the reaction conditions.

In certain embodiments, the aryl substrate and/or the amine, amide or the ligand is attached, either directly or via a tether, to a solid support.

In certain embodiments, the amine is a primary amine. In certain embodiments, the amine is lower alkyl amine. In certain embodiments, the amine is methylamine. In certain embodiments, a primary amine and a secondary amine are present within the same molecule, and the primary amine reacts selectively over the secondary amine in a cross-coupling reaction.

Alternatively, the corresponding salt of the amine, amide, or the like, may be prepared and used in place of the amine, amide, or the like. When the corresponding salt of the amine, amide, or the like is used in the reaction, an additional base may not be required.

It is contemplated that the "transition metal catalyst" of the present invention, as that term is used herein, shall include any catalytic transition metal and/or catalyst precursor as it is introduced into the reaction vessel and which is, if necessary, converted in situ into the active form, as well as the active form of the catalyst which participates in the reaction.

In certain embodiments, the transition metal catalyst complex is provided in the reaction mixture is a catalytic amount. In certain embodiments, that amount is in the range of 0.0001 to 20 mol %, and preferably 0.05 to 5 mol %, and most preferably 1-4 mol %, with respect to the limiting reagent, which may be either the aromatic compound the amine, boronic acid, ketone, or the like (or the corresponding salt thereof), depending upon which reagent is in stoichiometric excess. In the instance where the molecular formula of the catalyst complex includes more than one metal, the amount of the catalyst complex used in the reaction may be adjusted accordingly. By way of example, $Pd_2(dba)_3$ has two metal centers; and thus the molar amount of $Pd_2(dba)_3$ used in the reaction may be halved without sacrificing catalytic activity.

In certain embodiments, catalysts containing palladium and nickel are preferred. It is expected that these catalysts will perform similarly because they are known to undergo similar reactions, namely oxidative-addition reactions and reductive-elimination reactions, which are thought to be involved in the formation of the products of the present invention. The novel ligands are thought to modify the catalyst performance by, for example, modifying reactivity and preventing undesirable side reactions.

As suitable, the catalysts employed in the subject method involve the use of metals which can mediate cross-coupling of the aryl groups ArX and the amine, amide, or the like as defined above. In general, any transition metal (e.g., having d electrons) may be used to form the catalyst, e.g., a metal selected from one of Groups 3-12 of the periodic table or from the lanthanide series. However, in certain embodiments, the metal will be selected from the group of late transition metals, e.g., preferably from Groups 5-12 and even more preferably Groups 7-11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero valent transition metal, such as Pd or Ni with the ability to undergo oxidative addition to Ar—X bond. The zero-valent state, M(0), may be generated in situ, e.g., from M(II).

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom or carbon-carbon bond forming sequence. Thus, the metal center is desirably in the zero-valent state or is capable of being reduced to metal(0). Suitable soluble palladium complexes include, but are not limited to, tris(dibenzylideneacetone) dipalladium [$Pd_2(dba)_3$], bis(dibenzylideneacetone) palladium [$Pd(dba)_2$] and palladium acetate. Alternatively, particularly for nickel catalysts, the active species for the oxidative-addition step may be in the metal (+1) oxidation state.

Catalysts containing palladium and nickel are preferred. It is expected that these catalysts will perform comparably because they are known in the art to undergo similar reactions, namely cross-coupling reactions, which may be involved in the formation of the products of the present invention, e.g., arylamines, diaryls, α-arylketones, or the like.

The coupling can be catalyzed by a palladium catalyst which palladium may be provided in the form of, for illustrative purposes only, Pd/C, $PdCl_2$, $Pd(OAc)_2$, $(CH_3CN)_2PdCl_2$, $Pd[P(C_6H_5)_3]_4$, and polymer supported Pd(0). In other embodiments, the reaction can be catalyzed by a nickel catalyst which nickel may be provided in the form of, for illustrative purposes only, $Ni(acac)_2$, $NiCl_2[P(C_6H_5)]_2$, Ni(1,5-cyclooctadiene)$_2$, Ni(1,10-phenanthroline)$_2$, Ni(dppf)$_2$, $NiCl_2$(dppf), $NiCl_2$(1,10-phenanthroline), Raney nickel and the like, wherein "acac" represents acetylacetonate.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the products, rather than side reactions such as β-hydride elimination. The ligand, if chiral can be provided as a racemic mixture or a purified stereoisomer.

The catalyst complex may include additional supporting ligands as required to obtain a stable complex. Moreover, the ligand can be added to the reaction mixture in the form of a metal complex, or added as a separate reagent relative to the addition of the metal.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalytic metal center. In some preferred embodiments, the supporting ligand is a chelating ligand. Although not bound by any theory of operation, it is hypothesized that the supporting ligands suppress unwanted side reactions as well as enhance the rate and efficiency of the desired processes. Additionally, they typically prevent precipitation of the catalytic transition metal. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., amine, boronic acid, ketone or the like, or aromatic compound. The ratio of the supporting ligand to catalyst complex is typically in the range of about 1 to 20, and preferably in the range of about 1 to 4 and most preferably 2. These ratios are based upon a single metal complex and a single binding site ligand. In instances where the ligand contains additional binding sites (i.e., a chelating ligand) or the catalyst contains more than one metal, the ratio is adjusted accordingly. By way of example only, the supporting ligand BINAP contains two coordinating phosphorus atoms and thus the ratio of BINAP to catalyst is adjusted downward to about 1 to 10, preferably about 1 to 2 and most preferably 1. Conversely, $Pd_2(dba)_3$ contains two palladium metal centers and the ratio of a non-chelating ligand to $Pd_2(dba)_3$ is adjusted upward to 1 to 40, preferably 1 to 8 and most preferably 4.

In certain embodiments of the subject method, the transition metal catalyst includes one or more phosphine or aminophosphine ligands, e.g., as a Lewis basic ligand that controls the stability and electron transfer properties of the transition metal catalyst, and/or stabilizes the metal intermediates. Phosphine ligands are commercially available or can be prepared by methods similar to known processes. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis (diphenylphosphino)-1,1'-binaphthyl (BINAP), 1,2-bis (dimethylphosphino)ethane, 1,2-bis(diethylphosphino) ethane, 1,2-bis(dipropylphosphino)-ethane, 1,2-bis (diisopropylphosphino)ethane, 1,2-bis(dibutyl-phosphino) ethane, 1,2-bis(dicyclohexylphosphino)ethane, 1,3-bis (dicyclohexylphosphino)propane, 1,3-bis (diisopropylphosphino)propane, 1,4-bis (diisopropylphosphino)-butane and 2,4-bis (dicyclohexylphosphino)pentane. The aminophosphines may be monodentate, e.g., each molecule of aminophosphine donates to the catalytic metal atom only a Lewis basic nitrogen atom or a Lewis basic phosphorus atom. Alternatively, the aminophosphine may be a chelating ligand, e.g., capable of donating to the catalytic metal atom both a Lewis basic nitrogen atom and a Lewis basic phosphorus atom.

In some instances, it may be necessary to include additional reagents in the reaction mixture to promote reactivity of either the transition metal catalyst or activated aryl nucleus. In particular, it may be advantageous to include a suitable base. In general, a variety of bases may be used in practice of the present invention. It has not been determined at which point(s) in the mechanisms of the subject transformations the base participates. The base may optionally be sterically hindered to discourage metal coordination of the base in those circumstances where such coordination is possible, i.e., alkali metal alkoxides. Exemplary bases include such as, by way of example only: alkoxides such as sodium tert-butoxide; alkali metal amides such as sodium amide, lithium diisopropylamide, and alkali metal bis(trialkylsilyl)amide, e.g., such as lithium bis(trimethylsilyl)amide (LiHMDS) or sodium bis (trimethylsilyl)amide (NaHMDS); tertiary amines (e.g., triethylamine, trimethylamine, 4-(dimethylamino)pyridine (DMAP), 1,5-diazabicycl[4.3.0]non-5-ene (DBN), 1,5-diazabicyclo[5.4.0]undec-5-ene (DBU); alkali or alkaline earth carbonate, bicarbonate or hydroxide (e.g., sodium, magnesium, calcium, barium, potassium carbonate, phosphate, hydroxide and bicarbonate). By way of example only, suitable bases include NaH, LiH, KH, $K_2CO_3$, $Na_2CO_3$, $Tl_2CO_3$, $Cs_2CO_3$, K(Ot-Bu), Li(Ot-Bu), Na(Ot-Bu)K(OAr), Na(OAr), and triethylamine, or mixtures thereof. Preferred bases include CsF, $K_3PO_4$, DBU, NaOt-Bu, KOt-Bu, LiN(i-Pr)$_2$ (LDA), KN(SiMe$_3$)$_2$, NaN(SiMe$_3$)$_2$, and LiN(SiMe$_3$)$_2$.

Base is used in approximately stoichiometric proportions in the subject methods. The present invention has demonstrated that there is no need for large excesses of base in order to obtain good yields of the desired products under mild reaction conditions. No more than four equivalents of base, and preferably no more than two equivalents, are needed. Furthermore, in reactions using the corresponding salt of an amine, or the like, additional base may not be required.

As is clear from the above discussion, the products which may be produced by the reactions of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of alcohols by esters, acylation of amines and the like.

Anilines with Aryl Chlorides

There are two examples in the literature of cross-couplings reactions with anilines and aryl chlorides at low catalyst loadings. Nolan and co-workers have shown that they can use 0.01% catalyst loading but only with the bulky 2,6-diisopropylaniline. Marion, N.; Navarro, O.; Mei, J.; Stevens, E. D.; Scott, N. M.; Nolan, S. P. *J. Am. Chem. Soc.* 2006, 128, 4101-4111. Bellar and co-workers also have shown one example at 0.01% catalyst loading but they had to use a ligand:Pd ratio of 50:1 and a reaction temperature of 140° C. Rataboul, F.; Zapf, A.; Jackstell, R.; Harkal, S.; Riermeier, T.; Monsees, A.; Dingerdissen, U.; Beller, M. *Chem. Eur. J.* 2004, 10, 2983-2990.

As shown in FIG. 4, coupling reactions of anilines and aryl chlorides using 0.01% catalyst loading with a ligand:Pd ratio of 2:1 have been achieved. Aryl chlorides and anilines with ortho substituents (FIG. 4, Entries 1 and 2) and substrates that did not contain ortho substituents (FIG. 4, Entries 3 and 4) were all performed in excellent yields. In addition, fluorinated electron deficient anilines were also coupled with high efficiency (FIG. 4, Entries 5, 6, and 7).

A direct comparison of 1 with XPhos (13) (see FIG. 3) was performed in order to highlight both the stability and reactivity of this new class of ligands. When XPhos (13) was used in the coupling of p-phenetidine and 2-chloro-p-xylene the reaction had completed approximately one half-life and gave 44% yield after 1 h. With ligand 1 the same reaction had gone to completion and given a 93% isolated yield in the same amount of time (FIG. 4, Entry 1).

Anilines can be successfully coupled with aryl chlorides at catalyst loadings as low as 0.05 mol % when a catalyst system based on 13 is used. Fors, B. P.; Krattiger, P.; Strieter, E.; Buchwald, S. L. *Org. Lett.* 2008. ASAP. By switching to ligand 1, the catalyst loadings were lowered to 0.01 mol % while keeping the reaction times at 1 h (FIG. 12, Table 8, bottom row). This is the lowest palladium loading that has been reported in C—N bond-forming reactions of anilines with aryl chlorides. Marion, N.; Navarro, O.; Mei, J.; Stevens, E. D.; Scott, N. M.; Nolan, S. P. *J. Am. Chem. Soc.* 2006, 128, 4101. These results demonstrate clearly the exceptional reactivity of 1 in these reactions in comparison to previously reported catalyst systems.

Figure 18:
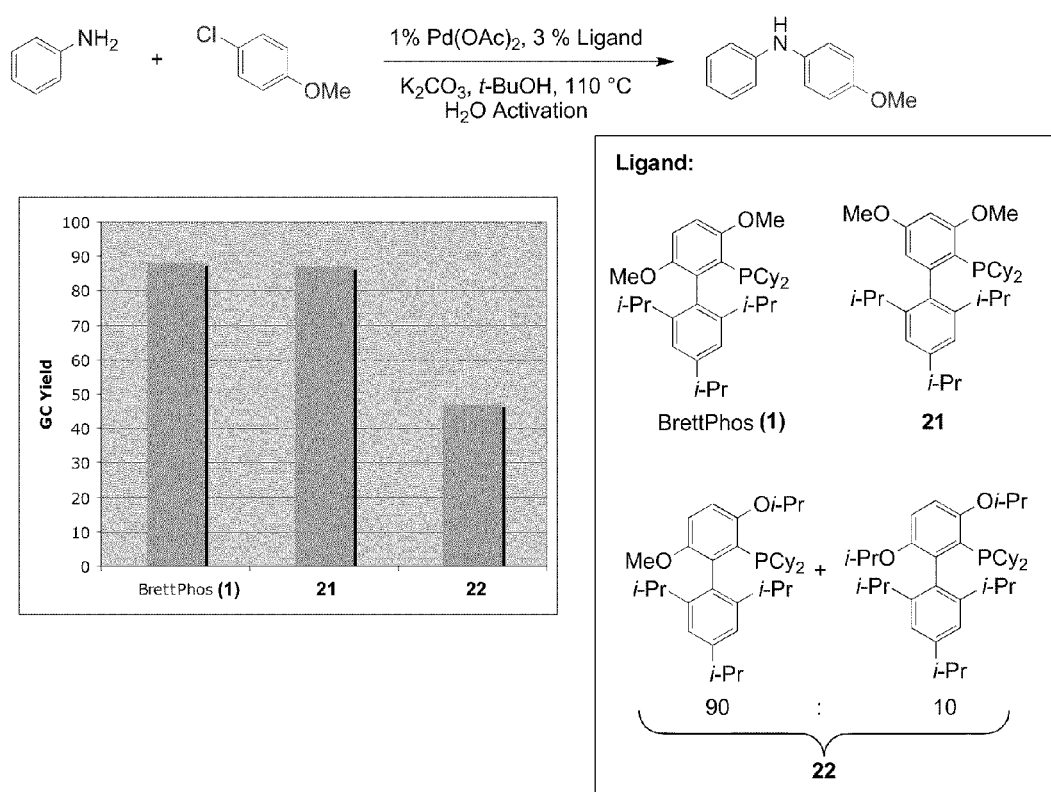
FIG. 18 depicts a comparison of the effectiveness of ligands 1, 21, and 22 in the coupling of aniline with 4-chloroanisole.

As depicted in FIG. 18, several ligands were screened for optimal yield in the coupling of aniline and 4-chloroanisole. Benchmark ligand 1 proved to be comparable to ligand 21, both ligands producing over 85% yield of the desired product after only 15 minutes of reaction time. A general procedure for these reactions is described in detail in Example 53.

Heteroarylamines with Aryl Chlorides

Figure 2:
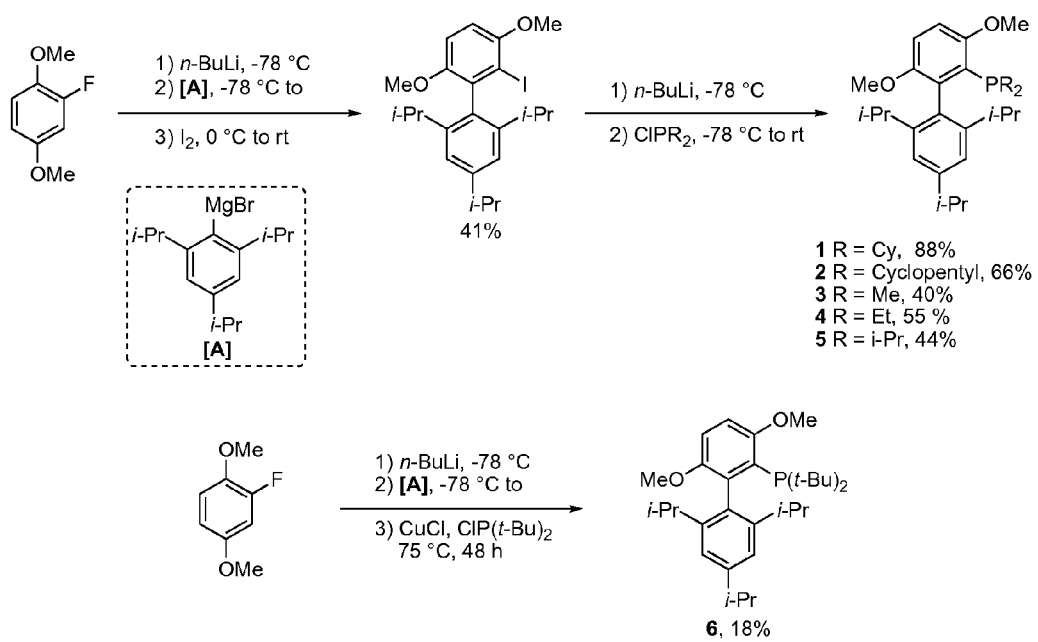
FIG. 2 depicts examples of syntheses of ligands of the invention.
Figure 5:
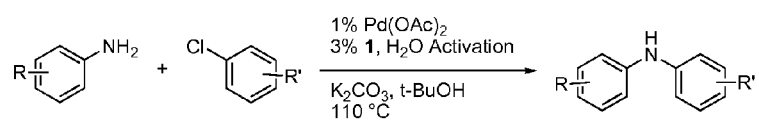
FIG. 5 depicts examples of cross-coupling reactions of heteroarylamines with aryl and heteroaryl chlorides using ligands of the invention.

FIG. 5 demonstrates the utility of ligand 1 in the cross-coupling reactions of heteroarylamines. While there are known catalyst systems that will couple aminopyrimidines, aminopyrazines, and aminopyridines, such the reactions took between 18 to 24 h and the yields were as low as 57%. Anderson, K. W.; Tundel, R. E.; Ikawa, T.; Altman, R. A.; Buchwald, S. L. *Angew. Chem. Int. Ed.* 2006, 45, 6523-6527. By using ligand 1, aminopyrimidines (FIG. 5, Entry 1), aminopyrazines (FIG. 5, Entry 2), and aminopyridines (FIG. 5, Entry 3) were all coupled successfully with short reaction times and in excellent yields.

In order to show the activity of 1 in reactions involving heteroarylamines a direct comparison with XPhos was performed. When XPhos was used in the coupling of 2-aminopyrimidine and 6-chloroquinoline the yield was 37% after 1.5 h. When 1 was used instead of XPhos the reaction had gone to completion after 1 h and the isolated yield was 91% (FIG. 5, Entry 1).

Amides with Aryl Chlorides

Figure 6:
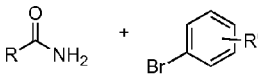
FIG. 6 depicts examples of cross-coupling reactions of amides with aryl and heteroaryl halides using ligands of the invention.

The effectiveness of inventive ligands in the coupling of amides was also explored (see FIG. 6). It is known that the coupling of acetamide with 2-chlorotoluene using ligand 7 (see FIG. 3) takes 18 h and gives a 71% yield. Ikawa, T.;

Barder, T. E.; Biscoe, M. R.; Buchwald, S. L. *J. Am. Chem. Soc.* 2007, 2183-2192. However, using ligand 6 the same coupling was performed in 1.5 h with a yield of 85% (FIG. 6, Entry 2).

Two additional examples were also performed in order to show that the catalyst system using ligand 6 can couple heterocyclic substrates (FIG. 6, Entries 3 and 4). In addition, the coupling of benzamide and p-chloroanisole was performed with both ligand 7 and ligand 6 and gave 79% and 92% yields respectively.

Primary Amines with Aryl Chlorides

Biphenyl-Based Ligands

Figure 10:
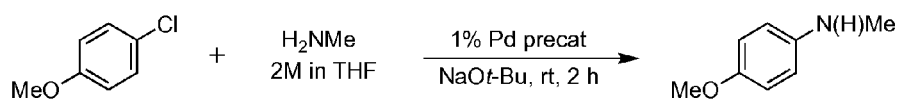
FIG. 10 depicts an evaluation of some ligands of the invention for use in the arylation of methylamine.

Examples of ligands of the invention also promote, for the first time, the highly selective monoarylation of primary amines using low catalyst loadings of a monophosphine-based catalyst. Because the catalytic systems of the present invention had shown a high level of reactivity in cross-coupling reactions in general, the monoarylation of primary amines utilizing these systems was examined. Using 10, methylamine was successfully coupled with 4-chloroanisole with a selectivity of >97:3 for monoarylation over diarylation (FIG. 10, Table 6, entry 1). The analogous reaction using 11 did not give any product at room temperature. By increasing the temperature to 80° C., the reaction proceeded but favored diarylation, reversing the selectivity to 20:80 (FIG. 10, Table 6, entry 3). Using the more bulky ligand 12, the selectivity increased to 82:18 (FIG. 10, Table 6, entry 4) but was still not nearly as selective as 1. Anderson, K. W.; Tundel, R. E.; Ikawa, T.; Altman, R. A.; Buchwald, S. L. *Angew. Chem. Int. Ed.* 2006, 45, 6523. For the reactions outlined in FIG. 10 and conducted at room temperature (Entry 1, 2, and 4), an extra equivalent of 1 was not required in order to create the most stable catalytic system. Additionally, the use of ligand 1 successfully inhibits reactions involving disubstituted amines and allows for the highly selective monoarylation of methylamine at room temperature (FIG. 11, Table 7).

The selective monoarylation of other primary aliphatic amines, which have been difficult to achieve using biarylphosphine ligands, was then examined. With a catalyst system using 1 as ligand, several primary aliphatic amines were successfully coupled to aryl chlorides in excellent yields at 0.05 mol % catalyst loading in 1 h (FIG. 12, Table 8, top row). It is also noteworthy that less than 1% of the diarylation product was observed in all cases. Common perception has been that chelating bisphosphine ligands are required for these couplings in order to suppress diarylation. However, these results not only show that biarylmonophosphines can efficiently support cross-coupling reactions involving primary aliphatic amines, but in some cases they are more efficient than bisphosphine systems. For example, the coupling of octylamine and 4-chloroanisole with a bisphosphine based catalyst system formerly required 0.1 mol % Pd and a reaction time of 48 h. Shen, Q.; Ogata, T.; Hartwig, J. F. *J. Am. Chem. Soc.* 2008, 130, 6586; Shen, Q.; Shekhar, S.; Stambuli, J. P.; Hartwig, J. F. *Angew. Chem. Int. Ed.* 2005, 44, 1371. With a catalyst system based on 1, the reaction of hexylamine and 4-chloroanisole (FIG. 12, Table 8, Entry 1) was complete after 1 h using only 0.05 mol % Pd.

Biphenyl-Based Ligands: Reactivity of Primary Amines Versus Secondary Amines

Figure 13:
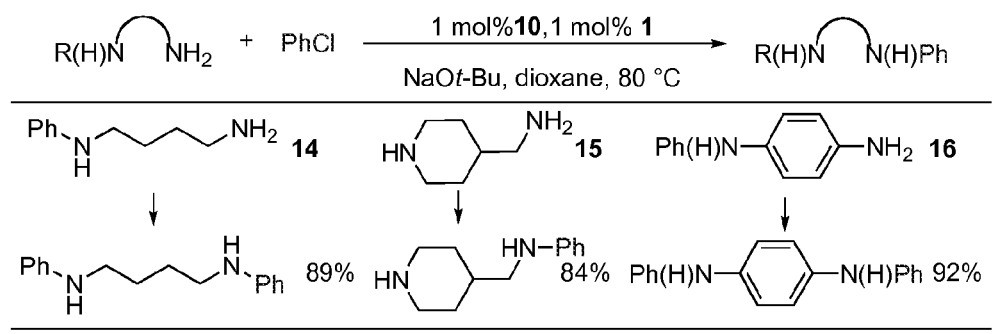
FIG. 13 depicts the selectivity for primary amines over secondary amines in examples of coupling reactions using an exemplary ligand of the invention.

The results described above suggested that high levels of chemoselectivity for the arylation of a primary amine over a secondary amine should be observed. Using 1, the primary amino group of 14 in the presence of a secondary anilino group was coupled with >40:1 selectivity (FIG. 13, Table 9). This result is complimentary to a previous report in which anilines reacted in preference to aliphatic amines. Biscoe, M. R.; Barder, T. E.; Buchwald, S. L. *Angew. Chem. Int. Ed.* 2007, 46, 7232. Further in the intramolecular competition between a primary and cyclic secondary amine in 15, and between a primary and secondary aniline in 16, the primary amino group was N-preferentially arylated and proceeded in excellent yields with selectivities of >20:1 (FIG. 13, Table 9). Cabello-Sanchez, N.; Jean, L.; Maddaluno, J.; Lasne, M.; Rouden, J. *J. Org. Chem.* 2007, 72, 2030.

Heteroaryl-Based Ligands

Figure 19:
FIG. 19 depicts a comparison of ligands 1 and 23 in the coupling of 4-chloroanisole and hexylamine; reaction times and ratios of mono- to di-arylation of the primary amine are noted.

A comparison of the reaction time and the ratio of mono- to di-arylation of the Pd-catalyzed cross-coupling of 4-chloroanisole and hexylamine, as aided by a biphenyl based ligand (1) or a heteroaryl-based ligand (23), can be found in FIG. 19. Although the time of the reaction utilizing the heteroaryl-based ligand (23) is significantly longer, this ligand gives a higher ratio of mono- to di-arylation products. A general procedure for these reactions can be found in Example 59.

Sodium Nitrite with Aryl Chlorides

Figure 20:
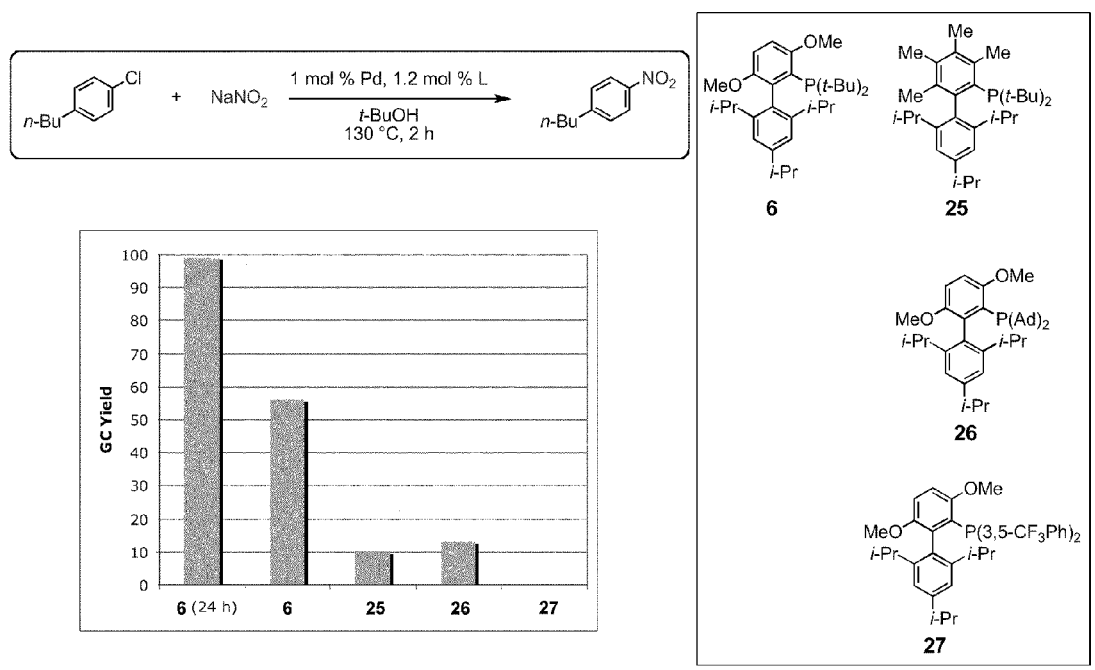
FIG. 20 depicts a comparison of various ligands (6, 25, 26, and 27) in the Pd-catalyzed nitration of an aryl chloride with sodium nitrite.
Figure 21:
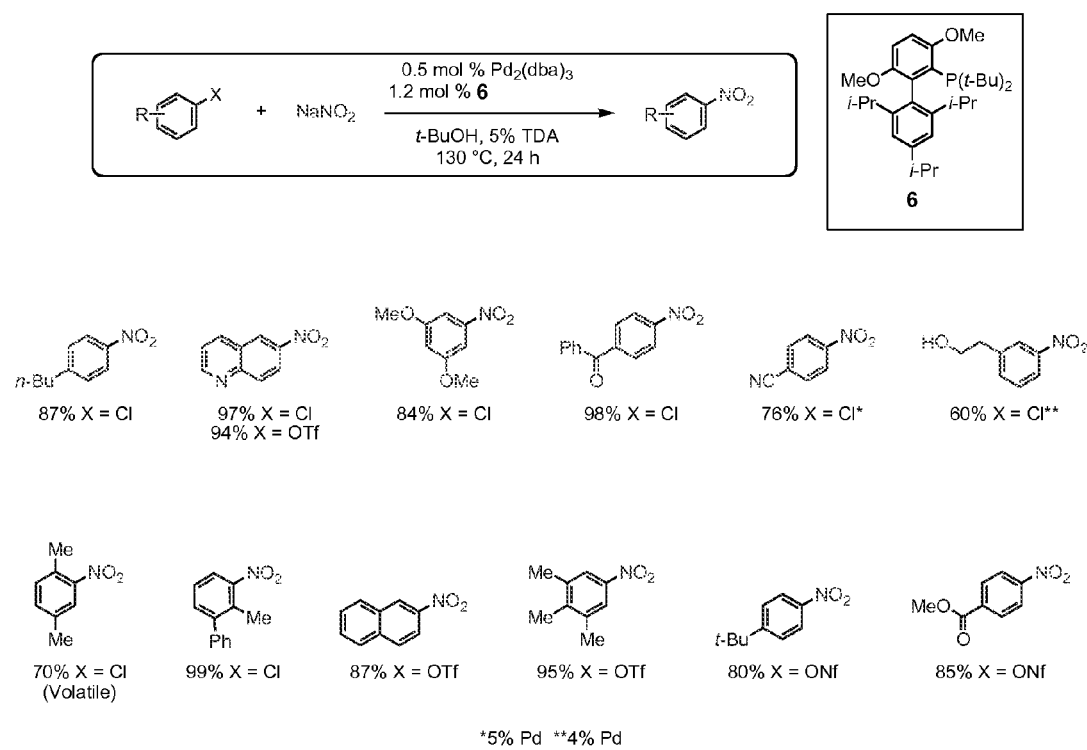
FIG. 21 depicts a variety of aryl chlorides and aryl sulfonates that were coupled with sodium nitrite using ligand 6.

Interestingly, these ligands also catalyze the nitration of aryl chlorides in the presence of sodium nitrite and an appropriate catalyst (FIGS. 20 and 21). As depicted in FIG. 1, ligand 6 produced over 50% yield (by GC) after only 2 h of reaction time. A reaction time of 24 h with ligand 6, however, yielded almost 100% of the desired nitration product. Ligands 25, 26, and 27 were less successful at catalyzing this reaction.

FIG. 21 depicts an array of aryl chlorides that can be coupled with sodium nitrite via ligand 6. Yields vary from 60% to 99%, depending on the substrate used. The nitration was successful for lectron-rich, electron-poor, electron-neutral, sterically-hindered, and highly-substituted aryl chlorides, reinforcing the versatility of these ligands.

Example 54 delineates a general procedure for these reactions.

Cyanates with Aryl Chlorides

Ligands of the present invention also proved successful in the synthesis of N-aryl carbamates from aryl chlorides and metal cyanates. In the presence of t-BuOH, ligand 6 catalyzed the synthesis of the desired product in 74% yield (FIG. 22). A general procedure for this reaction can be found in Example 55.

Anilines with Aryl Mesylates

Biphenyl-Based Ligands

The improved ligands of the invention enable the first aminations of aryl mesylates. In continued efforts to explore this effect, new ligands were prepared (FIG. 7), one of which contained methoxy substitution on the phosphine-containing arene (BrettPhos, 1, Example 9) and has been found to be effective in the amination of aryl mesylates.

Figure 8:
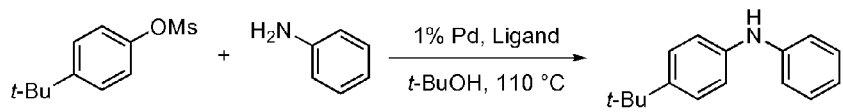
FIG. 8 depicts a screening of some ligands and some Pd sources for the coupling of aniline with 4-t-butylphenyl methanesulfonate.

Initial studies focused on the coupling of 4-t-butylphenyl methanesulfonate and aniline. Whereas catalyst systems based on the combination of $Pd_2(dba)_3$ and 1 failed to produce product (FIG. 8, Table 4, entry 1), precatalyst 10 provided a 98% yield in 3 h (FIG. 8, Table 4, entry 2). Biscoe, M. R.; Fors, B. P.; Buchwald, S. L. *J. Am. Chem. Soc.* 2008, 130, 6686. Similarly, utilization of water-mediated catalyst activation with 1 and $Pd(OAc)_2$ gave the desired product in 99% yield (Entry 3). Ozawa, F.; Kubo, A.; Hayashi, T. *Chem. Lett.* 1992, 2177; Amatore, C.; Carre, E.; Jutand, A.; M'Barki, M. A. *Organometallics* 1995, 14, 1818; Fors, B. P.; Krattiger, P.; Strieter, E.; Buchwald, S. L. *Org. Lett.* 2008. ASAP. In contrast, the use of ligand 13 (XPhos), which has been shown to be efficient in couplings of other aryl sulfonates, but lacks the methoxy groups, provided only trace amounts of product when used either as precatalyst 11 or with the water-mediated activation protocol (FIG. 8, Table 4, entries 4 and 5). Huang, X.; Anderson, K. W.; Zim, D.; Jiang, L.; Klapars, A.; Buchwald, S. L. *J. Am. Chem. Soc.* 2003, 125, 6653.

Because these results clearly implicate the importance of substitution in the upper arene in 1, the use of the tetra-methyl substituted ligand 7, a congener of a ligand which has been shown to be effective in amidation reactions, was also examined. Ikawa, T.; Barder, T. E.; Biscoe, M. R.; Buchwald S. L. *J. Am. Chem. Soc.* 2007, 129, 13001. Unlike reactions employing 1, reactions employing 7 failed to provide even detectable amounts of the desired product (FIG. 8, Table 4, entry 7). These results demonstrate that the nature of the arene substituent is critical to the performance of 1. Further, the importance of the 2',4',6'-triisopropylphenyl in 1 was demonstrated by comparison to dimethoxy ligand 9. As with 7, the use of 9 as the ligand failed to provide detectable product (FIG. 8, Table 4, entry 8). These results, taken together, reveal a cooperative effect between the methoxy substituents and the 2',4',6'-triisopropylphenyl ring and demonstrate that both are required for the observed reactivity in catalytic reactions employing ligand 1.

Having defined an efficient catalytic system, the scope of aryl mesylate coupling reactions was next explored. Highlighted in FIG. 9, Table 5, a number of electron-deficient anilines, which are less reactive in coupling reactions than electron-rich or -neutral anilines, were successfully reacted with both electron-rich and electron-deficient aryl mesylates in excellent yields. Hartwig, J. F. *Inorg. Chem.* 2007, 46, 1936. Ortho substituents on both the aniline and aryl mesylate and several functional groups were well tolerated (FIG. 9, Table 5).

Heteroaryl-Based Ligands

Heteroaryl-based ligands of the present invention, for example ligand 23, also proved successful at catalyzing the reaction of aryl mesylates and anilines. FIG. 23 depicts the use of this ligand in this reaction. A detailed procedure is provided in Example 60.

Amides with Aryl Mesylates

Figure 24:
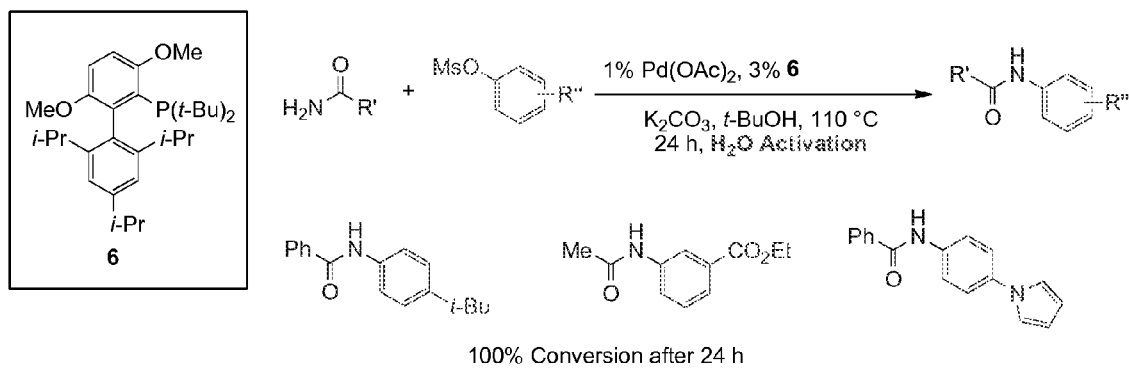
FIG. 24 depicts examples of compounds formed from the reaction of amides with aryl mesylates in the presence of ligand 6.

Other examples of the successful coupling of aryl mesylates are depicted in FIG. 24. Upon exposure to Pd(OAc)$_2$ and ligand 6, in the presence of K$_2$CO$_3$, t-BuOH, and water activation, a variety of amides were coupled to a variety of aryl mesylates, yielding 100% conversion of starting materials after 24 h. A general procedure for these reactions can be found in Example 56.

Sodium Nitrite with Aryl Triflates, Aryl Nonaflates

In addition to the success observed in the nitration of aryl chlorides, aryl triflates and aryl nonaflates were also successfully nitrated with the aid of ligands of the present invention. FIG. 21 depicts several examples of aryl triflates and aryl nonaflates coupled in reactions using ligand 6. Similarly to the case with aryl chlorides, the stereoelectronic nature of the substrate plays little to no role in the yield of the reaction. A general procedure for these reactions is outlined in Example 54.

Carbon-Carbon Coupling of Aryl Mesylates

Stille Cross-Coupling

Figure 25:
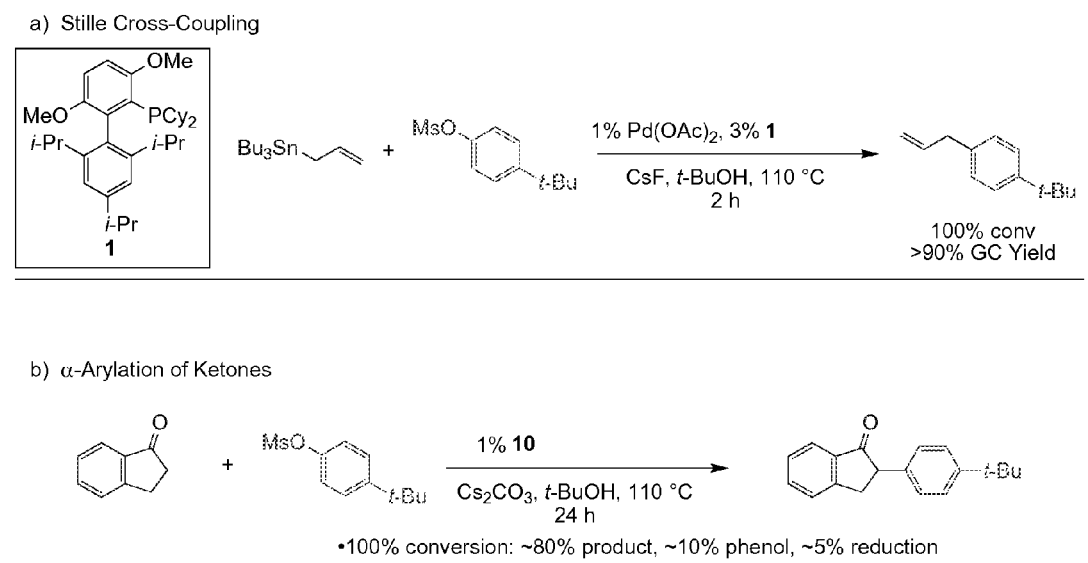
FIG. 25 depicts examples of the versatility of ligand 1 and precatalyst 10 in: a) an example of the Stille cross-coupling with an aryl mesylate, and b) the α-arylation of a ketone.
Figure 26:
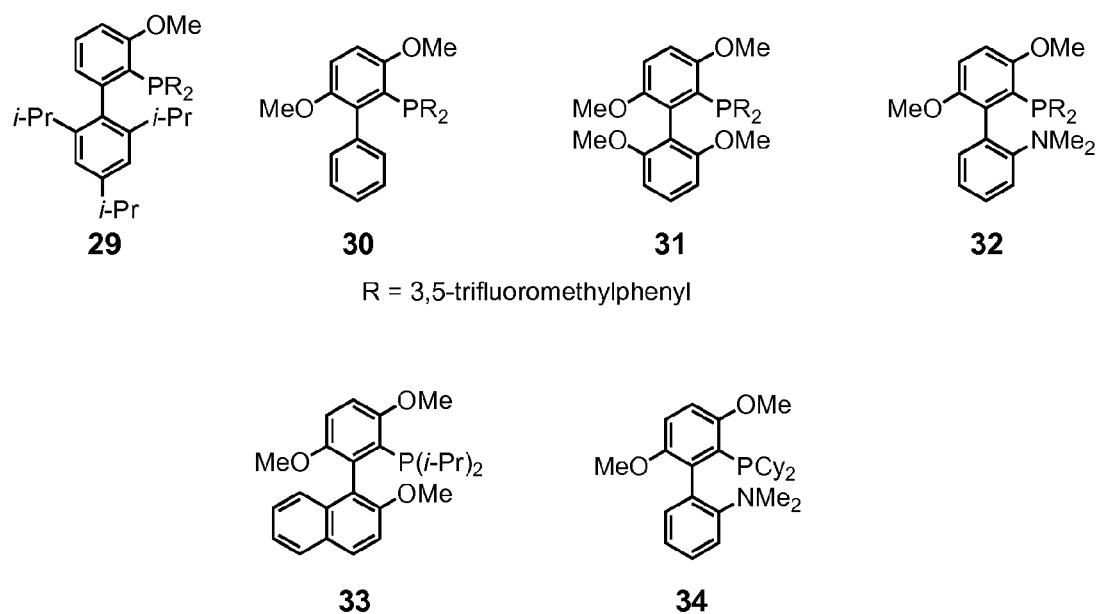
FIG. 26 depicts the structures of ligands 29, 30, 31, 32, 33, and 34.

The ligands of the present invention prove their extreme versatility in the catalysis of a Stille cross-coupling, as depicted in FIG. 25(*a*). Ligand 1 provided the desired product in 90% yield by GC after only 2 h.

α-Arylation of Ketones

Another example of the breadth of reactions catalyzed with the ligands of the present invention is shown in FIG. 25 (*b*). A ketone was successfully arylated with an aryl mesylate at the α-position of the ketone in approximately 80% yield of the desired product.

Ligand Structure

In an attempt to understand the unique reactivity of 1 compared to other ligands, a series of 1.Pd(II)ArX (X=Cl or Br, FIG. 14) complexes were prepared by combining (COD) Pd(CH$_2$SiPhMe$_2$)$_2$, 1 and ArX. Pan, Y.; Young, G. B. *J. Organomet. Chem.* 1999, 577, 257. These complexes exist in solution as a mixture of two well-defined conformational isomers. Examination of the reaction mixture by in situ $^{31}$P NMR revealed two products in an approximate 2:1 ratio. Addition of pentane to the solution induces precipitation of the Pd(II) complex, which crystallizes as a single conformer. Freshly prepared solutions of the isolated complexes display only signals from the major conformer ($^1$H and $^{31}$P NMR). However, rapid isomerization is observed, with the minor isomer becoming detectable within 5 minutes at room temperature. All concentrations in these experiments were measured versus an internal standard.

Figure 14:
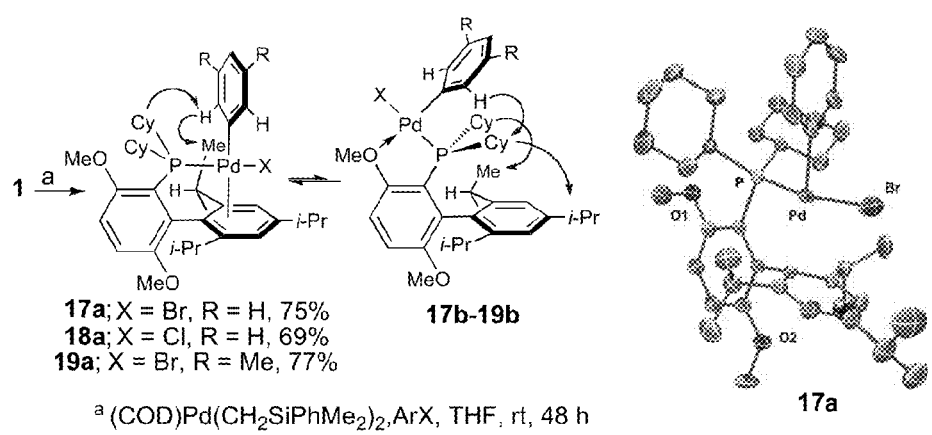

Subjecting either 13 or 7 to the conditions shown in FIG. 14 provided dramatically different results from those obtained using 1. The in situ $^{31}$P NMR spectrum from the reaction of 13 is complex and shows broad resonances that have yet to be deconvoluted. The reaction with 7 results in the formation of Pd black. These differences, to the extent that they reflect the behavior of the resulting Pd(II) complexes, may be related to the observed differences in reactivity observed with these ligands.

X-ray crystal analysis of 17 revealed that the complex exists as a monomer in solid state, and, although some disorder about the Br atom was observed, the resulting structure clearly demonstrates that the Pd center is bound over the tri-isopropylphenyl ring (FIG. 14). In solution, the conformations of the major and minor rotamers are analogous in 17, 18, and 19 ($^1$H NMR). In particular, the methoxy and isopropyl resonances are diagnostic in this assessment, see Examples 43, 44, and 45. For all three complexes, both conformers display $^1$H NMR resonances consistent with D$_2$ symmetry. NOESY NMR analysis of an equilibrated sample of 19 (2:1 mixture) allowed the assignment of the solution state conformation of both rotamers. The conformation of the major rotamer is the same as that observed in the solid state. In the minor isomer, the P—C$_{Ar}$ bond is rotated by 180°, and the palladium atom is chelated by the phosphine atom and the proximal methoxy group. Important cross-peaks used in these assignments are summarized in FIG. 14. 17, 18 and 19 are highly active precatalysts in C—N bond-forming reactions.

Two notable points arise from the structural data. First, the NMR data demonstrate that the Pd(II) aryl halide complexes of 1 likely remain monomeric in solution and are not in equilibrium with the non-D$_2$ symmetric dimeric form. Second, the observed monomeric equilibrium demonstrates that the proximal methoxy does not prevent rotation about the P—C$_{Ar}$ bond. Theoretical studies have shown that this rotation may play an important role in catalytic systems with other biarylphosphines. Ozawa, F.; Kubo, A.; Hayashi, T. *Chem. Lett.* 1992, 2177; Amatore, C.; Carre, E.; Jutand, A.; M'Barki, M. A. *Organometallics* 1995, 14, 1818; Fors, B. P.; Krattiger, P.; Strieter, E.; Buchwald, S. L. *Org. Lett.* 2008, ASAP. The implications of these findings are not yet fully understood, and further studies to clarify the role of the methoxy groups in 1 are ongoing.

Isolation of oxidative addition complexes of 1 has led to insight into the importance of the methoxy substitutent proximal to the phosphine for the reactivity of this catalyst system. Further studies into the origin of the reactivity of 1 are currently underway.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran, water and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants or a ligand anchored to a solid support.

In certain embodiments it is preferable to perform the reactions under an inert atmosphere of a gas such as nitrogen or argon.

In certain embodiments it is preferable to perform the reactions under microwave irradiation. The term "microwave" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared radiation but above those referred to as radio frequencies. Similarly, given the well-established inverse relationship between frequency and wavelength, microwaves have longer wavelengths than infrared radiation, but shorter than radio frequency wavelengths. Microwave-assisted chemistry techniques are generally well established in the academic and commercial arenas. Microwaves have some significant advantages in heating certain substances. In particular, when microwaves interact with substances with which they can couple, most typically polar molecules or ionic species, the microwaves can immediately create a large amount of kinetic energy in such species which provides sufficient energy to initiate or accelerate various chemical reactions. Microwaves also have an advantage over conduction heating in that the surroundings do not need to be heated because the microwaves can react instantaneously with the desired species.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion. In a order of events that, in some cases, can lead to an enhancement of the reaction rate, the base, e.g., t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

METHODS OF THE INVENTION

In one embodiment, the present invention relates to a method represented by Scheme 1:

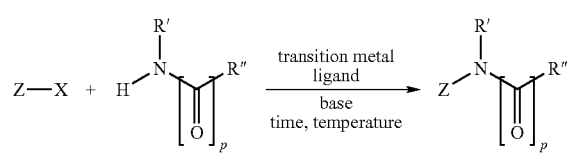

Scheme 1 wherein

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

R' and R" are selected, independently for each occurrence, from the group consisting of hydrogen, alkyl, heteroalkyl, aryl, heteroaryl, aralkyl, heteroaralkyl, alkoxyl, amino, aminoalkyl, heterocyclylalkyl, trialkylsilyl, and triarylsilyl; or R' and (C=O)$_p$R", taken together, form an optionally substituted ring consisting of 3-10 backbone atoms inclusive, said ring optionally comprising one, two or three heteroatoms in addition to the nitrogen to which the R' and (C=O)$_p$R" are bonded;

R' may be covalently linked to Z;

R" may be covalently linked to Z;

p is 0 or 1;

the transition metal is selected from the group consisting of Ni, Pd and Pt;

the base is selected from the group consisting of fluorides, hydrides, hydroxides, carbonates, phosphates, alkoxides, metal amides, and carbanions; and the ligand is any one of the above-mentioned biphenyl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

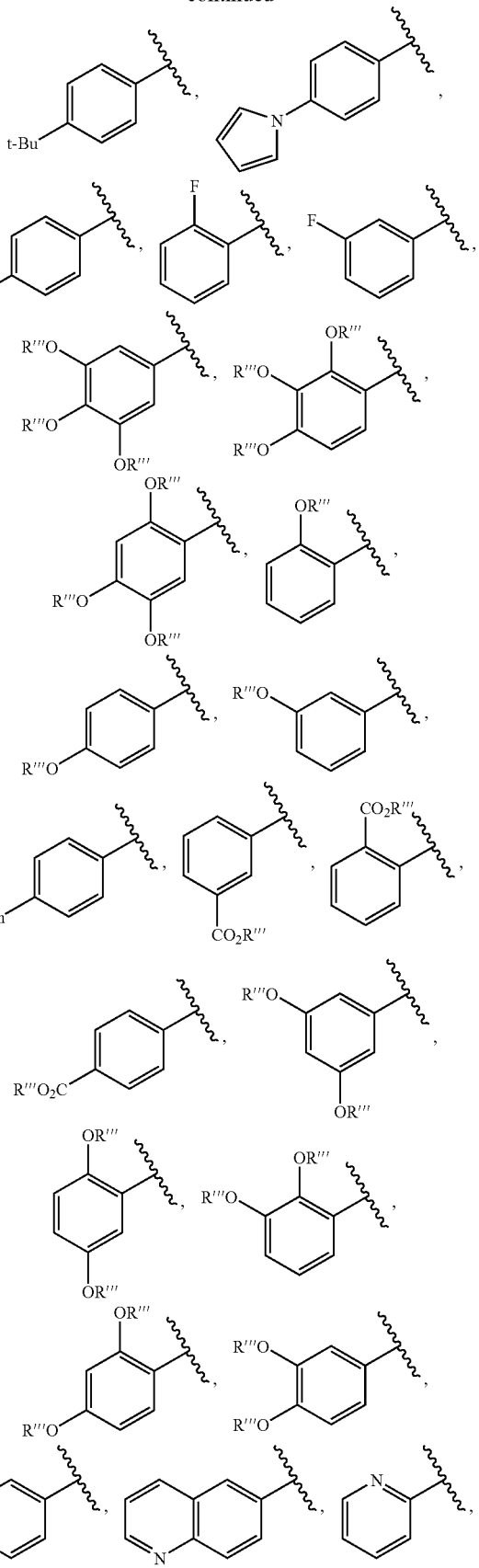

-continued

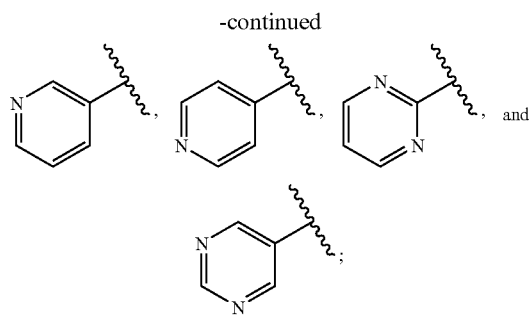

and R''' is lower alkyl.

In certain embodiments, the present invention relates to any one of the above-mentioned methods, wherein Z is selected from the group consisting of:

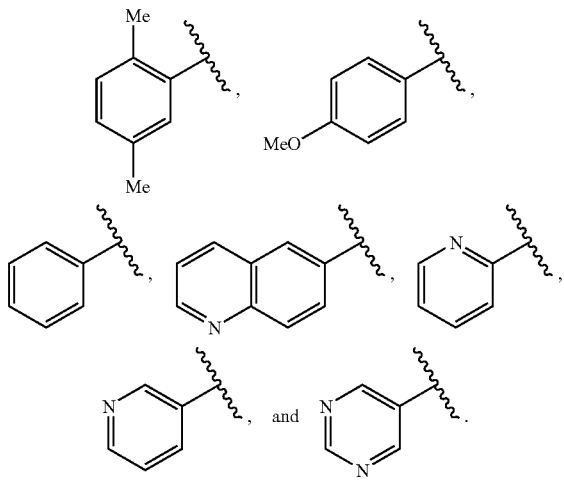

In certain embodiments, the present invention relates to any one of the above-mentioned methods, wherein Z is selected from the group consisting of:

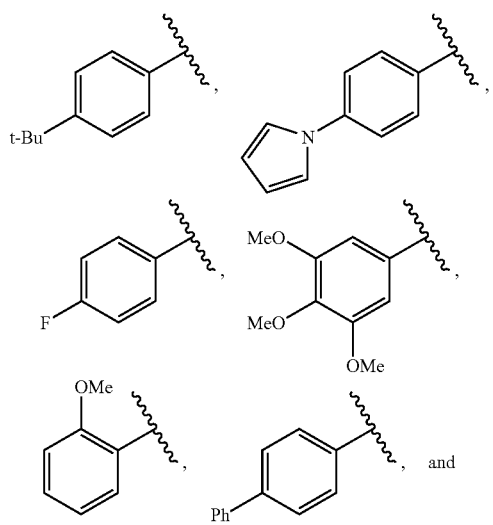

-continued

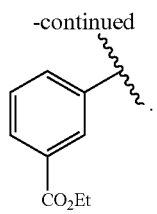

In certain embodiments, the present invention relates to any one of the above-mentioned methods, wherein Z is selected from the group consisting of:

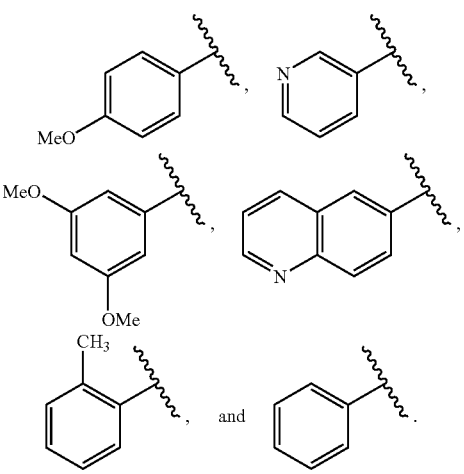

In certain embodiments, the present invention relates to any one of the above-mentioned methods, wherein X is $OS(O)_2CH_3$, $OS(O)_2CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is $OS(O)_2CH_3$, $OS(O)_2CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, Cl, Br, or I; Z is selected from the group consisting of:

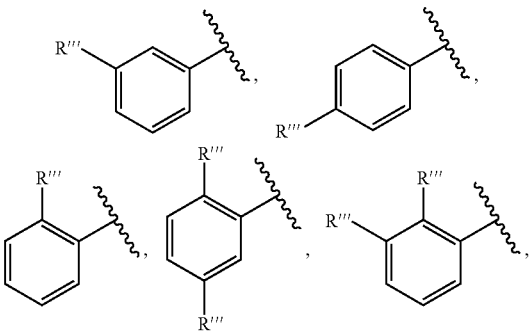

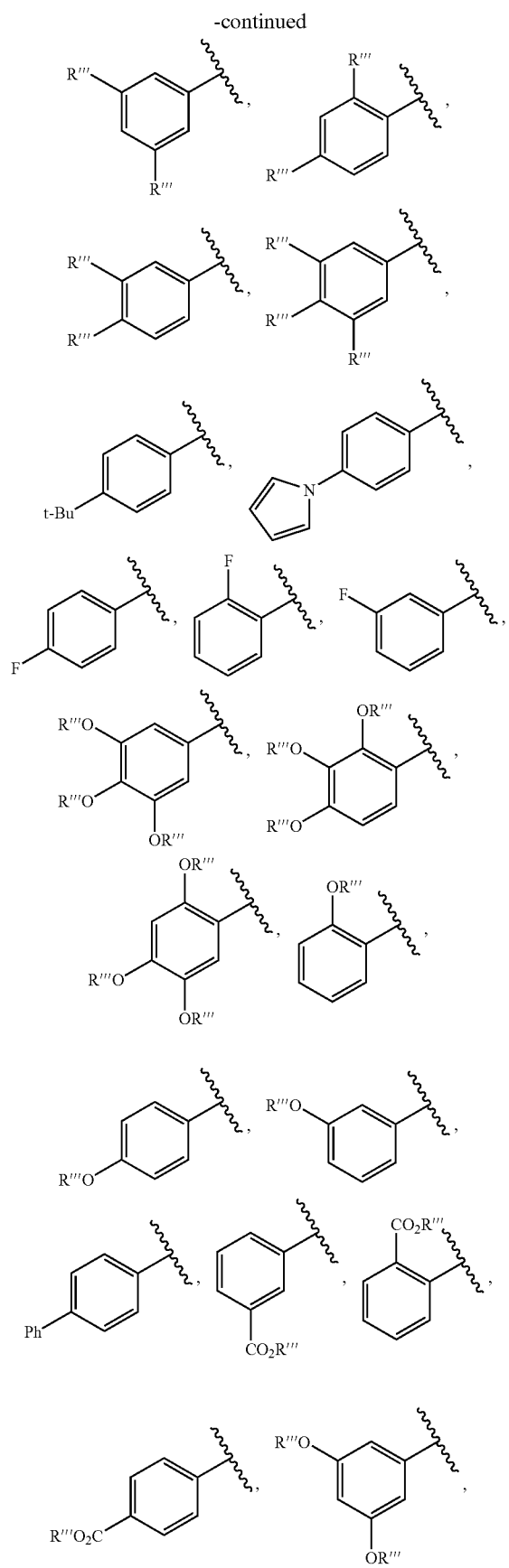
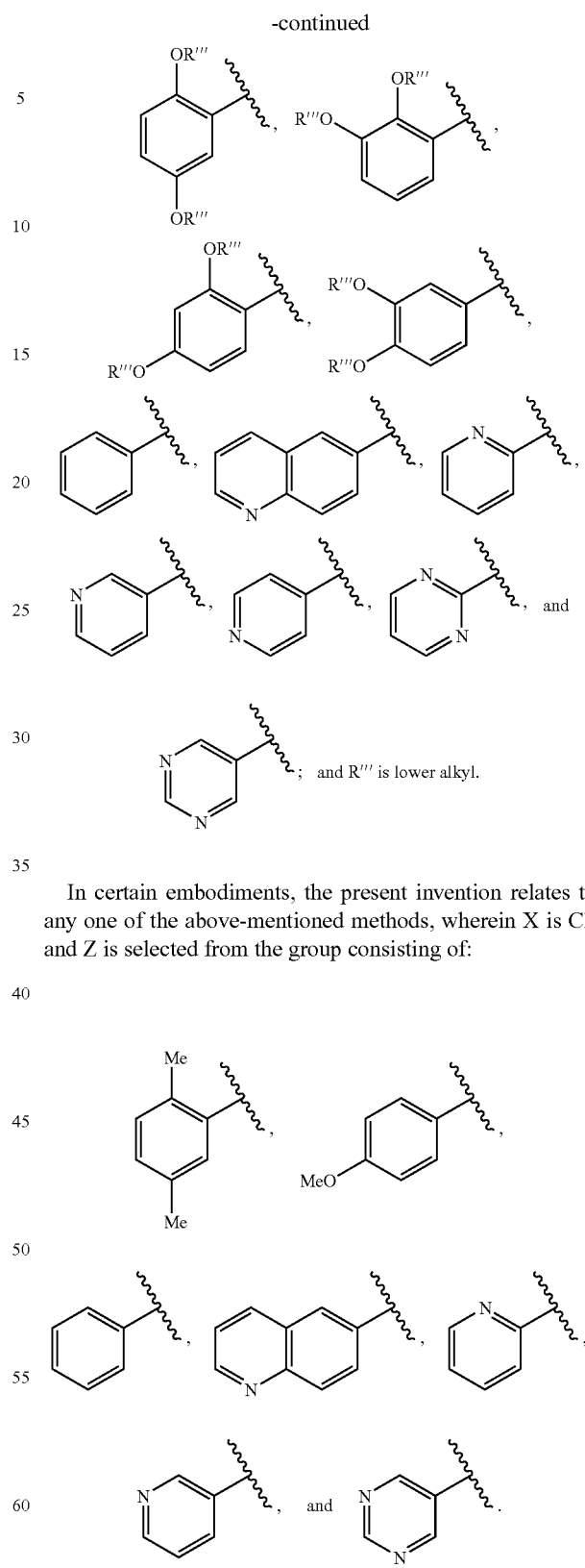
; and R′″ is lower alkyl.
In certain embodiments, the present invention relates to any one of the above-mentioned methods, wherein X is Cl; and Z is selected from the group consisting of:
In certain embodiments, the present invention relates to any one of the above-mentioned methods, wherein X is OS(O)$_2$CH$_3$; and Z is selected from the group consisting of:

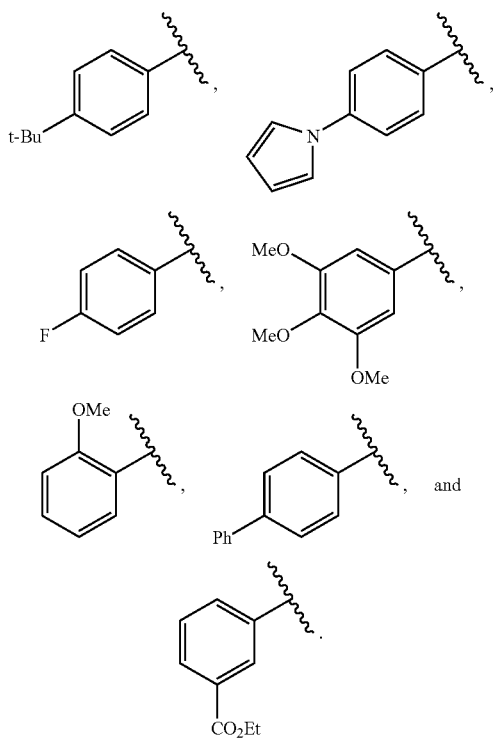

In certain embodiments, the present invention relates to any one of the above-mentioned methods, wherein X is Cl; and Z is selected from the group consisting of:

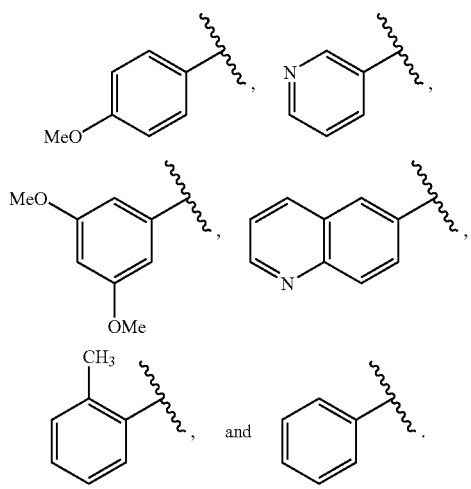

In certain embodiments, the present invention relates to any one of the above-mentioned methods, wherein R' and R" are selected, independently for each occurrence, from the group consisting of hydrogen, alkyl, heteroalkyl, aryl, heteroaryl, aralkyl, heteroaralkyl, alkoxyl, amino, aminoalkyl, heterocyclylalkyl, trialkylsilyl, and triarylsilyl.

In certain embodiments, the present invention relates to any one of the above-mentioned methods, wherein R' is selected from the group consisting of:

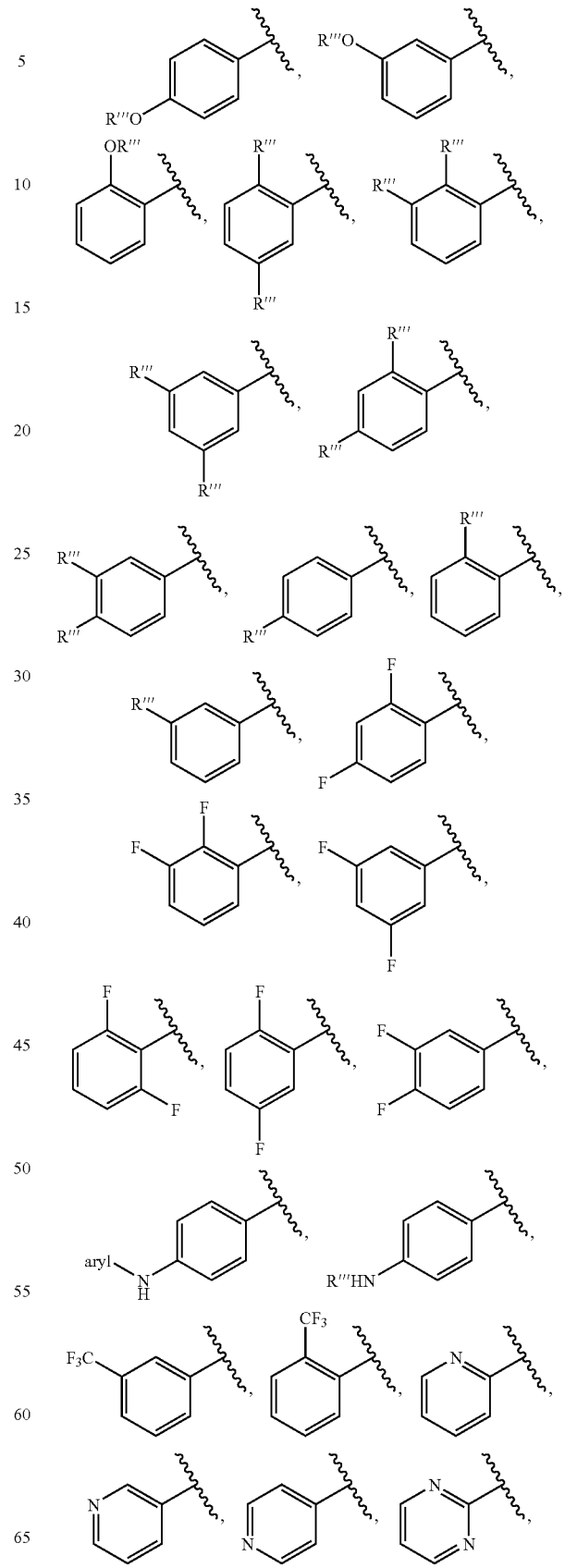

-continued

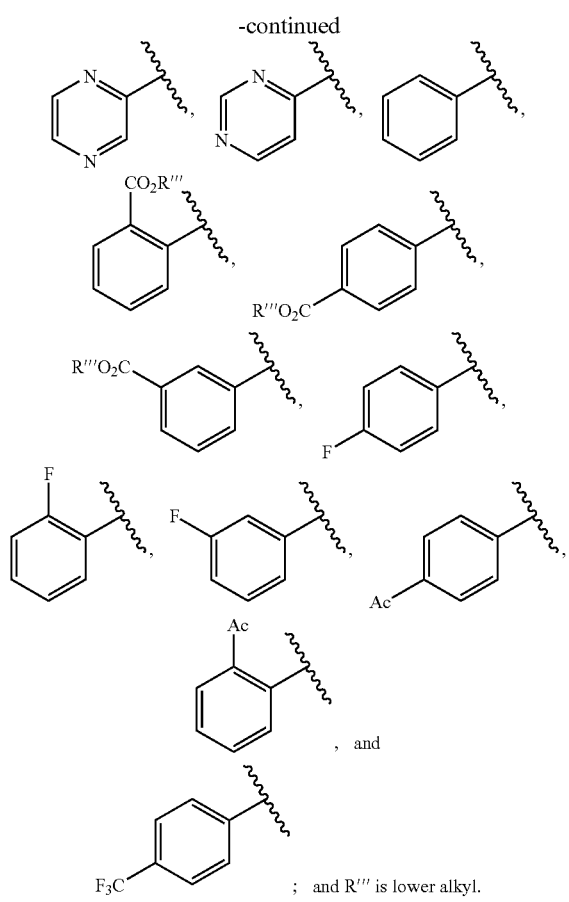

; and R''' is lower alkyl.

In certain embodiments, the present invention relates to any one of the above-mentioned methods, wherein R' is selected from the group consisting of:

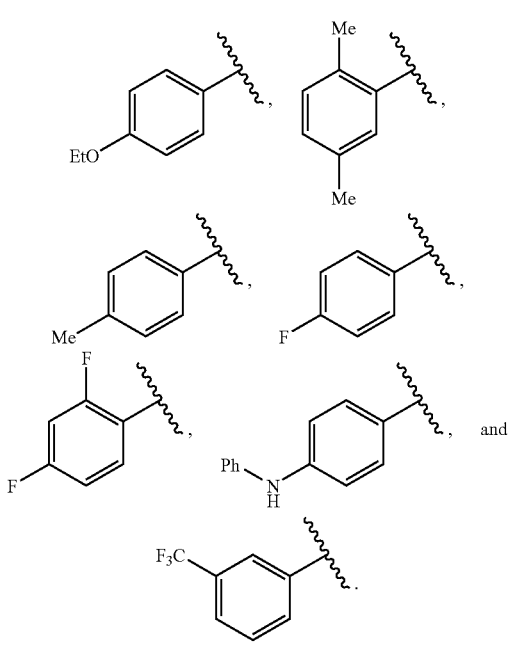

In certain embodiments, the present invention relates to any one of the above-mentioned methods, wherein R' is selected from the group consisting of:

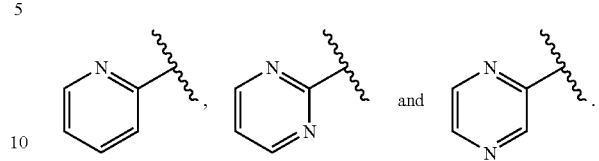

In certain embodiments, the present invention relates to any one of the above-mentioned methods, wherein R' is selected from the group consisting of:

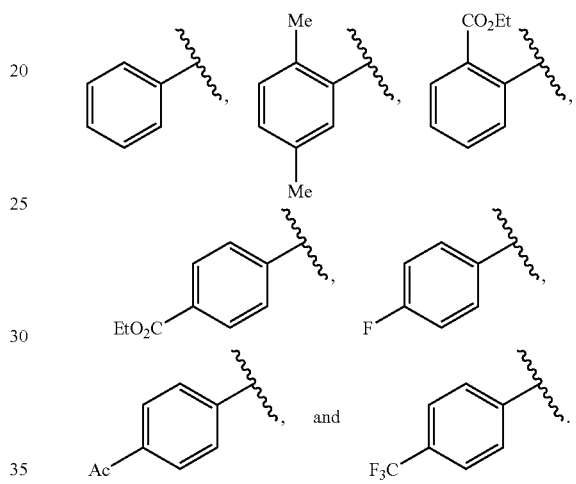

In certain embodiments, the present invention relates to any one of the above-mentioned methods, wherein R' is alkyl, aralkyl, aminoalkyl, or heterocyclylalkyl.

In certain embodiments, the present invention relates to any one of the above-mentioned methods, wherein R' is selected from the group consisting of methyl, ethyl, propyl, butyl, pentyl, hexyl, heptyl, octyl, and benzyl.

In certain embodiments, the present invention relates to any one of the above-mentioned methods, wherein R' is selected from the group consisting of

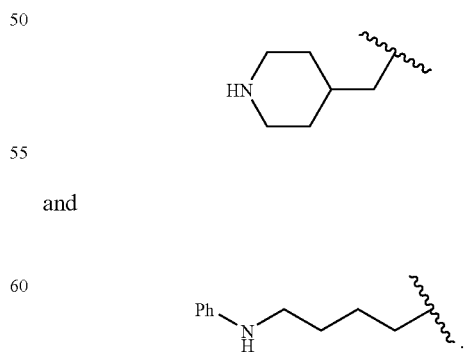

In certain embodiments, the present invention relates to any one of the above-mentioned methods, wherein R' is methyl.

In certain embodiments, the present invention relates to any one of the above-mentioned methods, wherein R' is hexyl.

In certain embodiments, the present invention relates to any one of the above-mentioned methods, wherein R' is benzyl.

In certain embodiments, the present invention relates to any one of the above-mentioned methods, wherein R' is selected from the group consisting of:

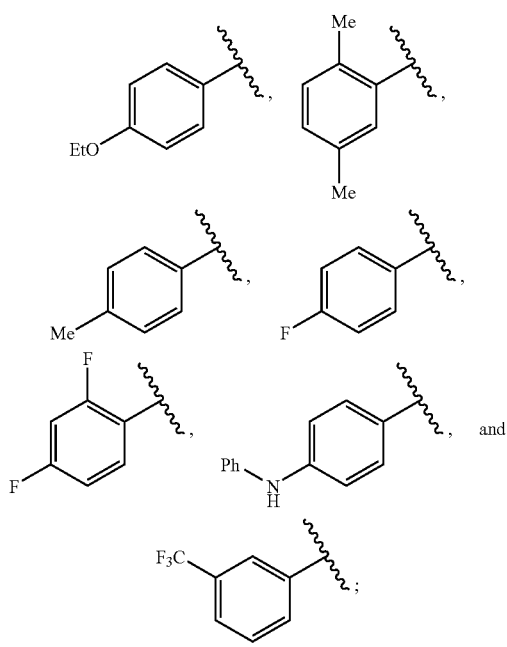

R" is hydrogen; and p is 0.

In certain embodiments, the present invention relates to any one of the above-mentioned methods, wherein R' is selected from the group consisting of:

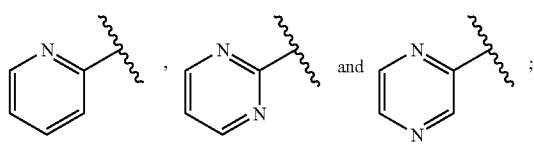

R" is hydrogen; and p is 0.

In certain embodiments, the present invention relates to any one of the above-mentioned methods, wherein R' is selected from the group consisting of:

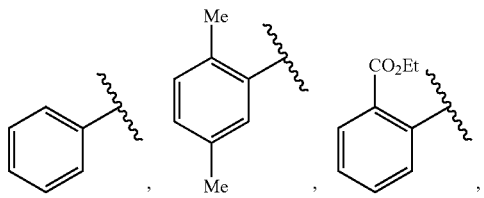

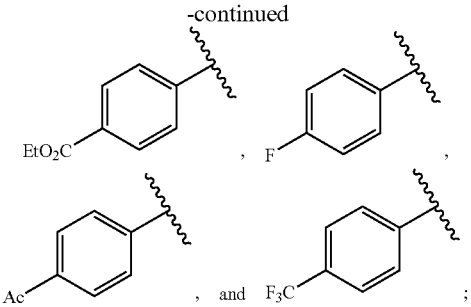

R" is hydrogen; and p is 0.

In certain embodiments, the present invention relates to any one of the above-mentioned methods, wherein R' is alkyl, aralkyl, aminoalkyl, or heterocyclylalkyl; R" is hydrogen; and p is 0.

In certain embodiments, the present invention relates to any one of the above-mentioned methods, wherein R' is selected from the group consisting of methyl, ethyl, propyl, butyl, pentyl, hexyl, heptyl, octyl, and benzyl; R" is hydrogen; and p is 0.

In certain embodiments, the present invention relates to any one of the above-mentioned methods, wherein R' is selected from the group consisting of

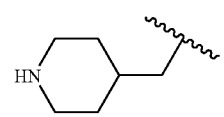

and

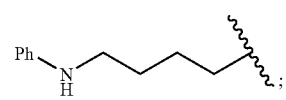

R" is hydrogen; and p is 0.

In certain embodiments, the present invention relates to any one of the above-mentioned methods, wherein R' is methyl; R" is hydrogen; and p is 0.

In certain embodiments, the present invention relates to any one of the above-mentioned methods, wherein R' is hexyl; R" is hydrogen; and p is 0.

In certain embodiments, the present invention relates to any one of the above-mentioned methods, wherein R' is benzyl; R" is hydrogen; and p is 0.

In certain embodiments, the present invention relates to any one of the above-mentioned methods, wherein R' is hydrogen.

In certain embodiments, the present invention relates to any one of the above-mentioned methods, wherein R" is selected from the group consisting of unsubstituted and substituted phenyl.

In certain embodiments, the present invention relates to any one of the above-mentioned methods, wherein R" is substituted phenyl.

In certain embodiments, the present invention relates to any one of the above-mentioned methods, wherein R" is lower alkyl or aryl.

In certain embodiments, the present invention relates to any one of the above-mentioned methods, wherein R" is methyl.

In certain embodiments, the present invention relates to any one of the above-mentioned methods, wherein R" is phenyl.

In certain embodiments, the present invention relates to any one of the above-mentioned methods, wherein R' and R", taken together, form an optionally substituted ring consisting of 3-10 backbone atoms inclusive, said ring optionally comprising one, two or three heteroatoms in addition to the nitrogen to which the R' and R" are bonded.

In certain embodiments, the present invention relates to any one of the above-mentioned methods, wherein R' and $(C=O)_pR"$, taken together, form an five-membered ring, inclusive of the nitrogen to which the R' and $(C=O)_pR"$ are bonded; and p is 1.

In certain embodiments, the present invention relates to any one of the above-mentioned methods, wherein R' and $(C=O)_pR"$, taken together, are $-(C=O)_pCH_2CH_2CH_2-$; and p is 1.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, $K_2CO_3$ or $K_3PO_4$.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is from about 30 minutes to about 2 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is $Bu_2O$, dioxane, or t-BuOH.

In one embodiment, the present invention relates to a method represented by Scheme 1:

Scheme 1

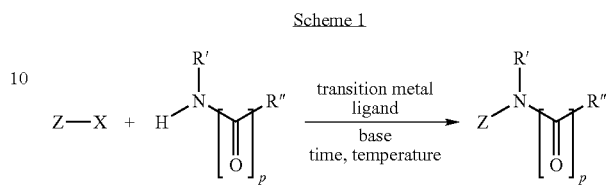

wherein, independently for each occurrence,
Z is selected from the group consisting of:

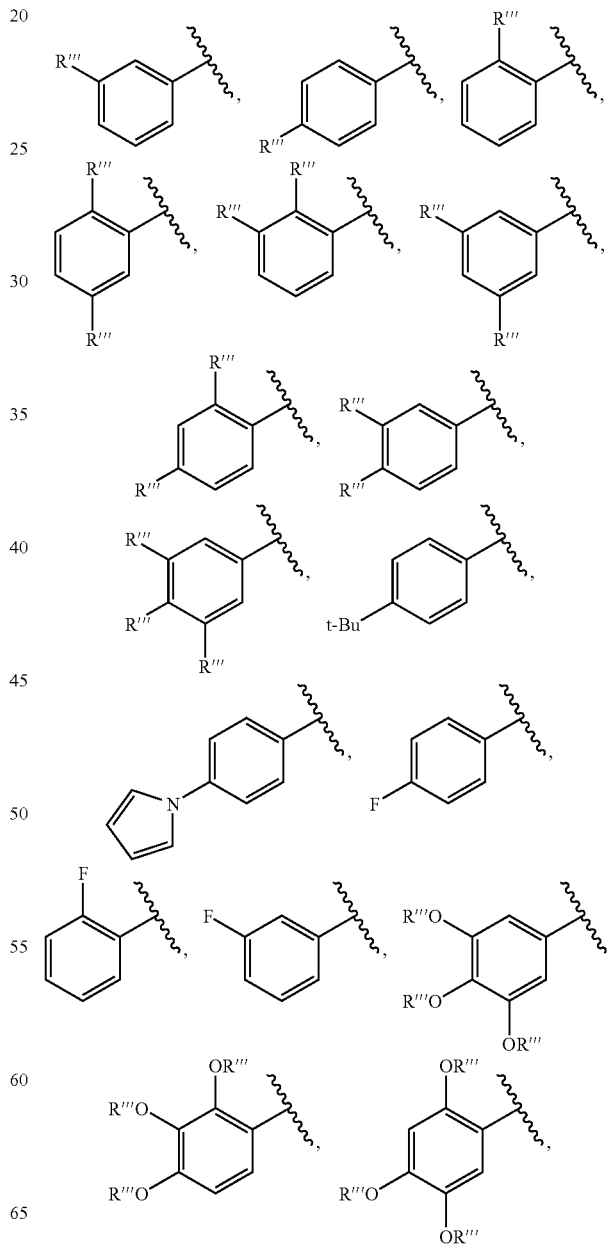

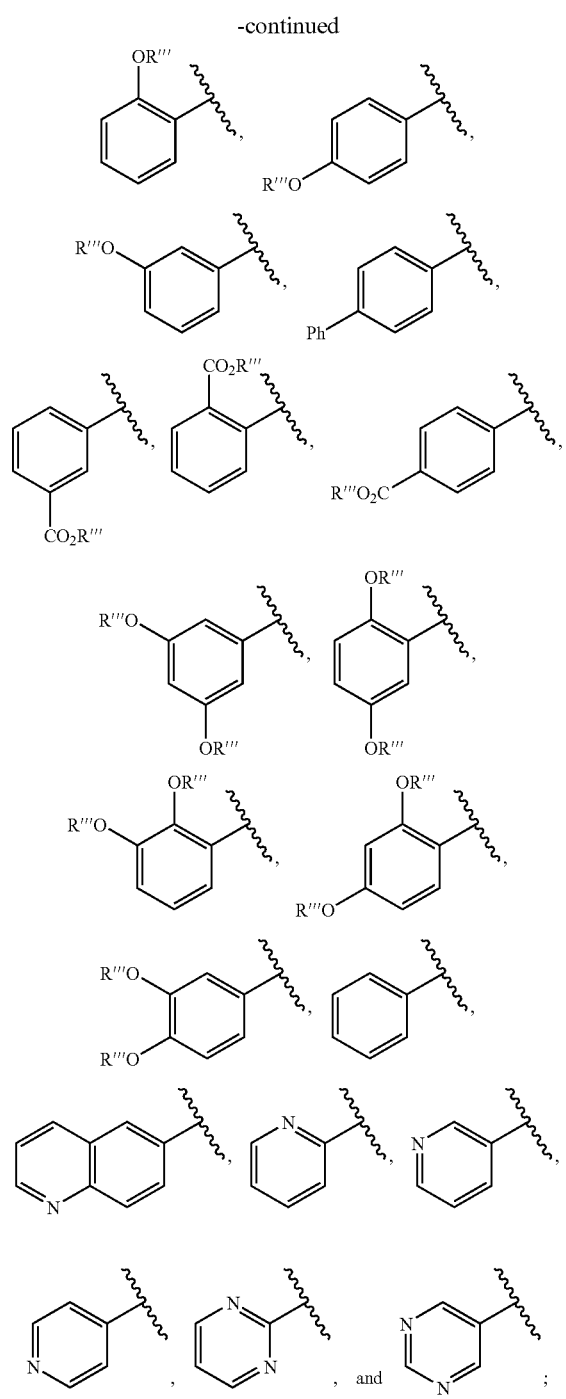
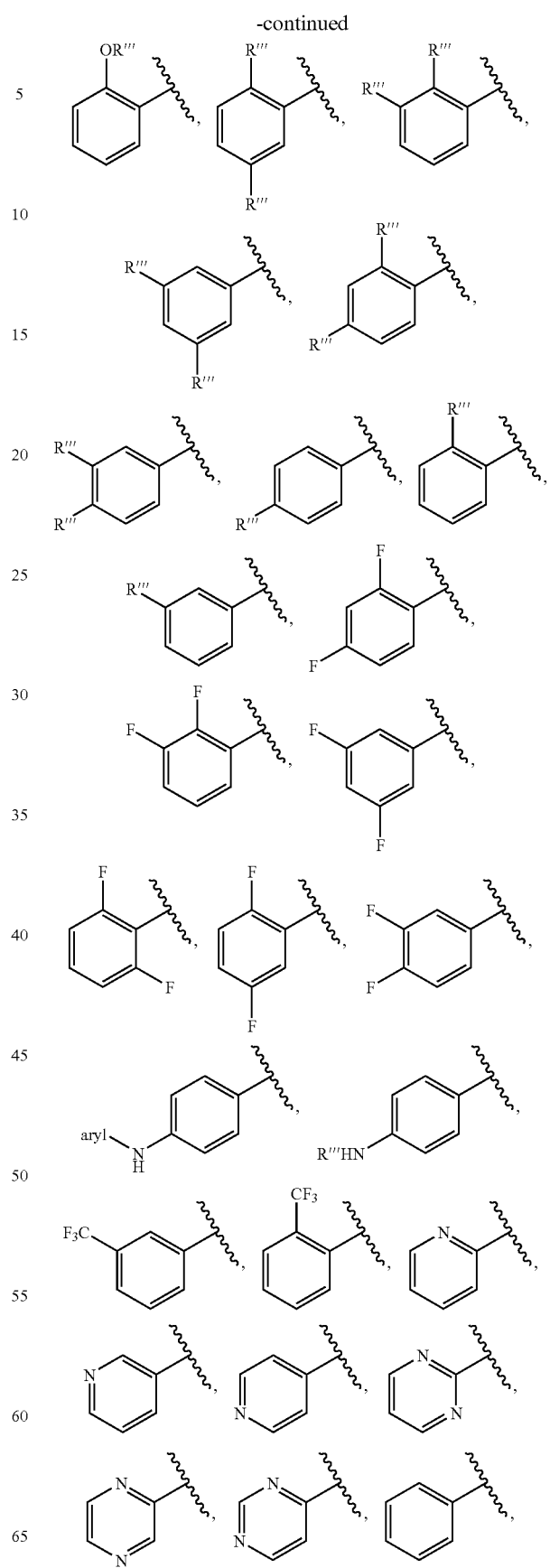
X is selected from the group consisting of $OS(O)_2CH_3$, $OS(O)_2CF_3$, Cl, Br, and I;
R' and R" are selected from the group consisting of:
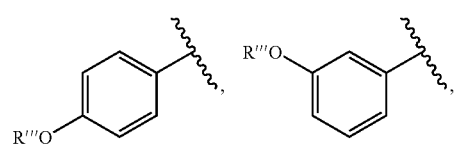

-continued

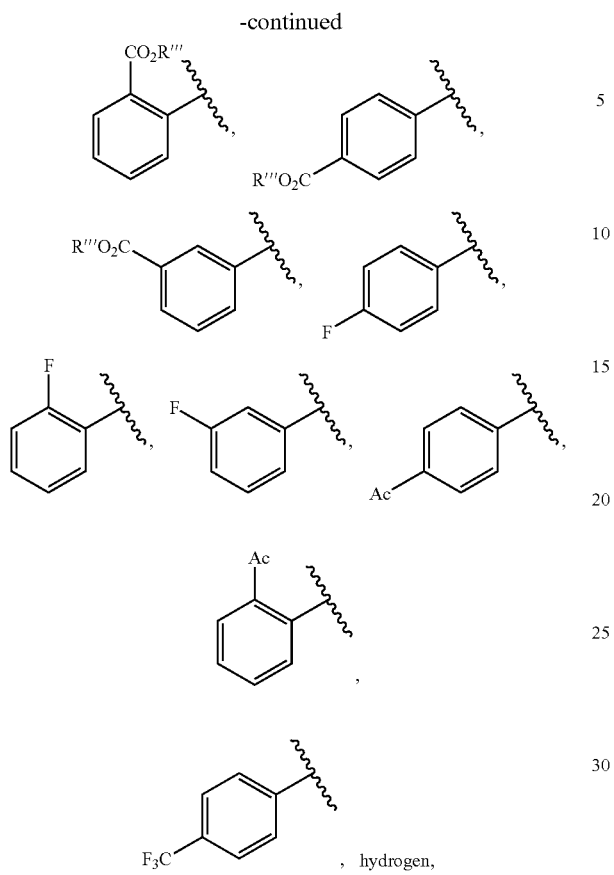

, hydrogen, alkyl, aralkyl, aminoalkyl, and heterocyclylalkyl; or R' and (C=O)$_p$R", taken together, form an optionally substituted ring consisting of 5-7 backbone atoms inclusive, said ring optionally comprising one, two or three heteroatoms in addition to the nitrogen to which the R' and (C=O)$_p$R" are bonded;

R''' is lower alkyl;

R' may be covalently linked to Z;

R" may be covalently linked to Z;

p is 0 or 1;

the transition metal is Pd or Pt;

the base is selected from the group consisting of hydroxides, carbonates, phosphates, and alkoxides; and the ligand is any one of the above-mentioned biphenyl-based ligands.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of:

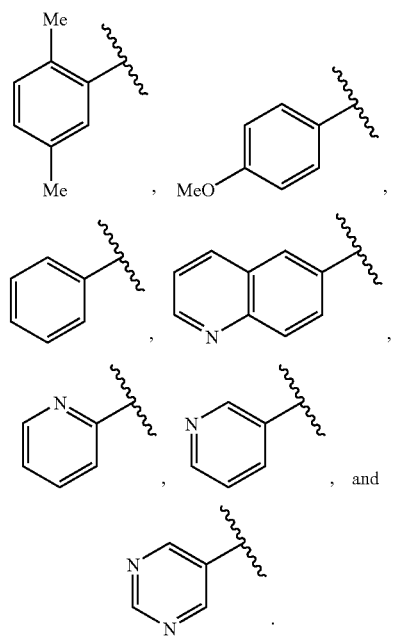

In certain embodiments, the present invention relates to any one of the above-mentioned methods, wherein Z is selected from the group consisting of:

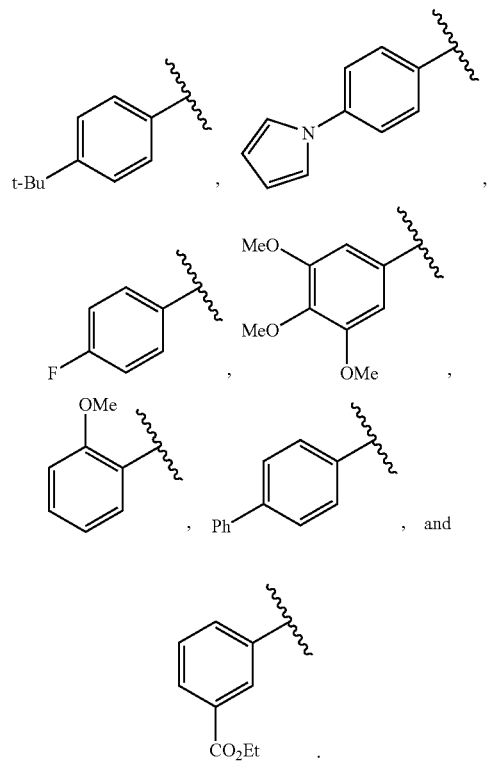

In certain embodiments, the present invention relates to any one of the above-mentioned methods, wherein Z is selected from the group consisting of:

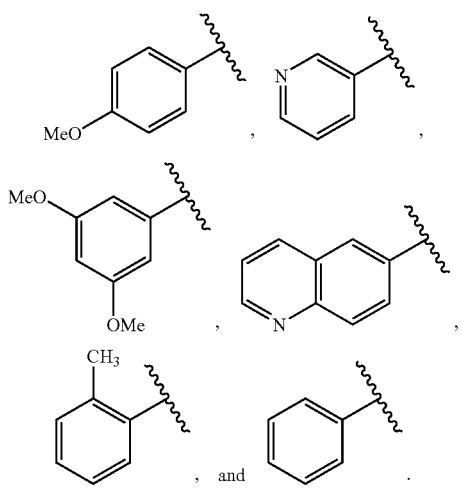

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is Cl; and Z is selected from the group consisting of:

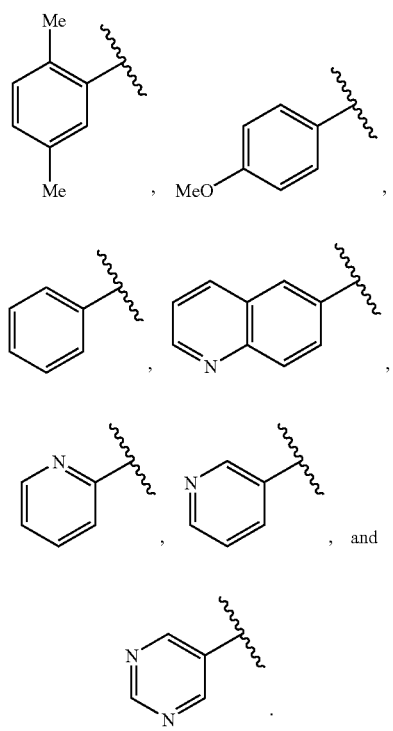

In certain embodiments, the present invention relates to any one of the above-mentioned methods, wherein X is $OS(O)_2CH_3$; and Z is selected from the group consisting of:

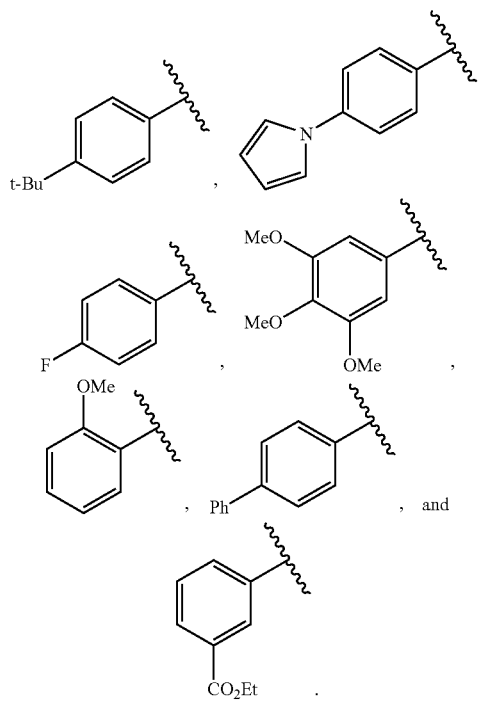

In certain embodiments, the present invention relates to any one of the above-mentioned methods, wherein X is Cl; and Z is selected from the group consisting of:

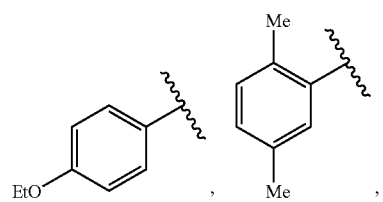

In certain embodiments, the present invention relates to any one of the above-mentioned methods, wherein R' is selected from the group consisting of:

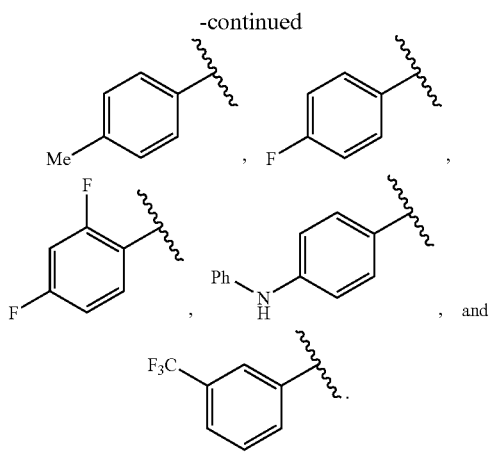

In certain embodiments, the present invention relates to any one of the above-mentioned methods, wherein R' is selected from the group consisting of:

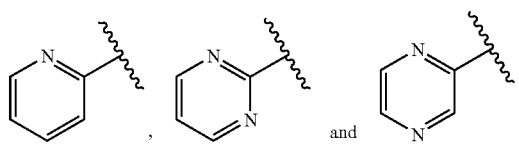

In certain embodiments, the present invention relates to any one of the above-mentioned methods, wherein R' is selected from the group consisting of:

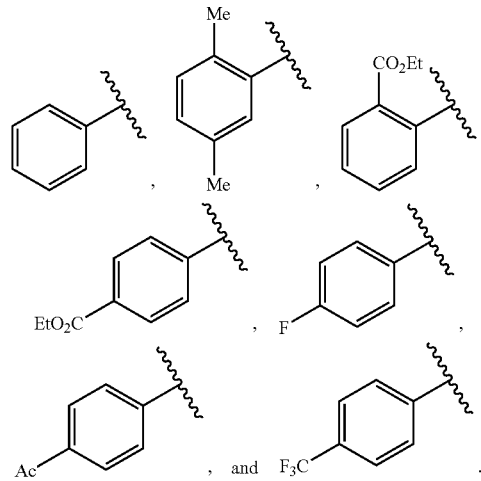

In certain embodiments, the present invention relates to any one of the above-mentioned methods, wherein R' is alkyl, aralkyl, aminoalkyl, or heterocyclylalkyl.

In certain embodiments, the present invention relates to any one of the above-mentioned methods, wherein R' is selected from the group consisting of methyl, ethyl, propyl, butyl, pentyl, hexyl, heptyl, octyl, and benzyl.

In certain embodiments, the present invention relates to any one of the above-mentioned methods, wherein R' is selected from the group consisting of

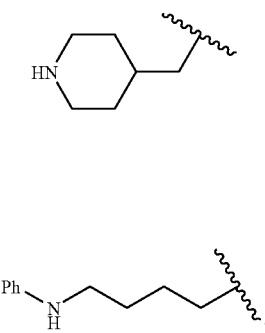

and

In certain embodiments, the present invention relates to any one of the above-mentioned methods, wherein R' is methyl.

In certain embodiments, the present invention relates to any one of the above-mentioned methods, wherein R' is hexyl.

In certain embodiments, the present invention relates to any one of the above-mentioned methods, wherein R' is benzyl.

In certain embodiments, the present invention relates to any one of the above-mentioned methods, wherein R' is selected from the group consisting of:

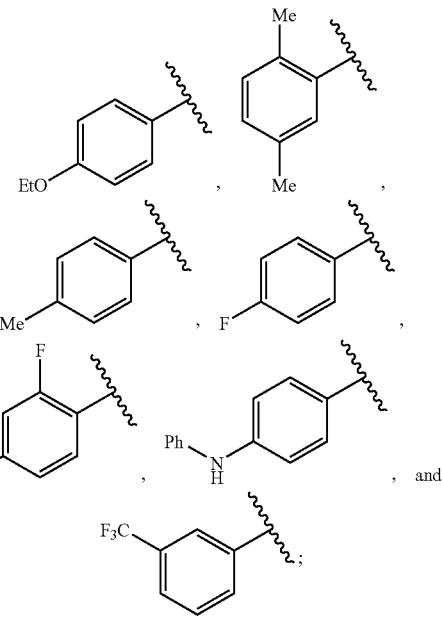

R" is hydrogen; and p is 0.

In certain embodiments, the present invention relates to any one of the above-mentioned methods, wherein R' is selected from the group consisting of:

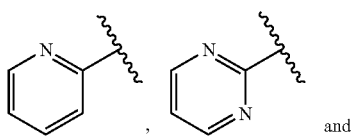

and

-continued

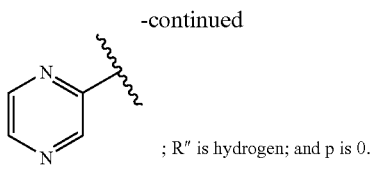

; R″ is hydrogen; and p is 0.

In certain embodiments, the present invention relates to any one of the above-mentioned methods, wherein R' is selected from the group consisting of:

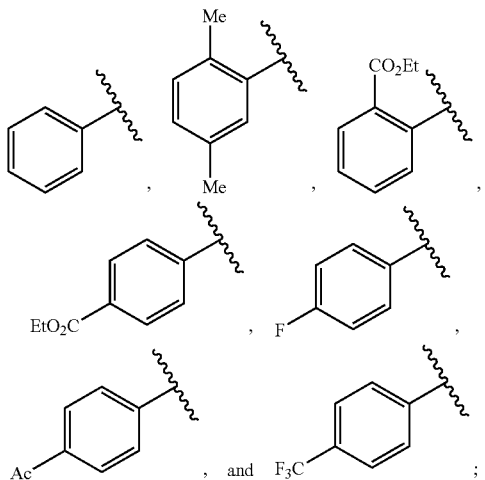

R″ is hydrogen; and p is 0.

In certain embodiments, the present invention relates to any one of the above-mentioned methods, wherein R' is alkyl, aralkyl, aminoalkyl, or heterocyclylalkyl; R″ is hydrogen; and p is 0.

In certain embodiments, the present invention relates to any one of the above-mentioned methods, wherein R' is selected from the group consisting of methyl, ethyl, propyl, butyl, pentyl, hexyl, heptyl, octyl, and benzyl; R″ is hydrogen; and p is 0.

In certain embodiments, the present invention relates to any one of the above-mentioned methods, wherein R' is selected from the group consisting of

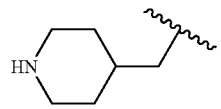

and

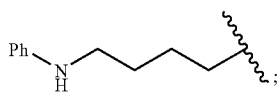

R″ is hydrogen; and p is 0.

In certain embodiments, the present invention relates to any one of the above-mentioned methods, wherein R' is methyl; R″ is hydrogen; and p is 0.

In certain embodiments, the present invention relates to any one of the above-mentioned methods, wherein R' is hexyl; R″ is hydrogen; and p is 0.

In certain embodiments, the present invention relates to any one of the above-mentioned methods, wherein R' is benzyl; R″ is hydrogen; and p is 0.

In certain embodiments, the present invention relates to any one of the above-mentioned methods, wherein R' is hydrogen.

In certain embodiments, the present invention relates to any one of the above-mentioned methods, wherein R″ is selected from the group consisting of unsubstituted and substituted phenyl.

In certain embodiments, the present invention relates to any one of the above-mentioned methods, wherein R″ is substituted phenyl.

In certain embodiments, the present invention relates to any one of the above-mentioned methods, wherein R″ is lower alkyl or aryl.

In certain embodiments, the present invention relates to any one of the above-mentioned methods, wherein R″ is methyl.

In certain embodiments, the present invention relates to any one of the above-mentioned methods, wherein R″ is phenyl.

In certain embodiments, the present invention relates to any one of the above-mentioned methods, wherein R' and $(C=O)_pR''$, taken together, form an five-membered ring, inclusive of the nitrogen to which the R' and $(C=O)_pR''$ are bonded; and p is 1.

In certain embodiments, the present invention relates to any one of the above-mentioned methods, wherein R' and $(C=O)_pR''$, taken together, are $—(C=O)_pCH_2CH_2CH_2—$; and p is 1.

In certain embodiments, the present invention relates to any one of the above-mentioned methods, wherein the transition metal is palladium.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is NaOt-Bu, $K_2CO_3$ or $K_3PO_4$.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is from about 30 minutes to about 2 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is Bu$_2$O, dioxane, or t-BuOH.

In one embodiment, the present invention relates to a method represented by Scheme 2:

Scheme 2

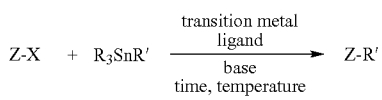

wherein,

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

R represents methyl, ethyl, propyl, butyl, or pentyl;

R' represents allyl, alkenyl, or aryl;

the transition metal is selected from the group consisting of Ni, Pd and Pt;

the base is selected from the group consisting of fluorides, hydrides, hydroxides, carbonates, phosphates, alkoxides, metal amides, and carbanions; and the ligand is any one of the above-mentioned biphenyl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

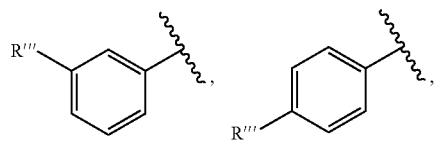

-continued

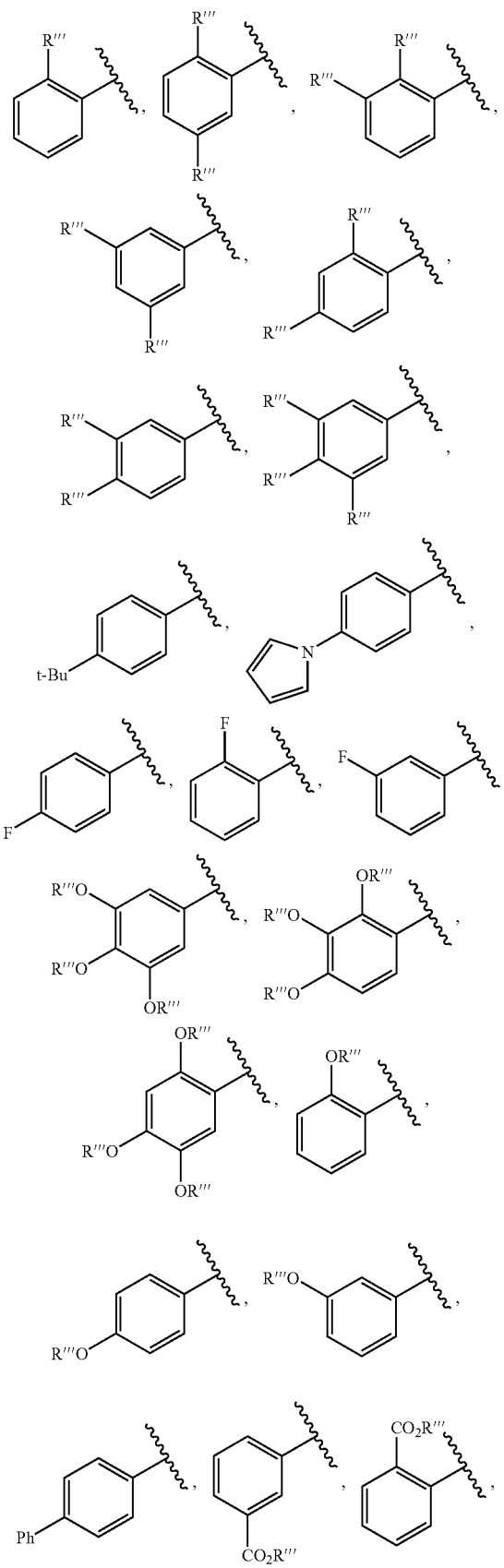

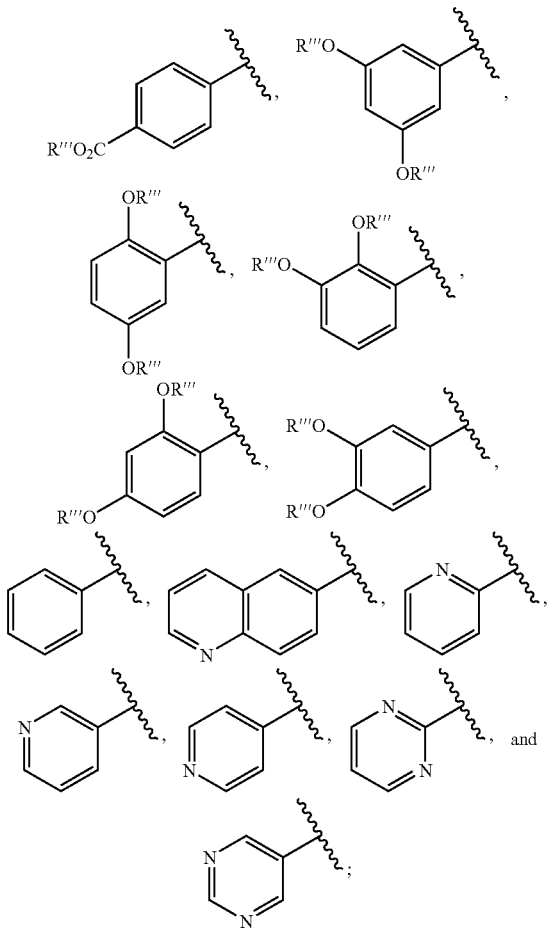

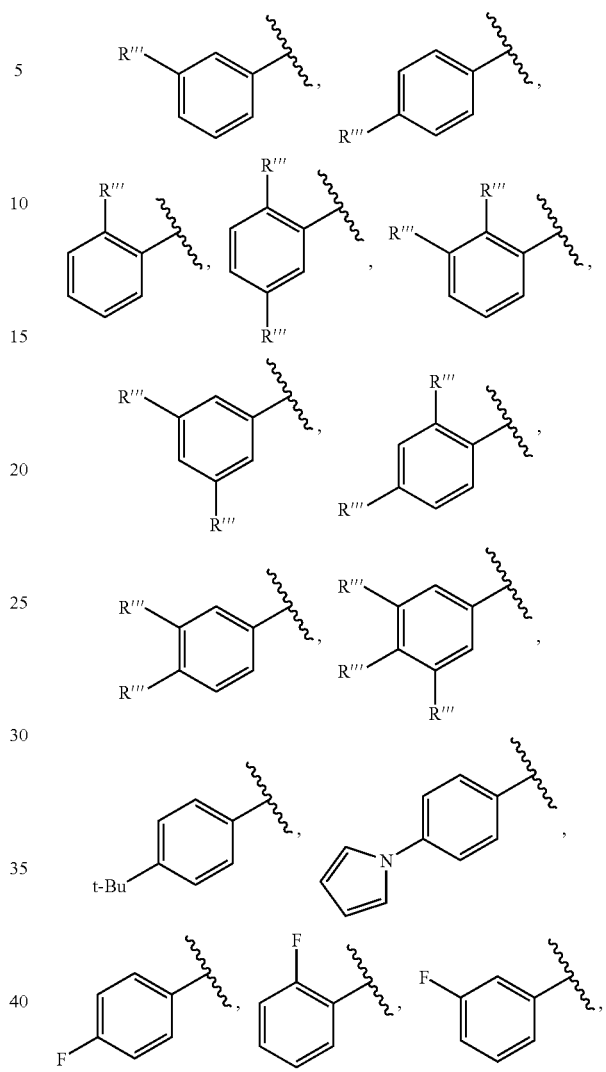

and R''' is lower alkyl.

In certain embodiments, the present invention relates to any one of the above-mentioned methods, wherein Z is

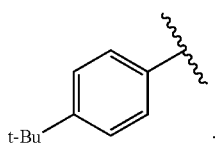

In certain embodiments, the present invention relates to any one of the above-mentioned methods, wherein X is $OS(O)_2CH_3$, $OS(O)_2CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is $OS(O)_2CH_3$, $OS(O)_2CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, Cl, Br, or I; Z is selected from the group consisting of:

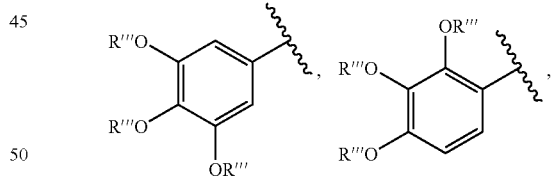

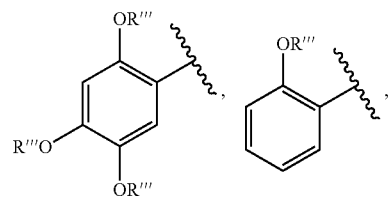

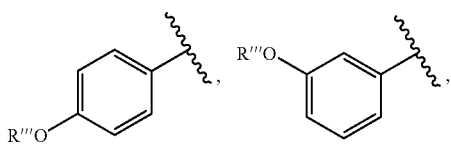

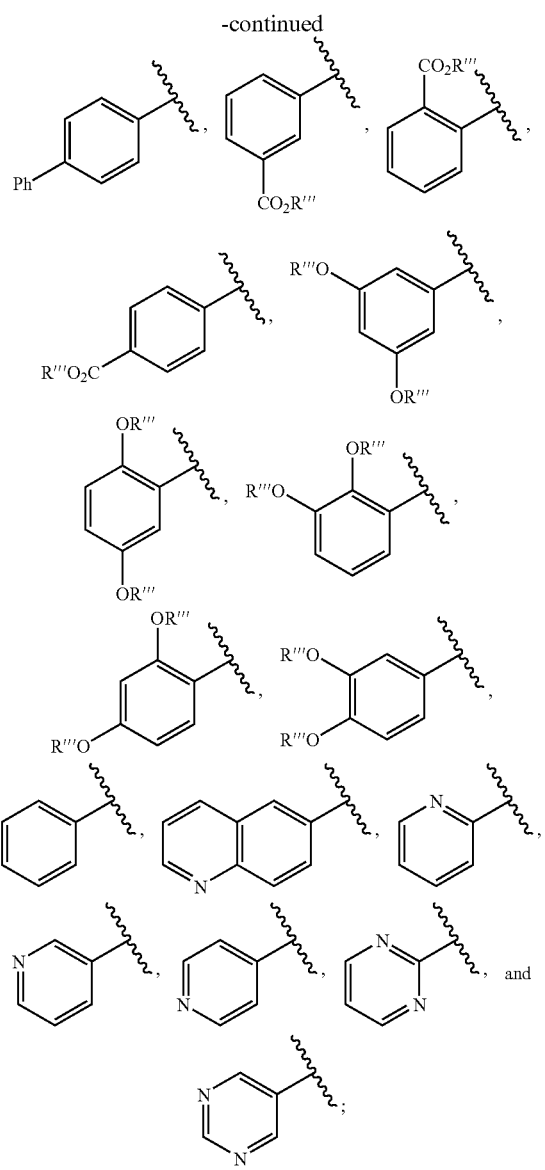

and R''' is lower alkyl.

In certain embodiments, the present invention relates to any one of the above-mentioned methods, wherein X is Cl; and Z is selected from the group consisting of:

In certain embodiments, the present invention relates to any one of the above-mentioned methods, wherein X is OS(O)$_2$CH$_3$; and Z is selected from the group consisting of:

In certain embodiments, the present invention relates to any one of the above-mentioned methods, wherein X is Cl; and Z is selected from the group consisting of:

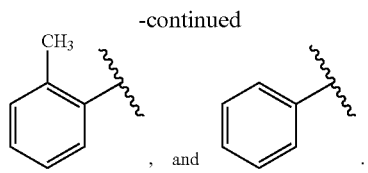
, and

In certain embodiments, the present invention relates to any one of the above-mentioned methods, wherein R is butyl.

In certain embodiments, the present invention relates to any one of the above-mentioned methods, wherein R' is allyl.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, $K_2CO_3$ or $K_3PO_4$.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is from about 30 minutes to about 2 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is $Bu_2O$, dioxane, or t-BuOH.

In certain embodiments, the present invention relates to any one of the above-mentioned methods, further comprising CsF.

In one embodiment, the present invention relates to a method represented by Scheme 3:

Scheme 3

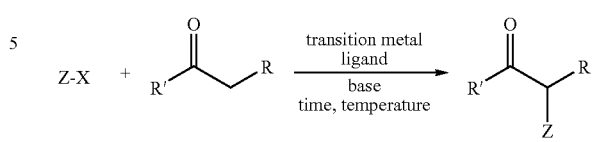

wherein,

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

R represents substituted or unsubstituted aryl, heteroaryl, or t-Bu;

R' represents alkyl, aryl, or heteroaryl;

R and R' may be covalently bonded together;

the transition metal is selected from the group consisting of Ni, Pd and Pt;

the base is selected from the group consisting of fluorides, hydrides, hydroxides, carbonates, phosphates, alkoxides, metal amides, and carbanions; and the ligand is any one of the above-mentioned biphenyl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

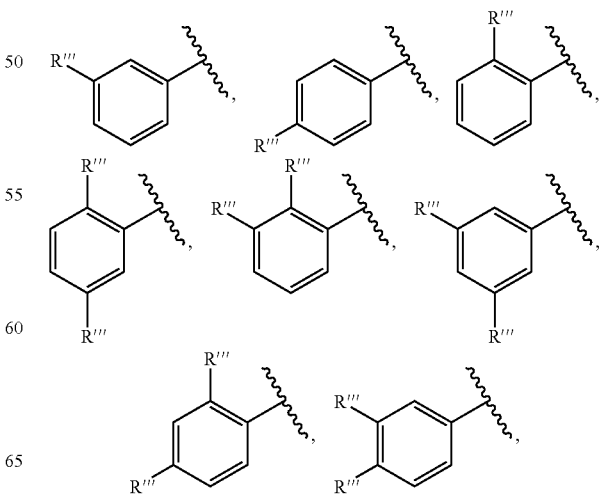

-continued

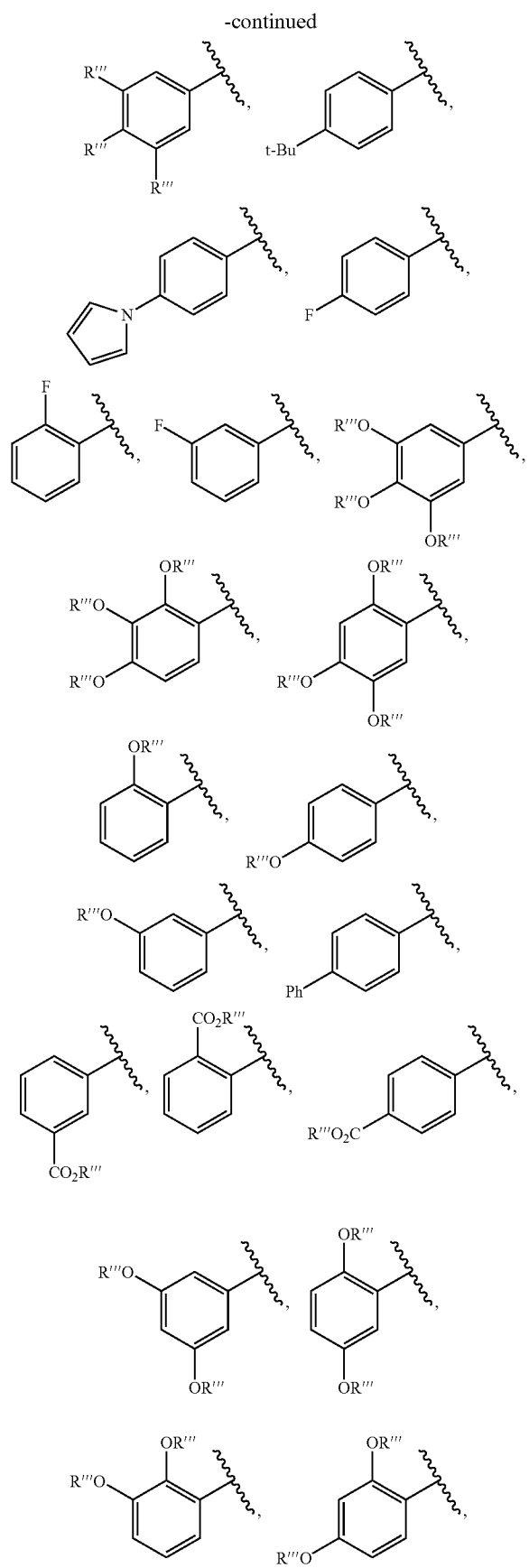

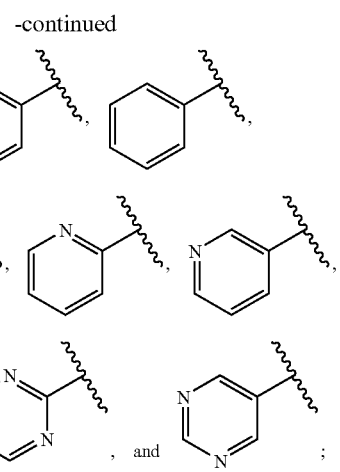

and R'''' is lower alkyl.

In certain embodiments, the present invention relates to any one of the above-mentioned methods, wherein Z is

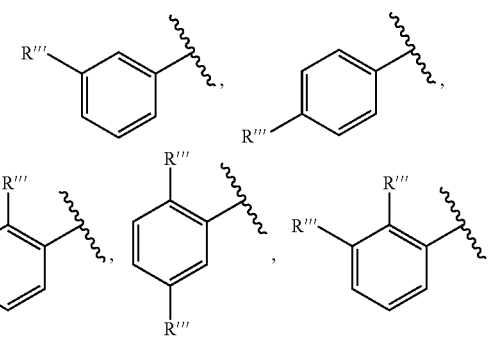

In certain embodiments, the present invention relates to any one of the above-mentioned methods, wherein X is $OS(O)_2CH_3$, $OS(O)_2CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is $OS(O)_2CH_3$, $OS(O)_2CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, Cl, Br, or I; Z is selected from the group consisting of:

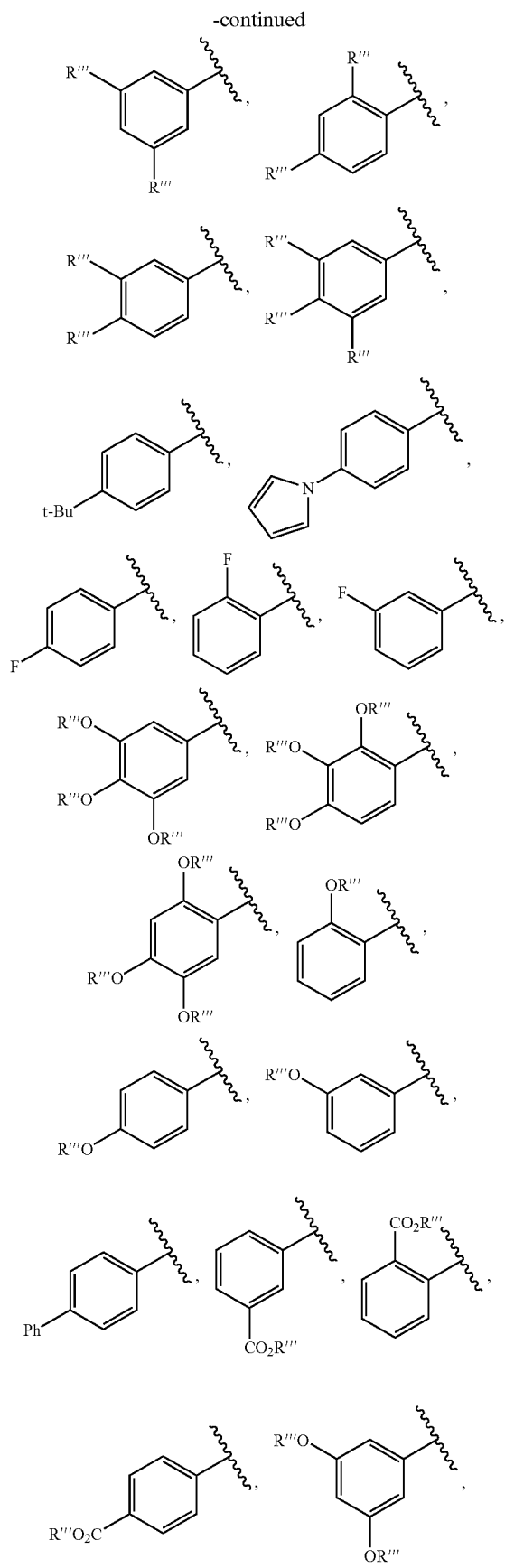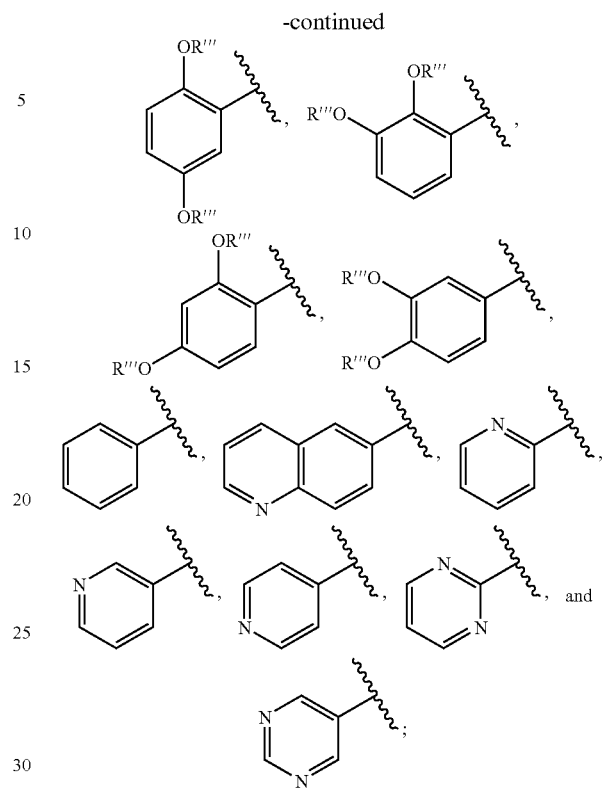
and R''' is lower alkyl.
In certain embodiments, the present invention relates to any one of the above-mentioned methods, wherein X is Cl; and Z is selected from the group consisting of:
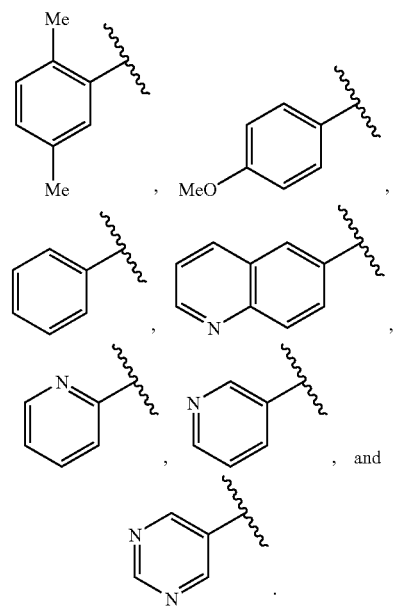
In certain embodiments, the present invention relates to any one of the above-mentioned methods, wherein X is OS(O)$_2$CH$_3$; and Z is selected from the group consisting of:

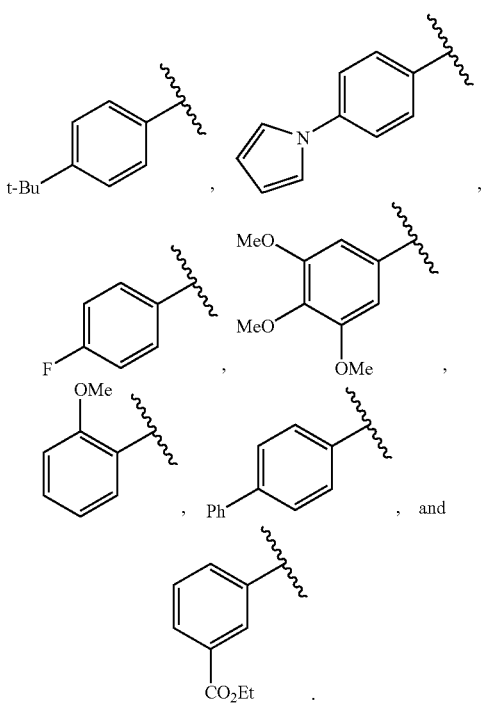

In certain embodiments, the present invention relates to any one of the above-mentioned methods, wherein X is Cl; and Z is selected from the group consisting of:

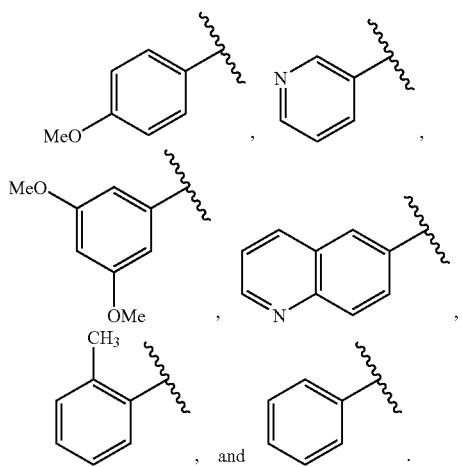

In certain embodiments, the present invention relates to any one of the above-mentioned methods, wherein R' is phenyl.

In certain embodiments, the present invention relates to any one of the above-mentioned methods, wherein R is —CH$_2$—; and R is covalently bonded to R', thereby forming a fused 6,5-ring system.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, Cs$_2$CO$_3$, K$_2$CO$_3$ or K$_3$PO$_4$.

In certain embodiments, the present invention relates to any one of the above-mentioned methods, wherein the period of time is from about 30 minutes to about 24 hours.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is Bu$_2$O, dioxane, or t-BuOH.

In one embodiment, the present invention relates to a method represented by Scheme 4:

Scheme 4

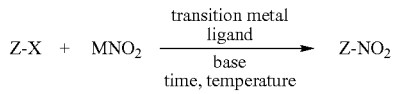

wherein,

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

M represents lithium, sodium, or potassium;

the transition metal is selected from the group consisting of Ni, Pd and Pt;

the base is selected from the group consisting of fluorides, hydrides, hydroxides, carbonates, phosphates, alkoxides, metal amides, and carbanions; and the ligand is any one of the above-mentioned biphenyl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

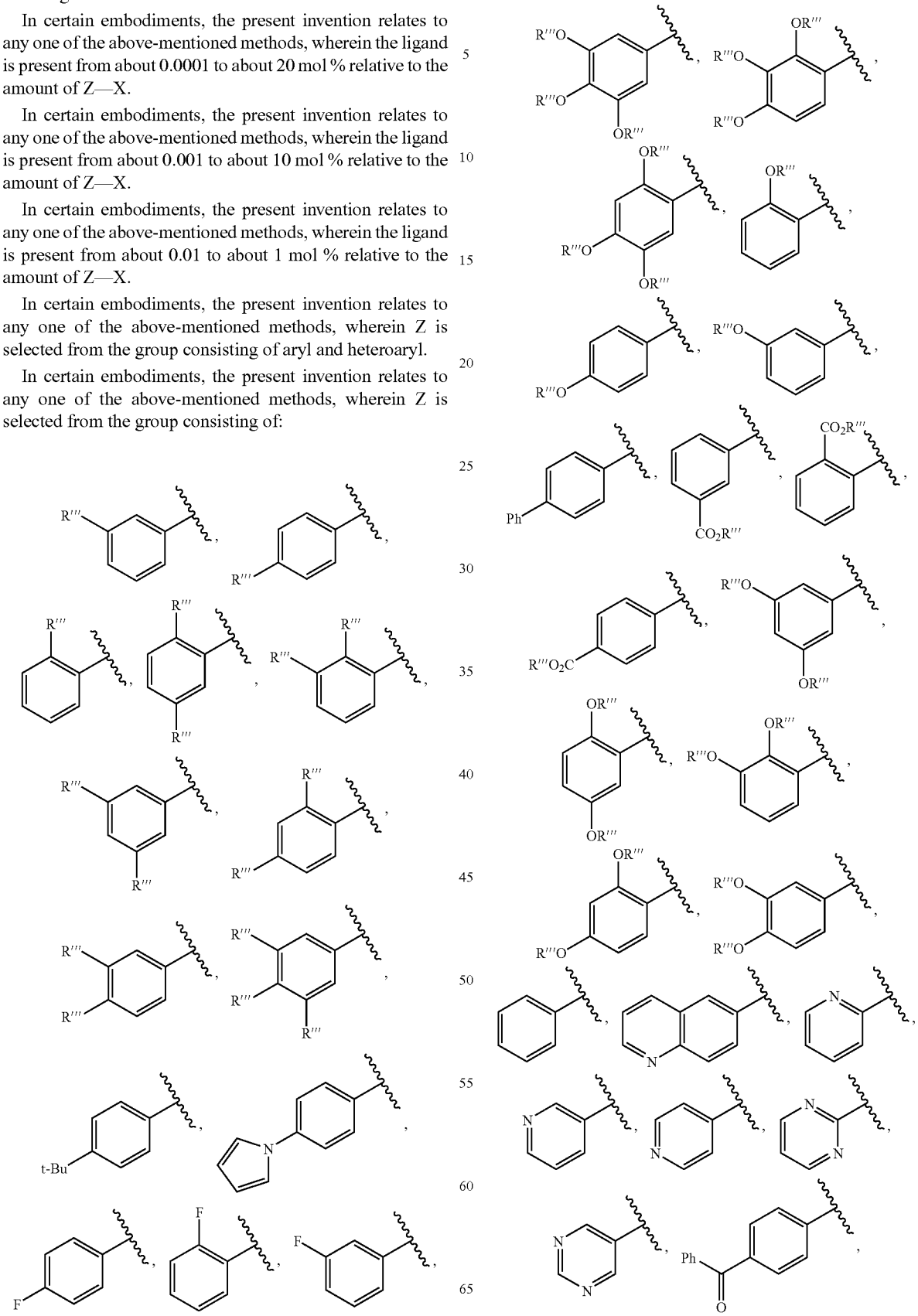

-continued

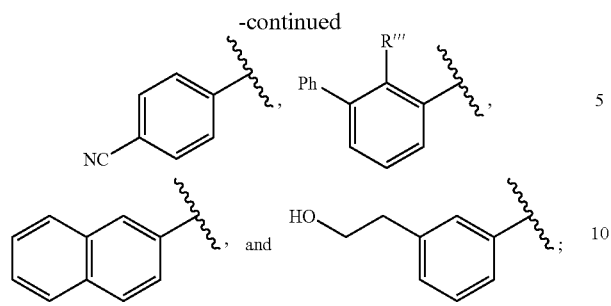

and R'''' is lower alkyl.

In certain embodiments, the present invention relates to any one of the above-mentioned methods, wherein Z is

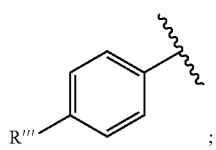

and R'''' is lower alkyl.

In certain embodiments, the present invention relates to any one of the above-mentioned methods, wherein Z is

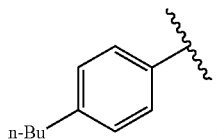

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is, $OS(O)_2(CF_2)_3CF_3$.

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I; Z is selected from the group consisting of:

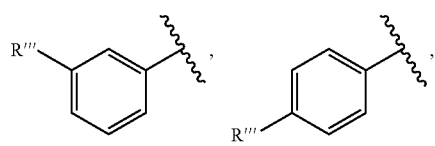

-continued

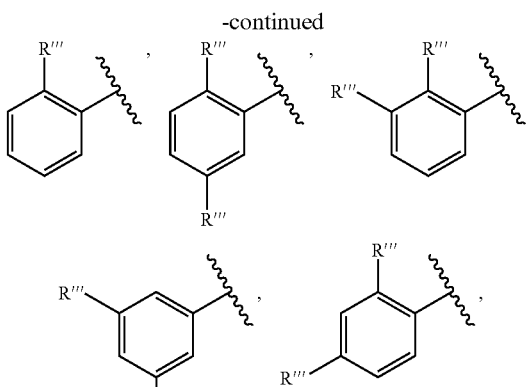

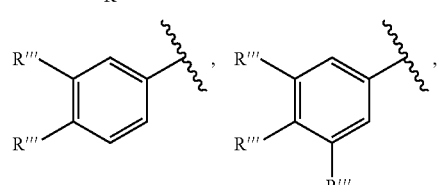

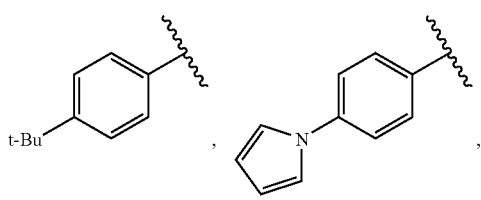

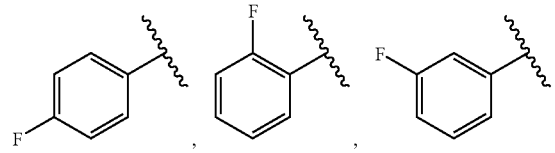

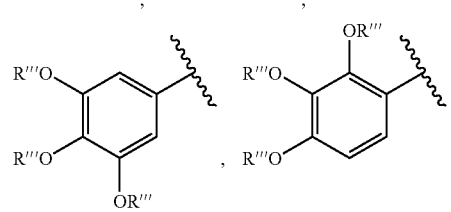

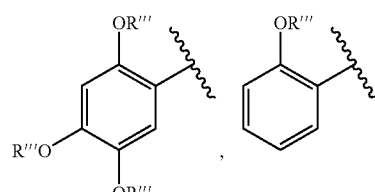

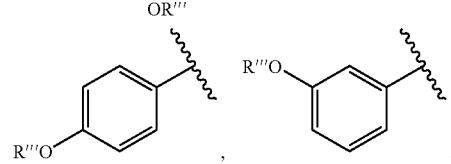

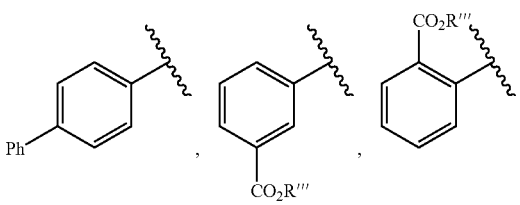

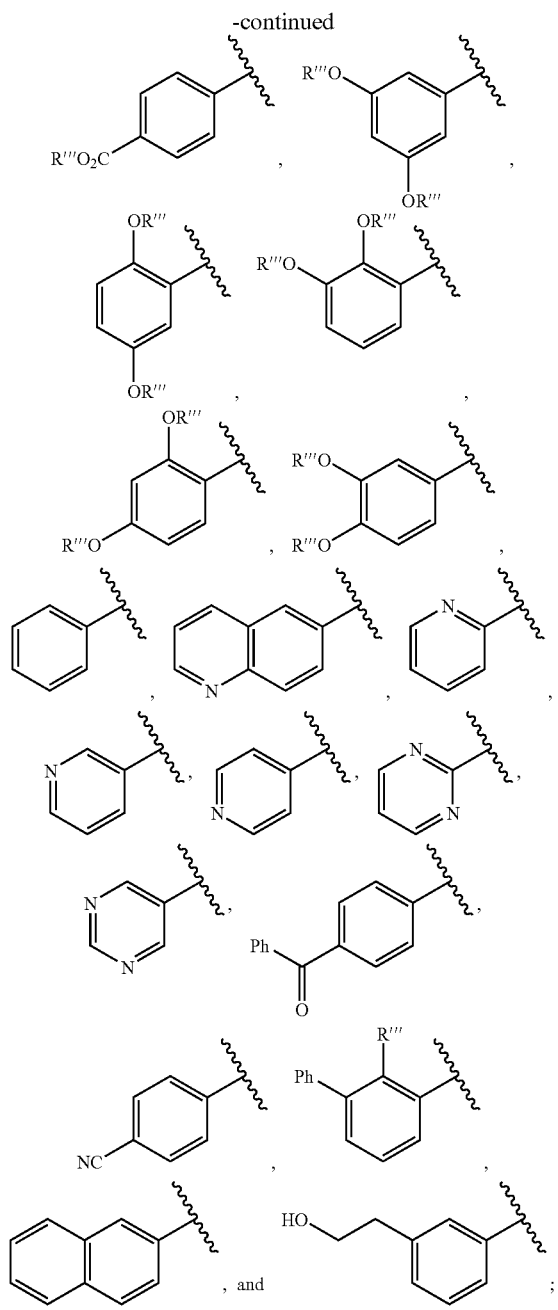

and R''' is lower alkyl.

In certain embodiments, the present invention relates to any one of the above-mentioned methods, wherein X is Cl; and Z is selected from the group consisting of:

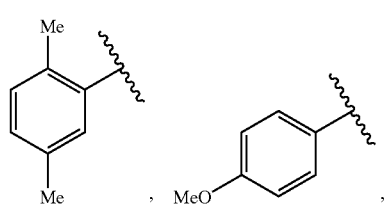

In certain embodiments, the present invention relates to any one of the above-mentioned methods, wherein X is Cl; and Z is selected from the group consisting of:

[structures shown in right column]

In certain embodiments, the present invention relates to any one of the above-mentioned methods, wherein X is $OS(O)_2(CF_2)_3CF_3$; and Z is selected from the group consisting of:

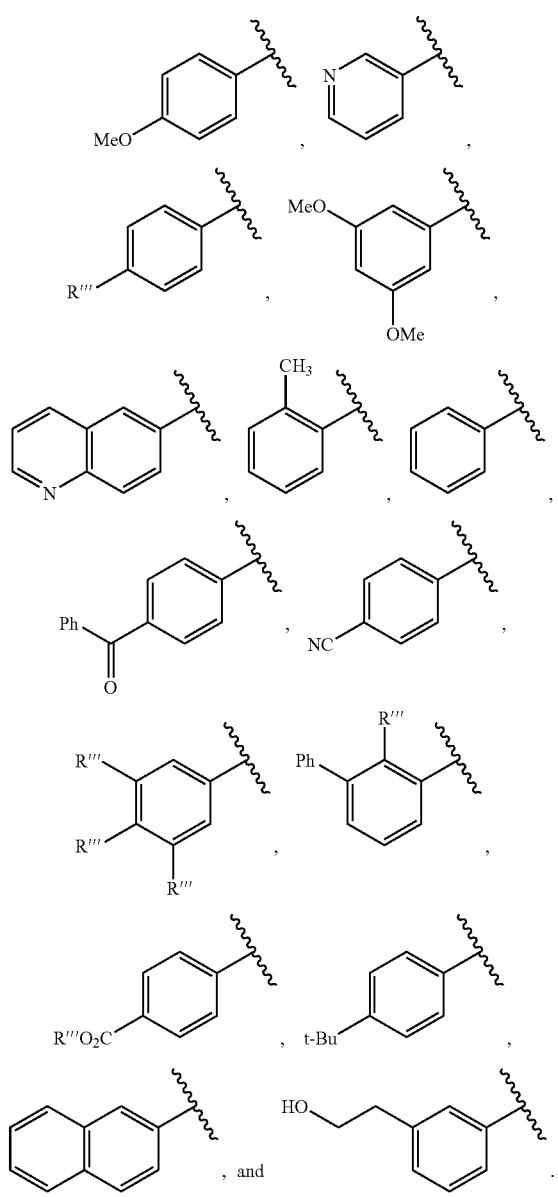

In certain embodiments, the present invention relates to any one of the above-mentioned methods, wherein X is OS(O)$_2$CF$_3$; and Z is selected from the group consisting of:

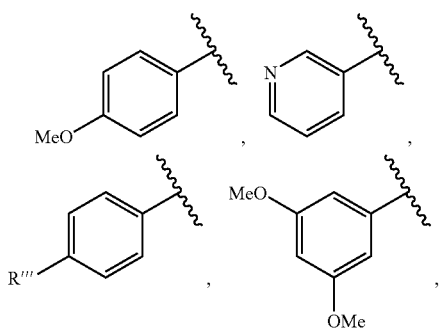

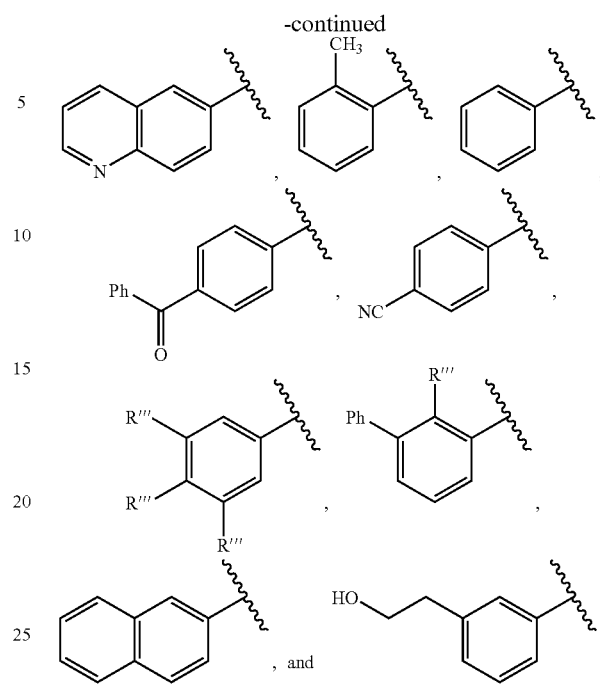

In certain embodiments, the present invention relates to any one of the above-mentioned methods, wherein M is sodium.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, Cs$_2$CO$_3$, K$_2$CO$_3$ or K$_3$PO$_4$.

In certain embodiments, the present invention relates to any one of the above-mentioned methods, wherein the period of time is from about 30 minutes to about 24 hours.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is $Bu_2O$, dioxane, or t-BuOH.

In one embodiment, the present invention relates to a method represented by Scheme 5:

Scheme 5

$$Z\text{-}X + MOCN \xrightarrow[\text{ROH}]{\text{transition metal} \atop \text{ligand}} \underset{\text{time, temperature}}{} Z\underset{}{\overset{H}{\underset{\parallel}{N}}}\underset{\parallel}{\overset{}{\underset{O}{C}}}OR$$

wherein,

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

M represents lithium, sodium, or potassium;

the transition metal is selected from the group consisting of Ni, Pd and Pt;

R is alkyl or aryl; and the ligand is any one of the above-mentioned biphenyl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

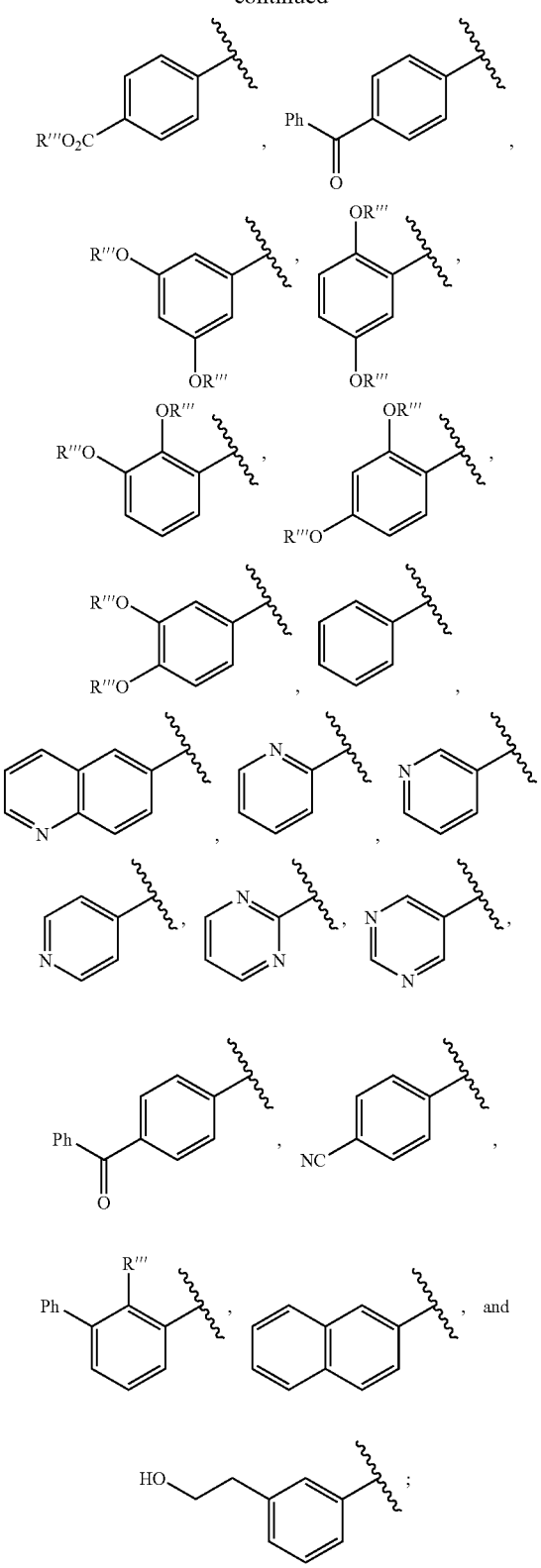

and R''' is lower alkyl.

In certain embodiments, the present invention relates to any one of the above-mentioned methods, wherein Z is

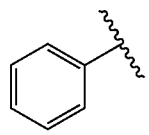

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, $OS(O)_2(CF_2)_3CF_3$, Cl, Br, or I; Z is selected from the group consisting of:

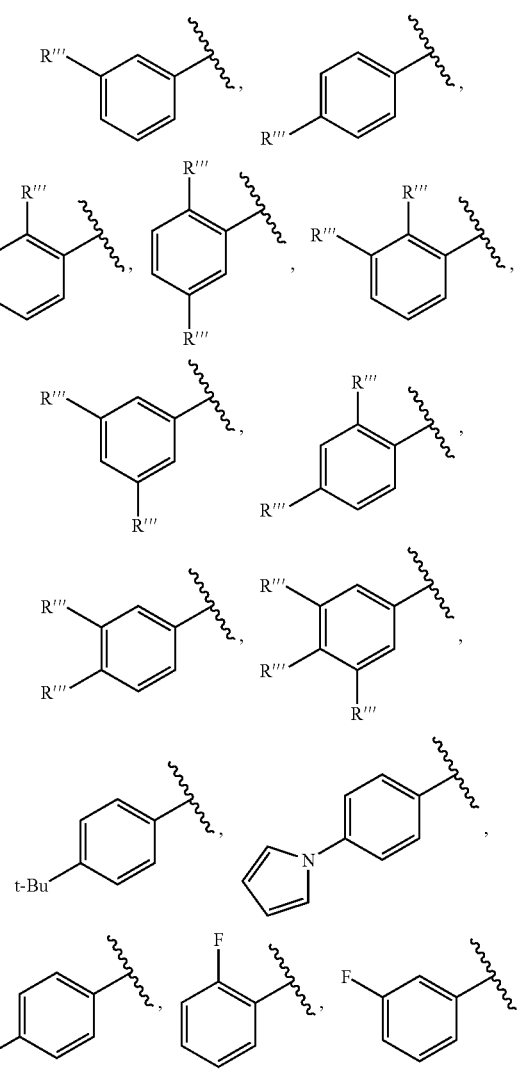

-continued

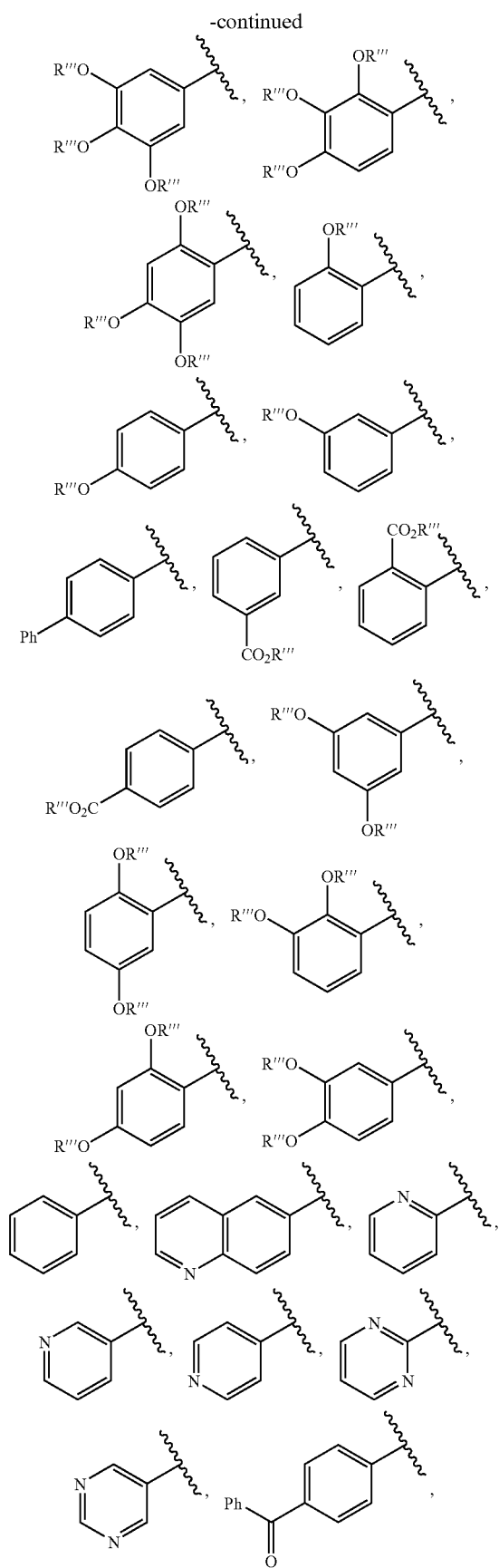

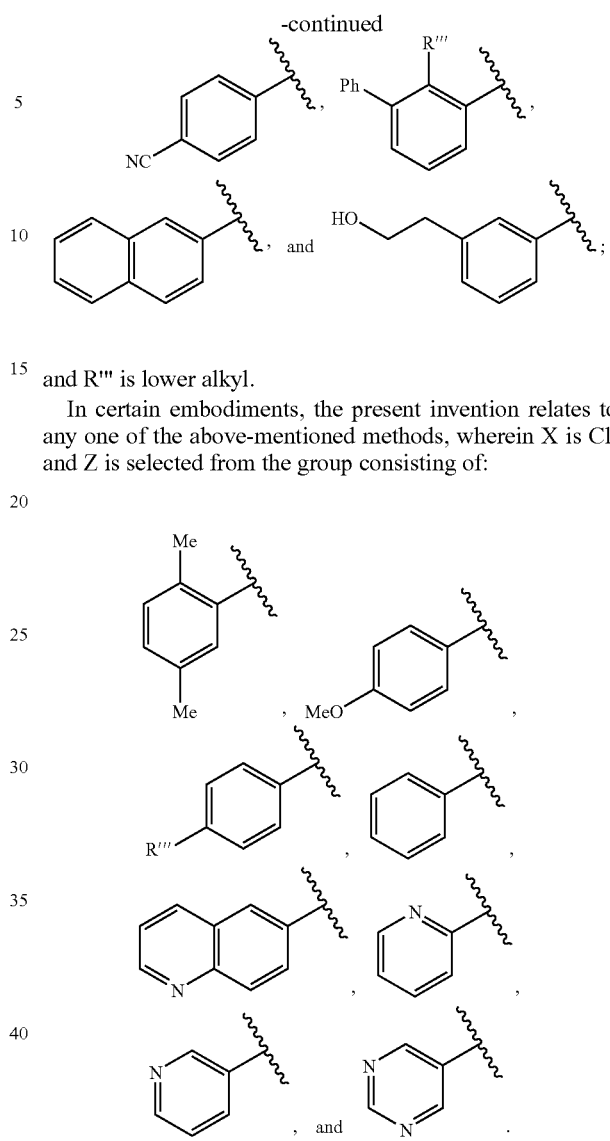

and R''' is lower alkyl.

In certain embodiments, the present invention relates to any one of the above-mentioned methods, wherein X is Cl; and Z is selected from the group consisting of:

In certain embodiments, the present invention relates to any one of the above-mentioned methods, wherein M is potassium.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, $Cs_2CO_3$, $K_2CO_3$ or $K_3PO_4$.

In certain embodiments, the present invention relates to any one of the above-mentioned methods, wherein the period of time is from about 30 minutes to about 24 hours.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, wherein R is alky.

In certain embodiments, the present invention relates to any one of the above-mentioned methods, wherein R is methyl, ethyl, propyl, or butyl.

In certain embodiments, the present invention relates to any one of the above-mentioned methods, wherein R is t-butyl.

In one embodiment, the present invention relates to a method represented by Scheme 1:

Scheme 1

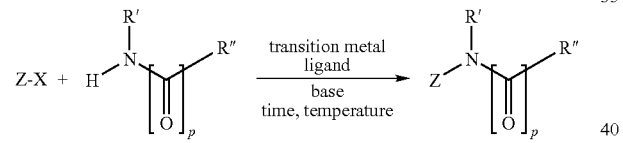

wherein

Z is selected from the group consisting of optionally substituted aryl, heteroaryl and alkenyl;

X is selected from the group consisting of —Cl, —Br, —I, —OS(O)$_2$alkyl, —OS(O)$_2$perfluoroalkyl, and —OS(O)$_2$aryl;

R' and R" are selected, independently for each occurrence, from the group consisting of hydrogen, alkyl, heteroalkyl, aryl, heteroaryl, aralkyl, heteroaralkyl, alkoxyl, amino, aminoalkyl, heterocyclylalkyl, trialkylsilyl, and triarylsilyl; or R' and (C=O)$_p$R", taken together, form an optionally substituted ring consisting of 3-10 backbone atoms inclusive, said ring optionally comprising one, two or three heteroatoms in addition to the nitrogen to which the R' and (C=O)$_p$R" are bonded;

R' may be covalently linked to Z;

R" may be covalently linked to Z;

p is 0 or 1;

the transition metal is selected from the group consisting of Ni, Pd and Pt;

the base is selected from the group consisting of fluorides, hydrides, hydroxides, carbonates, phosphates, alkoxides, metal amides, and carbanions; and the ligand is any one of the above-mentioned heteroaryl-based ligands.

In certain embodiments, the present invention relates to any one of the above-mentioned methods, wherein the ligand is present from about 0.0001 to about 20 mol % relative to the amount of Z—X.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is selected from the group consisting of aryl and heteroaryl.

In certain embodiments, the present invention relates to any one of the above-mentioned methods, wherein Z is selected from the group consisting of:

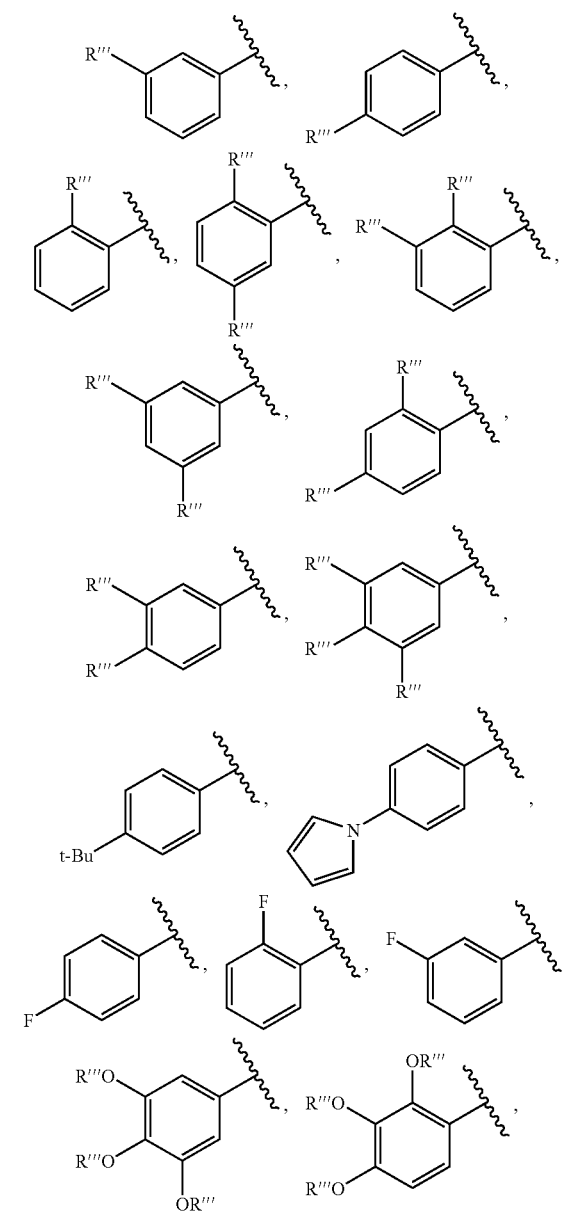

-continued

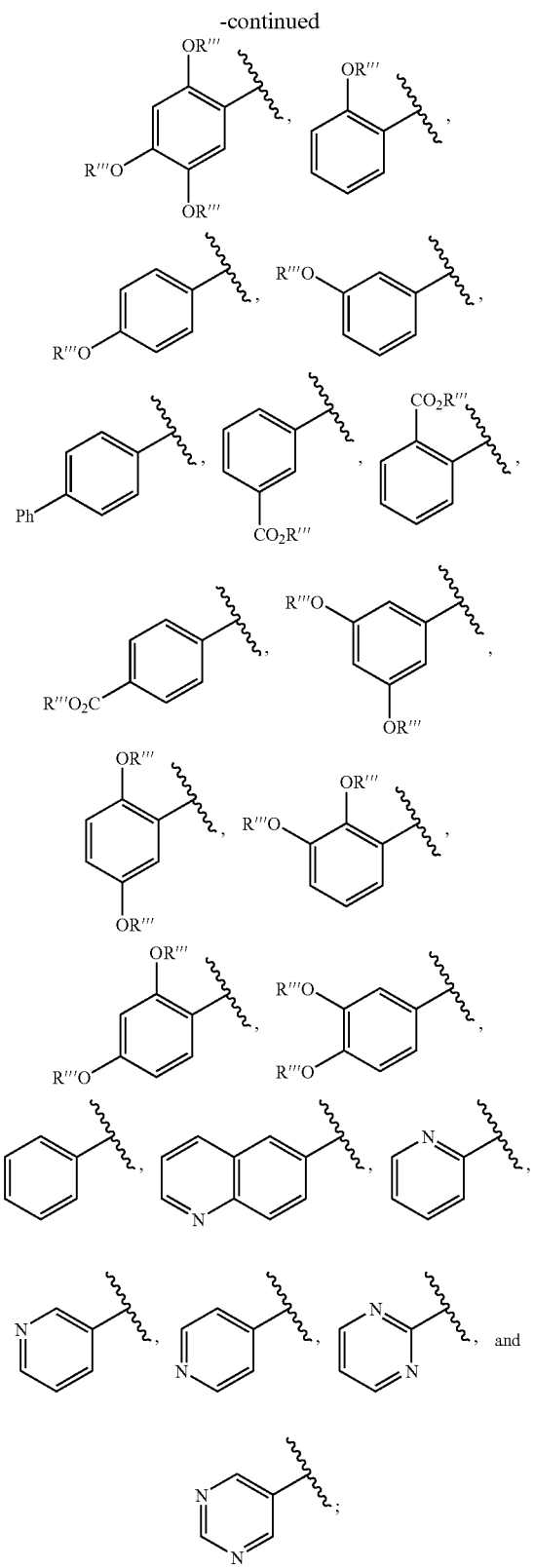

and R''' is lower alkyl.

In certain embodiments, the present invention relates to any one of the above-mentioned methods, wherein Z is

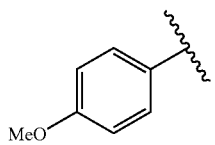

In certain embodiments, the present invention relates to any one of the above-mentioned methods, wherein Z is

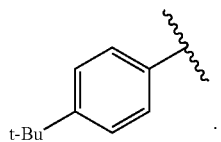

In certain embodiments, the present invention relates to any one of the above-mentioned methods, wherein X is $OS(O)_2CH_3$, $OS(O)_2CF_3$, Cl, Br, or I.

In certain embodiments, the present invention relates to any one of the above-mentioned methods, wherein X is Cl.

In certain embodiments, the present invention relates to any one of the above-mentioned methods, wherein X is $OS(O)_2CH_3$.

In certain embodiments, the present invention relates to any one of the above-mentioned methods, wherein X is $OS(O)_2CH_3$, $OS(O)_2CF_3$, Cl, Br, or I; and Z is selected from the group consisting of aryl and heteroaryl.

In certain embodiments, the present invention relates to any one of the above-mentioned methods, wherein X is $OS(O)_2CH_3$, $OS(O)_2CF_3$, Cl, Br, or I; Z is selected from the group consisting of:

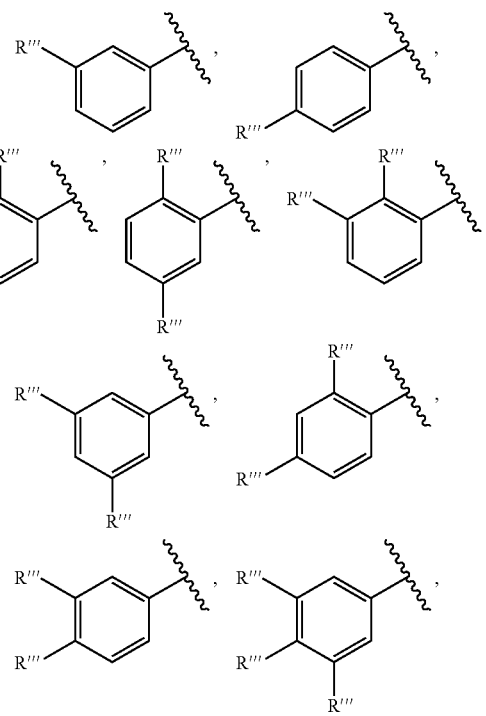

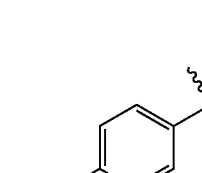

and R''' is lower alkyl.

In certain embodiments, the present invention relates to any one of the above-mentioned methods, wherein X is Cl; and Z is

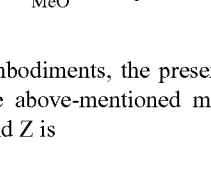

In certain embodiments, the present invention relates to any one of the above-mentioned methods, wherein X is OS(O)$_2$CH$_3$; and Z is

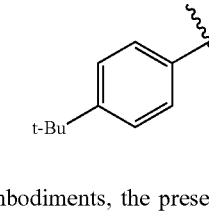

In certain embodiments, the present invention relates to any one of the above-mentioned methods, wherein R' and R'' are selected, independently for each occurrence, from the group consisting of hydrogen, alkyl, heteroalkyl, aryl, heteroaryl, aralkyl, heteroaralkyl, alkoxyl, amino, aminoalkyl, heterocyclylalkyl, trialkylsilyl, and triarylsilyl.

In certain embodiments, the present invention relates to any one of the above-mentioned methods, wherein R' is selected from the group consisting of alkyl,

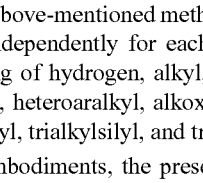

-continued

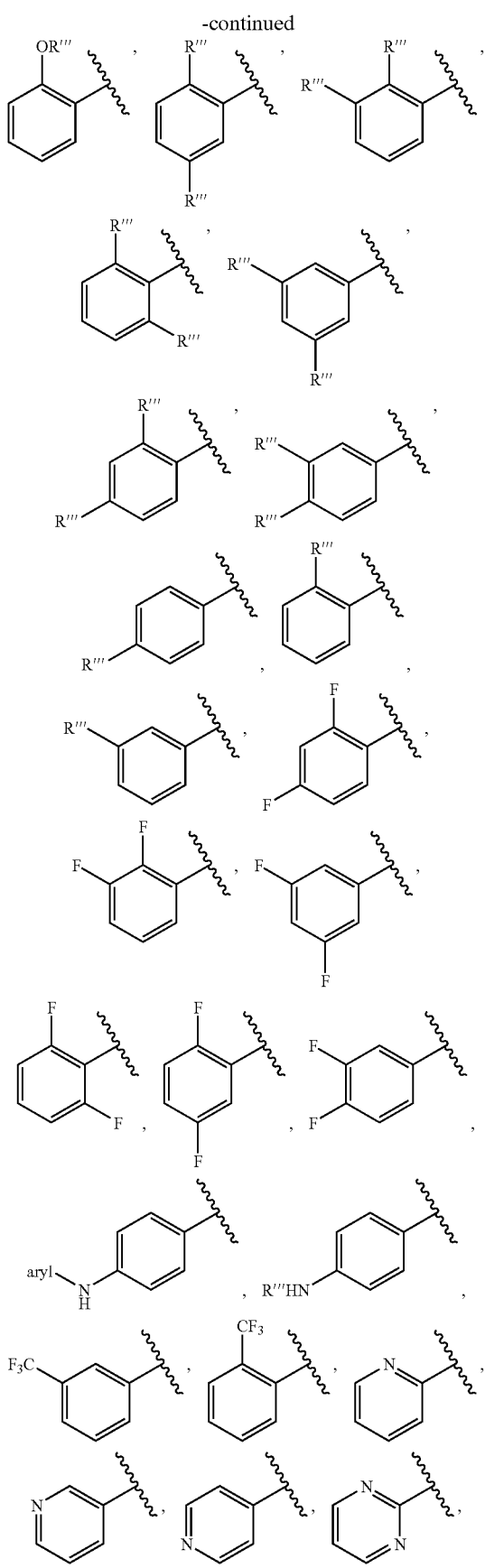

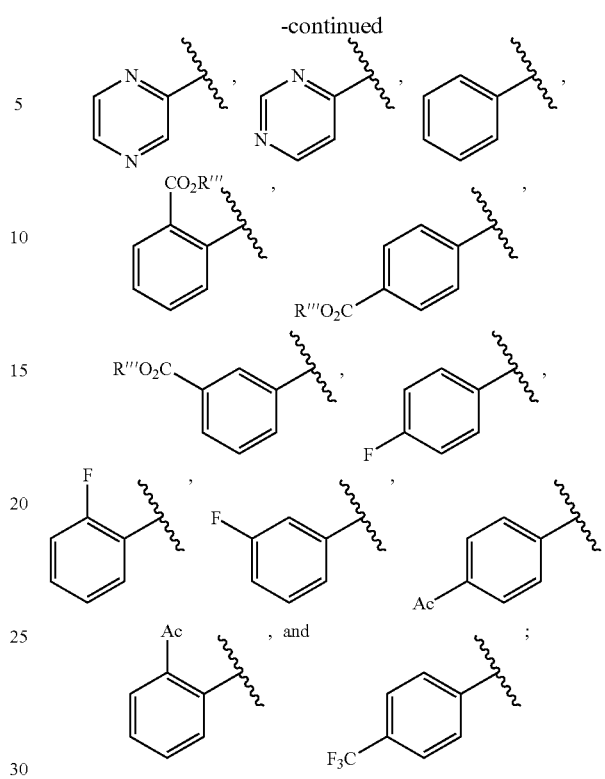

and R''' is lower alkyl.

In certain embodiments, the present invention relates to any one of the above-mentioned methods, wherein R' is

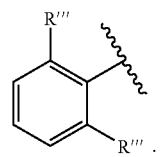

In certain embodiments, the present invention relates to any one of the above-mentioned methods, wherein R' is alkyl.

In certain embodiments, the present invention relates to any one of the above-mentioned methods, wherein R' is Me, Et, n-Pr, i-Pr, n-Bu, i-Bu, s-Bu, pentyl, or hexyl.

In certain embodiments, the present invention relates to any one of the above-mentioned methods, wherein R' is hexyl.

In certain embodiments, the present invention relates to any one of the above-mentioned methods, wherein R'' is hydrogen.

In certain embodiments, the present invention relates to any one of the above-mentioned methods, wherein R' is

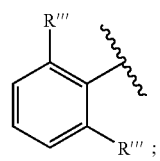

R'' is hydrogen; and p is 0.

In certain embodiments, the present invention relates to any one of the above-mentioned methods, wherein R' is alkyl; R" is hydrogen; and p is 0.

In certain embodiments, the present invention relates to any one of the above-mentioned methods, wherein R' is Me, Et, n-Pr, i-Pr, n-Bu, i-Bu, s-Bu, pentyl, or hexyl; R" is hydrogen; and p is 0.

In certain embodiments, the present invention relates to any one of the above-mentioned methods, wherein R' is hexyl; R" is hydrogen; and p is 0.

In certain embodiments, the present invention relates to any one of the above-mentioned methods, wherein the transition metal is palladium.

In certain embodiments, the present invention relates to any one of the above-mentioned methods, wherein the transition metal is present from about 0.0001 to about 20 mol % relative to the amount of Z—X.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is an alkoxide, amide, phosphate, or carbonate.

In certain embodiments, the present invention relates to any one of the above-mentioned methods, wherein the base is NaOt-Bu, $K_2CO_3$ or $K_3PO_4$.

In certain embodiments, the present invention relates to any one of the above-mentioned methods, wherein the period of time is from about 30 minutes to about 24 hours.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is about 3 hours.

In certain embodiments, the present invention relates to any one of the above-mentioned methods, wherein the period of time is about 2 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is $Bu_2O$, dioxane, or t-BuOH.

In one embodiment, the present invention relates to a method represented by Scheme 1:

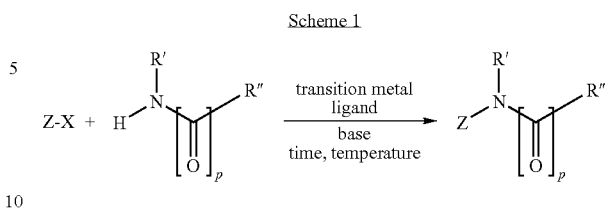

wherein, independently for each occurrence,

Z is selected from the group consisting of:

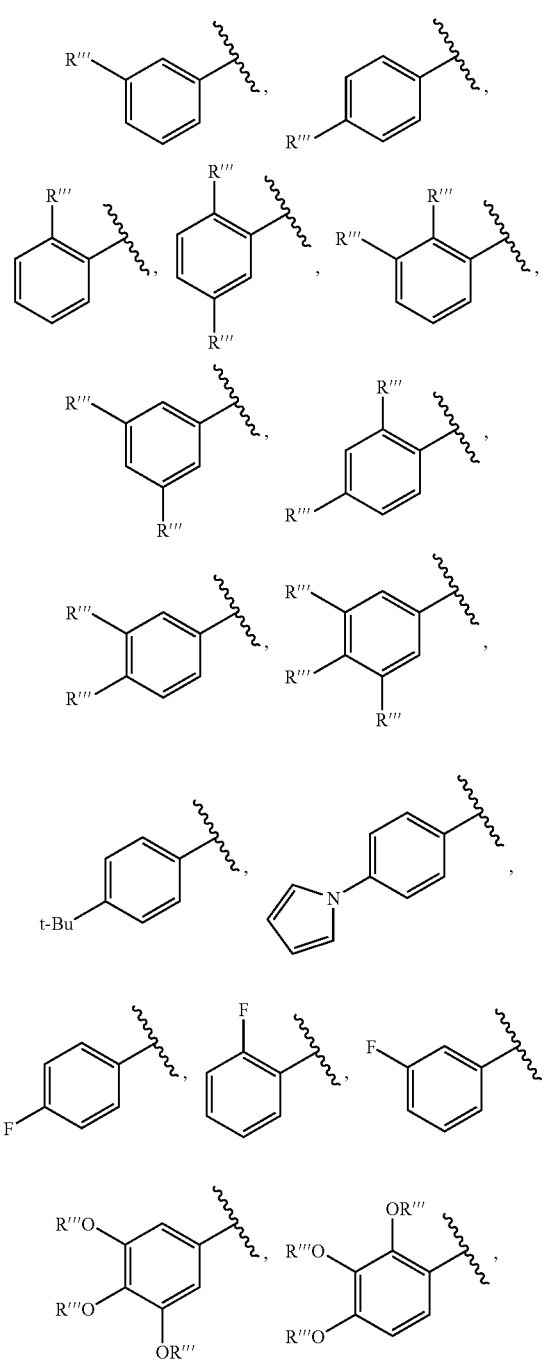

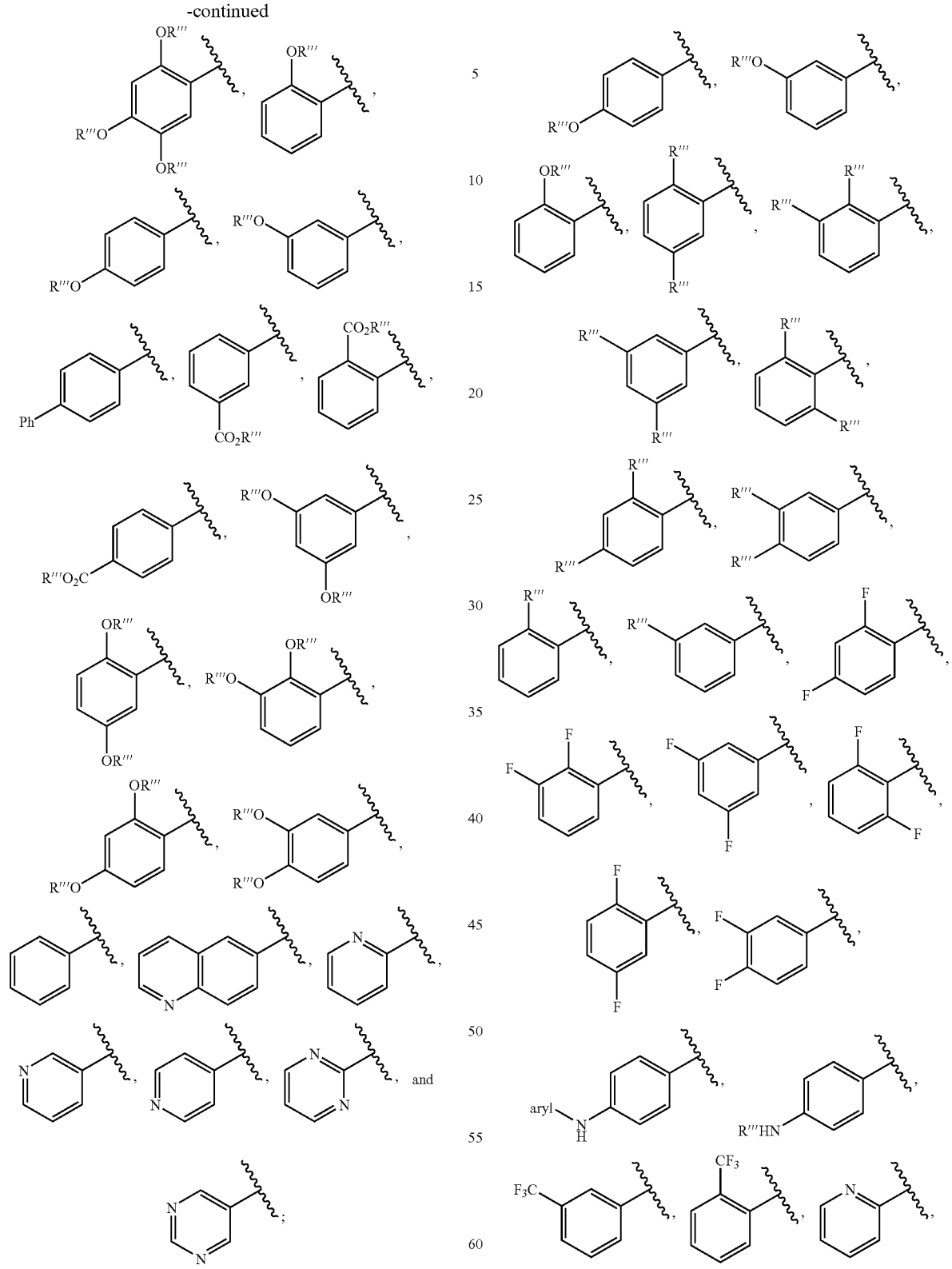
X is selected from the group consisting of OS(O)$_2$CH$_3$, OS(O)$_2$CF$_3$, Cl, Br, and I;
R' and R" are selected from the group consisting of hydrogen, alkyl, -continued

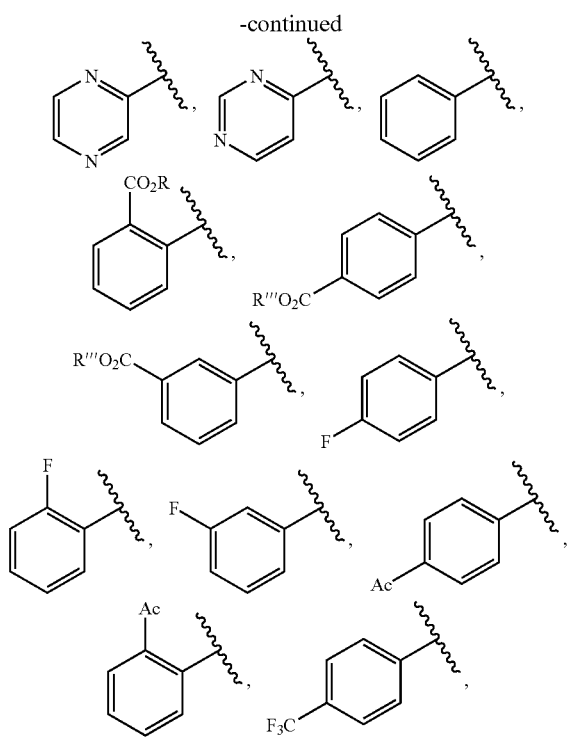

hydrogen, alkyl, aralkyl, aminoalkyl, and heterocyclylalkyl; or R' and (C=O)$_p$R", taken together, form an optionally substituted ring consisting of 5-7 backbone atoms inclusive, said ring optionally comprising one, two or three heteroatoms in addition to the nitrogen to which the R' and (C=O)$_p$R" are bonded;

R'" is lower alkyl;
R' may be covalently linked to Z;
R" may be covalently linked to Z;
p is 0 or 1;
the transition metal is Pd or Pt;
the base is selected from the group consisting of hydroxides, carbonates, phosphates, and alkoxides; and
the ligand is any one of the above-mentioned heteroaryl-based ligands.

In certain embodiments, the present invention relates to any one of the above-mentioned methods, wherein the ligand is present from about 0.001 to about 10 mol % relative to the amount of Z—X.

In certain embodiments, the present invention relates to any one of the above-mentioned methods, wherein the ligand is present from about 0.01 to about 1 mol % relative to the amount of Z—X.

In certain embodiments, the present invention relates to any one of the above-mentioned methods, wherein Z is

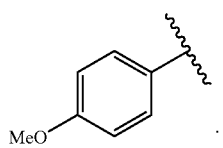

In certain embodiments, the present invention relates to any one of the above-mentioned methods, wherein Z is

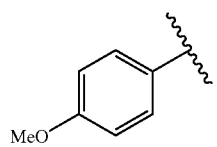

In certain embodiments, the present invention relates to any one of the above-mentioned methods, wherein X is Cl.

In certain embodiments, the present invention relates to any one of the above-mentioned methods, wherein X is OS(O)$_2$CH$_3$.

In certain embodiments, the present invention relates to any one of the above-mentioned methods, wherein X is Cl; and Z is

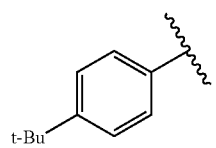

In certain embodiments, the present invention relates to any one of the above-mentioned methods, wherein X is OS(O)$_2$CH$_3$; and Z is

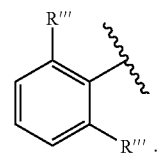

In certain embodiments, the present invention relates to any one of the above-mentioned methods, wherein R' is selected from the group consisting of alkyl or

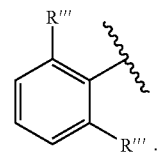

In certain embodiments, the present invention relates to any one of the above-mentioned methods, wherein R' is

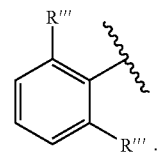

In certain embodiments, the present invention relates to any one of the above-mentioned methods, wherein R' is alkyl.

In certain embodiments, the present invention relates to any one of the above-mentioned methods, wherein R' is methyl, ethyl, propyl, butyl, pentyl, hexyl, heptyl, octyl, or benzyl.

In certain embodiments, the present invention relates to any one of the above-mentioned methods, wherein R" is hydrogen.

In certain embodiments, the present invention relates to any one of the above-mentioned methods, wherein R' is hexyl.

In certain embodiments, the present invention relates to any one of the above-mentioned methods, wherein R' is

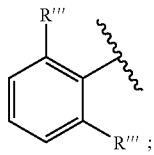

R" is hydrogen; and p is 0.

In certain embodiments, the present invention relates to any one of the above-mentioned methods, wherein R' is alkyl; R" is hydrogen; and p is 0.

In certain embodiments, the present invention relates to any one of the above-mentioned methods, wherein R' is methyl, ethyl, propyl, butyl, pentyl, hexyl, heptyl, octyl, or benzyl; R" is hydrogen; and p is 0.

In certain embodiments, the present invention relates to any one of the above-mentioned methods, wherein R' is hexyl; R" is hydrogen; and p is 0.

In certain embodiments, the present invention relates to any one of the above-mentioned methods, wherein the transition metal is palladium.

In certain embodiments, the present invention relates to any one of the above-mentioned methods, wherein the transition metal is present from about 0.001 to about 10 mol % relative to the amount of Z—X.

In certain embodiments, the present invention relates to any one of the above-mentioned methods, wherein the transition metal is present from about 0.01 to about 1 mol % relative to the amount of Z—X.

In certain embodiments, the present invention relates to any one of the above-mentioned methods, wherein the base is NaOt-Bu, $K_2CO_3$ or $K_3PO_4$.

In certain embodiments, the present invention relates to any one of the above-mentioned methods, wherein the period of time is from about 30 minutes to about 24 hours.

In certain embodiments, the present invention relates to any one of the above-mentioned methods, wherein the period of time is from about 30 minutes to about 4 hours.

In certain embodiments, the present invention relates to any one of the above-mentioned methods, wherein the period of time is about 3 hours.

In certain embodiments, the present invention relates to any one of the above-mentioned methods, wherein the period of time is about 2 hours.

In certain embodiments, the present invention relates to any one of the above-mentioned methods, wherein the period of time is about 1 hour.

In certain embodiments, the present invention relates to any one of the above-mentioned methods, wherein the temperature is about 23° C.

In certain embodiments, the present invention relates to any one of the above-mentioned methods, wherein the temperature is about 80° C.

In certain embodiments, the present invention relates to any one of the above-mentioned methods, wherein the temperature is about 110° C.

In certain embodiments, the present invention relates to any one of the above-mentioned methods, further comprising a solvent.

In certain embodiments, the present invention relates to any one of the above-mentioned methods, wherein said solvent is an ether or alcohol.

In certain embodiments, the present invention relates to any one of the above-mentioned methods, wherein said solvent is $Bu_2O$, dioxane, or t-BuOH.

EXEMPLIFICATION

The invention now being generally described, it will be more readily understood by reference to the following examples which are included merely for purposes of illustration of certain aspects and embodiments of the present invention, and are not intended to limit the invention.

Example One

Synthesis of 2-iodo-2',4',6'-triisopropyl-3,6-dimethoxybiphenyl

An oven-dried three-neck 100 mL round bottom flask, which was equipped with a magnetic stir bar and charged with magnesium shavings (360 mg, 15.36 mmol), was fitted with a reflux condenser, glass stopper, and rubber septum. The flask was evacuated and backfilled with argon (this process was repeated a total of 3 times) and then THF (40 mL) and 2,4,6-triisopropylbromobenzene (3.62 g, 12.8 mmol) were added via syringe. The reaction was heated to reflux and 1,2-dibromethane (40 μL) was added dropwise. The reaction was allowed to stir at reflux for 1 h and then was cooled to room temperature. A separate oven-dried 500 mL round bottom flask, which was equipped with a magnetic stir bar and fitted with a septum, was evacuated and backfilled with argon (this process was repeated a total of 3 times) and then THF (160 mL) and 1,4-dimethoxy-2-fluorobenzene (2 g, 12.8 mmol) were added to the flask via syringe. The reaction was cooled to −78° C. and n-BuLi (2.5 M in Hexane, 5.12 mL, 12.8 mmol) was added dropwise over a 15 min period. The solution was stirred for 30 min and the Grignard reagent, which was prepared in the first reaction vessel, was added via cannula transfer over a 20 min period and allowed to stir at −78° C. for 1 h. The reaction was warmed to room temperature slowly where it was stirred for an additional 1.5 h. The reaction was then cooled to 0° C. and a solution of Iodine in THF (0.38 M, 40 mL, 15.36 mmol) was added dropwise over a 15 min period and then the dark red solution was warmed to room temperature and stirred for 1 h. The reaction was concentrated on a rotary evaporator, taken up in $CH_2Cl_2$, washed with a saturated solution of sodium sulfite, and washed with brine. The organic layer was then dried over $MgSO_4$, filtered, and concentrated on a rotary evaporator to give a yellow solid. The crude material was recrystallized from EtOAc to yield 2.471 g (41%) of product as a white solid. (See Examples 8 and 46 for alternative syntheses of this molecule).

Example Two

General Procedure for the Synthesis of Compounds 1 through 5

An oven-dried 25 mL round bottom flask, which was equipped with a magnetic stir bar and charged with 2-iodo-2',4',6'-triisopropyl-3,6-dimethoxybiphenyl (1 g, 2.15 mmol), was evacuated and backfilled with argon (this process was repeated a total of 3 times). THF (10 mL) was added via syringe and the reaction was cooled to −78° C. and n-BuLi (2.5 M in Hexane, 940 µL, 2.36 mmol) was added dropwise over a 10 min period. The solution was stirred for 30 min and then the ClPR$_2$ (2.26 mmol) was added dropwise over a 10 min period. The reaction was stirred for 1 h at −78° C. and then warmed slowly to room temperature and stirred for an additional 1.5 h. The solution was filtered through a plug of Celite layered on a plug of silica (eluting with EtOAc) and then concentrated on a rotary evaporator to give a white solid. The crude material was recrystallized from acetone (ligands 2 through 5 were recrystallized from MeOH) to yield white crystals of the desired product.

Example Three

Synthesis of Ligand 6

An oven-dried three-neck 100 mL round bottom flask, which was equipped with a magnetic stir bar and charged with Magnesium shavings (360 mg, 15.36 mmol), was fitted with a reflux condenser, glass stopper, and rubber septum. The flask was evacuated and backfilled with argon (this process was repeated a total of 3 times) and then THF (40 mL) and 2,4,6-triisopropylbromobenzene (3.62 g, 12.8 mmol) were added via syringe. The reaction was heated to reflux and 1,2-dibromethane (40 µL) was added dropwise. The reaction was allowed to stir at reflux for 1 h and then was cooled to room temperature. A separate oven-dried 500 mL round bottom schlenk flask, which was equipped with a magnetic stir bar and fitted with a septum, was evacuated and backfilled with argon (this process was repeated a total of 3 times) and then THF (160 mL) and 1,4-dimethoxy-2-fluorobenzene (2 g, 12.8 mmol) were added to the flask via syringe. The reaction was cooled to −78° C. and n-BuLi (2.5 M in Hexane, 5.12 mL, 12.8 mmol) was added dropwise over a 15 min period. The solution was stirred for 30 min and the Grignard reagent, which was prepared in the first reaction vessel, was added via cannula transfer over a 20 min period and allowed to stir at −78° C. for 1 h. The reaction was warmed to room temperature slowly where it was stirred for an additional 3 h. Under a constant flow of argon the septum was removed and anhydrous CuCl (1.267 g, 12.8 mmol) was added quickly. The ClP(t-Bu)$_2$ (2.44 mL, 12.8 mmol) was then added via syringe and the schlenk tube was sealed with a Teflon screw cap. The reaction was heated to 75° C. for 48 h and then cooled to room temperature. The reaction was quenched with 30% aqueous NH$_4$OH (100 mL) and the resulting suspension was extracted with EtOAc (200 mL). The organic layer was washed with 30% aqueous NH$_4$OH (3×100 mL) and brine (100 mL), dried over MgSO$_4$, filtered, and concentrated on a rotary evaporator to yield a thick yellow oil. The crude material was taken up in minimum amount of hot MeOH and placed in a −25° C. freezer over night to yield 1.11 g (18%) of white crystals.

Example Four

General Procedure for Cross-Couplings Reactions with Anilines and Aryl Chlorides In a glovebox an oven-dried test tube, which was equipped with a magnetic stir bar, was charged with the NaOt-Bu (1.2 equiv.), the aryl chloride (1.0 equiv.), amine (1.2 equiv.), and Bu$_2$O (2 mL/mmol). A solution of the pre-catalyst and ligand 1 in Toluene (0.002 M, 0.01%) were added and the tube was capped and taken out of the glovebox where it was heated to 110° C. until the starting material had been completely consumed as monitored by GC. The reaction was then cooled to room temperature, diluted with EtOAc, washed with water, concentrated in vacuo, and purified via the Biotage SP4 (silica-packed 25+M cartridge).

Example Five

General Procedure for Cross-Coupling Reactions of Heteroarylamines

An oven-dried test tube, which was equipped with a magnetic stir bar and fitted with a Teflon screw cap septum, was charged with Pd(OAc)$_2$ (0.01 mmol) and 1 (0.03 mmol). The vessel was evacuated and backfilled with argon (this process was repeated a total of 3 times) and then t-BuOH (2 mL) and degassed H$_2$O (0.04 mmol) were added via syringe. After addition of the water the solution was heated to 80° C. for 1 minute.

A second oven-dried reaction vessel, which was equipped with a magnetic stir bar and fitted with a Teflon screw cap septum, was charged with K$_2$CO$_3$ (1.4 mmol). The vessel was evacuated and backfilled with argon (this process was repeated a total of 3 times) and then the aryl chloride (1.0 mmol) and amine (1.2 mmol) were added via syringe (aryl chlorides or amines that were solids at room temperature were added with the base) and the activated catalyst solution was transferred from the first reaction vessel via cannula. The solution was heated to 110° C. until the starting material had been completely consumed as monitored by GC. The reaction was then cooled to room temperature, diluted with EtOAc, washed with water, concentrated in vacuo, and purified via the Biotage SP4 (silica-packed 25+M cartridge).

Example Six

General Procedure for Coupling of Amides

An oven-dried test tube, which was equipped with a magnetic stir bar and fitted with a Teflon screw cap septum, was charged with Pd(OAc)$_2$ (0.01 mmol) and 6 (0.022 mmol). The vessel was evacuated and backfilled with argon (this process was repeated a total of 3 times) and then t-BuOH (2 mL) and degassed H$_2$O (0.04 mmol) were added via syringe. After addition of the water the solution was heated to 110° C. for 1.5 minute.

A second oven-dried reaction vessel, which was equipped with a magnetic stir bar and fitted with a Teflon screw cap septum, was charged with K$_3$PO$_4$ (1.4 mmol). The vessel was evacuated and backfilled with argon (this process was repeated a total of 3 times) and then the aryl chloride (1.0 mmol) and amide (1.2 mmol) were added via syringe (aryl chlorides or amides that were solids at room temperature were added with the base) and the activated catalyst solution was transferred from the first reaction vessel via cannula. The solution was heated to 110° C. until the starting material had been completely consumed as monitored by GC. The reaction was then cooled to room temperature, diluted with EtOAc, washed with water, concentrated in vacuo, and purified via the Biotage SP4 (silica-packed 25+M cartridge).

Example Seven

General Information Pertaining to Examples 8-45

General Reagent Information

All reactions were carried out under an argon atmosphere. The methylamine solution, 1,4-dioxane, THF, and tert-butanol were purchased from Aldrich Chemical Co. in Sure-Seal bottles and were used as received. Dibutyl ether was purchased from Aldrich Chemical Co., anhydrous, and was distilled from sodium metal. Pentane was purchased from Aldrich, in a Sure-Seal bottle, $N_2$-sparged and stored over activated 3 Å molecular sieves in a glovebox. $Pd(OAc)_2$ was a gift from BASF and aryl halides and amines were purchased from Aldrich Chemical Co., Alfa Aesar, Parkway Scientific, or TCI America. The 1,4-dimethoxyfluorobenzene was purchased from Synquest Labs, Inc., and used as received. All amines that were a liquid and the aryl chlorides used in FIG. 12, Table 8 were distilled from calcium hydride and stored under argon. Amines that were a solid and all other aryl halides were used as purchased without further purification. Distilled water was degassed by brief (30 sec) sonication under vacuum. Both potassium carbonate and sodium tert-butoxide were purchased from Aldrich Chemical Co. and used as received. The bulk of the bases were stored in a $N_2$ glovebox. Small portions were taken outside the box in glass vials and weighed in the air. Ligands 13 and 8 and precatalyst 10 were synthesized using literature procedures. Huang, X.; Anderson, K. W.; Zim, D.; Jiang, L.; Klapers, A.; Buchwald, S. L. *J. Am. Chem. Soc.* 2003, 125, 6653; Anderson, K. W.; Tundel, R. E.; Ikawa, T.; Altman, R. A.; Buchwald, S. L. *Angew. Chem. Int. Ed.* 2006, 45, 6523; Biscoe, M. R.; Fors, B. P.; Bucwhald, S. L. *J. Am. Chem. Soc.* 2008, 130, 2754.

General Analytical Information

All compounds were characterized by $^1H$ NMR, $^{13}C$ NMR, and IR spectroscopy. Nuclear Magnetic Resonance spectra were recorded on a Varian 300 MHz instrument and Bruker 400 MHz instrument. All $^1H$ NMR experiments are reported in δ units, parts per million (ppm), and were measured relative to the signals for residual chloroform (7.26 ppm) in the deuterated solvent, unless otherwise stated. All $^{13}C$ NMR spectra are reported in ppm relative to deuterochloroform (77.23 ppm), unless otherwise stated, and all were obtained with $^1H$ decoupling. All IR spectra were taken on a Perkin-Elmer 2000 FTIR. All GC analyses were performed on an Agilent 6890 gas chromatograph with a FID detector using a J & W DB-1 column (10 m, 0.1 mm I.D.). Elemental analyses were performed by Atlantic Microlabs Inc., Norcross, Ga.

Example Eight

Alternative Synthesis of 2-iodo-2',4',6'-triisopropyl-3,6-dimethoxybiphenyl

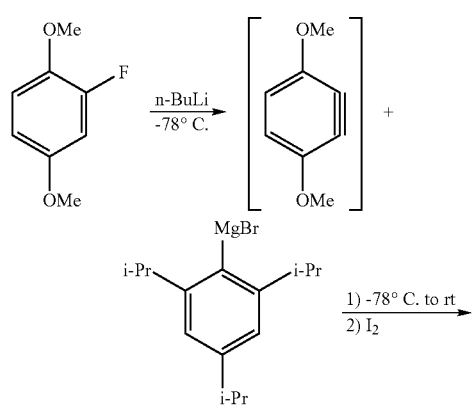

-continued

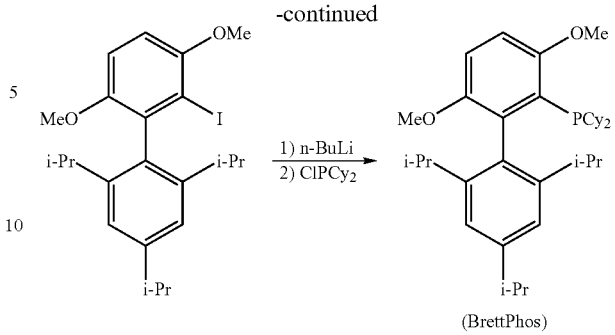

(BrettPhos)

An oven-dried three-neck 500 mL round bottom flask, which was equipped with a magnetic stir bar and charged with magnesium shavings (1.48 g, 61 mmol), was fitted with a reflux condenser, glass stopper, and rubber septum. The flask was purged with argon and then THF (120 mL) and 2,4,6-triisopropylbromobenzene (14.48 g, 51.2 mmol) were added via syringe. The reaction was heated to reflux and 1,2-dibromomethane (40 uL) was added via syringe. The reaction mixture was allowed to stir at reflux for 1 h and was then cooled to room temperature. A separate oven-dried 1 L round bottom flask, which was equipped with a magnetic stir bar and fitted with a septum, was purged with argon and then THF (300 mL) and 1,4-dimethoxy-2-fluorobenzene (8 g, 51.2 mmol) were added to the flask via syringe. The reaction vessel was cooled via a −78° C. bath and n-BuLi (2.5 M in Hexane, 20.5 mL, 51.2 mmol) was added in a dropwise fashion over a 15 min period. The solution was stirred for an additional 30 min and the Grignard reagent, which was prepared in the first reaction vessel, was added via cannula over a 20 min period and the reaction mixture was allowed to stir at −78° C. for 1 h. The reaction mixture was slowly warmed to room temperature where it was stirred for an additional 1.5 h. The mixture was then cooled to 0° C. and a solution of Iodine in THF (1 M, 61 mL, 61 mmol) was added via syringe over a 15 min period and then the dark red solution was warmed to room temperature and stirred for 1 h. The solvent was removed with the aid of a rotary evaporator, and the remaining dark brown oil was taken up in $CH_2Cl_2$, washed with a saturated solution of sodium sulfite, and with brine. The organic layer was then dried over $MgSO_4$, filtered, and the solvent was removed with the aid of a rotary evaporator to give a yellow solid. The crude material was recrystallized from EtOAc to yield the product as white crystals (3.430 g). The mother liquor was then concentrated and the remaining yellow solid was recrystallized from EtOAc to yield additional white crystals (3.728 g, 31% overall yield), mp 189-191° C. $^1H$ NMR (300 MHz, $CDCl_3$) δ: 7.07 (s, 2H), 6.90 (d, J=9.0 Hz, 1H), 6.81 (d, J=9.0 Hz, 1H), 3.90 (s, 3H), 3.67 (s, 3H), 2.98 (septet, J=7.0 Hz, 1H), 2.39 (septet, J=7.0 Hz, 2H), 1.33 (d, J=7.0 Hz, 6H), 1.20 (d, 7.0 Hz, 6H), 1.02 (d, J=7.0 Hz, 6H) ppm. $^{13}C$ NMR (75 MHz, $CDCl_3$) δ: 152.7, 152.5, 148.4, 145.9, 136.4, 136.1, 121.0, 110.3, 109.4, 96.6, 57.0, 55.8, 34.3, 31.1, 24.8, 24.3, 23.9 ppm. IR (neat, $cm^{-1}$): 2957, 2865, 1567, 1460, 1428, 1257, 1032, 755. Anal. Calcd. for $C_{23}H_{31}IO_2$: C, 59.23; H, 6.70. Found: C, 59.23; H, 6.72.

Example Nine

Synthesis of Ligand 1

An oven-dried 25 mL round bottom flask, which was equipped with a magnetic stir bar and charged with 2-iodo- 2',4',6'-triisopropyl-3,6-dimethoxybiphenyl (1 g, 2.15 mmol), was evacuated and backfilled with argon (this process was repeated a total of 3 times). THF (10 mL) was added via syringe and the reaction was cooled to −78° C. and n-BuLi (2.5 M in Hexane, 940 μL, 2.36 mmol) was added in a dropwise fashion over a 10 min period. The solution was stirred for 30 min and then the ClPCy$_2$ (527 mg, 2.26 mmol) was added via syringe over 10 min. The reaction mixture was stirred for 1 h at −78° C. and then warmed slowly to room temperature where it was stirred for an additional 1.5 h. The solution was filtered through a plug of Celite layered on a plug of silica (eluting with EtOAc) and then the solvent was removed with the aid of a rotary evaporator to give a white solid. The crude material was recrystallized from acetone to yield the desired product as white crystals. The mother liquor was then concentrated and the remaining white solid was recrystallized from acetone to yield additional white crystals (1.012 g total, 88% yield), mp 191-193° C. $^1$H NMR (300 MHz, CDCl$_3$) δ: 6.96 (s, 2H), 6.85 (d, J=9.0 Hz, 1H), 6.78 (d, J=9.0 Hz, 1H), 3.82 (s, 3H), 3.56 (s, 3H), 2.93 (septet, J=7.0 Hz, 1H), 2.42 (septet, J=7.0 Hz, 2H), 2.19 (m, 2H), 1.82-1.60 (m, 8H), 1.41-0.90 (m, 12H), 1.31 (d, J=7.0 Hz, 6H), 1.16 (d, J=7.0 Hz, 6H), 0.92 (d, J=7.0 Hz, 6H) ppm. $^{13}$C NMR (75 MHz, CDCl$_3$) δ: 156.5, 156.5, 152.5, 152.4, 147.1, 146.2, 146.1, 139.5, 139.0, 132.9, 132.8, 127.0, 126.6, 120.4, 120.3, 110.9, 108.8, 55.3, 54.9, 54.8, 36.9, 36.7, 34.0, 33.3, 32.9, 31.2, 31.0, 30.7, 28.2, 28.1, 27.9, 27.7, 26.7, 25.3, 24.2, 23.8 ppm (Observed complexity is due to P—C splitting). $^{31}$P NMR (121 MHz, CDCl$_3$) δ: −1.62 ppm. IR (neat, cm$^{-1}$): 3378, 2849, 1654, 1654, 1457, 1423, 1384, 1249, 1053. Anal. Calcd. for C$_{35}$H$_{53}$O$_2$P: C, 78.32; H, 9.95. Found: C, 78.44; H, 10.09.

Example Ten

Synthesis of Ligand 7

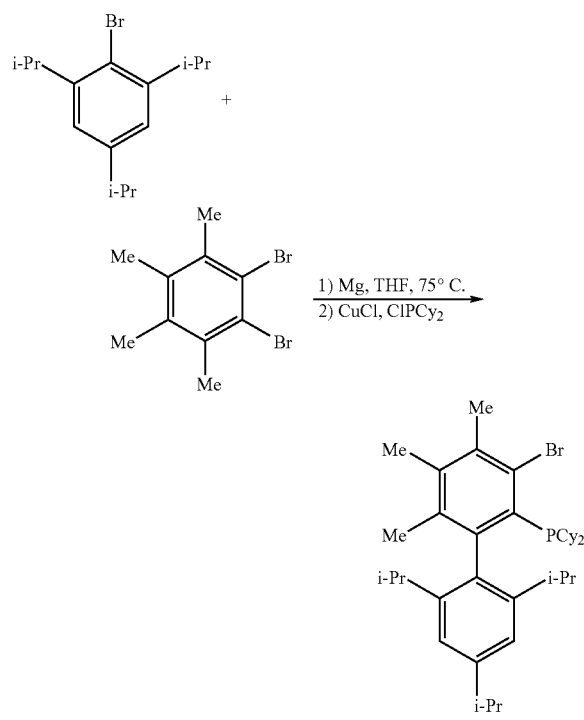

An oven-dried three-neck 250 mL round bottom flask, which was equipped with a magnetic stir bar and charged with magnesium shavings (559 mg, 24.3 mmol), was fitted with a reflux condenser, addition funnel, and glass stopper. The flask was purged with argon and then THF (15 mL) and 2,4,6-triisopropylbromobenzene (2.83 g, 10 mmol) were added via syringe. The reaction mixture was heated to reflux and 1,2-dibromethane (40 uL) was added via syringe. The reaction was allowed to stir at reflux for 1 h and then the addition funnel, which was charged with 1,2-dibromo-3,4,5,6-tetramethylbenzene (2.92 g, 10 mmol) in 40 mL of THF, was opened and the solution was added over a 1 h period. The mixture was stirred for 5 h at reflux and then cooled to room temperature where CuCl (1.0 g, 10 mmol) was added quickly to the reaction mixture. Next, ClPCy$_2$ (2.65 mL, 10 mmol) was then added in a dropwise fashion and the reaction mixture was heated to 75° C. for 60 h. The reaction mixture was then cooled to room temperature, diluted with EtOAc, washed 3 times with 30% NH$_4$OH, dried over MgSO$_4$, and concentrated under reduced pressure. The crude material was recrystallized from benzene to yield the product as a white solid (1.507 g, 28% yield). $^1$H NMR (300 MHz, CDCl$_3$) δ: 7.36 (s, 5H), 7.15 (s, 2H), 2.99 (septet, J=7.0 Hz, 1H), 2.44 (s, 3H), 2.35-2.14 (m, 11H), 1.98 (s, 2H), 1.80-1.44 (m, 14H), 1.39-1.04 (m, 22H), 0.91 (d, J=6.5 Hz, 6H) ppm. $^{13}$C NMR (75 MHz, CDCl$_3$) δ: 150.9, 145.8, 145.4, 144.6, 140.0, 138.5, 135.8, 135.6, 135.5, 135.5, 128.6, 124.3, 40.2, 39.9, 35.4, 35.2, 34.5, 30.7, 29.5, 27.8, 27.7, 27.4, 27.2, 25.9, 25.0, 24.6, 21.2, 20.8, 17.7, 17.3 ppm (Observed complexity is due to P—C splitting). $^{31}$P NMR (121 MHz, CDCl$_3$) δ: 16.33 ppm.

Example Eleven

Synthesis of Ligand 9

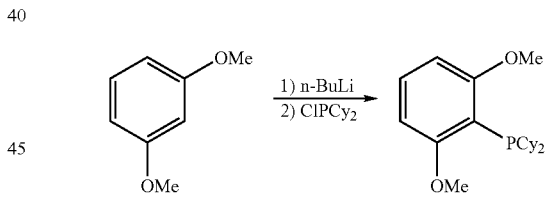

To a 0° C. solution of 1,3-dimethoxybenzene (2.0 mL, 15.3 mmol) in THF (35 mL) was added n-BuLi (6.20 mL, 2.5 M in hexanes, 15.5 mmol) via syringe over a 10 min period. The mixture was then allowed to warm to room temperature and stirred for 5 h. The mixture was re-cooled to 0° C. and ClPCy$_2$ (3.07 mL, 13.9 mmol) was added via syringe over a 10 min period. The reaction mixture was allowed to warm to room temperature where it was stirred for 12 h. The solution was then filtered through a plug of silica, eluting with EtOAc, and concentrated under reduced pressure to yield the product as a white solid (4.89 g, 96% yield). $^1$H NMR (300 MHz, CDCl$_3$) δ: 7.21 (t, J=8.0 Hz, 1H), 6.46 (d, J=8.0 Hz, 2H), 3.74 (s, 6H), 2.26 (m, 2H), 1.86 (m, 2H), 1.70 (m, 2H), 1.56 (m, 4H), 1.42-0.89 (m, 12H) ppm. $^{13}$C NMR (75 MHz, CDCl$_3$) δ: 164.5, 164.4, 131.1, 111.6, 111.2, 104.1, 55.8, 34.3, 34.1, 32.5, 32.2, 30.5, 30.4, 27.6, 27.5, 27.5, 27.3, 26.7 ppm (Observed complexity is due to P—C splitting). $^{31}$P NMR (121

MHz, CDCl$_3$) δ: −11.8 ppm. IR (neat, cm$^{-1}$): 2921, 2847, 1581, 1463, 1428, 1242, 1103, 777.

Example Twelve

Synthesis of Precatalyst 10

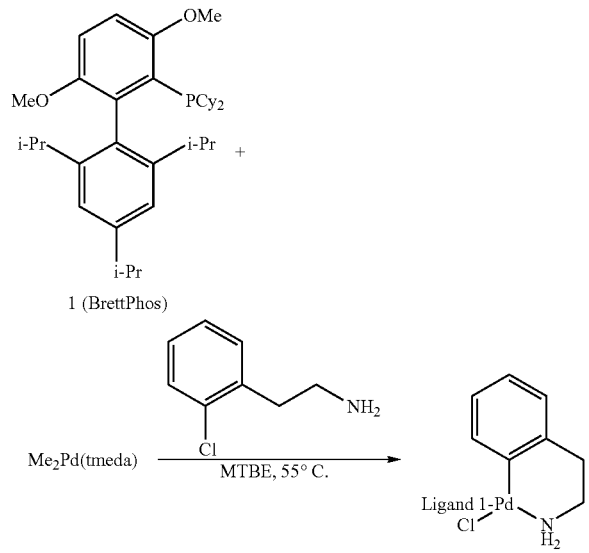

An oven-dried schlenk tube, which was equipped with a magnetic stir bar and fitted with a rubber septum, was charged with Me$_2$Pd(TMEDA) (253 mg, 1 mmol) and 1 (537 mg, 1 mmol). The vessel was evacuated and backfilled with argon (this process was repeated a total of 3 times) and the 2-(2-chorophenyl)ethylamine (156 mg, 1 mmol) and MTBE (8 mL) were added via syringe and the reaction mixture was heated to 55° C. for 5 h. The reaction mixture was then cooled to 0° C. and a white precipitate was filtered and washed with cold MTBE. The white product was then taken up in CH$_2$Cl$_2$ and concentrated under reduced pressure (done to remove any remaining MTBE) to yield the product as a white solid (645 mg, 93% yield). $^1$H NMR (300 MHz, CDCl$_3$) δ: 7.17 (s, 2H), 7.09-6.84 (m, 6H), 3.85 (s, 3H), 3.38 (s, 3H), 3.17-0.00 (m, 49H) ppm. $^{31}$P NMR (121 MHz, CDCl$_3$) δ: 42.2 ppm. IR (neat, cm$^{-1}$): 3303, 2929, 1658, 1462, 1384, 1256, 1010, 755.

Example Thirteen

Experimental Procedures for Reactions Described in Table 4, FIG. 8

General Procedure Using the Precatalysts

An oven-dried test tube, which was equipped with a magnetic stir bar and fitted with a teflon septum, was charged with the precatalyst (1 mol %), ligand (1 mol %), 4-t-butylphenyl methanesulfonate (0.5 mmol, 114 mg), and K$_2$CO$_3$ (97 mg, 0.7 mmol). The vessel was evacuated and backfilled with argon (this process was repeated a total of 3 times) and then the aniline (55 μL, 0.6 mmol) and tert-butanol (6 mL) were added via syringe. The solution was heated to 110° C. for 4 h, cooled to room temperature, diluted with Ethyl acetate, and washed with water. Dodecane was then added as an internal standard and the reaction was analyzed by GC.

General Procedure for Water-Mediated Catalyst Preactivation

An oven-dried test tube, which was equipped with a magnetic stir bar and fitted with a teflon septum, was charged with Pd(OAc)$_2$ (1 mol %) and ligand (3 mol %). The vessel was evacuated and backfilled with argon (this process was repeated a total of 3 times) and the tert-butanol (1 mL) and degassed H$_2$O (8 mol %) were added via syringe. After addition of the water, the solution was heated to 110° C. for 1 min.

A second oven-dried test tube, which was equipped with a magnetic stir bar and fitted with a Teflon septum, was charged with 4-t-butylphenyl methanesulfonate (0.5 mmol, 114 mg) and K$_2$CO$_3$ (97 mg, 0.7 mmol). The vessel was evacuated and backfilled with argon (this process was repeated a total of 3 times) and then the aniline (55 μL, 0.6 mmol) and tert-butanol (5 mL) were added via syringe and the activated catalyst solution was transferred from the first reaction vessel into the second via cannula. The solution was heated to 110° C. for 4 h, cooled to room temperature, diluted with Ethyl acetate, and washed with water. Dodecane was then added as an internal standard and the reaction was analyzed by GC.

Example Fourteen

Experimental Procedures for Reactions Described in Table 5, FIG. 9

General Procedure A

An oven-dried test tube, which was equipped with a magnetic stir bar and fitted with a teflon septum, was charged with 10 (1 mol %) 1 (1 mol %) and K$_2$CO$_3$ (97 mg, 0.7 mmol). The vessel was evacuated and backfilled with argon (this process was repeated a total of 3 times) and then the aryl mesylate (0.5 mmol), amine (0.6 mmol), and tert-butanol (6 mL) were added via syringe (aryl chlorides or amines that were solids at room temperature were added with the catalyst and base). The solution was heated to 110° C. until the starting material was completely consumed as monitored by GC. The reaction mixture was then cooled to room temperature, diluted with ethyl acetate, washed with water, concentrated in vacuo, and purified via the Biotage SP4 (silica-packed 25+M cartridge).

Example Fifteen

Synthesis of N-(4-(1H-pyrrol-1-yl)phenyl)-2,5-dimethylaniline (FIG. 9, Table 5, Entry 1)

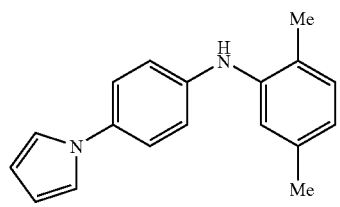

Following general procedure A, a mixture of 4-(1H-pyrrol-1-yl)phenylmethanesulfonate (119 mg, 0.5 mmol), 2,5-dimethylaniline (75 μL, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 0-30% EtOAc/hexanes) to provide the title compound as a white solid (138 mg, 95%), mp 97-98° C. $^1$H NMR (300 MHz, CDCl$_3$) δ: 7.31 (d, J=9.0 Hz, 2H), 7.14 (d, J=7.5 Hz, 1H), 7.04 (m, 5H), 6.82 (d, J=7.5 Hz, 1H), 6.37 (t, J=2.5 Hz, 2H), 5.40 (s, 1H), 2.33 (s, 3H), 2.27 (s, 3H) ppm. $^{13}$C NMR (75 MHz, CDCl$_3$) δ: 142.4, 141.1, 136.9, 134.4, 131.2, 125.6, 123.3, 122.3, 119.9, 119.8, 118.5, 110.0, 21.5, 17.8 ppm. IR (neat, cm$^{-1}$): 3386, 2920, 1519, 1310, 1072, 829, 726. Anal. Calcd. for C$_{18}$H$_{18}$N$_2$: C, 82.41; H, 6.92. Found: C, 82.03; H, 7.03.

Example Sixteen

Synthesis of ethyl 2-(4-fluorophenylamino)benzoate (FIG. 9, Table 5, Entry 2)

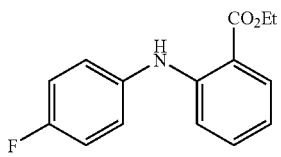

Following general procedure A, a mixture of 4-fluorophenylmethanesulfonate (95 mg, 0.5 mmol), ethyl 2-aminobenzoate (89 μL, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 0-20% EtOAc/hexanes) to provide the title compound as a yellow oil (118 mg, 91%). $^1$H NMR (300 MHz, CDCl$_3$) δ: 9.44 (s, 1H), 7.99 (d, J=8.0 Hz, 1H), 7.30 (t, J=7.5 Hz, 1H), 7.21 (m, 2H), 7.07 (m, 3H), 6.73 (t, J=7.5 Hz, 1H), 4.37 (q, J=7.5 Hz, 2H), 1.42 (t, J=7.5 Hz, 3H) ppm. $^{13}$C NMR (75 MHz, CDCl$_3$) δ: 168.8, 161.3, 158.1, 148.8, 136.9, 136.9, 134.4, 131.9, 125.4, 125.3, 117.1, 116.5, 116.2, 113.6, 112.0, 60.9, 14.6 ppm. IR (neat, cm$^{-1}$): 3316, 2982, 1683, 1583, 1513, 1455, 1260, 1233, 1082, 749. Anal. Calcd. for C$_{15}$H$_{14}$FNO$_2$: C, 69.49; H, 5.44. Found: C, 70.14; H, 5.64.

Example Seventeen

Synthesis of N-(4-fluorophenyl)-3,4,5-trimethoxyaniline (FIG. 9, Table 5, Entry 3)

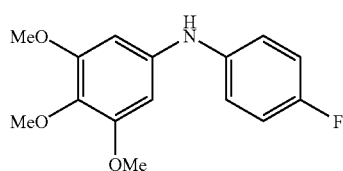

Following general procedure A, a mixture of 3,4,5-trimethoxyphenylmethanesulfonate (131 mg, 0.5 mmol), 4-fluoroaniline (57 μL, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 5-40% EtOAc/hexanes) to provide the title compound as a yellow oil (120 mg, 87%). $^1$H NMR (300 MHz, CDCl$_3$) δ: 6.99 (m, 4H), 6.22 (s, 2H), 5.57 (s, 1H), 3.80 (s, 3H), 3.78 (s, 6H) ppm. $^{13}$C NMR (75 MHz, CDCl$_3$) δ: 159.7, 156.5, 154.1, 140.5, 139.6, 132.5, 120.4, 120.3, 116.4, 116.1, 95.2, 61.3, 56.2 ppm. IR (neat, cm$^{-1}$): 3360, 2937, 1597, 1499, 1454, 1216, 1129, 1007, 785. Anal. Calcd. for C$_{15}$H$_{16}$FNO$_3$: C, 64.97; H, 5.82. Found: C, 65.24; H, 6.00.

Example Eighteen

Synthesis of ethyl 4-(2-methoxyphenylamino)benzoate (FIG. 9, Table 5, Entry 4)

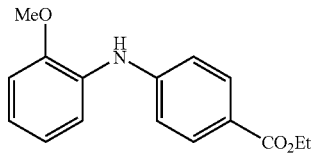

Following general procedure A, a mixture of 2-methoxyphenylmethanesulfonate (101 mg, 0.5 mmol), ethyl 4'-aminobenzoate (99 mg, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 0-30% EtOAc/hexanes) to provide the title compound as a clear oil (117 mg, 87%). $^1$H NMR (300 MHz, CDCl$_3$) δ: 7.96 (d, J=9.0 Hz, 2H), 7.41 (d, J=7.0 Hz, 1H), 7.09 (d, J=9.0 Hz, 2H), 6.97 (m, 3H), 6.42 (s, 1H), 4.35 (q, J=7.0 Hz, 2H), 3.87 (s, 3H), 1.39 (t, J=7.0 Hz, 3H) ppm. $^{13}$C NMR (75 MHz, CDCl$_3$) δ: 166.8, 149.7, 147.7, 131.6, 130.8, 122.4, 121.7, 121.0, 117.9, 115.4, 111.1, 60.7, 55.8, 14.7 ppm. IR (neat, cm$^{-1}$): 3354, 2979, 1704, 1593, 1526, 1276, 1175, 1105, 1027, 746. Sapountzis, I.; Knochel, P. J. Am. Chem. Soc. 2002, 124, 9390.

Example Nineteen

Synthesis of 1-(4-(biphenyl-4-ylamino)phenyl)ethanone (FIG. 9, Table 5, Entry 5)

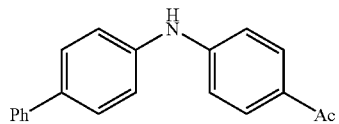

Following general procedure A, a mixture of 4-biphenylmethanesulfonate (124 mg, 0.5 mmol), 4'-aminoacetophenone (81 mg, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 15-50% EtOAc/hexanes) to provide the title compound as a white solid (139 mg, 97%), mp 136-139° C. $^1$H NMR (300 MHz, CDCl$_3$) δ: 7.90 (d, J=9.0 Hz, 2H), 7.59 (m 4H), 7.45 (t, J=7.0 Hz, 2H), 7.35 (t, J=7.0 Hz, 1H), 7.25 (d, J=9.0 Hz, 2H), 7.05 (d, J=9.0 Hz, 2H), 6.35 (s 1H), 2.55 (s, 3H) ppm. $^{13}$C NMR (75 MHz, CDCl$_3$) δ: 196.8, 148.4, 140.7, 140.2, 136.2, 130.9, 129.3, 129.1, 128.4, 127.3, 127.0, 120.9, 114.9, 26.5 ppm. IR (neat, cm$^{-1}$): 3324, 1656, 1586, 1524, 1487, 1339, 1278, 1178, 827, 763.

Example Twenty

Synthesis of ethyl 3-(4-(trifluoromethyl)phenylamino)benzoate (FIG. 9, Table 5, Entry 6)

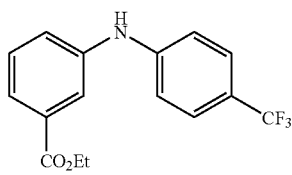

Following general procedure A, a mixture of ethyl 3-(methylsulfonyloxy)benzoate (122 mg, 0.5 mmol), 4-(trifluoromethyl)aniline (75 µL, 0.6 mmol), K$_2$CO$_3$ (97 mg, 0.7 mmol), 10 (4 mg, 1 mol %), 1 (2.5 mg, 1 mol %), and t-BuOH (6 mL) was heated to 110° C. for 16 h. The crude product was purified via the Biotage SP4 (silica-packed 25+M; 0-30% EtOAc/hexanes) to provide the title compound as a white solid (144 mg, 93%), mp 106-108° C. $^1$H NMR (300 MHz, CDCl$_3$) δ: 7.81 (s, 1H), 7.71 (d, J=7.0 Hz, 1H), 7.49 (d, J=8.5 Hz, 2H), 7.36 (m, 2H), 7.07 (d, J=8.5 Hz, 2H), 6.13 (s 1H), 4.38 (q, J=7.0 Hz, 2H), 1.39 (t, J=7.0 Hz, 3H) ppm. $^{13}$C NMR (75 MHz, CDCl$_3$) δ: 166.7, 146.3, 141.8, 132.1, 130.1, 129.8, 127.1, 127.0, 127.0, 126.9, 126.6, 123.8, 123.8, 123.0, 122.6, 122.2, 120.6, 116.0, 61.5, 14.5 ppm. IR (neat, cm$^{-1}$): 3358, 1701, 1620, 1543, 1333, 1158, 1108, 1070, 751. Anal. Calcd. for C$_{16}$H$_{14}$F$_3$O$_2$N: C, 62.13; H, 4.56. Found: C, 61.97; H, 4.46.

Example Twenty-One

Synthesis of Aryl Mesylates

All known aryl mesylates were synthesized using literature procedures. Munday, R. H.; Martinelli, J. R.; Buchwald, S. L. *J. Am. Chem. Soc.* 2008, 130, 2754. Ritter, T.; Stanek, K.; Larrosa, I.; Carreira, E. M. *Org. Lett.* 2004, 6, 1513. Fujikawa, N.; Ohta, T.; Yamaguchi, T.; Fukuda, T.; Ishibashi, F.; Iwao, M. *Tetrahedron* 2006, 62, 594.

Example Twenty-Two

Synthesis of Ethyl 3-(methylsulfonyloxy)benzoate

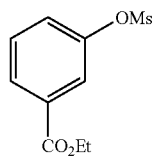

To a stirred solution of ethyl 3-hydroxybenzoate (3.32 g, 20 mmol) in dichloromethane (20 mL) cooled to 0° C. was added triethylamine (4.17 mL, 30 mmol). To this was added mesyl chloride (1.94 mL, 25 mmol) dropwise over 15 min. The reaction was stirred at 0° C. for 15 min then quenched with water and the phases separated. The aqueous layer was extracted with dichloromethane and the combined organics were dried over MgSO$_4$ and concentrated in vacuo. The crude material was purified via the Biotage SP4 (silica-packed 25+M; 0-50% EtOAc/hexanes) to provide the title compound as a white solid (2.698 g, 55%). $^1$H NMR (300 MHz, CDCl$_3$) δ: 7.98 (m, 1H), 7.89 (s, 1H), 7.47 (m, 2H), 4.35 (q, J=7.0 Hz, 2H), 3.16 (s, 3H), 1.37 (t, J=7.0 Hz, 3H) ppm. $^{13}$C NMR (75 MHz, CDCl$_3$) δ: 165.3, 149.3, 132.9, 130.3, 128.7, 126.9, 123.2, 61.8, 37.8, 14.5 ppm. IR (neat, cm$^{-1}$): 1721, 1384, 1369, 1268, 1194, 1168, 1098, 936, 840, 798.

Example Twenty-Three

General Experimental Procedures for Examples Described in FIG. 11, Table 7

General Procedure B

An oven-dried test tube, which was equipped with a magnetic stir bar and fitted with a teflon septum, was charged with the precatalyst (0.01 equiv.) and NaOt-Bu (120 mg, 1.2 mmol). The vessel was evacuated and backfilled with argon (this process was repeated a total of 3 times) and then the aryl chloride (1.0 mmol), 2M methylamine solution in THF (1 mL, 2.0 mmol), and t-BuOH (1 mL) were added in succession via syringe (aryl chlorides that were solids at room temperature were added with the precatalyst and base). The solution was allowed to stir at room temperature until starting aryl chloride was completely consumed as monitored by GC. The reaction mixture was then diluted with ethyl acetate, washed with aqueous NH$_4$Cl, dried over Na$_2$SO4 concentrated in vacuo, and purified via column chromatography on silica gel.

Procedure C

General procedure A was used with the following modification: 2 M methylamine solution in THF (1 mL, 2.0 mmol), and t-BuOH (4 mL) were premixed and added to the reaction vessel.

Example Twenty-Four

Synthesis of 4-Methoxy-N-methylaniline (FIG. 11, Table 7, Entry 1)

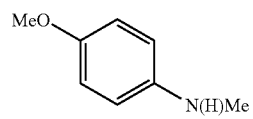

Following general procedure A, a mixture of 4-chloroanisole (123 µL, 1.0 mmol), 2M methylamine (1 mL, 2.0 mmol), NaOt-Bu (120 mg, 1.2 mmol), BrettPhos precatalyst 10 (8 mg, 0.01 mmol), and t-BuOH (1 mL) was stirred at room temperature for 2 h. The crude product was purified via column chromatography (20:1 CH$_2$Cl$_2$/MeOH) to provide the title compound as a yellow liquid that turned into a tan solid upon standing (126 mg, 92%). $^1$H NMR (400 MHz, CDCl$_3$) δ: 6.80 (dt, J=9.0, 2.3 Hz, 2H), 6.59 (dt, J=9.0, 2.3 Hz, 2H), 3.76 (s, 3H), 3.46 (bs, 1H), 2.81 (s, 3H) ppm. $^{13}$C NMR (75 MHz, CDCl$_3$) δ: 152.2, 143.9, 115.1, 113.8, 56.1, 31.8 ppm. Ali, H. I.; Tomita, K.; Akaho, E.; Kambara, H.; Miura, S.;

Hayakawa, H.; Ashida, N.; Kawashima, Y.; Yamagishi, T.; Ikeya, H.; Yoneda, F.; Nagamatsu, T. *Bioorg. Med. Chem.* 2007, 15, 242.

Example Twenty-Five

Synthesis of 3,5-Dimethoxy-N-methylaniline (FIG. 11, Table 7, Entry 2)

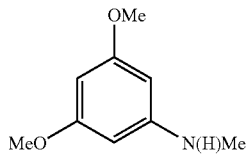

Following general procedure A, a mixture of 3,5-dimethoxychlorobenzene (173 mg, 1.0 mmol), 2M methylamine (1 mL, 2.0 mmol), NaOt-Bu (120 mg, 1.2 mmol), BrettPhos precatalyst 10 (8 mg, 0.01 mmol), and t-BuOH (1 mL) was stirred at room temperature for 2 h. The crude product was purified via column chromatography (80:20 to 50:50 Hexanes/EtOAc gradient) to provide the title compound as a pale yellow liquid (150 mg, 90%). $^1$H NMR (400 MHz, CDCl$_3$) δ: 5.89 (t, J=2.2 Hz, 1H), 5.80 (t, J=2.2 Hz, 2H), 3.76 (s, 7H), 2.81 (s, 3H) ppm. $^{13}$C NMR (75 MHz, CDCl$_3$) δ: 161.9, 151.5, 91.4, 89.7, 55.3, 30.9 ppm. Brown, F. J.; Bernstein, P. R.; Cronk, L. A.; Dosset, D. L.; Hebbel, K. C.; Maduskuie, T. P.; Shapiro, H. S.; Vacek, E. P.; Yee, Y. K.; Willard, A. K.; Krell, R. D.; Snyder, D. W. *J. Med. Chem.* 1989, 32, 807.

Example Twenty-Six

Synthesis of N-Methylpyridin-3-amine (FIG. 11, Table 7, Entry 3)

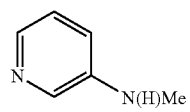

Following general procedure B, a mixture of 3-chloropyridine (95 μL, 1.0 mmol), 2M methylamine (1 mL, 2.0 mmol), NaOt-Bu (120 mg, 1.2 mmol), BrettPhos precatalyst 10 (8 mg, 0.01 mmol), and t-BuOH (4 mL) was stirred at room temperature for 2 h. The crude product was purified via column chromatography (20:1 CH$_2$Cl$_2$/MeOH) to provide the title compound as a pale yellow liquid (97 mg, 90%). The isolated product was a 35:1 mixture of mono:diarylation methylamine. $^1$H NMR (400 MHz, CDCl$_3$) δ: 8.02 (d, J=2.9, 1H), 7.95 (dd, J=4.7, 1.3, 1H), 7.09 (dd, J=8.3, 4.7, 1H), 6.86 (ddd, J=8.2, 2.9, 1.3, 1H), 3.79 (bs, 1H), 2.85 (d, J=5.1, 3H) ppm. $^{13}$C NMR (75 MHz, CDCl$_3$) δ: 145.3, 138.9, 136.0, 123.9, 118.2, 30.5 ppm. Watanabe, T.; Tanaka, Y.; Sekiya, K.; Akita, Y.; Ohta, A. *Synthesis* 1980, 39.

Example Twenty-Seven

Synthesis of N-methylquinolin-6-amine (FIG. 11, Table 7, Entry 4)

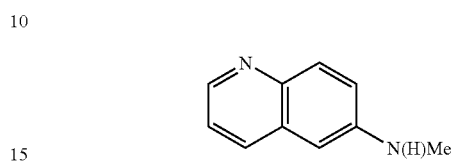

Following general procedure A, a mixture of 6-chloroquinoline (164 mg, 1.0 mmol), 2M methylamine (1 mL, 2.0 mmol), NaOt-Bu (120 mg, 1.2 mmol), BrettPhos precatalyst 10 (8 mg, 0.01 mmol), and t-BuOH (1 mL) was stirred at room temperature for 17 h. The crude product was purified via column chromatography (99:1 to 97:3 CH$_2$Cl$_2$/MeOH gradient) to provide the title compound as a yellow oil (150 mg, 95%). $^1$H NMR (400 MHz, CDCl$_3$) δ: 8.62 (dd, J=4.2, 1.7 Hz, 1H), 7.94 (d, J=8.3 Hz, 1H), 7.88 (d, J=9.1 Hz, 1H), 7.26 (dd, J=8.3, 4.2 Hz, 1H), 7.09 (dd, J=9.1, 2.6 Hz, 1H), 6.68 (d, J=2.6 Hz, 1H), 4.19 (bs, 1H), 2.93 (s, 3H) ppm. $^{13}$C NMR (75 MHz, CDCl$_3$) δ: 147.4, 146.1, 143.3, 133.9, 130.3, 130.2, 121.5, 102.4, 30.8 ppm.

Example Twenty-Eight

Experimental Procedures for Reactions Described in FIG. 12, Table 8

General Procedure D

An oven-dried test tube, which was equipped with a magnetic stir bar and fitted with a teflon septum, was charged with 10 (0.05 mol %) 1 (0.05 mol %) and NaOt-Bu (1.15 g, 12 mmol). The vessel was evacuated and backfilled with argon (this process was repeated a total of 3 times) and then the aryl chlorodie (10 mmol), amine (14 mmol), and Bu$_2$O (3 mL) were added via syringe. The solution was heated to 85° C. until the starting material was completely consumed as monitored by GC. The reaction mixture was then cooled to room temperature, diluted with ethyl acetate, washed with water, concentrated in vacuo, and purified via the Biotage SP4 (silica-packed 100 g snap cartridge).

General Procedure E

An oven-dried test tube, which was equipped with a magnetic stir bar, was taken into a nitrogen filled dry-box and charged with NaOt-Bu (115 mg, 1.2 mmol), amine (1.2 mmol), aryl chloride (1.0 mmol), and Bu$_2$O (1 mL). A solution of 1 and 10 in toluene (50 μL, 0.02 M, 0.01 mol % 1, 0.01 mol % 10) was added and then the reaction vessel was sealed, removed from the dry-box and heated to 110° C. until the starting material was completely consumed as monitored by GC. The reaction mixture was then cooled to room temperature, diluted with ethyl acetate, washed with water, concentrated in vacuo, and purified via the Biotage SP4 (silica-packed 25+M cartridge).

Example Twenty-Nine

Synthesis of N-hexyl-4-methoxyaniline (FIG. 12, Table 8, Entry 1)

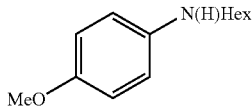

Following general procedure D, a mixture of 4-chloroanisole (1.23 mL, 10 mmol), hexylamine (1.83 mL, 14 mmol), NaOt-Bu (1.15 g, 12 mmol), 10 (4 mg, 0.05 mol %), 1 (2.5 mg, 0.05 mol %), and Bu$_2$O (3 mL) was heated to 85° C. for 1 h. The crude product was purified via the Biotage SP4 (silica-packed 100 g; 0-50% EtOAc/hexanes) to provide the title compound as a yellow oil (1.828 g, 88%). $^1$H NMR (300 MHz, CDCl$_3$) δ: 6.84 (d, J=9.0 Hz, 2H), 6.62 (d, J=9.0 Hz, 2H), 3.78 (s, 3H), 3.40 (s, 1H), 3.09 (t, J=7.0 Hz, 2H), 1.64 (pentet, J=7.5 Hz, 2H), 1.42 (m, 6H), 0.97 (t, J=7.0 Hz, 3H) ppm. $^{13}$C NMR (75 MHz, CDCl$_3$) δ: 152.2, 143.2, 115.1, 114.2, 56.0, 45.3, 32.0, 30.0, 27.2, 23.0, 14.4 ppm. IR (neat, cm$^{-1}$): 3394, 2929, 2857, 2831, 1513, 1466, 1237, 1180, 1040, 819, 520.

Example Thirty

Synthesis of N-benzyl-4-methoxyaniline (FIG. 12, Table 8, Entry 2)

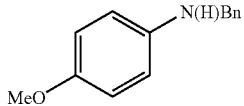

Following general procedure D, a mixture of 4-chloroanisole (1.23 mL, 10 mmol), benzylamine (1.52 mL, 14 mmol), NaOt-Bu (1.15 g, 12 mmol), 10 (4 mg, 0.05 mol %), 1 (2.5 mg, 0.05 mol %), and Bu$_2$O (3 mL) was heated to 85° C. for 1 h. The crude product was purified via the Biotage SP4 (silica-packed 25+M; 0-50% EtOAc/hexanes) to provide the title compound as a yellow oil (2.059 g, 97%). $^1$H NMR (300 MHz, CDCl$_3$) δ: 7.63-7.52 (m, 5H), 7.06 (d, J=9.0 Hz, 2H), 6.81 (d, J=9.0 Hz, 2H), 4.46 (s, 2H), 4.05 (s, 1H), 3.92 (s, 3H) ppm. $^{13}$C NMR (75 MHz, CDCl$_3$) δ: 152.6, 143.1, 140.5, 129.2, 128.1, 127.7, 115.4, 114.6, 56.1, 49.5 ppm. IR (neat, cm$^{-1}$): 3414, 3029, 2832, 1513, 1453, 1235, 1036, 820, 743, 698. Anal. Calcd. for C$_{14}$H$_{15}$NO: C, 78.84; H, 7.09. Found: C, 78.61; H, 7.10.

Example Thirty-One

Synthesis of N-Hexylaniline (FIG. 12, Table 8, Entry 3)

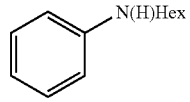

Following general procedure D, a mixture of chlorobenzene (1.02 mL, 10 mmol), hexylamine (1.83 mL, 14 mmol), NaOt-Bu (1.15 g, 12 mmol), 10 (4 mg, 0.05 mol %), 1 (2.5 mg, 0.05 mol %), and Bu$_2$O (3 mL) was heated to 85° C. for 1 h. The crude product was purified via the Biotage SP4 (silica-packed 50 g; 0-50% EtOAc/hexanes) to provide the title compound as a clear oil (1.607 g, 91%). $^1$H NMR (300 MHz, CDCl$_3$) δ: 7.33 (t, J=7.5 Hz, 2H), 6.85 (t, J=7.5 Hz, 1H), 6.74 (d, J=7.5 Hz, 2H), 3.70 (s, 1H), 3.23 (t, J=7.0 Hz, 2H), 1.74 (pentet, J=7.0 Hz, 2H), 1.51 (m, 6H), 1.09 (t, J=7.0 Hz, 3H) ppm. $^{13}$C NMR (75 MHz, CDCl$_3$) δ: ppm 148.9, 129.6, 117.4, 113.0, 44.4, 32.1, 29.9, 27.3, 23.1, 14.5. IR (neat, cm$^{-1}$): 3412, 2956, 2928, 1603, 1507, 1321, 1259, 748, 692. Anal. Calcd. for C$_{12}$H$_{19}$N: C, 81.30; H, 10.80. Found: C, 81.37; H, 10.73.

Example Thirty-Two

Synthesis of N-benzylaniline (FIG. 12, Table 8, Entry 4)

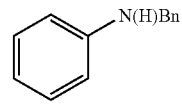

Following general procedure D, a mixture of chlorobenzene (1.02 mL, 10 mmol), benzylamine (1.52 mL, 14 mmol), NaOt-Bu (1.15 g, 12 mmol), 10 (4 mg, 0.05 mol %), 1 (2.5 mg, 0.05 mol %), and Bu$_2$O (3 mL) was heated to 85° C. for 1 h. The crude product was purified via the Biotage SP4 (silica-packed 25+M; 0-50% EtOAc/hexanes) to provide the title compound as a yellow oil (1.646 g, 90%). $^1$H NMR (300 MHz, CDCl$_3$) δ: 7.69-7.61 (m, 5H), 7.53 (t, J=7.5 Hz, 2H), 7.09 (t, J=7.5 Hz, 1H), 6.92 (d, J=7.5 Hz, 2H), 4.57 (s, 2H), 4.22 (s, 1H) ppm. $^{13}$C NMR (75 MHz, CDCl$_3$) δ: 148.8, 140.2, 129.9, 129.3, 128.1, 127.8, 118.1, 113.5, 48.7 ppm. IR (neat, cm$^{-1}$): 3419, 3052, 3026, 2841, 1603, 1506, 1453, 1325, 750, 693. Anal. Calcd. for C$_{13}$H$_{13}$N: C, 85.21; H, 7.15. Found: C, 85.04; H, 7.15.

Example Thirty-Three

Synthesis of N-hexyl-2-methylaniline (FIG. 12, Table 8, Entry 5)

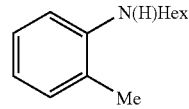

Following general procedure D, a mixture of 2-chlorotoluene (1.17 mL, 10 mmol), hexylamine (1.82 mL, 14 mmol), NaOt-Bu (1.15 g, 12 mmol), 10 (4 mg, 0.05 mol %), 1 (2.5 mg, 0.05 mol %), and Bu$_2$O (3 mL) was heated to 85° C. for 1 h. The crude product was purified via the Biotage SP4 (silica-packed 50 g snap; 0-50% EtOAc/hexanes) to provide the title compound as a clear oil (1.732 g, 91%). $^1$H NMR (300 MHz, CDCl$_3$) δ: 7.33 (t, J=7.5 Hz, 1H), 7.25 (d, J=7.5 Hz, 1H), 6.83 (m, 2H), 3.61 (s, 1H), 3.33 (t, J=7.0 Hz, 2H), 2.32 (s, 3H), 1.85 (septet, J=7.0 Hz, 2H), 1.58 (m, 6H), 1.14 (t, J=7.0 Hz, 3H) ppm. $^{13}$C NMR (75 MHz, CDCl$_3$) δ: 146.8, 130.4, 127.6, 122.0, 117.0, 110.0, 44.4, 32.2, 30.0, 27.4, 23.2, 17.9, 14.5 ppm. IR (neat, cm$^{-1}$): 3430, 2956, 2924, 2856, 1607, 1514, 1473, 1317, 1260, 745. Anal. Calcd. for C$_{13}$H$_{21}$N: C, 81.61; H, 11.06. Found: C, 81.81; H, 11.02.

Example Thirty-Four

Synthesis of 2,5-dimethyl-N-(3-(trifluoromethyl)phenyl)aniline (FIG. 12, Table 8, Entry 6)

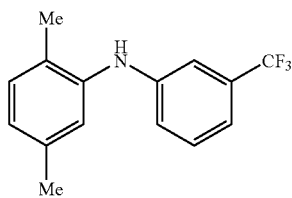

Following general procedure E, a mixture of 2-chloro-p-xylene (134 μL, 1.0 mmol), 3-(trifluoromethyl)aniline (150 μL, 1.2 mmol), NaOt-Bu (115 mg, 1.2 mmol), 10 (0.08 mg, 0.01 mol %), 1 (0.05 mg, 0.01 mol %), and Bu$_2$O (1 mL) was heated to 110° C. for 1 h. The crude product was purified via the Biotage SP4 (silica-packed 25+M; 0-30% EtOAc/hexanes) to provide the title compound as a clear oil (248 mg, 94%). $^1$H NMR (300 MHz, CDCl$_3$) δ: 7.38 (t, J=8.0 Hz, 1H), 7.22 (d, J=8.0 Hz, 1H), 7.16 (m, 3H), 7.08 (d, J=8.0 Hz, 1H), 6.95 (d, J=8.0 Hz, 1H), 5.53 (s, 1H), 2.39 (s, 3H), 2.28 (s, 3H) ppm. $^{13}$C NMR (75 MHz, CDCl$_3$) δ: 145.5, 139.8, 137.1, 132.6, 132.2, 131.8, 131.8, 131.4, 130.1, 130.0, 127.5, 126.4, 124.9, 124.9, 124.8, 122.8, 122.1, 122.0, 119.2, 119.1, 116.3, 116.3, 112.8, 21.4, 17.7 ppm. IR (neat, cm$^{-1}$): 3391, 3021, 2924, 1613, 1485, 1337, 1165, 1124, 787, 699. Anal. Calcd. for C$_{15}$H$_{14}$F$_3$N: C, 67.91; H, 5.32. Found: C, 68.02; H, 5.31.

Example Thirty-Five

Synthesis of N-(4-ethoxyphenyl)-2,5-dimethylaniline (FIG. 12, Table 8, Entry 7)

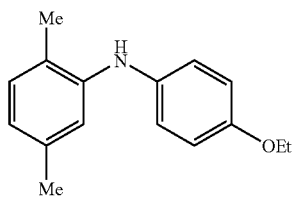

Following general procedure E, a mixture of 2-chloro-p-xylene (134 μL, 1.0 mmol), 4-ethoxyaniline (154 μL, 1.2 mmol), NaOt-Bu (115 mg, 1.2 mmol), 10 (0.08 mg, 0.01 mol %), 1 (0.05 mg, 0.01 mol %), and Bu$_2$O (1 mL) was heated to 110° C. for 1 h. The crude product was purified via the Biotage SP4 (silica-packed 25+M; 0-30% EtOAc/hexanes) to provide the title compound as a white solid (235 mg, 98%), mp 56-58° C. $^1$H NMR (300 MHz, CDCl$_3$) δ: 7.10 (m, 3H), 6.95 (m, 3H), 6.72 (d, J=7.5 Hz, 1H), 5.26 (s, 1H), 4.09 (q, J=7.0 Hz, 2H), 2.33 (s, 3H), 2.29 (s, 3H), 1.51 (t, J=7.0 Hz, 3H) ppm. $^{13}$C NMR (75 MHz, CDCl$_3$) δ: 154.7, 143.5, 136.8, 136.5, 130.9, 122.5, 121.0, 116.1, 116.1, 115.6, 64.1, 21.6, 17.7, 15.3 ppm. IR (neat, cm$^{-1}$): 3402, 2978, 2923, 1511, 1478, 1292, 1238, 1117, 1049, 798. Anal. Calcd. for C$_{16}$H$_{19}$NO: C, 79.63; H, 7.94. Found: C, 79.70; H, 8.01.

Example Thirty-Six

Synthesis of 4-fluoro-N-(4-methoxyphenyl)aniline (FIG. 12, Table 8, Entry 8)

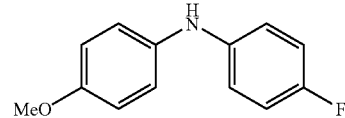

Following general procedure E, a mixture of 4-chloroanisole (123 μL, 1.0 mmol), 4-fluoroaniline (114 μL, 1.2 mmol), NaOt-Bu (115 mg, 1.2 mmol), 10 (0.08 mg, 0.01 mol %), 1 (0.05 mg, 0.01 mol %), and Bu$_2$O (1 mL) was heated to 110° C. for 1 h. The crude product was purified via the Biotage SP4 (silica-packed 25+M; 0-30% EtOAc/hexanes) to provide the title compound as a white solid (209 mg, 94%), mp 59-60° C. $^1$H NMR (300 MHz, CDCl$_3$) δ: 7.03-6.86 (m, 8H), 5.41 (s, 1H), 3.81 (s, 3H) ppm. $^{13}$C NMR (75 MHz, CDCl$_3$) δ: 159.0, 155.8, 155.2, 141.4, 136.8, 121.0, 118.0, 117.9, 116.2, 115.9, 115.0, 55.8 ppm. IR (neat, cm$^{-1}$): 3391, 3007, 1508, 1314, 1243, 1221, 1027, 814, 772, 591. Anal. Calcd. for C$_{13}$H$_{12}$FNO: C, 71.87; H, 5.57. Found: C, 71.89; H, 5.62.

Example Thirty-Seven

Synthesis of 4-ethoxy-N-(4-methoxyphenyl)aniline (FIG. 12, Table 8, Entry 9)

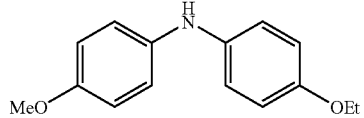

Following general procedure E, a mixture of 4-chloroanisole (123 μL, 1.0 mmol), 4-ethoxyaniline (154 μL, 1.2 mmol), NaOt-Bu (115 mg, 1.2 mmol), 10 (0.08 mg, 0.01 mol %), 1 (0.05 mg, 0.01 mol %), and Bu$_2$O (1 mL) was heated to 110° C. for 1 h. The crude product was purified via the Biotage SP4 (silica-packed 25+M; 0-30% EtOAc/hexanes) to provide the title compound as a white solid (229 mg, 94%), mp 73-75° C. $^1$H NMR (300 MHz, CDCl$_3$) δ: 6.95 (m, 4H), 6.84 (m, 4H), 5.34 (s, 1H), 4.01 (q, J=7.0 Hz, 2H), 3.80 (s, 3H), 1.43 (t, J=7.0 Hz, 3H) ppm. $^{13}$C NMR (75 MHz, CDCl$_3$) δ: 154.4, 153.8, 138.2, 138.1, 119.8, 119.7, 115.7, 114.9, 64.1, 55.9, 15.3 ppm. IR (neat, cm$^{-1}$): 3421, 2983, 2956, 1513, 1298, 1253, 1116, 1052, 1037, 814. Anal. Calcd. for C$_{15}$H$_{17}$NO$_2$: C, 74.05; H, 7.04. Found: C, 73.95; H, 7.06.

Example Thirty-Eight

Synthesis of N-(4-methoxyphenyl)-2,5-dimethylaniline (FIG. 12, Table 8, Entry 10)

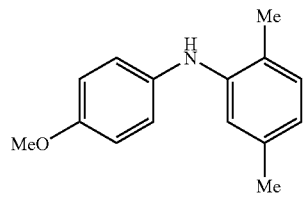

Following general procedure E, a mixture of 4-chloroanisole (123 µL, 1.0 mmol), 2,5-dimethylaniline (149 µL, 1.2 mmol), NaOt-Bu (115 mg, 1.2 mmol), 10 (0.08 mg, 0.01 mol %), 1 (0.05 mg, 0.01 mol %), and Bu$_2$O (1 mL) was heated to 110° C. for 1 h. The crude product was purified via the Biotage SP4 (silica-packed 25+M; 0-30% EtOAc/hexanes) to provide the title compound as a white solid (220 mg, 97%), mp 40-41° C. $^1$H NMR (300 MHz, CDCl$_3$) δ: 7.11 (m, 3H), 6.96 (m, 3H), 6.75 (d, J=7.5 Hz, 1H), 5.27 (s, 1H), 3.88 (s, 3H), 2.33 (s, 3H), 2.30 (s, 3H) ppm. $^{13}$C NMR (75 MHz, CDCl$_3$) δ: 155.3, 143.5, 136.8, 136.7, 131.0, 122.7, 122.5, 121.1, 116.2, 115.0, 55.9, 21.7, 17.7 ppm. IR (neat, cm$^{-1}$): 3400, 2921, 1579, 1511, 1463, 1292, 1241, 1037, 828, 800. Anal. Calcd. for C$_{15}$H$_{17}$NO: C, 79.26; H, 7.54. Found: C, 79.11; H, 7.59.

Example Thirty-Nine

Experimental Procedures for Reactions Described in FIG. 13, Table 9

General Procedure F

An oven-dried test tube, which was equipped with a magnetic stir bar and fitted with a teflon septum, was charged with 10 (1 mol %) 1 (1 mol %) and NaOt-Bu (2.0 equiv). The vessel was evacuated and backfilled with argon (this process was repeated a total of 3 times) and then the aryl chlorodie (1.0 equiv), amine (1.2 equiv), and dioxane (1 mL/mmol) were added via syringe. The solution was heated to 80° C. until the starting material was completely consumed as monitored by GC. The reaction mixture was then cooled to room temperature, diluted with ethyl acetate, washed with water, concentrated in vacuo, and purified via the Biotage SP4 (silica-packed 50 g snap cartridge).

Example Forty

Synthesis of N$^1$,N$^4$-diphenylbutane-1,4-diamine (FIG. 13, Table 9, Entry 1)

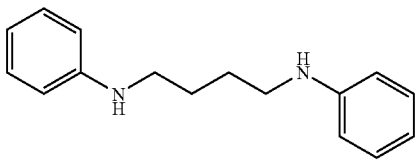

Following general procedure F, a mixture of chlorobenzene (51 µL, 0.5 mmol), N$^1$-phenylbutane-1,4-diamine (98 mg, 0.6 mmol), NaOt-Bu (97 mg, 1.0 mmol), 10 (4 mg, 1 mol %), 1 (2.5 mg, 1 mol %), and dioxane (0.5 mL) was heated to 80° C. for 2 h. The crude product was purified via the Biotage SP4 (silica-packed 50 g snap; 0-75% EtOAc/hexanes) to provide the title compound as a clear oil (108 mg, 91%). $^1$H NMR (300 MHz, CDCl$_3$) δ: 7.28 (t, J=7.0 Hz, 4H), 6.80 (t, J=7.0 Hz, 2H), 6.68 (d, J=7.0 Hz, 4H), 3.68 (s, 2H), 3.22 (m, 4H), 1.78 (m, 4H) ppm. $^{13}$C NMR (75 MHz, CDCl$_3$) δ: 148.6, 129.6, 117.6, 113.1, 44.0, 27.4 ppm. IR (neat, cm$^{-1}$): 3407, 3050, 2934, 2861, 1603, 1507, 1477, 1321, 1257, 1179, 749, 693. Anal. Calcd. for C$_{16}$H$_{20}$N$_2$: C, 79.96; H, 8.39. Found: C, 80.20; H, 8.48.

Example Forty-One

Synthesis of N-(piperidin-4-ylmethyl)aniline (FIG. 13, Table 9, Entry 2)

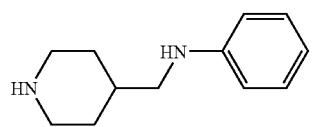

Following general procedure F, a mixture of chlorobenzene (102 µL, 1.0 mmol), 4-(aminomethyl)piperidine (137 mg, 1.2 mmol), NaOt-Bu (192 mg, 2.0 mmol), 10 (8 mg, 1 mol %), 1 (5 mg, 1 mol %), and dioxane (1 mL) was heated to 80° C. for 15 h. The crude product was purified via the Biotage SP4 (silica-packed 50 g snap; 7-9% MeOH/CH$_2$Cl$_2$) to provide the title compound as a white solid (159 mg, 84%), mp 60-61° C. $^1$H NMR (300 MHz, DMSO) δ: 7.02 (t, J=7.5 Hz, 2H), 6.52 (d, J=8.0 Hz, 2H), 6.46 (t, J=8.0 Hz, 1H), 5.58 (s, 1H), 3.11 (s, 1H), 2.92 (d, J=11.5 Hz, 2H), 2.82 (t, J=6.0 Hz, 2H), 2.41 (t, J=10 Hz, 2H), 1.64 (m, 3H), 1.02 (m 2H) ppm. $^{13}$C NMR (75 MHz, DMSO) δ: 149.8, 129.5, 115.8, 112.5, 50.0, 46.5, 36.2, 31.7 ppm. IR (neat, cm$^{-1}$): 3326, 2919, 1602, 1509, 1427, 1325, 1263, 749, 694.

Example Forty-Two

Synthesis of N$^1$, N$^4$-diphenylbenzene-1,4-diamine (FIG. 13, Table 9, Entry 3)

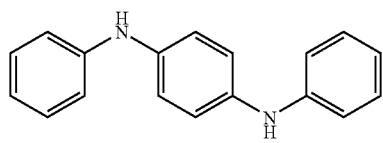

Following general procedure F, a mixture of chlorobenzene (102 µL, 1.0 mmol), N$^1$-phenylbenzene-1,4-diamine (221 mg, 1.2 mmol), NaOt-Bu (192 mg, 2.0 mmol), 10 (8 mg, 1 mol %), 1 (5 mg, 1 mol %), and dioxane (1 mL) was heated to 80° C. for 2 h. The crude product was purified via the Biotage SP4 (silica-packed 50 g snap; 0-50% EtOAc/Hexane) to provide the title compound as a off-white solid (260 mg, 99%), mp 152-154° C. $^1$H NMR (300 MHz, CDCl$_3$) δ: 7.27 (t, J=7.5 Hz, 4H), 7.08 (s, 4H), 7.00 (d, J=8.0 Hz, 4H), 6.90 (t, J=7.5 Hz, 2H), 5.59 (s, 2H) ppm. $^{13}$C NMR (75 MHz, CDCl$_3$) δ: 144.7, 137.4, 129.6, 121.2, 120.2, 116.5 ppm. IR (neat, cm$^{-1}$): 3389, 1601, 1512, 1496, 1382, 1313, 1271, 820, 742, 695. Anal. Calcd. for $C_{18}H_{16}N_2$: C, 83.04; H, 6.19. Found: C, 82.81; H, 6.22.

Example Forty-Three

Synthesis of BrettPhosPdPhBr (17)

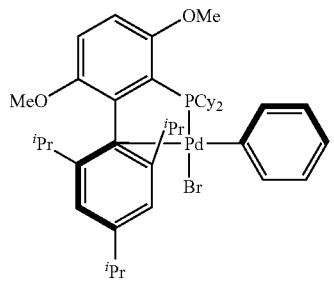

In a nitrogen filled glovebox, a solution of BrettPhos (1, 23.6 mg, 44 μmol), bromobenzene (30 μL) and THF (2 mL) was added to solid (COD)Pd(CH$_2$SiPhMe$_2$)$_2$ (20.4 mg, 40 μmol) (COD=1,5-cyclooctadiene) in an oven-dried 20 mL vial. (The THF used in this experiment was prepared as described in the general procedures set forth in Example 7, then sparged with N$_2$ for 30 min and stored over activated 3 Å molecular sieves in a glovebox prior to use.) Pan, Y.; Young, G. B. *J. Organomet. Chem.* 1999, 577, 257. The vial was capped, and the resulting yellow solution was allowed to stand for 48 h at rt. After this time, pentane (8 mL) was layered on top of the THF solution and the vial was allowed to stand for 24 h resulting in the formation of crystals. After 24 h, the crystals were collected via vacuum filtration in the glovebox, and dried under vacuum to provide 17 (24 mg, 75%) as light-yellow needles as a THF mono-solvate: $^1$H NMR (400 MHz, CD$_2$Cl$_2$, mixture of rotomers) δ 7.26-7.29 (m, 2H—minor), 7.00-7.06 (m, major and minor), 6.82-6.92 (m, major and minor), 6.75-6.79 (m, 1H—minor, 1H—major), 4.33 (s, 3H—minor), 3.79 (s, 3H—major), 3.59 (s, 3H—minor), 3.33 (s, 3H—major), 3.00-3.08 (m, 1H—major), 2.88-2.92 (m, 1H—major), 2.72-2.82 (m, 2H—major), 2.46-2.53 (m, 2H—major), 2.32-2.37 (m, 2H—minor), 1.50-1.90 (m, major and minor), 1.05-1.45 (m), 0.75-0.90 (m, 12H—major and minor), 0.55-0.65 (m, 2H—minor); $^{31}$P NMR (162 MHz, CD$_2$Cl$_2$, mixture of rotomers) δ 44.9 (minor), 36.9 (major).

Example Forty-Four

Synthesis of BrettPhosPdPhCl (18)

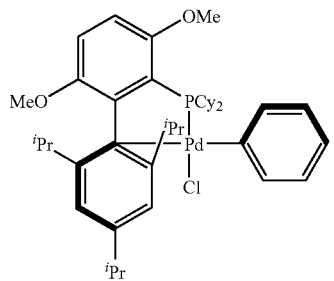

In a nitrogen filled glovebox, a solution of BrettPhos (1, 51.0 mg, 96 μmol), chlorobenzene (100 μL) and THF (4 mL) was added to solid (COD)Pd(CH$_2$SiPhMe$_2$)$_2$ (40.8 mg, 80 μmol) in an oven-dried 20 mL vial. The vial was capped, and the resulting yellow solution was allowed to stand for 48 h at rt. After this time, pentane (14 mL) was layered on top of the THF solution and the vial was allowed to stand for 24 h resulting in the formation of crystals. After 24 h, the crystals were collected via vacuum filtration in the glovebox, and dried under vacuum to provide 18 (42 mg, 69%) as light-yellow microcrystalline powder: $^1$H NMR (400 MHz, CD$_2$Cl$_2$, mixture of rotomers) δ 7.28-7.30 (m, 2H—minor), 7.07-7.10 (m, 2H—minor), 7.04 (s, 2H—major), 7.02 (s, 2H—minor), 6.82-6.92 (m, major and minor), 6.76-6.82 (m, 1H—minor, 1H—major), 4.29 (s, 3H—minor), 3.79 (s, 3H—major), 3.59 (s, 3H—minor), 3.34 (s, 3H—major), 2.96-3.03 (m, 1H—major), 2.88-2.95 (m, 1H—major), 2.71-2.80 (m, 2H—major), 2.46-2.53 (m, 2H—major), 2.32-2.37 (m, 2H—minor), 1.50-1.90 (m, major and minor), 1.08-1.45 (m), 0.78-0.92 (m, major and minor), 0.55-0.65 (m, 2H—minor); $^{31}$P NMR (162 MHz, CD$_2$Cl$_2$, mixture of rotomers) δ 46.8 (minor), 38.6 (major). Anal Calc for $C_{41}H_{58}ClO_2PPd$: C, 65.16; H, 7.74;. Found: C, 65.42; H, 7.53.

Example Forty-Five

Synthesis of BrettPhosPd(3,5-dimethylphenyl)Br (19)

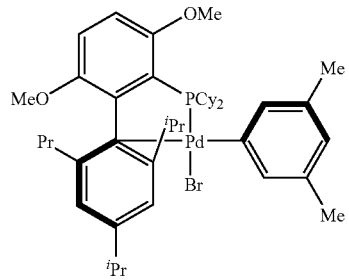

In a nitrogen filled glovebox, a solution of BrettPhos (1, 172 mg, 321 μmol), 3,5-dimethylbromobenzene (225 μL) and THF (15 mL) was added to solid (COD)Pd(CH$_2$SiPhMe$_2$)$_2$ (150 mg, 292 μmol) in an oven-dried 100 mL round bottom flask. The flask was capped, and the resulting yellow solution was allowed to stand for 48 h at rt. After this time, pentane (60 mL) was layered on top of the THF solution and the vial was allowed to stand for 24 h resulting in the formation of crystals. After 24 h, the crystals were collected via vacuum filtration in the glovebox, and dried under vacuum to provide 19 (185 mg, 77%) as light-yellow microcrystalline powder as a THF mono-solvate: $^1$H NMR (400 MHz, CD$_2$Cl$_2$, mixture of rotomers) δ 7.01-7.08 (m, 2H—major, 4H—minor), 6.90 (s, 2H—minor), 6.89 (dd, J=9.2, 2.8, 1H—major), 6.83 (d, J=8.8 Hz, 1H—major), 6.64 (s, 2H—major), 6.41 (s, 1H—minor, 2H—major), 4.31 (s, 3H—minor), 3.78 (s, 3H—major), 3.59 (s, 3H—minor), 3.32 (s, 3H—major), 3.03-3.06 (m, 1H—major), 2.88-2.92 (m, 1H—major), 2.70-2.79 (m, 2H—major), 2.45-2.51 (m, 2H—major), 2.32-2.37 (m, 2H—minor), 2.14 (s, 6H—major), 2.12 (s, 6H—minor), 1.50-1.90 (m, major and minor), 1.05-1.45 (m), 0.75-0.90 (m, 12H—major and minor), 0.55-0.65 (m, 2H—minor); $^{31}$P NMR (162 MHz, CD$_2$Cl$_2$, mixture of rotomers) δ 45.0 (minor), 37.5 (major). Anal Calc $C_{43}H_{62}BrO_2PPd$: C, 62.36; H, 7.55. Found: C, 62.52; H, 7.68.

Example Forty-Six

Optimized Synthesis of 2-iodo-2',4',6'-triisopropyl-3,6-dimethoxybiphenyl

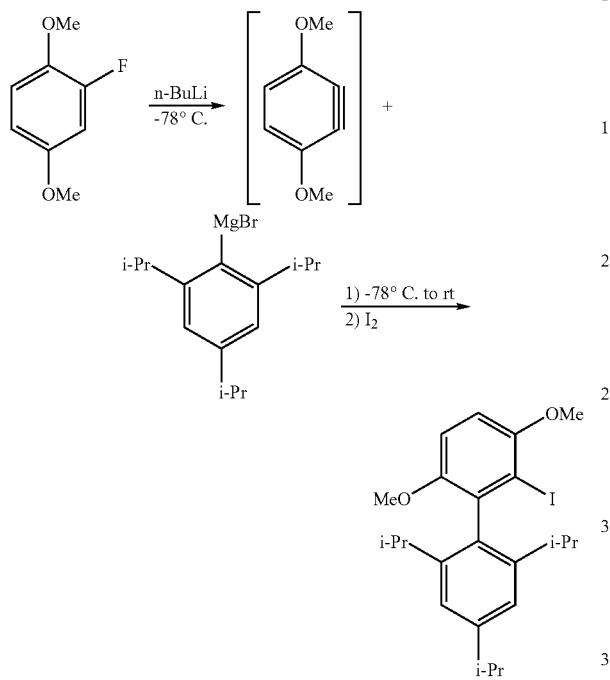

2-iodo-2',4',6'-triisopropyl-3,6-dimethoxybiphenyl. An oven-dried three-neck 500 mL round-bottom flask, which was equipped with a magnetic stir bar and charged with magnesium shavings (2.8 g, 116 mmol), was fitted with a reflux condenser, glass stopper, and rubber septum. The flask was purged with argon and then THF (100 mL) and 2,4,6-triisopropylbromobenzene (24.3 mL, 96 mmol) were added via syringe. The reaction mixture was heated to reflux and 1,2-dibromethane (40 uL) was added via syringe. The reaction was allowed to stir at reflux for 1.5 h and was then cooled to room temperature. A separate oven-dried 2 L round bottom flask, which was equipped with a magnetic stir bar and fitted with a septum, was purged with argon and then THF (500 mL) and 1,4-dimethoxy-2-fluorobenzene (7.49 g, 48 mmol) were added to the flask via syringe. The reaction mixture was cooled to −78° C. and n-BuLi (2.5 M in Hexane, 19.4 mL, 48.5 mmol) was added in a dropwise fashion over a 40 min period. The solution was stirred for 1 h and the Grignard reagent, which was prepared in the first reaction vessel, was added via cannula over a 30 min period and allowed to stir at −78° C. for 1 h. The reaction mixture was warmed to room temperature slowly where it was stirred for an additional 12 h. The mixture was then cooled to 0° C. and a solution of Iodine in THF (1 M, 96 mL, 96 mmol) was added via syringe over a 15 min period and then the dark red solution was warmed to room temperature and stirred for 1 h. The solvent was removed via a rotary evaporator, and the remaining dark brown oil was taken up in $Et_2O$, washed with a saturated solution of sodium sulfite, and washed with brine. The organic layer was then dried over $MgSO_4$, filtered, and the solvent was removed via rotary evaporator to give a yellow solid. The crude material was triturated with hexanes and filtered to give the desired product as an off-white solid (16.199 g, 72%, mp 189-191° C.). $^1H$ NMR (300 MHz, $CDCl_3$) δ: 7.07 (s, 2H), 6.90 (d, J=9.0 Hz, 1H), 6.81 (d, J=9.0 Hz, 1H), 3.90 (s, 3H), 3.67 (s, 3H), 2.98 (septet, J=7.0 Hz, 1H), 2.39 (septet, J=7.0 Hz, 2H), 1.33 (d, J=7.0 Hz, 6H), 1.20 (d, 7.0 Hz, 6H), 1.02 (d, J=7.0 Hz, 6H) ppm. $^{13}C$ NMR (75 MHz, $CDCl_3$) δ: 152.7, 152.5, 148.4, 145.9, 136.4, 136.1, 121.0, 110.3, 109.4, 96.6, 57.0, 55.8, 34.3, 31.1, 24.8, 24.3, 23.9 ppm. IR (neat, $cm^{-1}$): 2957, 2865, 1567, 1460, 1428, 1257, 1032, 755. Anal. Calcd. for $C_{23}H_{31}IO_2$: C, 59.23; H, 6.70. Found: C, 59.23; H, 6.72.

Example Forty-Seven

Synthesis of 2-iodo-2',4',6'-triisopropyl-3,5-dimethoxybiphenyl

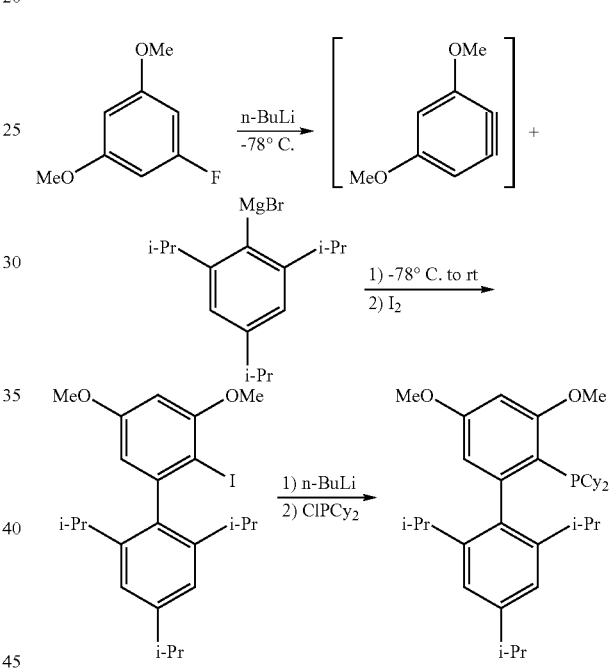

2-iodo-2',4',6'-triisopropyl-3,5-dimethoxybiphenyl. An oven-dried three-neck 500 mL round bottom flask, which was equipped with a magnetic stir bar and charged with magnesium shavings (2.8 g, 116 mmol), was fitted with a reflux condenser, glass stopper, and rubber septum. The flask was purged with argon and then THF (45 mL) and 2,4,6-triisopropylbromobenzene (11.4 mL, 45 mmol) were added via syringe. The reaction mixture was heated to reflux and 1,2-dibromethane (40 uL) was added via syringe. The reaction was allowed to stir at reflux for 1.5 h and was then cooled to room temperature. A separate oven-dried 2 L round bottom flask, which was equipped with a magnetic stir bar and fitted with a septum, was purged with argon and then THF (200 mL) and 3,5-dimethoxyfluorobenzene (3 mL, 22.5 mmol) were added to the flask via syringe. The reaction mixture was cooled to −78° C. and n-BuLi (2.5 M in Hexane, 9.2 mL, 23 mmol) was added in a dropwise fashion over a 40 min period. The solution was stirred for 1 h and the Grignard reagent, which was prepared in the first reaction vessel, was added via cannula over a 30 min period and allowed to stir at −78° C. for 1 h. The reaction mixture was warmed to room temperature slowly where it was stirred for an additional 12 h. The mixture was then cooled to 0° C. and a solution of Iodine in THF (1 M, 50 mL, 50 mmol) was added via syringe over a 15 min period and then the dark red solution was warmed to room temperature and stirred for 1 h. The solvent was removed via a rotary evaporator, and the remaining dark brown oil was taken up in Et$_2$O, washed with a saturated solution of sodium sulfite, and washed with brine. The organic layer was then dried over MgSO$_4$, filtered, and the solvent was removed via rotary evaporator to give a yellow solid. The crude material was triturated with hexanes and filtered to give the desired product as an off-white solid (5.059 g, 48%).

Example Forty-Eight

Figure 16:
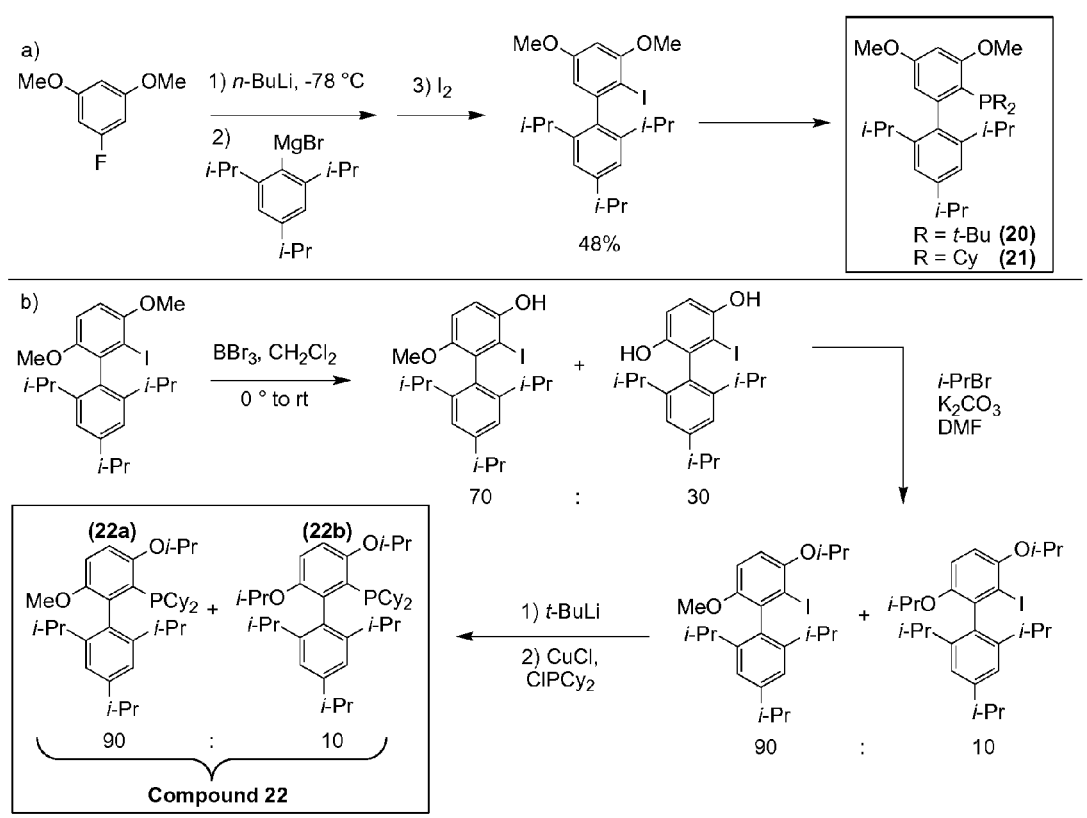
FIG. 16 depicts syntheses of ligands 20, 21, and 22.

Synthesis of 2-dicyclohexylphosphine-2',4',6'-triisopropyl-3,5-dimethoxybiphenyl (21) (FIG. 16)

2-dicyclohexylphosphine-2',4',6'-triisopropyl-3,5-dimethoxybiphenyl (21). An oven-dried 25 mL round bottom flask, which was equipped with a magnetic stir bar and charged with 2-iodo-2',4',6'-triisopropyl-3,5-dimethoxybiphenyl (2 g, 4.29 mmol), was evacuated and backfilled with argon (this process was repeated a total of 3 times). THF (10 mL) was added via syringe and the reaction was cooled to −78° C. and n-BuLi (2.5 M in Hexane, 1.8 mL, 4.5 mmol) was added in a dropwise fashion over a 10 min period. The solution was stirred for 30 min and then the ClPCy$_2$ (1.038 mL, 4.7 mmol) was added via syringe over 10 min. The reaction was stirred for 1 h at −78° C. and then warmed slowly to room temperature where it was stirred for an additional 1.5 h. The solution was filtered through a plug of celite layered on a plug of silica (eluting with EtOAc) and then the solvent was removed via a rotary evaporator to give a white solid. The crude material was recrystallized from acetone to yield the desired product as white crystals. The mother liquor was then concentrated and the remaining white solid was recrystallized from acetone to yield additional white crystals.

Example Forty-Nine

Synthesis of 2-di(tert-butyl)phosphine-2',4',6'-triisopropyl-3,5-dimethoxybiphenyl (20) (FIG. 16)

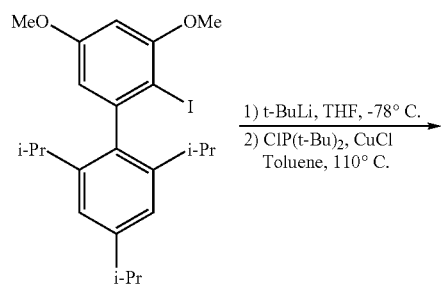

1) t-BuLi, THF, −78° C.
2) ClP(t-Bu)$_2$, CuCl
Toluene, 110° C.

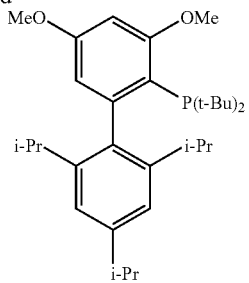

2-di(tert-butyl)phosphine-2',4',6'-triisopropyl-3,5-dimethoxybiphenyl (20). An oven-dried 100 mL schlenk flask, which was equipped with a magnetic stir bar and charged with 2-iodo-2',4',6'-triisopropyl-3,5-dimethoxybiphenyl (3 g, 6.44 mmol), was evacuated and backfilled with argon (this process was repeated a total of 3 times). THF (15 mL) was added via syringe and the reaction was cooled to −78° C. and t-BuLi (1.7 M in Hexane, 7.6 mL, 12.8 mmol) was added in a dropwise fashion over a 10 min period. The solution was stirred for 30 min and then the ClP(t-Bu)$_2$ (1.35 mL, 7.08 mmol) was added via syringe over 10 min. The reaction was stirred for 1 h at −78° C. and then warmed slowly to room temperature where solid CuCl (638 mg, 12.8 mmol) was added quickly under a positive pressure of argon. Toluene (30 mL) was added via syringe and then the reaction vessel was sealed with a Teflon stopper and heated to 110° C. for 24 h. The reaction mixture was cooled to room temperature, diluted with ethyl acetate, washed with NH$_4$OH (this process was repeated a total of 3 times), dried over MgSO$_4$, filtered, and concentrated to yield a yellow oil. The oil was taken up in a minimum amount of hot methanol and cooled in a −25° C. freezer overnight to yield the title compound (20) as white crystals.

Example Fifty

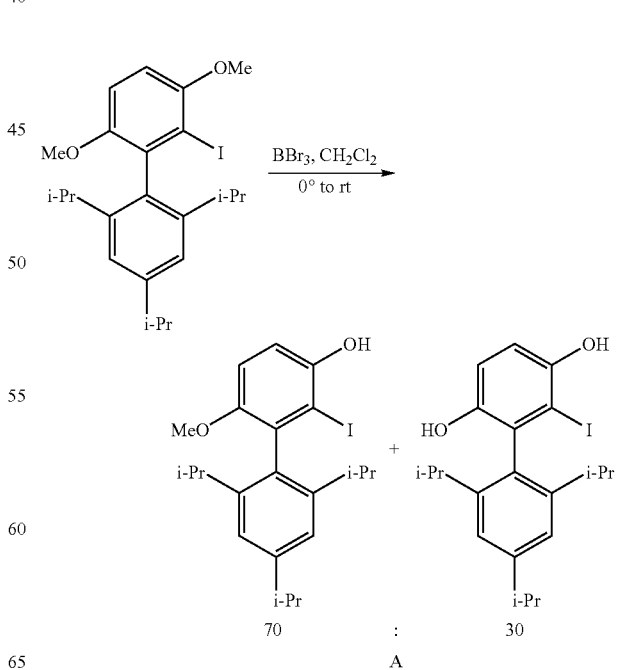

A

Mixture A. An oven-dried 100 mL round bottom flask, which was equipped with a magnetic stir bar and rubber septum, was charged with 2-iodo-2',4',6'-triisopropyl-3,6-dimethoxybiphenyl (3 g, 6.44 mmol) and purged with argon. CH$_2$Cl$_2$ (12 mL) was added via syringe and then the reaction mixture was cooled to 0° C. where BBr$_3$ (1 M in CH$_2$Cl$_2$, 13 mL, 12.9 mmol) was added in a dropwise fashion over a 20 min period. The solution was warmed to room temperature and allowed to stir for 6 h. The solution was then diluted with CH$_2$Cl$_2$, washed with 1 M NaOH, dried over MgSO$_4$, and concentrated to yield a 70:30 mixture of the title compounds as an off-white solid.

Example Fifty-One

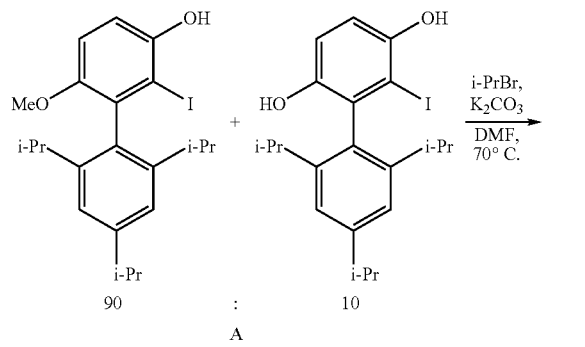

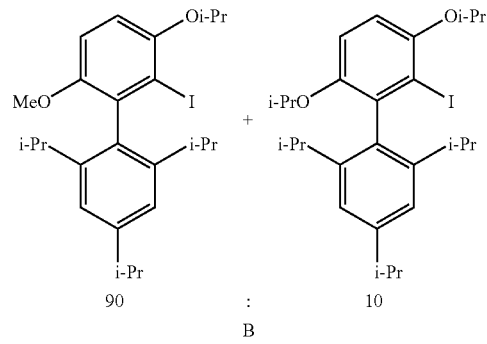

Mixture B. An oven-dried 50 mL schlenk flask, which was equipped with a magnetic stir bar and rubber septum, was charged with mixture A (1.5 g, 3.3 mmol), K$_2$CO$_3$ (2.7 g, 19.8 mmol), and purged with argon. DMF (6.6 mL) and i-PrBr (1.86 mL, 19.8 mmol) were added via syringe and then the reaction vessel was sealed with a Teflon screw cap and heated to 70° C. for 24 h. The solution was cooled to room temperature, diluted with ethyl acetate, washed with water, dried with MgSO$_4$, and concentrated to give a yellow oil. The crude material was purified via flash chromatography (Biotage 100 g snap column, 0-20% EtOAc/Hexanes) to yield a 80:20 mixture of the title compounds. The material was then purified a second time via flash chromatography (Biotage 100 g snap column, 0-20% EtOAc/Hexanes) to yield a 90:10 mixture of the title compounds.

Example Fifty-Two

Synthesis of 22 (FIG. 16)

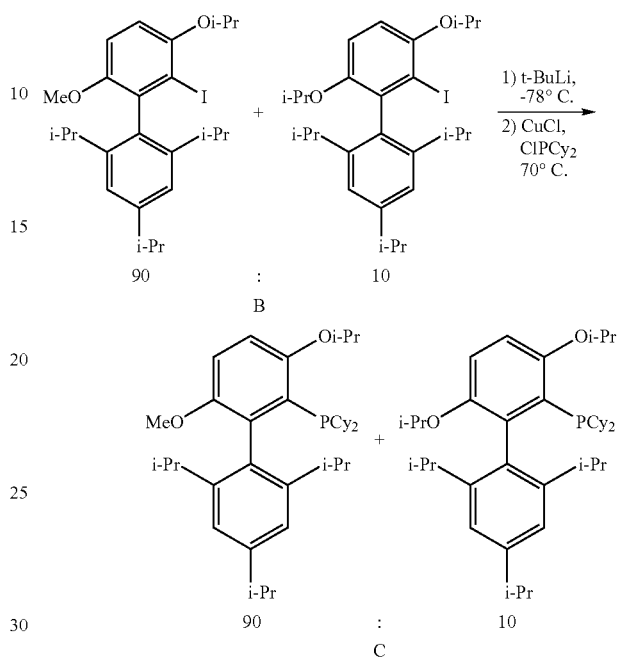

Mixture C (22a+22b). An oven-dried 50 mL schlenk flask, which was equipped with a magnetic stir bar and charged with mixture B (1.625 g, 2.88 mmol), was evacuated and back-filled with argon (this process was repeated a total of 3 times). THF (10 mL) was added via syringe and the reaction was cooled to –78° C. and t-BuLi (1.6 M in Hexane, 3.6 mL, 5.76 mmol) was added in a dropwise fashion over a 10 min period. The solution was stirred for 30 min and then the ClPCy$_2$ (642 uL, 2.90 mmol) was added via syringe over 10 min. The reaction was stirred for 1 h at –78° C. and then warmed slowly to room temperature where solid CuCl (285 mg, 2.88 mmol) was added quickly under a positive pressure of argon. The reaction vessel was sealed with a Teflon stopper and heated to 70° C. for 2 days. The reaction mixture was cooled to room temperature, diluted with ethyl acetate, washed with NH$_4$OH (this process was repeated a total of 3 times), dried over MgSO$_4$, filtered, and concentrated to yield a yellow solid. The crude material was purified via flash chromatography (Biotage 100 g snap column, 0-20% EtOAc/Hexanes) to yield a 90:10 mixture of the title compounds as a white solid.

Example Fifty-Three

General Procedure for Ligand Screen for Aniline and 4-Chloroanisole (FIG. 18)

An oven dried test tube, which was equipped with a magnetic stir bar and fitted with a teflon septum, was charged with Pd(OAc)$_2$ (1 mol %) and the ligand (1, 21, or 22) (3 mol %). The vessel was evacuated and backfilled with argon (this process was repeated a total of 3 times) and t-BuOH (2 mL)

and degassed H$_2$O (4 mol %) were added via syringe. After addition of the water, the solution was heated to 110° C. for 1.5 min.

A second oven dried test tube, which was equipped with a magnetic stir bar and fitted with a Teflon septum, was charged with K$_2$CO$_3$ (1.4 mmol). The vessel was evacuated and backfilled with argon (this process was repeated a total of 3 times) and then the 4-chloroanisole (123 uL, 1.0 mmol) and aniline (110 uL, 1.2 mmol) were added via syringe and the activated catalyst solution was transferred from the first reaction vessel into the second via cannula. The solution was heated to 110° C. for 15 min and then was cooled to room temperature and dodecane was added as an internal standard. The reaction mixture was diluted with ethyl acetate, washed with water, and analyzed by GC.

Example Fifty-Four

General Procedure for Pd-Catalyzed Nitrations of Aryl Chlorides and Aryl Sulfonates (FIGS. 20 and 21)

An oven-dried schlenk tube, which was equipped with a magnetic stir bar and fitted with a rubber septum, was charged with the Pd$_2$(dba)$_3$ (0.5 mol %), ligand (6, 25, 26, or 27) (1.2 mol %), and NaNO$_2$ (138 mg, 2.0 mmol) (aryl halides* that were solids at room temperature were added with the catalyst). The vessel was evacuated and backfilled with argon (this process was repeated a total of 3 times) and then the aryl halide* (1.0 mmol), tris(3,6-dioxaheptyl)amine (5 mol %), and tert-butanol (2 mL) were added via syringe. The reaction vessel was sealed with a Teflon screw cap and heated to 110° C. for 24 h. The solution was cooled to room temperature, diluted with Ethyl acetate, washed with water, and purified via flash chromatography.
*Includes aryltriflates and arylnonaflates.

Example Fifty-Five

General Procedure for Synthesis of N-Aryl Carbamates (FIG. 22)

An oven-dried test tube, which was equipped with a magnetic stir bar and fitted with a teflon septum, was charged with Pd$_2$(dba)$_3$ (1 mol %), t-BuBrettPhos (6) (2 mol %), and sodium cyanate (2.2 mmol). The vessel was evacuated and backfilled with argon (this process was repeated a total of 3 times) and then the aryl chloride (1.0 mmol) and tert-butanol (2 mL) were added via syringe. The reaction mixture was heated to 110° C. for 24 h, cooled to room temperature, diluted with Ethyl acetate, and washed with water. The organic phase was concentrated on a rotary evaporator and the crude material was purified via flash chromatography.

Example Fifty-Six

General Procedure for Coupling of Amides and Aryl Mesylates (FIG. 24)

An oven dried test tube, which was equipped with a magnetic stir bar and fitted with a teflon septum, was charged with Pd(OAc)$_2$ (1 mol %) and the t-BuBrettPhos (6) (3 mol %). The vessel was evacuated and backfilled with argon (this process was repeated a total of 3 times) and t-BuOH (2 mL) and degassed H$_2$O (8 mol %) were added via syringe. After addition of the water, the solution was heated to 110° C. for 1.5 min.

A second oven dried test tube, which was equipped with a magnetic stir bar and fitted with a Teflon septum, was charged with K$_3$PO$_4$ (0.7 mmol). The vessel was evacuated and backfilled with argon (this process was repeated a total of 3 times) and then the arylmesylate (0.5 mmol) and amide (0.7 mmol) were added via syringe and the activated catalyst solution was transferred from the first reaction vessel into the second via cannula. The solution was heated to 110° C. for 24 h and then was cooled to room temperature and dodecane was added as an internal standard. The reaction mixture was diluted with ethyl acetate, washed with water, and analyzed by GC.

Example Fifty-Seven

Figure 17:
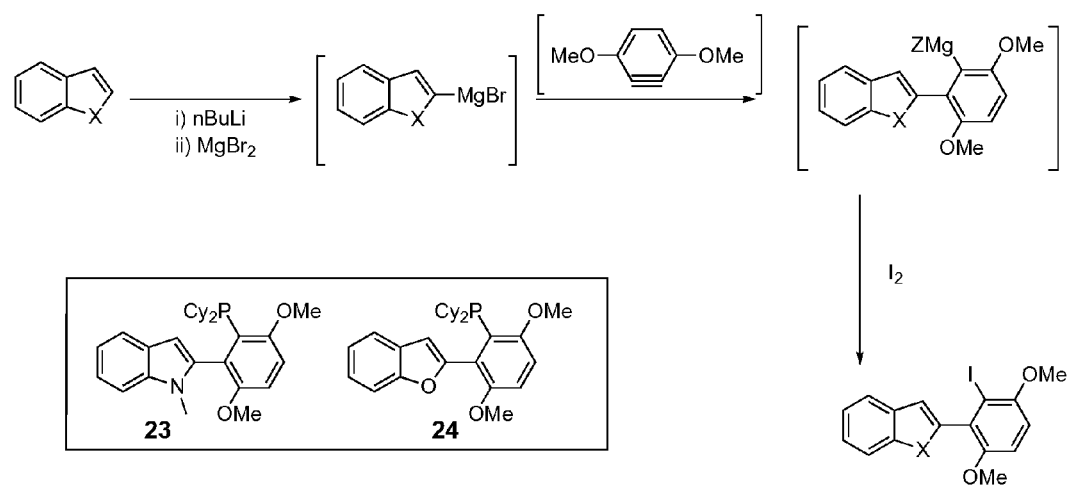
FIG. 17 depicts syntheses of heteroaryl-based ligands 23 and 24.

Synthesis of Ligand 23 (FIG. 17)

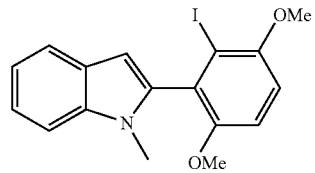

In a round-bottomed flask nBuLi (10 mmol, 4 mL of a 2.5 M solution in hexanes) was added drop-wise to a solution of 1,4-dimethoxyfluorobenzene (10 mmol, 1.56 g) in THF (120 mL) at −78° C. The mixture was stirred at −78° C. for a further 30 min, generating solution A. nBuLi (20 mmol, 8 mL of a 2.5 M solution in hexanes) was added drop-wise to a solution of 1-methylindole (20 mmol, 2.62 g, 2.50 mL) in THF (30 mL) at 0° C. After 2 h at this temperature the mixture was cooled to −78° C. and magnesium bromide (20 mmol, 3.68 g) added and this mixture stirred until the solid dissolved. This solution was then added via cannula to solution A and the mixture maintained at −78° C. for 1 h. The solution was then allowed to warm to room temperature overnight. The solution was then cooled to 0° C. and a solution of iodine (12 mmol, 3.5 g) in THF added via cannula. The mixture was allowed to warm to room temperature and sodium sulfite (saturated aq. solution) added. The mixture was extracted with EtOAc, the organic layer washed (water, then brine), dried and the solvent removed under reduced pressure. The residue was purified in 2 batches by column chromatography on a Biotage SP4 (hexane-EtOAc, 98:2-80:20) to give the iodide.

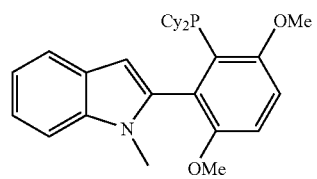

nBuLi was added drop-wise to a stirred solution of iodide (0.31 mmol, 120 mg) in THF at −78° C. After 30 min at this temperature chlorodicyclohexylphosphine (0.34 mmol, 78 mg, 74 μL) in THF was added drop-wise and the solution allowed to warm to room temperature. The solution was maintained at room temperature for 1.5 h and then MeOH (1 mL) added. The solution was then filtered a layer of SiO$_2$ and a layer of Celite, eluting with EtOAc. The solvent was removed under reduced pressure and the residue purified by recrystallization (MeOH) to give the phosphine (23).

Example Fifty-Eight

Synthesis of Ligand 24 (FIG. 17)

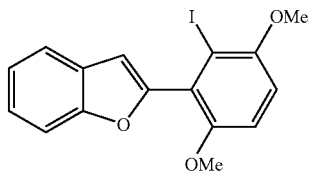

In a round-bottomed flask nBuLi (10 mmol, 4 mL of a 2.5 M solution in hexanes) was added drop-wise to a solution of 1,4-dimethoxyfluorobenzene (10 mmol, 1.56 g) in THF (120 mL) at −78° C. The mixture was stirred at −78° C. for a further 30 min, generating solution A. nBuLi (20 mmol, 8 mL of a 2.5 M solution in hexanes) was added drop-wise to a solution of 2,3-benzofuran (20 mmol, 2.36 g, 2.20 mL) in THF (30 mL) at 0° C. After 2 h at this temperature the mixture was cooled to −78° C. and magnesium bromide (20 mmol, 3.68 g) added and this mixture stirred until the solid dissolved. This solution was then added via cannula to solution A and the mixture maintained at −78° C. for 1 h. The solution was then allowed to warm to room temperature overnight. The solution was then cooled to 0° C. and a solution of iodine (12 mmol, 3.5 g) in THF added via cannula. The mixture was allowed to warm to room temperature and sodium sulfite (saturated aq. solution) added. The mixture was extracted with EtOAc, the organic layer washed (water, then brine), dried and the solvent removed under reduced pressure. The residue was purified in 2 batches by column chromatography on a Biotage SP4 (hexane-EtOAc, 98:2-80:20) to give the iodide.

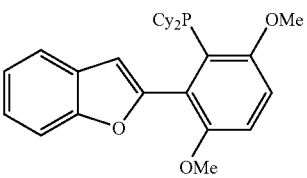

24 nBuLi was added drop-wise to a stirred solution of iodide (0.31 mmol, 120 mg) in THF at −78° C. After 30 min at this temperature chlorodicyclohexylphosphine (0.34 mmol, 78 mg, 74 µL) in THF was added drop-wise and the solution allowed to warm to room temperature. The solution was maintained at room temperature for 1.5 h and then MeOH (1 mL) added. The solution was then filtered a layer of $SiO_2$ and a layer of Celite, eluting with EtOAc. The solvent was removed under reduced pressure and the residue purified by recrystallization (MeOH) to give the phosphine (24).

Example Fifty-Nine

Effect of Ligand Structure on Coupling of Hexylamine and 4-Chloroanisole (FIG. 19)

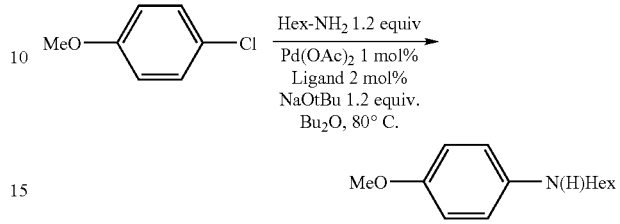

Pd(OAc)$_2$ (1 mol %, 1.1 mg), ligand (1 or 23) (2 mol %) and NaOtBu (0.6 mmol, 61 mg) were weighed into test-tube fitted with a screw cap. The tube was evacuated and back-filled with argon and di-n-butylamine (1 mL), 4-chloroanisole (0.5 mmol, 71 mg, 61 µL) and hexylamine (0.6 mmol, 61 mg, 79 µL) added via syringe. The tube was the stirred at 80° C. and the progress of the reaction followed by GC analysis of aliquots. Full conversion was reached at 150 mins.

Example Sixty

Coupling of Anilines and Aryl Mesylates by Ligand 23 (FIG. 23)

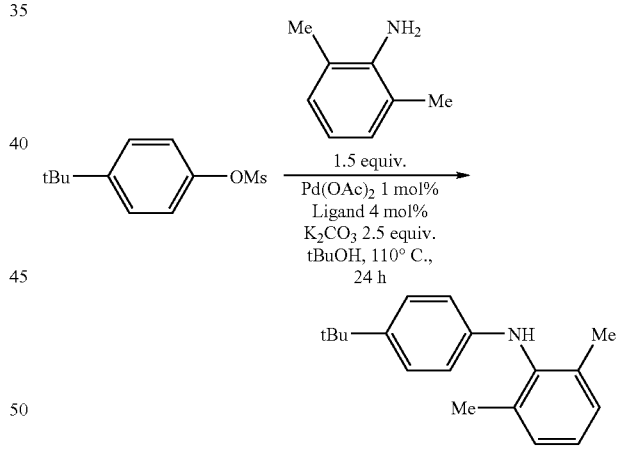

Pd(OAc)$_2$ (1 mol %, 1.1 mg) and ligand 23 were placed in Sclenk tube and the tube evacuated and back-filled with argon. CH$_2$Cl$_2$ (1 mL) and triethylamine (0.05 mL) were then added and the solution gently warmed and swirled for 1 min. The solution was then allowed to cool to room temperature and the solvent removed under vacuum. Potassium carbonate (1.25 mmol, 173 mg), the aryl mesylate (0.5 mmol, 114 mg) and phenylboronic acid (4 mol %, 2.5 mg) were then added up a stream of argon and the tube evacuated and back-filled with argon. The aniline (0.75 mmol, 91 mg, 92 µL), dodecane (0.5 mmol, as internal standard) and tBuOH (2 mL) were then added via syringe and the tube sealed with a Teflon screw seal and the mixture stirred at room temperature for 2 min. The tube was then placed in a pre-heated oil bath at 110° C. for 24 h. At the end of this time GC analysis revealed 85% conversion of aryl mesylate, 63% yield of desired product.

Example Sixty-One

Synthesis of 2-iodo-2',4',6'-triisopropyl-3-methoxy-biphenyl

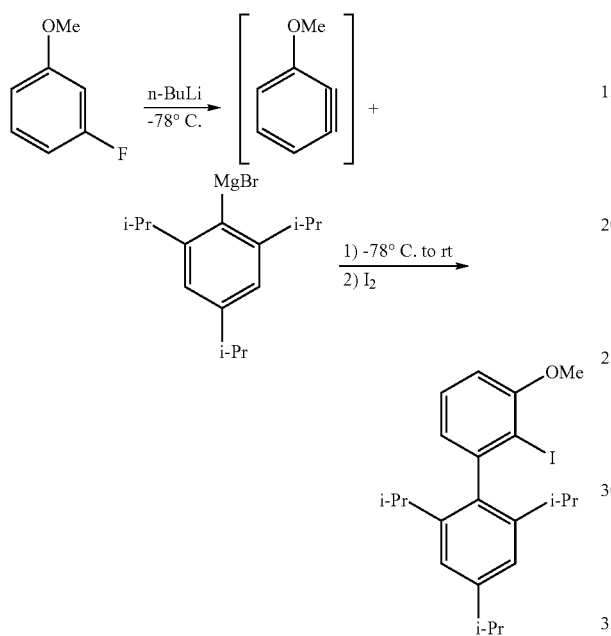

2-iodo-2',4',6'-triisopropyl-3-methoxybiphenyl. An oven-dried three-neck round bottom flask, which was equipped with a magnetic stir bar and charged with magnesium shavings (2.4 equiv), was fitted with a reflux condenser, glass stopper, and rubber septum. The flask was purged with argon and then THF (1 mL/mmol) and 2,4,6-triisopropylbromobenzene (2 equiv) were added via syringe. The reaction mixture was heated to reflux and 1,2-dibromethane (40 uL) was added via syringe. The reaction was allowed to stir at reflux for 1.5 h and was then cooled to room temperature. A separate oven-dried round bottom flask, which was equipped with a magnetic stir bar and fitted with a septum, was purged with argon and then THF (10 mL/mmol) and 3-fluoroanisole (1 equiv) were added to the flask via syringe. The reaction mixture was cooled to −78° C. and n-BuLi (1.05 equiv) was added in a dropwise fashion over a 40 min period. The solution was stirred for 1 h and the Grignard reagent, which was prepared in the first reaction vessel, was added via cannula over a 30 min period and allowed to stir at −78° C. for 1 h. The reaction mixture was warmed to room temperature slowly where it was stirred for an additional 12 h. The mixture was then cooled to 0° C. and a solution of Iodine in THF (1 M, 2 equiv) was added via syringe over a 15 min period and then the dark red solution was warmed to room temperature and stirred for 1 h. The solvent was removed via a rotary evaporator, and the remaining dark brown oil was taken up in Et$_2$O, washed with a saturated solution of sodium sulfite, and washed with brine. The organic layer was then dried over MgSO$_4$, filtered, and the solvent was removed via rotary evaporator to give a yellow solid. The crude material was recrystallized to give the desired product as a white solid.

Example Sixty-Two

Synthesis of Ligand 29

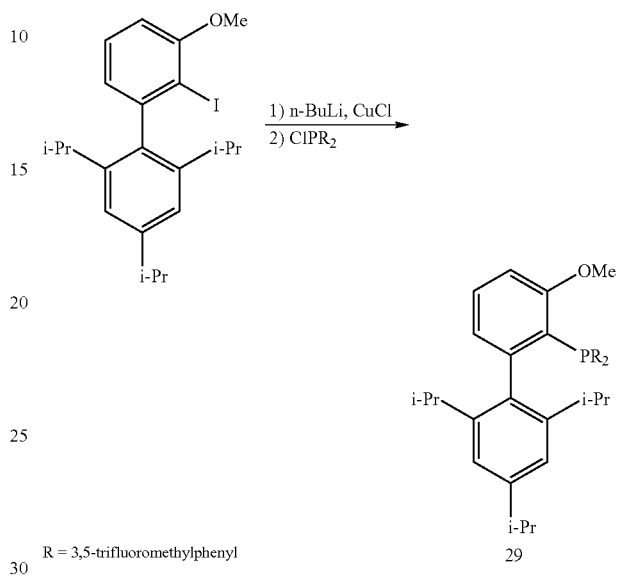

R = 3,5-trifluoromethylphenyl

Synthesis of 29. An oven-dried round bottom flask, which was equipped with a magnetic stir bar and charged with 2-iodo-2',4',6'-triisopropyl-3-methoxybiphenyl (1 equiv), was evacuated and backfilled with argon (this process was repeated a total of 3 times). THF (5 mL/mmol) was added via syringe and the reaction was cooled to −78° C. and n-BuLi (1 equiv) was added in a dropwise fashion over a 10 min period. The solution was stirred for 1 h and then the CuCl (1 equiv) was added. The reaction was stirred for 1 h at −78° C. and then warmed slowly to room temperature where a solution of the chlorophosphine in THF was added. The reaction mixture was heated to 70° C. for 24 h, then cooled to room temperature, diluted with Et$_2$O, and washed with aqueous NH$_4$OH (this process was repeated a total of 3 times). The organic layer was then dried over MgSO$_4$ and concentrated via reduced pressure. The crude material was recrystallized to give the desired product.

Example Sixty-Three

General Procedure for Iodoaryl Ligand Precursor

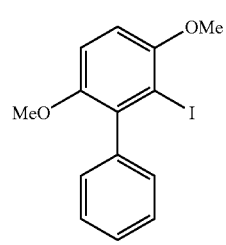

B

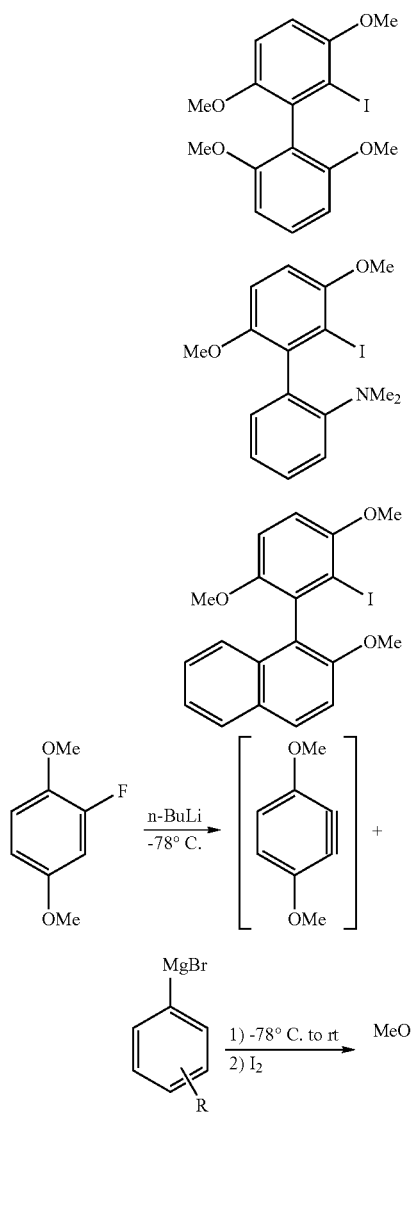

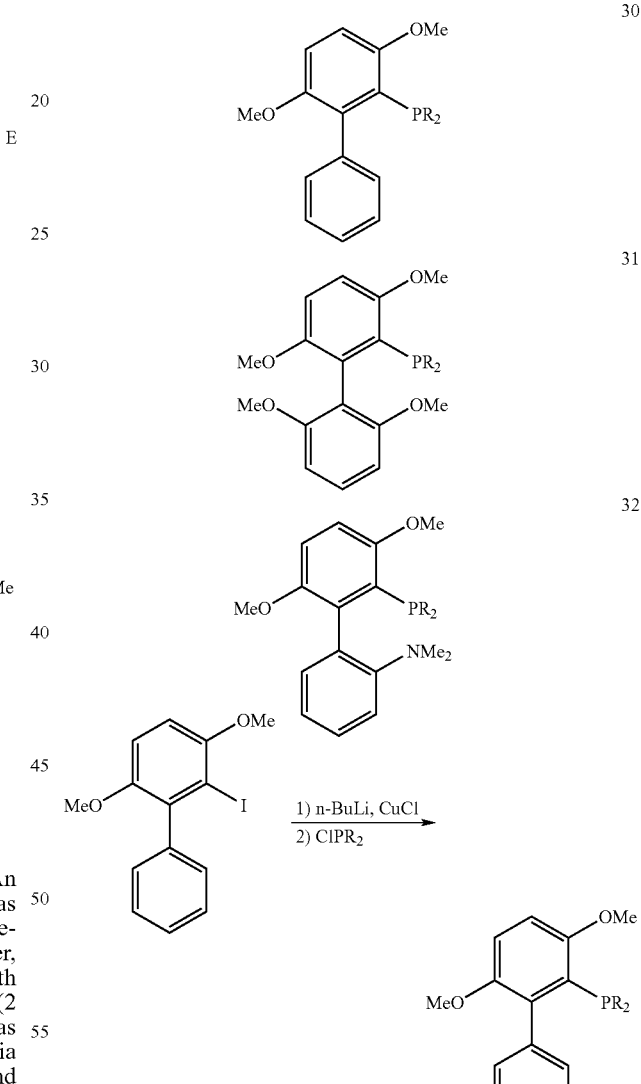

General procedure for the synthesis of B, C, D, and E. An oven-dried three-neck round bottom flask, which was equipped with a magnetic stir bar and charged with magnesium shavings (2.4 equiv), was fitted with a reflux condenser, glass stopper, and rubber septum. The flask was purged with argon and then THF (1 mL/mmol) and the bromo arene (2 equiv) were added via syringe. The reaction mixture was heated to reflux and 1,2-dibromethane (40 uL) was added via syringe. The reaction was allowed to stir at reflux for 1.5 h and was then cooled to room temperature. A separate oven-dried round bottom flask, which was equipped with a magnetic stir bar and fitted with a septum, was purged with argon and then THF (10 mL/mmol) and 1,4-dimethoxy-2-fluorobenzene (1 equiv) were added to the flask via syringe. The reaction mixture was cooled to −78° C. and n-BuLi (1.05 equiv) was added in a dropwise fashion over a 40 min period. The solution was stirred for 1 h and the Grignard reagent, which was prepared in the first reaction vessel, was added via cannula over a 30 min period and allowed to stir at −78° C. for 1 h. The reaction mixture was warmed to room temperature slowly where it was stirred for an additional 12 h. The mixture was then cooled to 0° C. and a solution of Iodine in THF (1 M, 2 equiv) was added via syringe over a 15 min period and then the dark red solution was warmed to room temperature and stirred for 1 h. The solvent was removed via a rotary evaporator, and the remaining dark brown oil was taken up in $Et_2O$, washed with a saturated solution of sodium sulfite, and washed with brine. The organic layer was then dried over $MgSO_4$, filtered, and the solvent was removed via rotary evaporator. The crude material was recrystallized to give the desired product.

Example Sixty-Four

Synthesis of Ligands 30, 31, and 32

R = 3,5-trifluoromethylphenyl

Synthesis of 30, 31, and 32. An oven-dried round bottom flask, which was equipped with a magnetic stir bar and charged with the iodo arene (1 equiv), was evacuated and backfilled with argon (this process was repeated a total of 3 times). THF (5 mL/mmol) was added via syringe and the reaction was cooled to −78° C. and n-BuLi (1 equiv) was added in a dropwise fashion over a 10 min period. The solution was stirred for 1 h and then the CuCl (1 equiv) was added. The reaction was stirred for 1 h at −78° C. and then warmed slowly to room temperature where a solution of the chlorophosphine in THF was added. The reaction mixture was heated to 70° C. for 24 h, then cooled to room temperature, diluted with Et₂O, and washed with aqueous NH₄OH (this process was repeated a total of 3 times). The organic layer was then dried over MgSO₄ and concentrated via reduced pressure. The crude material was recrystallized to give the desired product.

Example Sixty-Five

Synthesis of Ligand 33

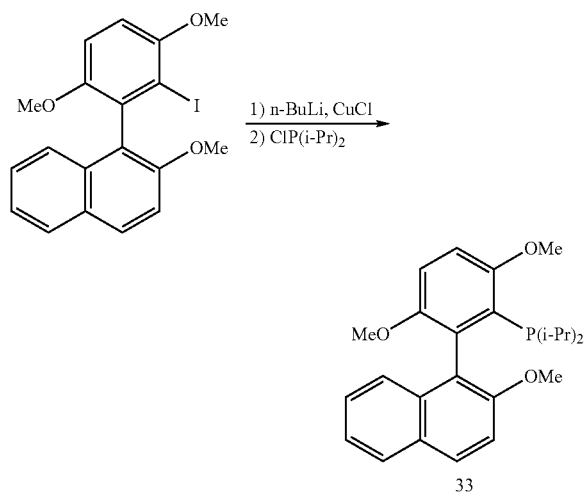

Synthesis of 33. nBuLi (1.1 equiv) was added dropwise to a stirred solution of aryl iodide (1 equiv) in THF in a Schlenk tube at −78° C. The mixture was stirred at −78° C. for 30 min and copper(I) iodide (1 equiv) was added. Diisopropylchlorophospine (1.1 equiv) was next added and the mixture heated to 70° C. The mixture was maintained at this temperature for 48 h and then allowed to cool to room temperature. MeOH was then added, the mixture diluted with EtOAc and the organic layer washed repeatedly with aq. NH₃ solution. The organic phase was separated, dried, the solvent removed under reduced pressure and the residue purified by Flash chromatography (hexane-EtOAc, 1:1).

Example Sixty-Six

Synthesis of Ligand 34

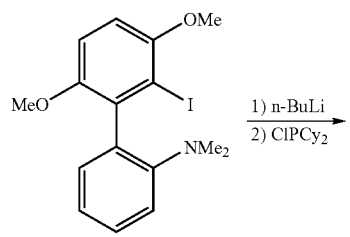

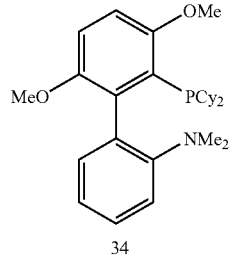

Synthesis of 34. An oven-dried round bottom flask, which was equipped with a magnetic stir bar and charged with the iodo arene (1 equiv), was evacuated and backfilled with argon (this process was repeated a total of 3 times). THF (5 mL/mmol) was added via syringe and the reaction was cooled to −78° C. and n-BuLi (1.05 equiv) was added in a dropwise fashion over a 10 min period. The solution was stirred for 30 min and then the ClPCy₂ (1.05 equiv) was added via syringe over 10 min. The reaction was stirred for 1 h at −78° C. and then warmed slowly to room temperature where it was stirred for an additional 1.5 h. The solution was filtered through a plug of celite layered on a plug of silica (eluting with EtOAc) and then the solvent was removed via a rotary evaporator to give a white solid. The crude material was recrystallized to yield the desired product.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:
1. A ligand represented by I:

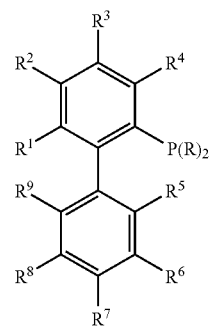

wherein
R is selected independently for each occurrence from the group consisting of alkyl, cycloalkyl, aryl, heteroaryl, aralkyl, heteroaralkyl, and —(CH₂)$_m$—R¹⁰;
R¹, R², R³, and R⁴ are selected independently for each occurrence from the group consisting of hydrogen, halogen, alkyl, cycloalkyl, heterocycloalkyl, aryl, heteroaryl, aralkyl, heteroaralkyl, —OR¹¹, —N(R¹¹)₂, —Si(R¹¹)₃, and —(CH₂)$_m$—R¹⁰; or any two adjacent instances of $R^1$, $R^2$, $R^3$ and $R^4$, taken together with the carbons to which they are bound, form a five- or six-membered substituted or unsubstituted aryl or heteroaryl ring;

provided that at least two of $R^1$, $R^2$, $R^3$ and $R^4$ are —$OR^{11}$;

$R^5$, and $R^9$ are selected independently for each occurrence from the group consisting of hydrogen, alkyl, cycloalkyl, heterocycloalkyl, aryl, heteroaryl, aralkyl, heteroaralkyl, —$Si(R^{11})_3$, and —$(CH_2)_m$—$R^{10}$;

$R^7$ is selected independently for each occurrence from the group consisting of alkyl, cycloalkyl, heterocycloalkyl, aryl, heteroaryl, aralkyl, heteroaralkyl, —$Si(R^{11})_3$, —$(CH_2)_m$—$R^{10}$, —OH, —$OR^{11}$, —$NH_2$, —$NHR^{11}$, and —$N(R^{11})_2$;

$R^6$ and $R^8$ are selected independently for each occurrence from the group consisting of hydrogen, lower alkyl and halogen;

or any two adjacent instances of $R^5$, $R^6$, $R^7$, $R^8$, or $R^9$, taken together with the carbons to which they are bound, form a five- or six-membered substituted or unsubstituted aryl or heteroaryl ring;

$R^{10}$ represents an unsubstituted or substituted aryl, cycloalkyl, cycloalkenyl, heterocycle, or polycycle, wherein polycycle refers to two or three rings, each ring independently selected from the group consisting of cycloalkyls, cycloalkenyls, cycloalkynyls, aryls and heterocyclyls, in which two or more carbons are shared by adjoining rings;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

2. The ligand of claim 1, wherein $R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$.

3. The ligand of claim 1, wherein R is alkyl, aryl, or cycloalkyl.

4. The ligand of claim 1, wherein R is Cy, i-Pr, $C_5H_{11}$, Me, Et, 1-adamantyl, t-Bu,

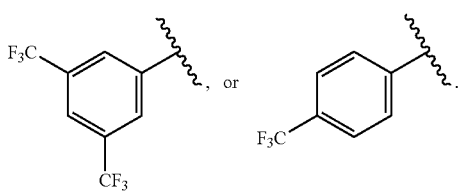

5. The ligand of claim 1, wherein $R^1$, $R^2$, $R^3$, and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)R^{10}$.

6. The ligand of claim 1, wherein $R^1$ and $R^4$ are —$OR^{11}$.

7. The ligand of claim 1, wherein $R^1$ and $R^4$ are —$OR^{11}$; and $R^{11}$ is alkyl.

8. The ligand of claim 1, wherein $R^2$ and $R^3$ are —$OR^{11}$.

9. The ligand of claim 1, wherein $R^2$ and $R^3$ are —$OR^{11}$; and $R^{11}$ is alkyl.

10. The ligand of claim 1, wherein $R^2$ and $R^4$ are —$OR^{11}$.

11. The ligand of claim 1, wherein $R^2$ and $R^4$ are —$OR^{11}$; and $R^{11}$ is alkyl.

12. The ligand of claim 1, wherein $R^5$, $R^7$ and $R^9$ are alkyl.

13. A ligand represented by II:

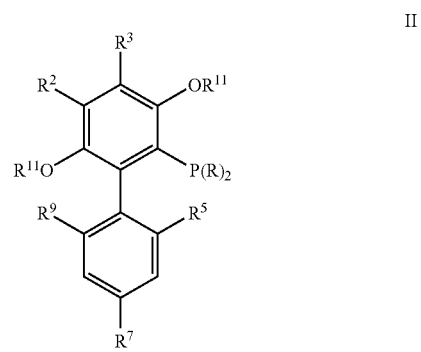

wherein

R is selected independently for each occurrence from the group consisting of alkyl, cycloalkyl, aryl, heteroaryl, aralkyl, heteroaralkyl, and —$(CH_2)_m$—$R^{10}$;

$R^2$ and $R^3$ are selected independently for each occurrence from the group consisting of hydrogen, halogen, alkyl, cycloalkyl, heterocycloalkyl, aryl, heteroaryl, aralkyl, heteroaralkyl, —$OR^1$, —$N(R^{11})_2$, —$Si(R^{11})_3$, and —$(CH_2)_m$—$R^{11}$; or any two adjacent instances of $R^2$ and $R^3$, taken together with the carbons to which they are bound, form a five or six-membered, substituted or unsubstituted, aryl or heteroaryl ring;

$R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$;

$R^6$ and $R^8$ are selected independently for each occurrence from the group consisting of hydrogen, lower alkyl and halogen;

$R^{10}$ represents an unsubstituted or substituted aryl, cycloalkyl, cycloalkenyl, heterocycle, or polycycle, wherein polycycle refers to two or three rings, each ring independently selected from the group consisting of cycloalkyls, cycloalkenyls, cycloalkynyls, aryls and heterocyclyls, in which two or more carbons are shared by adjoining rings;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand is achiral or, when chiral, is a single stereoisomer or a mixture of stereoisomers.

14. The ligand of claim 13, wherein R is alkyl, aryl, or cycloalkyl.

15. The ligand of claim 13, wherein R is Cy, i-Pr, $C_5H_{11}$, Me, Et, 1-adamantyl, t-Bu,

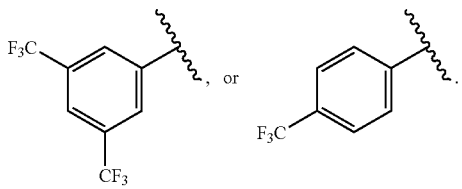

16. The ligand of claim 13, wherein $R^{11}$ is alkyl.
17. The ligand of claim 13, wherein $R^2$ and $R^3$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, $Si(R^{11})_3$, and —$(CH_2)_m$—$R^{10}$.
18. The ligand of claim 13, wherein $R^2$ and $R^3$ are —$OR^{11}$.
19. The ligand of claim 13, wherein $R^2$ and $R^3$ are —$OR^{11}$; and $R^{11}$ is alkyl.
20. The ligand of claim 13, wherein $R^2$ and $R^3$ are alkyl.
21. The ligand of claim 13, wherein $R^5$, $R^7$ and $R^9$ are alkyl.
22. A ligand represented by III:

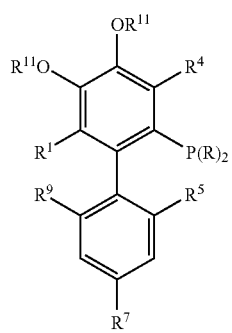

wherein
R is selected independently for each occurrence from the group consisting of alkyl, cycloalkyl, aryl, heteroaryl, aralkyl, heteroaralkyl, and —$(CH_2)_m$—$R^{10}$;
$R^1$ and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$;
$R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$;
$R^6$ and $R^8$ are selected independently for each occurrence from the group consisting of hydrogen, lower alkyl and halogen;
$R^{10}$ represents an unsubstituted or substituted aryl, cycloalkyl, cycloalkenyl, heterocycle, or polycycle, wherein polycycle refers to two or three rings, each ring independently selected from the group consisting of cycloalkyls, cycloalkenyls, cycloalkynyls, aryls and heterocyclyls, in which two or more carbons are shared by adjoining rings;
$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and
the ligand, when chiral, is a mixture of stereoisomers or a single enantiomer.
23. The ligand of claim 22, wherein R is alkyl, aryl, or cycloalkyl.
24. The ligand of claim 22, wherein R is Cy, i-Pr, $C_5H_{11}$, Me, Et, 1-adamantyl, t-Bu,

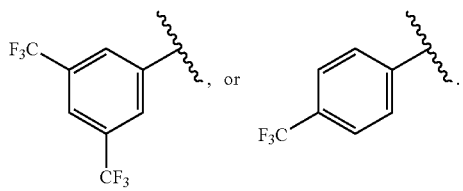

25. The ligand of claim 22, wherein $R^{11}$ is alkyl.
26. The ligand of claim 22, wherein $R^1$ and $R^4$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$.
27. The ligand of claim 22, wherein $R^1$ and $R^4$ are —$OR^{11}$.
28. The ligand of claim 22, wherein $R^1$ and $R^4$ are —$OR^{11}$; and $R^{11}$ is alkyl.
29. The ligand of claim 22, wherein $R^1$ and $R^4$ are alkyl.
30. The ligand of claim 22, wherein $R^5$, $R^7$ and $R^9$ are alkyl.
31. A ligand represented by IV:

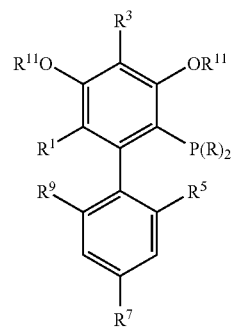

wherein
R is selected independently for each occurrence from the group consisting of alkyl, cycloalkyl, aryl, heteroaryl, aralkyl, heteroaralkyl, and —$(CH_2)_m$—$R^{10}$;
$R^1$ and $R^3$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)_m$—$R^{10}$;
$R^5$, $R^7$ and $R^9$ are selected independently for each occurrence from the group consisting of alkyl, cycloalkyl, heterocycloalkyl, aryl, heteroaryl, aralkyl, heteroaralkyl, —$Si(R^{11})_3$, and —$(CH_2)_m$—$R^{10}$;
$R^6$ and $R^8$ are selected independently for each occurrence from the group consisting of hydrogen, lower alkyl and halogen;
$R^{10}$ represents an unsubstituted or substituted aryl, cycloalkyl, cycloalkenyl, heterocycle, or polycycle, wherein polycycle refers to two or three rings, each ring independently selected from the group consisting of cycloalkyls, cycloalkenyls, cycloalkynyls, aryls and heterocyclyls, in which two or more carbons are shared by adjoining rings;

$R^{11}$ is selected independently for each occurrence from the group consisting of alkyl, cycloalkyl, heterocycloalkyl, aryl, heteroaryl, aralkyl, and heteroaralkyl;

m is independently for each occurrence an integer in the range 0 to 8 inclusive; and the ligand, when chiral, is a mixture of stereoisomers or a single enantiomer.

32. The ligand of claim 31, wherein R is alkyl, aryl, or cycloalkyl.

33. The ligand of claim 31, wherein R is Cy, i-Pr, $C_5H_{11}$, Me, Et, 1-adamantyl, t-Bu,

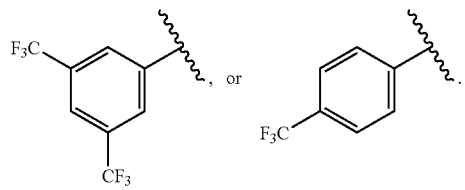

34. The ligand of claim 31, wherein $R^{11}$ is alkyl.

35. The ligand of claim 31, wherein $R^1$ and $R^3$ are selected independently for each occurrence from the group consisting of hydrogen, halogen, alkyl, cycloalkyl, heterocycloalkyl, aryl, heteroaryl, aralkyl, heteroaralkyl, —$OR^{11}$, —$N(R^{11})_2$, —$Si(R^{11})_3$, and —$(CH_2)R^{10}$.

36. The ligand of claim 31, wherein $R^1$ and $R^3$ are —$OR^{11}$.

37. The ligand of claim 31, wherein $R^1$ and $R^3$ are —$OR^{11}$; and $R^{11}$ is alkyl.

38. The ligand of claim 31, wherein $R^1$ and $R^3$ are alkyl.

39. The ligand of claim 31, wherein $R^5$, $R^7$ and $R^9$ are alkyl.

40. The ligand of claim 1, wherein said ligand is selected from the group consisting of:

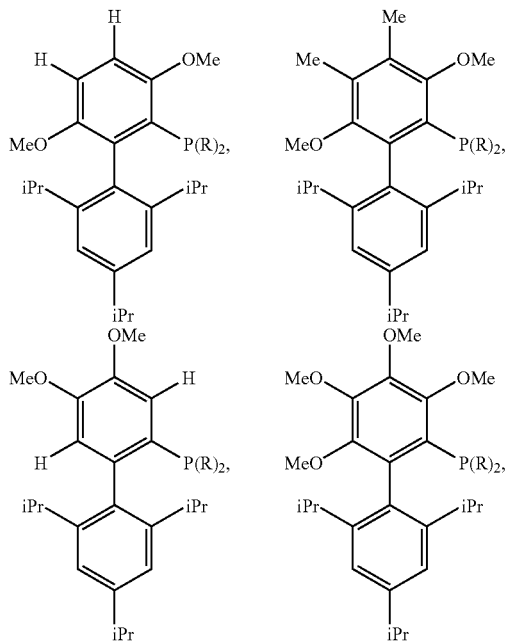

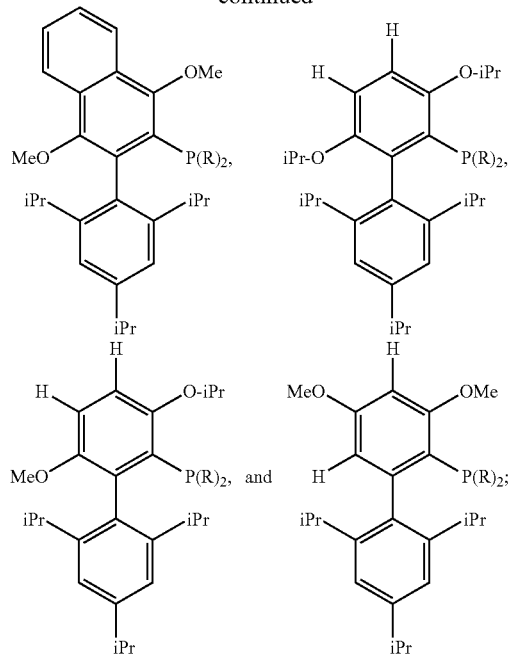

wherein R is selected independently for each occurrence from the group consisting of alkyl, aryl, and cycloalkyl.

41. The ligand of claim 40, wherein R is Cy, i-Pr, $C_5H_{11}$, Me, Et, 1-adamantyl, t-Bu,

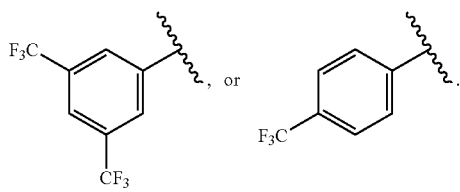

42. The ligand of claim 40, wherein said ligand is represented by

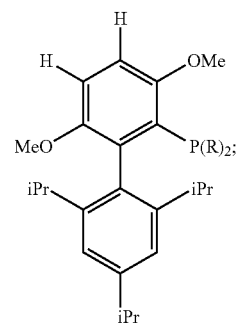

wherein R is Cy or t-Bu.

* * * * *